(12) United States Patent
Botstein et al.

(10) Patent No.: US 8,350,008 B2
(45) Date of Patent: Jan. 8, 2013

(54) WISP POLYPEPTIDES AND NUCLEIC ACIDS ENCODING SAME

(75) Inventors: David Botstein, Belmont, CA (US); Robert L. Cohen, San Mateo, CA (US); Audrey D. Goddard, San Francisco, CA (US); Austin L. Gurney, Belmont, CA (US); Kenneth J. Hillan, San Francisco, CA (US); David A. Lawrence, San Francisco, CA (US); Arnold J. Levine, New York, NY (US); Diane Pennica, Burlingame, CA (US); Margaret Ann Roy, San Francisco, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/117,051

(22) Filed: May 26, 2011

(65) Prior Publication Data

US 2011/0311540 A1 Dec. 22, 2011

Related U.S. Application Data

(60) Continuation of application No. 12/648,425, filed on Dec. 29, 2009, now abandoned, which is a continuation of application No. 11/488,375, filed on Jul. 17, 2006, now abandoned, which is a division of application No. 10/112,267, filed on Mar. 27, 2002, now Pat. No. 7,101,850, which is a division of application No. 09/182,145, filed on Oct. 29, 1998, now Pat. No. 6,387,657.

(60) Provisional application No. 60/063,704, filed on Oct. 29, 1997, provisional application No. 60/073,612, filed on Feb. 4, 1998, provisional application No. 60/081,695, filed on Apr. 14, 1998.

(51) Int. Cl.
*C12P 21/08* (2006.01)
*C07K 16/00* (2006.01)
*C07K 16/18* (2006.01)

(52) U.S. Cl. ............... 530/387.3; 530/388.1; 530/387.9; 530/388.24

(58) Field of Classification Search ........................ None
See application file for complete search history.

(56) References Cited

U.S. PATENT DOCUMENTS

| | | | |
|---|---|---|---|
| 5,408,040 A | 4/1995 | Grotendorst et al. |
| 5,536,637 A | 7/1996 | Jacobs |
| 5,585,087 A | 12/1996 | Lustig et al. |
| 5,840,569 A | 11/1998 | Hillman |
| 6,100,060 A | 8/2000 | Barnes et al. |
| 6,387,657 B1 | 5/2002 | Botstein et al. |

FOREIGN PATENT DOCUMENTS

| | | |
|---|---|---|
| EP | 307247 B1 | 3/1989 |
| WO | WO 89/06692 | 7/1989 |
| WO | WO 95/17416 | 6/1995 |
| WO | WO 98/21236 A1 | 5/1998 |
| WO | WO 98/25956 | 6/1998 |
| WO | WO 98/58063 A1 | 12/1998 |
| WO | WO 99/14327 A2 | 3/1999 |
| WO | WO 02/088081 | 7/2002 |

OTHER PUBLICATIONS

Adams et al., "Initial assessment of human gene diversity and expression patterns based upon 83 million nucleotides of cDNA sequence", Nature, 377(6547 SUPPL): 3-174, (1995).
Adams, et al., "Initial assessment of human gene diversity and expression patterns based on upon 83 million nucleotides of cDNA sequence", Nature, vol. 377, pp. 3-17, (1995).
Adams, MD et al., "EST90040 Synovial membrane *Homo sapiens* cDNA 5' end" *Database EmBL*=trIEST18 Entry Hszz82583, Acc. No. AA377456', (1997).
Aligenicht, LH et al, "Low-level c-myc amplificatIonin human cedóhic carcinoma cell lines and tumors: a frequent', p53-independent mutation associated with improved outcome in a randomized multi-institutional trial" Cancer Research 57(9): 1769-1775, (1997).
Alitalo and Schwab, "Oncogene amplification in tumor cells" Advances in *Cancer* Research 47: 235-281 (1986).
Altschul and Gish, "Local Alignment Statistics" *Methods in Enzymology* 266:460-480 (1990).
Attisano et al., "TOP-beta receptors and actions" *Biochimica et Biophysica Acta* 122(1): 71-80, (1994).
Ausubel et al., Current Protocols in Molecular Biology, N.Y.:Green Publishing Associates and Wiley Interscience (1989).
Babic AM et al., "CYR61, a product of a growth factor-inducible immediate early gene, promotes angiogenesis and tumor growth", Proc. Natl. Acad. Sci. USA 95(11): 6355-6360 (1998).
Baker, N., "Embryonic and imaginal requirements for wingless, a segment-polarity gene in brosophil", Dev. Biol. 125: 96-108, (1988).
Barfod et al., "Cloning and expression of a human CDC42 GTPasc-activating protein reveals a functional SH3-binding domain", Journal of Biological Chemistry 268(35): 26059-26062, (Dec. 15, 1993).
Baselga et al., "HER2 Overexpression and Paclitaxel Sensitivity in Breast Cancer: Therapeutic Implications", Oncology (Supplement No. 2) 11(3): 43-48, (Mar. 1997).
Baselga et al., "Phase II Study of Weekly Xntravenous keco mi binant Humanized KEICI-p185mcRd Monoclonal Antibody in Patients With HER2/neu-Overexpressing Metastatic Breast Cancer", J. Olin. Oncol. 14(3): 737-744, (Mar. 1996).
Beier et al, "MDB0332 Mouse brain, Stratagene Mum musculus cDNA 3• end similar to promo-oncogene (Wnt-5a) (human)", Database EMBL-EMEST19, Entry MM953, Acc. No. R74953, (1996).

(Continued)

*Primary Examiner* — Daniel C Gamett
(74) *Attorney, Agent, or Firm* — Traci Ropp; Ginger R. Dreger; Arnold & Porter LLP

(57) ABSTRACT

Wnt-1-Induced Secreted Proteins (WISPs) are provided, whose genes are induced at least by Wnt-1. Also provided are nucleic acid molecules encoding those polypeptides, as well as vectors and host cells comprising those nucleic acid sequences, chimeric polypeptide molecules comprising the polypeptides fused to heterologous polypeptide sequences, antibodies which bind to the polypeptides, and methods for producing the polypeptides.

5 Claims, 49 Drawing Sheets

OTHER PUBLICATIONS

Bennett et al., "Extracellular Domain-IgG Fusion Proteins for Three Human Natriurctic Peptide Receptors. Hormone Pharmacology and Application to Solid Phase Screening of Synthetic Peptide Antisera", The Journal of Biological Chemistry 266(34): 23060-23067 (1991).

Bishop, "Molecular themes in oncogenesie", Cell 64(2): 235-248 (1991).

Bolivar, "Construction and characterization of new cloning vehicles. II. A multipurpose cloning system" Gene 2(2): 95-113, (1997).

Boring et al., "Cancer Statistics, 1993" CA: A Cancer Journal for Clinicians 43(1): 7-26 (Jan.-Feb. 1993).

Bradbury et al., "Wnt-4 expression induces a pregnancy-like growth pattern in reconsdituted mammary glands in virgin mice", Dev. Biol. 170: 553-563, (1995).

Bradley and Brown, "The proto-oncogene int-1 encodes a secreted protein associated with the extracellular matrix", EMBO Journal 9: 1569-1575, (1990).

Bradley et al., "Expression of Wnt-1 in PC-12 cells results in modulation of plakoglobin and E-cadherin and increased cellular adhesion", Journal of Cell Biology 123(6, Pt.2 ▶ 1857-1865, (Dec. 1993).

Brown et al., "A retroVirUs vector expressing the putative mammary oncogene int-1 causes partial transformation of a mammary epithelial cell line" Cell 46(7): 1001-1009, (Sep. 26, 1986).

Brown, "Characterization of the FunctioYial gene and several processed pseudogenes in the human triosephoaphate isomerase gene family", Mol Cell Biol 5(7): 1694-1706, (Jul. 1985).

Cadigan and Nusse, "Wnt signaling: a common time in animal development" Genes & Development 11(24): 3286-3305, (Dec. 15, 1997.

Christiansen et al., Murine Wnt-11 and Wht=12 have temporally and spatially restricted expression patterns during embryonic development Mech. Dev. 51(2-3): 341-350, (1995).

Cornelis et al., "Allele toss patterns on chromosome 17q and 109 in breast carcinomas indicate at least two distinct target regions", Oncogene 8(3): 781-785, (Mar. 1993).

Cropp, et al., "Loss of heterozygosity on chromosomes 17 and 18 in breast carcinoma: two additional regions identified", Proc. Natl. Acad. Sci. USA 87(19): 7737-7741, (Oct. 1990).

Darzynkiewicz et al., Features of apoptotic Palls measured by flow cytometry Cytometry 13(8): 795-808, (1992).

Database accession No. AA000708, "mg36a12.r1 Soarcs mouse embryo NbME13.5 14.5 Mus musculus cDNA clone, mRNA sequence", (1996).

Database accession No. AA034677, "mi41b01.r1 Soares mouse embryo NbME13.5 14.5 Mus musculus cDNA clone, mRNA sequence", (1996).

Database accession No. AA238083, "mw97e08.r1 Soares mouse NML Mus musculus cDNA clone, mRNA sequence", (1997).

Database accession No. AA265159, "mx90c09.r1 Soares mouse NML Mus musculus cDNA clone, mRNA sequence", (2000).

Database accession No. AA278092, "vc34c10.r1 Barstead MPLRB1 Mus musculus cDNA clone, mRNA sequence", (1997).

Database accession No. W77228, "me63e12.r1 Soares mouse embryo NbME13.5 14.5 Mus musculus cDNA clone, mRNA sequence", (1996).

Database EMBL, "EST90040 synovial membrane Homo sapiens cDNA 5 end", XP002094095, (1997).

Database EMBL, "EST99434 thyroid Homo sapiens cDNA 5 end" XP002508626, (1997).

Database EMBL, "Homo sapiens connective tissue growth factor-like protein precursor, mRNA, complete cds", XP002508627, (2008).

Diatchehlco et al, "Suppression subtractive hybridization: a method for generating differentially regulated or tissue-specific cDNA probes and libraries", Proc. Natl. Acad. Sci. USA 93: 6025-6030, (1996).

Didsbury et al., "rac, a novel ras-related family of proteins that are botulinum toxin substrates", Journal of Biological Chemistry 264(28): 16378-16382, (Oct. 5, 1989).

Dzicrzck and Mcdvinsky, "Mouse chryonic hematopoicsis", Trends Genet. 11: 359-366, (1995).

Fendly, B.M. et al., "Characterization of Murine Monoclonal.Antibodies Reactive to Either the Human Epidermal Growth Factor Receptor or HER2/neu Gene Product" Cancer Research 50: 1550-1558, (Mar. 1, 1990).

Fracker PJ, et al., "Protein and cell membrane iodinations with a sparingly soluble chloroamide, 1,3,4,6-tetrachloro-3a, 6a-dephrenylglycoluril" Biochem Biophys Res Commun 80(4): 849-857 (Feb. 28, 1978).

Gavin et al., "Expression of multiple novel Wnt-1lint-rrelated genes during fetal andadult mouse development", Genes Dev. 4: 2319-2332, (1990).

Glinka at al., "Dickkopf-1 is a Member of a New Family of Secreted Proteins and Functions in Head Induction." Nature. 391(6665): 357-362, (Jan. 22, 1998).

Godowaki et al., "Characterization of the human growth hormone receptor gene and demonstration of a partial gene deletion in two patients with Laron-type dwarfism" Proc. Natl. Acad. Sci. USA 86: 8083-8087 (1989).

Green, "Phrap" UffEiAiclifilrr of Washington, Scatle, Washington: http://bozeman.mbt.washington.edu/Ohrap/HEifl, (1994).

Haataja et al., "Characterization of RAC3, a nove member of the Rho family", Journal of Biological Chemistry 272(33): 20384-20388, (Aug. 15, 1997).

Hashimoto et al., "Expression of the Elml gene, a novel gene of the CCN (connective tissue growth factor, Cyr61/Cef10, and neuroblastoma overexpressed gene) family, suppresses In vivo tumor growth and metastasis of K-1735 murine melanoma cells" Journal of Experimental Medicine 187(3): 289-296, (1998).

Haynes, et al, Electrophoresis 19: 1862-1871, (1998).

Herman and Horvitz, "The Caenorhabditis elegans gene lin-44 controls the polarity of asymmetric cell divisions", Development 120: 1035-1047 (1994).

Hiller et al (GenBank EST accession No. AA133248), (Nov. 1996).

Hiller et al., z117h12.r1 Soares pregnant uterus NbHPU Homosapiesn cbiens cONA clone 502247 5'IC C Database EMBL-EMEST15, Entry Hsaa33248, Acc. No. AA133248, (1996).

Hiller, "Yb42e03.r1 Homo sapiens cDNA clone 71852 5 r" Database EMBL-EMEST10, Entry 0501627, Acc. No. T5501, (1995).

Holland et al., "Gene duplications and the origins of vertebrate development" Development pp. 125-133, (1994).

Holmes et al, "Structure and Functional Expression of a. Human Interleukin-8 Receptor" Science 253(5025): 1279-1280, (1991).

Hunter, "Cooperation between oncogenes" Cell 64(2): 249-270 (Jan. 25, 1991).

Hynes and Stern., "The Biology of crbB-2/neufKER-2 and Its Role in Cancer." Bionhimica et Biophysica Acta 1198(2-3): 165-184, (Dec. 30, 1994).

Jue et al., "The mouse Wnt-1 gene can act via a paracrine mechanism in transformation of mammary epithelial cells" Molecular & Cellular Biology 12(1): 321-328, (Jan. 1992).

Kanateu and Nishikawa, "In vitro analysis of epiblast tissue potency for hematopoietic cell differentiation" Development 122: 823-830, (1996).

Kay et al., "Xenopus laevis: Practical uses in Cell and Molecular Biology" Methods in Cell Biology 36 (1991).

Kearney et al, "A new mouse myeloma cell line that has lost immunoglobulin expression but permits the construction of antibody-secreting hybrid cell lines" J. Immunol 123(4): 1548-1550, (Oct. 1979).

Kim et al., "Identification of a family of low-affinity insulin-like growth factor binding proteins (IGFBPs): Characterization of connective tissue growth factor as a member of the IGFBP superfamily", Proc. Natl. Acad. Sci. USA 94(24): 12981-12986, (Nov. 25, 1997).

Klein et al., "Selection for Genes Encoding Secreted Proteins and Receptors" Proc. Natr. Acad. Sci. USA 93(14): 7108-7113, (1996).

Klingensmith and Nusse, "Signaling by wingless in Drosophila" Dev. Biol. 166:396-414, (1994).

Kumar, et al., "Identification and cloning of CTGF-L from human osteoblasts, a novel cysteine rich protein containing an IGF binding domain", vol. 23, No. 5., p. S240, (1998).

Lee et al., "Insertional mutagenesis identifies a member of the Wnt gene family as a candidate oncogene in the mammary epithelium of int-2/Fgf-3 transgenic mice" Proc. Natl. Acad. Sci. 92(6): 2268-2272, (1995).

Lu and Gillett., "An Optimized Protocol for In Situ Hybridization Using PCR-Generated 33P-Labeled Riboprobes." Cell Vision. 1(2):169-176, (1994).

Maquat et al., "Human triosephosphate isomerase cDNA and protein structure. Studies of triosephosphate isomerase deficiency in man" J Biol Chem 260(6):3748-3753, (1985).

Marra et al., "md87all.rl Soares mouse embryo NbME13.5 14.5 Mus musculus cDNA clone 375356 5'" Database EMBL-MM71928, Entry MM71928, Acc. No. W64719, (1996).

Marra et al., "me63e12.r1 Soares mouse embryo NbME13.5 14.5 Mus musculus cDNA clone 400270 5'" Database EMBL-EMEST19, Entry MM22832, Acc. No. W77228, (1996).

Marra M et al, "va79b05.r1 Soares mouse NML Mus musculus cDNA clone 737553 5'" Database EMBL-EMEST18, Entry MM1181119, Acc. No. AA277108, (1997).

Marra M et al., "mw97e08.r1 Soares mouse NML Mus musculus cDNA clone 678662 5'" Database EMBL-EMEST18, Entry MM1155850, Acc. No. AA238083, (1997).

Marra M et al., "vuO5a03.r1 Soares mouse mammary gland NbMMg Mus musculus cDNA Clone 1179724 5' similar to SW:G25B human P21181 G25K GTP-binding protein, brain isoform" Database EMBL-EMEST2, Entry/acc. No. Aa672834, (1997).

Marra M et al., oug99b06.r1 Soares mouse hypothalamus NMHy Mus musculus cDNA clone 1616531 5', mRNA sequence Database EMBL-EMESTS, Entry/acc. No. Aa981401, (1998).

Marra M et al., vc34c10.r1 Barstead MPLRB1 Mus musculus cDNA clone 776466 5' Database EMBL-EMEST18, Entry MM1182282, Acc. No. AA278092, (1997).

Marra, M et al., "mg36a12.r1 Soares mouse embryo NbME13.5 14.5 Mus Musculus ZUM Clone 425854 5'" Database EMBL-EMEST19, Entry MMA00708, Acc. No. AA000708, (1996).

Marra, M et al., "mi41b01.r1 Soares mouse embryo NbME13.5 14.5 Mus musculus cDNA clone 466057 5'" Database EMBL-EMEST19, Entry mma34677, Acc. No. AA034677 (es), (1996).

Marra, M et al., mj41h08.r1 Soares mouse embryo NbME13.5 14.5 Mus musculus cDNA clone 478719 5' Database EMBL-EMEST19, Entry MMAA51212, Acc. No. AA051212, (1996).

Martinerie C, et al., "Physical mapping of human locihomologous to the chicken nov proto-oncogene" Oncogene 7(12):2529-2534, (1992).

Martinerie et al., "Regulation of nov by WT1: a potential role for nov in nephrogenesis" Oncogene, 12(7):1479-1492, (1996).

Martinerie et al., Structural analysis of the human nov proto-oncogene and expression in Wilms tumors Oncogene 9(9):2729-2732, (1994).

McMahon and Bradley, "The Wnt-1 lint-1) proto-oncogene is required for development of a large region of the mouse brain" Cell 62:1073-1085 (1990).

McMahon, A., "The Wnt Family of Developmental Regulators" Trends in Genetics (71): 236-242, (1992).

Meese, "Molecular mapping of the oncogene MYB and rearrangements in malignant melanoma" Genes, Chromosomes Cancer 1(1):88-94, (1989).

Moll et al., "The murine raci gene: cDNA cloning, tissue distribution and regulated expression of raci mRNA by disassembly of actin microfilaments" Oncogene 6(5):863-866 (1991).

Morata and Lawrence, "The development of wingless, a homeotic mutation of *Drosophila*" Dev. Biol. 56:227-240, (1977).

Nieuwkoop et al, "Normal Table of *Xenopus laevis*: (Daudin)", Amsterdam: North—Holland (1967).

Nilsson, et al., Prot. Exp . and Purification 11: 1-16, (1997).

Nusse and Vermus, Many tumors induced by the mouse mammary tumor virus contain a provirus integrated in the same region of the host genome Cell 31:99-109 (1982).

Oemar and Luscher, "Connective tissue growth factor. Friend or foe?" Arteriosclerosis, Thrombosis & Vascular Biology 17(8):1483-1489 (1997).

Oemar, et al., "Connective tissue growth factor, friend or foe?", Arteriosclerosis, thrombosis and vascular biology, vol. 17, No. 8, pp. 1483-1489, (1997).

Olson and Papkoff, "Regulated expression of Wnt Family Members during Proliferation of C57mg Mammary Cells" Cell Growth & Differentiation 5(2):197-206 (1994).

O'Reilley et al. Baculovirus Expression Vectors: A Laboratory Manual, Oxford: Oxford University Press (1994).

Ousse and Varmus, "Wnt genes" Cell 69:1073-1087 (1992).

Papkoff and Sdhryver, "Secreted int-1 protein is associated with the cell surface" Mole. Cell. Biol. 10:2723-2730, (1990).

Parr and McMahon, "Dorsalizing signal Wnt-7a required for normal polarity of D-V and A-P axes of mouse limb" Nature 374:350-353, (1995).

Pennica D, et al., "WISP, genes are members of the connective tissue growth factor family that are up-regulated in wnt-1-transformed cells and aberrantly expressed in human colon tumors" Proc. Natl. Acad. Sci. USA 95(25):14717-22 (1998).

Pennica, et al., "WISP genes are members of the connective tissue growth factor family that are up-regulated in Wnt-1-transformed cells and aberrantly expressed in human colon tumors", Proc. Natl. Acad. Sci., vol. 95, pp. 14717-14722, (1998).

Peppel at al., J. Exp Med., 174: 1483-1489, (1991).

Picker et al., "Control of lymphocyte recirculation in man. I. Differential regulation of the peripheral lymph node homing receptor L-aelectin on T cells during the virgin to memory cell transition" Journal of Immunology 150(3):1105-1121 (1993).

Possee R.D. et al., "Nucleotide sequence of the Autographa californica nuclear polyhedrosis 9.4 kbp EcoRI-I and -R(polyhedrin gene) region" Virology 185(1):229-241, (1991).

Price et al., "Tumorigenicity and metastasis of human breast carcinoma cell lines in nude mice" Cancer Research 50(3):717-721, (1990).

Ravdin and Chamness, "The c-erbB-2 proto-oncogene as a prognostic and predictive marker in breast cancer: a paradigm for the development of other macromolecular markers—a review" Gene 159(1):19-27, (1995).

Rijsewijk et al., "The *Drosophila* homolog of the mouse mammary oncogene int-1 is identical to the segment polarity gene wingless" Cell 50:649-657 (1987).

Ruppert et al., "Cloning and Expression of Human TAF11250: a TBP-associated Factor Implicated in Cell-cycle Regulation" Nature 362:175-179 (1993).

Sambrook et al, "Molecular Cloning: A Laboratory Manual", Cold Spring Harbor Laboratory Press, New York (1989).

Saxena, et al., "Differential expression of WISP-1 and WISP-2 genes in normal and transformed human breast cell lines", Molecular and cellular biochemistry, vol. 228, pp. 99-104, (2001).

Schwab and Amler, "Amplification of cellular oncogenes: a predictor of clinical outcome in human cancer" Genes, Chromosomes & Cancer 1(3):181-193, (1990).

Shirsat et al., "A member of the ras *gene* superfamily is expressed specifically in T, B and myeloid hemopoietic cells" Oncogene 5(5):769-772, (1990).

Sigel R., et al., "Production of Antibodies by Inoculation into Lymph Nodes" Methods in Enzymology, New York: Academic Press vol. 93 (1983).

Slamon et al., "Human Breast Cancer: Correlation of Aelapse and Survival with Amplification of the HER-2/neu Oncogene" Science 235:177-182 (1987).

Slamon et al., "Studies of the HER-2/neu Proto-Oncogene in Human Breast and Ovarian Cancer" Science 244:707-712, (1989).

Sokol S, et al., "Injected Wnt RNA induces a complete body axis in *Xenopus* embryos" Cell 67(4):741-752, (1991).

Sompayrac et al., "Efficient infection of monkey *cells* with DNA of simian virus 40" Proc. Natl. Acad. Sci. USA 78(12):7575-7578, (1981).

Soon et al., J. Biol. Chem., vol. 278, Issue 13, 11465-11470, (2003).

Stark et al., "Epithelial transformation of metanephric mesenchyme in the developing kidney regulated by Wnt-4" Nature 372:679-683, (1994).

Strausberg, R., "nnO3e01.81 NCI_CGAP_Pr4.1 *Homo sapiens* CDNA clone IMAGE:1076664 similar to TR:g984956 G984956 connective tissue growth factor" Database EMBL-EMEST1, Entry Aa592984, Acc. No. AA592984, (1997).

Suva et al., "A parathyroid hormone-related protein implicated in malignant hypercalcemia: cloning and expression" Science 237(4817):893-896, (1987).

Takada et al., "Wnt-3a regulates somite and tailbud formation in the mouse embryo" Genes Dev. 8: 174-189, (1994).

Takahashi, "Mapping of the MYC gene to band 8q24.12—q24.13 by R-banding and distal to fra($^8$T($9^{24}$-$^{11}$), FRA8E, by fluorescence in situ hybridization" Cytogenet Cell Genet 57(2):109-111 (1991).

Thimmappaya et al., "Adenovirus VAT RNA is required for efficient translation of viral mRNAs at late times after infection" Cell 31(3 Pt 2):543-551, (1982).

Thomas and Cappcchi, "Targeted disruption of the murine int-I proto-oncogene resulting in. severe abnormalities in midbrain and cerebellar development" Nature 346:847-850, (1990).

Tubby, B., "*Homo sapiens* DNA sequence from PAC 142L7 on chromosome 6q21. Contains a Tisse growth factor'" Database EMBL-EMHUM1, Entry Hs14217, Acc. No. Z99289, (1997).

Vant Veer et al., Molecular cloning and chromosomal assignment of the human homolog of int-1, a mouse gene implicated in mammary tumorigenesis Mole. Cell. Biol. 4:2532-2534, (1984).

Van't Veer, "molecular cloning and chromosomal assignment of the human homolog of int-1, a mouse gene implicated in mammary tumorigenesis" Mol Cell Biol 4(11):2532-2534, (1984).

Wong et al., "Differential transformation of mammary epithelial cells by Wnt genes" Molecular & Cellular Biology 14(9):6278-6286 (Sep. 1994).

Yamanaka et al., "Inhibition of insulin receptor activation by insulin-like growth factor binding proteins" Journal of Biological Chemistry 272(49):30729-30734, (1997).

Zhang A et al., "Identification of rCop-1, a new member of the CCN protein family, as a negative regulator for cell transformation" Mol Cell Biol 18(10):6131-6141, (1998).

Zhang et al., "Relative malignant potential of human breast carcinoma cell lines established from pleural effusions anda brain metastasis" Invasion Metastasis 11(4):204-215, (1991).

Zhang, et al., "Identification of rCop-1, a new member of the ccn protein family, as a negative regulator for cell transformation", Molecular and cellular Biology, vol. 18, No. 10, pp. 6131-6141, (1998).

Zheng S et al, "The induction of Wnt-1 in PC12 cells results in modulation of plakoglcibin and Z-cadherin and increased cellular. adhesion" Journal of Cell Biology 123(6,pt2):1857-1865, (1993).

Zheng S et al., "The induction of ret by Wnt-1 in PC12 cells is atypically dependent on continual Wnt-1 expression" Oncogene 12(3): 555-562, (1996).

Zon, et al., "In Gluckman and Coulombel, ed., Colloque, INSERM" presented at the Joint International Workshop on Foetal and Neonatal Hematopoisis and Mechanism of Bone Marrow Failure, Paris, France, Apr. 3-6, 1995 235:17-22, (1995).

Zoubine, et al., "WISP-2: A Serum-inducible gene differentially expressed in human normal breast epithelial cells and in mcf-7 breast tumor cells", Biochemical and Biophysical Research Communications, vol. 282, pp. 421-425, (2001).

FIG._1A

```
 901  GCTGTGTACC AGCCAGAGGA GGCCACGAAC TTCACTCTCG CAGGCTGTGT CAGCACACGC ACCTACCGAC CCAAGTACTG CGGAGTCTGT ACTGACAATA
      CGACACATGG TCGGTCTCCT CCGGTGCTTG AAGTGAGAGC GTCCGACACA GTCGTGTGCG TGGAGGCTG GGTTCATGAC GCCTCAGACA TGACTGTTAT
 275   A  V  Y   Q  P  E   E  A  T   N  F  T   L  A  G   C  V  Q   H  T  T   Y  R  P   K  Y  C   G  V  C   T  D  N  R

1001  GGTGTTGCAT CCCCTACAAG TCCAAGACCA TCAGTGTGGA TTTCCAGTGT AAAGGTCACCT CCAGAGGGGC CAGGTTTCTC CCGGCAGGTC CTATGGATTA ATGCTTCTT
      CCACAACGTA GGGGATGTTC AGGTTCTGGT AGTCACACCT AAAGGTCACA GTTCCAGTGG TTTCCAGTGG GTCCAAAGAG GGCCGTCCAG GATACCTAAT TACGAAGAA
 309   C  C  I   P  Y  K   S  K  T   I  S  V   D  F  Q   C  K  G   H  P  E   G  P  G   F  S  R   Q  V  L   W  I  N   A  C  F

1101  CTGCAACCTG AGTGCAGGA TATCTTTGCT GACTTGGAAT CTTCGAAGAG ATTGCCAATT AGTGGGTGT GTGGCTCAGG
      GACGTTGGAC TCGACGTCCT ATAGAAACGA CTGAACCTTA GAAGCTTCTC TAACGGTTAA TCCACCCACA CACCGAGTCC
 342   C  N  L   S  C  R   N  P  N  D   I  F  A   D  L  E  S   Y  P  D   F  E  E   I  A  N  Q

1201  GTAAAGTTCC ATGCTGCAAA CTTTGTGGTC CAGGACCAGC CAATTGAGCC TTATTTCATC TGGGACAATT CTACATCATT CCAAGGAAAA
      CATTTCAAGG TACGACGTTT GAAACACCAG GTCCTGGTCG GTTAACTCGG AATAAAGTAG ACCCTGTAA GATGTAGTAA GGTTCCTTT

1301  TCTGTTCCTG TTTTGACAAT GCAGCCAGG CTGCTCAGGC CAGGAGAGTG GGTTCCTCCT CAATTGAGCC GGGACAATT GTCCAAGAA ATTCCCAGTT
      AGACAAGGAC AAAACTGTTA CGTCGGTCAC GACGAGTCCG GTCCTCTCAC CCAAGGAGGA ACCCTGTAA AGTCTTCAAC CAGGTTCCTT TAAGGGTCAA

1401  CACATCTCTG ACTGTTCACA ATGGAAGCAA AGCTAGTTCT GCTCCAGCCT GGGCAAGCT TCAGAAGTTG GCCGTTCAAC TGGATGGGAT GTCCAAGGAA
      GTGTAGAGAC TGACAAGTGT TACCTTCGTT TCGATCAAGA CGAGGTCGGA CCCGTTCGA AGTCTTCAAC CGGCAAGTTG ACCTACCCTA CAGGTTCCTT

1501  AAGCATCAGC TGAAGAACCA GTATCATGAA CCTTGCCAAG GTCCTTCCTC AGATGCCAAG CCTAGGGGAT CTGGGATCCT TTCAGACAGA TGGGGACACA
      TTCGTAGTCG ACTTCTTGGT CATAGTACTT GGAACGGTTC CAGGAAGGAG TCTACGGTTC GGATCCCCTA GACCCTAGGA AAGTCTGTCT ACCCTGTGT

1601  GGAATAAGCT ATTATTTTAC CCTTGCCAAA TGATACTATC CTGGTATTT CTGCCTAAAA ACATACCAAA AGTGTTCTTG TTCCACTGAT CTGTATATCA
      CCTTATTCGA TAATAAAATG GGAACGGTTT ACTATGATAG GACCATAAA GACGGATTTT TGTATGGTTT TCACAAGAAC AAGGTTGACTA GACATATAGT

1701  CAAGTCACCA AACATTTCC AGGTGAGGAC GTCATTCTCT GTTTGCCAATT GAAAAAA
      GTTCAGTGGT TTGTAAAAGG TCCACTCCTG CAGTAAGACA AAACGGTTAA CTTTTT
```

FIG._1B

```
  1 CCCACGCGTC CGGCTCCTG ATCTCCAGAG GACCCGGGGC TGGGACAGGG GCCTTGGCGA GCCTGCTGCAG GCCTGTGGGA TGGAGGTCTT
    GGGTGCGCAG GCCGAGGAC TAGAGGTCTC CTGGGCCCG ACCCTGTCCC CGGAACCGTC CGGACGACCT ATCGAACCCT ACCTCCAGAA

101 TCTTGCTGGG AACTGAGAG CTGAGAGGCT CCTGTCAGGC TCCTGTCCTA AACTCTTGGC ACTTGGGCTT CACACACTGT CAGACACCTT
    AGAACGACCC TTGACTCCTC GACTCTCCGA GGACAGTCCG AGGACAGGAT TTGAGAACCG TGAACGCCAC CGAACCCGAA GTCTGTGGAA

201 CTTGGTGGCC TCCTCGGCCT CAGGTTTGAA GCTGGCTCCA CAAGGACACA GGTGACATGA CTTCTGGCCA TTTCCTTCCT
    GAACCACGG AGGAGCCCGA GTCCAAACTT CGACCGAGGT GTTCCCTGTG CCACTGTACT TGACTAGGTA GAAGACCCGT AAAGGAAGA
                                                                        M   R                              S    F    L

301 CTGCATTCTC TCAATGGTGT ATTCCCAGCT GTGCCCAGCA CCCTGTGCCT GTCCTTGGAC ACCACCCCAG TGCCCACCGG GGGTACCCCT GGTGCTGGAT
    GACGTAAGAG AGTTACCACA TAAGGGTCGA CACGGGTCGT GGGACACGGA CAGGAACCTG TGGTGGGGTC ACGGGTGGCC CCCATGGGGA CCACGACCTA
     16  C    I    L    S    M    V    Y    S    Q    L    C    P    A    P    C    A    C    P    W    T    P    P    P    Q    C    P    P    G    V    P    L    V    L    D

401 GGCTGTGGCT GCTGTCGAGT GTGTGCACGG AGTCCTGCGA CCACCTGCAT GTCTGCGACC CCAGCCAGGG CCTGGTTTGT CAGCCTGGGG
    CCGACACCGA CGACAGCTCA CACACGTGCC TCAGGACGCT GGTGGACGTA CAGACGCTG GGTCGGTCCC GGACCAAACA GTCGGACCCC
     49  C    A    R    V    C    G    C    C    R    L    G    E    S    C    D    H    L    H    V    C    D    P    S    Q    G    L    V    C    Q    P    G    A

501 CAGGCCCCAG TGGCCGTGGT GCTGTGTGCC TCTTCGAAGA AGCTGTGAGG TGAATGGCGG CAGGTACCTG GATGGGGAGA CCTTTAAACC
    GTCCGGGGTC ACCGGCACCA CGACACACGG AGAAGCTTCT TCGACACTCC ACTTACCGCC GTCCATGGAC CTACCCCTCT GGAAATTTGG
     83  G    P    S    G    R    G    A    V    C    L    F    E    E    D    D    G    S    C    E    V    N    G    R    R    Y    L    D    G    E    T    F    K    P

601 CAATTGCAGG GTTTTGTGCC GCTGTGATGA CGGTGGTTTC ACCTGCCTGC CGGTGGTTTG TGTGTGACCA GGCAGTGATG CCCACGCCCC
    GTTAACGTCC CAAAACACGG CGACACTACT GCCACCAAAG TGGACGGACG GCCACCAAAC ACACACTGGT CCGTCACTAC GGGTGCGGGG
    116  N    C    R    V    L    C    R    C    D    D    G    G    F    T    C    L    P    L    C    S    E    D    V    R    L    P    S    W    D    C    P    R    P

701 AGGAGAATAC AGGTGCCAGG AAGTGCTGCC ATGGCCCCTG GCATCTGCCC CTCAACTGGG AGCACAGCCT CAGCGCCCTC TCCAGCCCAA TGTGGGTTGG GCATAGCCAC
    TCCTCTTATG TCCACGGTCC TTCACGACGG TACCGGGGAC CGTAGACGGG GAGTTGACCC TCGTGTCGGA GTCGCGGGAT AGGTCGGGTT ACACCCAACC CGTATCGGTG
    149  R    R    I    Q    V    P    G    R    C    C    D    G    G    P    E    W    V    C    D    Q    A    V    M    Q    P    A    I    Q    P    S    A    Q    G    H    Q    L

801 TTTCTGCCCT TGTCACTCCT GCATCTGCCG ATGGCCCCTG ACCAGAACCC CTCAACTGGG AGCACAGCCT CAGCGCCCTC TCCAGCCCAA TGTGGGTTGG GCATAGCCAC
    AAAGACGGGA ACAGTGAGGA CGTAGACGGC TACCGGGGAC TGGTCTTGGG GAGTTGACCC TCGTGTCGGA GTCGCGGGAT AGGTCGGGTT ACACCCAACC CGTATCGGTG
    183  S    A    L    V    T    P    A    S    A    D    G    P    C    S    T    F    C    G    L    G    I    A    T

901 CCGAGTATCC AACCAGAACC GATTCTGCCA CAGGAGATC ACTGGAGATG TGTGTCTGTC CAGACCCTGC CTGGGGAACG CTCATGGAAC CTCATGGAAC
    GGCTCATAGG TTGGTCTTGG CTAAGACGGT GTCCTCTAG TGACCTCTAC ACACAGACAG GTCTGGGACG GACCCCTTGC GAGTACCTTG
    216  R    V    S    N    Q    N    R    F    C    Q    L    E    I    Q    R    R    L    C    L    S    R    P    C    L    A    S    R    S    H    G    S    W    N
```

FIG._2A

```
1001 AGTGCCTTCT AGAGCCATTG CGGGGATGTG GATACAGGGC CTGCCATTCT CAGCAAATGT CCCTAGGACC AGGCCCTGGA CTGATGGTAG ATGCCCCTCT
     TCACGGAAGA TCTCGGTAAC GCCCCTACAC CTATGTCCCG GACGGTAAGA GTCGTTTACA GGGATCCTGG TCCGGGACCT GACTACCATC TACGGGGAGA
249    S   A   F   Q

1101 CCATGCTCTT GGCTGCAGTT AACTGTCCTG GGTGGATTCA GTGTCCAGAG CCTCTGAGCG ATCCCTGCTC TGTCTGAGGT GGGGAAGCA GGTGACCAGC
     GGTACGAGAA CCGACGTCAA TTGACAGGAC CCACCTAAGT CACAGGTCTC GGAGACTCGC TAGGGACGAG ACAGACTCCA CCCCTTCGT CCACTGGTCG

1201 TCCATTCTC TGGATTCTGA CCCAGGCTTC TGGGTTCTCC TGGCTAGTTC CTCAAAACTT CCCTGTATGA AAAGGACAAC CAAAAGGACC TTTAAAGCTA
     AGGTAAAGAG ACCTAAGACT GGGTCCGAAG ACCCAAGAGG ACCGATCAAG GAGTTTTGAA GGGACATACT TTTCCTGTTG GTTTTCCTGG AAATTTCGAT

1301 AGCTGTACTG GGCAAGCCTG GCCACCATGC TGGGGATAGT GACAGTAATA GGTACCAGGC AGCAGATTGC CTGAAACATC CAGGTCCCTT CTTGGACTTC
     TCGACATGAC CCGTTCGGAC CGGTGGTACG ACCCCTATCA CTGTCATTAT CCATGGTCCG TCGTCTAACG GACTTTGTAG GTCCAGGGAA GAACCTGAAG

1401 TATGTGCTTG TCCCAAAGAT TATGGGTGAC CTTGTAAGTG TGCCTTTCCT GATCTGAGAA CACCCTGCCC GGCTGGGAAG AATTTTCTGG GAACATGAAG
     ATACACGAAC AGGGTTTCTA ATACCCACTG GAACATTCAC ACGGAAAGGA CTAGACTCTT GTGGGACGGG CCGACCCTTC TTAAAAGACC CTTGTACTTC

1501 AGATGGAATC ACACTATTCT TAAGAGCGTT TGCCAAGTCC AGGAACTTGA CCTTTGTATT TGTAAAAATA CACATCTCTT AAATGCTCAC AAAGCAAGAG
     TCTACCTTAG TGTGATAAGA ATTCTCGCAA ACGGTTCAGG TCCTTGAACT GGAAACATAA ACATTTTTAT GTGTAGAGAA TTTACGAGTG TTTCGTTCTC

1601 GCTCCACACT TCTGGCAGGC CAGGGCCTTT CTCTTCAGCA TGAGAGAGAC AAGGAACAGT AGAGTACCCT CCTCTGGAGG ACTGGCCCGG TCTGGAATAA
     CGAGGTGTGA AGACCGTCCG GTCCCGGAAA GAGAAGTCGT ACTCTCTCTG TTCCTTGTCA TCTCATGGGA GGAGACCTCC TGACCGGGCC AGACCTTATT

1701 ACACCCAAAT CAAGTGTGGA AAAAAAAAAA AAAA
     TGTGGGTTTA GTTCACACCT TTTTTTTTTT TTTT
```

```
 901 GAAGTGTCTG GCTGTGTACC AGCCAGAGGC ATCCATGAAC TTCACACTTG CGGGCTGCAT CAGCACACGC TCCTATCAAC CCAAGTACTG TGGAGTTTGC
     CTTCACAGAC CGACACATGG TCGGTCTCCG TAGGTACTTG AAGTGTGAAC GCCCGACGTA GTCGTGTGCG AGGATAGTTG GGTTCATGAC ACCTCAAACG
 272  K  C  L   A  V  Y  Q   P  E  A    S  M  N   F  T  L  A   G  C  I    S  T  R    S  Y  Q  P   K  Y  C    G  V  C

1001 ATGGACAATA GGTGCTGCAT CCCCTACAAG TCTAAGACTA TCGACGTGTC CTTCCAGTGT CCTGATGGGC TTGGCTTCTC CCGCCAGGTC CTATGATTA
     TACCTGTTAT CCACGACGTA GGGGATGTTC AGATTCTGAT AGCTGCACAG AAGGTCACA  GGACTACCCG AACCGAAGAG GGCGGTCCAG GATACCTAAT
 305  M  D  N   R   C  C  I   P  Y  K   S  K  T  I    D  V  S    F  Q  C    P  D  G  L   G  F  S    R  Q  V   L  W  I  N

1101 ATGCCTGCTT CTGTAACCTG AGCTGTAGGA CATCTTTGCT GACTTGGAAT CCTACCCTGA CTTCTCAGAA ATTGCCAACT AGGCAGGCAC
     TACGGACGAA GACATTGGAC TCGACATCCT GTAGAAACGA CTGAACCTTA GGATGGGACT GAAGAGTCTT TAACGGTTGA TCCGTCCGTG
 339  A  C  P    C  N  L    S  C  R  N    P  N  D    I  F  A    D  L  E  S    Y  P  D    F  S  E    I  A  N  Q

1201 AAATCTTGGG TCTTGGGGAC TAACCCAATG CCTGTGAAGC TATGGCCAAT AACTTTTCAC CAATGAGCCT TAGTTACCCT GATCTGGACC
     TTTAGAACCC AGAACCCCTG ATTGGGTTAC GGACACTTCG ATACCGGTTA ATGAAAAGTG GTTACTCGGA ATCAATGGGA CTAGACCTGG

1301 CTTGGCCTCC ATTTCTGTCT CTAACCATTC AAATGACGCC GCTCAGGCCC ANGCTATGAG TTTTCTCCTT GATATCATTC AGCATCTACT
     GAACCGGAGG TAAAGACAGA GATTGGTAAG TTTACTGCGG ACTACCACGA CGAGTCCGGG TACGATACTC AAAAGAGGAA CTATAGTAAG TCGTAGATGA

1401 CTAAAGAAAA ATGCCTGTCT CTAGCCTGAA TGGACTACAC CCAAGCCTGA TTCTTTTAGAT AGAGTCCTG CTGGATCTTG CCTAAATCCC
     GATTTCTTTT TACGGACAGA GATCGGACAT ACCTGATGTG GGTTCGGACT AAGAAATCTA TCTTCAGGAC GACCTAGAAC GGATTAGGG

1501 AAGAAATGGA ATCAGGTAGA CTTTTAATAT CACTAATTTC TGCCAAGAGG GGTAATTCTG AAGACTCTTT GGGTCCATTC AGATGAATAG ATGGAATTTG
     TTCTTTACCT TAGTCCATCT GAAATTATA  GTGATTAAAG ACGGTTCTCC CCAATTAAGAC TTCTGAGAA  CCCAGGTAAG TCTACTTATC TACCTAAAC

1601 GAACAATAGA ATAATCTATT ATTTGGAGCC TGCCAAGAGG TACTGTAATG ACGGTTCTCC ACGTCAGCTG ACCAAAACTA TCCTGATTCC AAATATGTAT
     CTTGTTATCT TATTAGATAA TAAACCTCGG ACGGTTCTCC ATGACATTAC TGCCAAGAC TGCAGTCGAC TGGTTTTGAT AGGACTAAGG TTTATACATA

1701 GCACCTCAAG GTCATCAAAC ATTTGCCAAG TGAGTTGAAT AGTTGCTTAA TTTTGATTTT AAAACTAAAA TTGTATCCAT TTGTTCATGG ATTGTTGAGG
     CGTGGAGTTC CAGTAGTTTG TAAACGGTTC ACTCAACTTA TCAACGAATT AAAACTAAAA TTTTGATTTT TTGATTTAAA AACATAGGTA TAACAACTCC

1801 TTAAGTTTCT CTTCACCCCT ACACTGTGTC GGGTACAGAT TAAGGTTTGTC CCAGTCAGAA TAAGGTTTTC ATAAACATTG CTGTTGATGG GAAAAGCCCC
     AATTCAAGA AGAGTGGGGGA TGTGACACTT CCCATGTCTA ATCCAAACAG GGTCAGTCTT TATTTTGTAAG TATTTGTAAC GACAACTACC CTTTCGGGG

1901 CAGTAATAAC TCCAGAGACA GGGAAAGGTC AGCCCATTTC AGAGGACCA ATTGACTCTC ACACTGAATTG TAACTGAGAG AGCTGCTGAC TGGCAGGGCT TTGGGCAGTT
     GTCAATTATG AGGTCTCTGT CCCTTTCCAG TCGGGTAAAG TCTCCTGGT TAACTGAGAG ATTGACTTAG TCGACGACTG ACCGCCGTCA AACCCGTCAA
```

*FIG._3B*

```
2001 GGCCAGGCTC TTCCCTGAAT CTTCTCCCTT GTCCTGCTTG GGTTCATAGG AATTGGTAAG GCCTCTCGAC TGGCCTGTCT GGCCCCTGAG AGTGGTGCCC
     CCGGTCCGAG AAGGAACTTA GAAGAGGGAA CAGGACGAAC CCAAGTATCC TTAACCATTC CGGAGACCTG ACCGGACAGA CCGGGGACTC TCACCACGGG

2101 TGGAACACTC CTCTACTCTT ACAGAGCCTT GAGAGACCCA GCTGCAGACC ATGCCAGACC CACTGAAATG ACCAAGACAG GTTCAGGTAG GGGTGTGGGT
     ACCTTGTGAG GAGATGAGAA TGTCTCGGAA CTCTCTGGGT CGACGTCTGG TACGGTCTGG GTGACTTGAC TGGTTCTGTC CAAGTCCATC CCCACACCCA

2201 CAAACCAAGA AGTGGGTGCC CTTGGTAGCA ACCTCTAGAG CTGGAGGCTG TGGGACTCCA GGGGCCCCCG TGTTCAGGAC ACATCTATTG
     GTTTGGTTCT TCACCCACGG GAACCATCGT TGGAGATCTC GACCTCCGAC ACCCTGAGGT CCCCGGGGGC ACAAGTCCTG TGTAGATAAC

2301 CAGAGACTCA TTTCGTTCTG CTGACCAAAT GGCCAGTTTT CTGGTAGGAA GATGGAGGTT TACCAGTTGT TTAGAAACAG AAATAGACTT
     GTCTCTGAGT AAAGCAAGAC GACTGGTTTA CCGGTCAAAA GACCATCCTT CTACCTCCAA ATGGTCAACA AATCTTTGTC TTTATCTGAA

2401 AATAAAGGTT TAAAGCTGAA GAGGTTGTTG CTAAAAGGAA AAGGTTGTTG TTAATGAATA TCAGGCTATT ATTTATTGTA ATAATATTTA
     TTATTTCCAA ATTTCGACTT CTCCAACTTC GATTTTCCTT TTCCAACATT AGTCCGATAA TAAATAACAT TATTATAAAT

2501 CTGTTAGAAT TCTTTTATTT AGGGCCTTTT CTGTGCCAGA CATTGCTCTC AGTGCTTTGC TTCACTGAATC TGTTGAGAAG
     GACAATCTTA AGAAAATAAA TCCCGGAAAA GACACGGTCT GTAACGAGAG TCACGAAAACG AAGTGCTGTT ACAACTCTTC

2601 TTCCCATTAT TATTTCTGTT CTTACAAATG TGAAACGGAA ACTTTGCCTT GTGAGAAAAC TCAACCAGAG TCACCCAGTT AAAGTTAGGA
     AAGGGTAATA ATAAAGACAA GAATGTTTAC ACTTTGCCTT CACTCTCTG AGTTGGTCTC AGTGGGTCAA CCACTGACCC TTTCAATCCT

2701 TTCAGATCGA AATTGGACTG TCTTTATAAC CCCTGTTTT TAGAGCTTCC AAATGTGTCA GAATAGGAAA ACATTGCAAT AAATGGCTTG
     AAGTCTAGCT TTAACCTGAC AGAAATATTG GGGACAAAA ATCTCGAAGG TTTACACAGT CTTATCCTTT TGTAACGTTA TTTACCGAAC

2801 ATTTTTTAAA AAAAAAAAAA AAAAAAAAA
     TAAAAAATTT TTTTTTTTT TTTTTTTTT
```

```
 901  CCACCATGCA GAACACCAAT ATTAACACGC TGCCTGGTCT GTCTGGATCC CGAGGTATGG CAGAGGTGCA AGACCTAGTC CCCTTTCCTC TAACTCACTG
      GGTGGTACGT CTTGTGGTTA TAATTGTGCG ACGGACCAGA CAGAGCCTAGG GCTCCATACC GTCTCCACGT TCTGGATCAG GGGAAAGGAG ATTGAGTGAC

1001  CCTAGGAGGC TGGCCAAGGT GTCCAGGGTC CTCTAGCCCA CTCCCCTGCCT ACACACACAG CCTATATCAA ACATGCACAC GGGCGAGCTT TCTCTCCGAC
      GGATCCTCCG ACCGGTTCCA CAGGTCCCAG GAGATCGGGT GAGGGACGGA TGTGTGTGTC GGATATAGTT TGTACGTGTG CCCGCTCGAA AGAGAGGCTG

1101  TTCCCCTGGG CAAGAGATGG GACAAGCAGT CCCTTAATAT TGAGGCTGCA GCAGGTGCTG GCCATTTTTC TGGGGGTAGG ATGAAGAGAA
      AAGGGGACCC GTTCTCTACC CTGTTCGTCA GGGAATTATA ACTCCGACGT CGTCCACGAC CGGTAAAAAG ACCCCCATCC TACTTCTCTT

1201  GGCACACAGA GATTCTGGAT CTCCCTGCTGC GTTTGTAAAA TTGTTCCTGA ATACAAGCCT ATGCGTGAAA AAAAAAAAAA AAA
      CCGTGTGTCT CTAAGACCTA GAGGACGACG CAAACATTTT AACAAGGACT TATGTTCGGA TACGCACTTT TTTTTTTTTT TTT
```

*FIG._4B*

| | |
|---|---|
| 1 | 5'-CTGCAGGGGACATGAGAGGCACACCGAAGACCCACCTCCTGGCCTTCTC |
| 51 | CCTCCTCTGCCTCCTCTCAAAGGTGCGTACCCAGCTGTGCCCGACACCAT |
| 101 | GTACCTGCCCCTGGCCACCTCCCCGATGCCCGCTGGGAGTACCCCTGGTG |
| 151 | GTGGATGGCTGTGGCTGCTGCCGGGTATGTGCACGGCGGCTGGGGAGCC |
| 201 | CTGCGACCAACTCCACGTCTGCGACGCCAGCCAGGGCCTGGTCTGCCAGC |
| 251 | CCGGGGCAGGACCCGGTGGCCGGGGGCCCTGTGCCTCTTGGCAGAGGAC |
| 301 | GACAGCAGCTGTGAGGTGAACGGCCGCCTGTATCGGGAAGGGGAGACCTT |
| 351 | CCAGCCCCACTGCAGCATCCGCTGCCGCTGCGAGGACGGCGGCTTCACCT |
| 401 | GCGTGCCGCTGTGCAGCGAGGATGTGCGGCTGCCCAGCTGGGACTGCCCC |
| 451 | CACCCCAGGAGGGTCGAGGTCCTGGGCAAGTGCTGCCCTGAGTGGGTGTG |
| 501 | CGGCCAAGGAGGGGACTGGGGACCAGCCCTTCCAGCCCAAGGACCCC |
| 551 | AGTTTTCTGGCCTTGTCTCTTCCCTGCCCCTGGTGTCCCCTGCCCAGAA |
| 601 | TGGAGCACGGCCTGGGGACCCTGCTCGACCACCTGTGGGCTGGGCATGGC |
| 651 | CACCCGGGTGTCCAACCAGAACCGCTTCTGCCGACTGGAGACCCAGCGCC |
| 701 | GCCTGTGCCTGTCCAGGCCCTGCCCACCCTCCAGGGGTCGCAGTCCACAA |
| 751 | AACAGTGCCTTCTAGAGCCGGGCTGGGAATGGGGACACGGTGTCCACCAT |
| 801 | CCCCAGCTGGTGGCCCTGTGCCTGGGCCCTGGGCTGATGGAAGA |

FIG._5

```
  1 GTGGGGTTTGCAGAGGAGACAGGGGAGCTTTGTGTACCGGAGCAATGAACAAGCGGCGACTTCTCTACC
    CACCCCAAACGTCTCCTCTGTCCCCTCGAAACACATGGGCCTCGTTGTTCGCCGCTGAAGAGATGG
  1                                                  M  N  K  R  R  L  L  Y  P

71 CCTCAGGGTGGCTCCACGGTGCCAGGGTCGCTGT
    GGAGTCCCACCGAGGTGCCAGGGTCGCTGTCCGT
 10  S  G  W  L  H  G  P  S  D  M

101 TGCAGGGGCTCCTCCTTCTCCACTCTTCTGCTGGCCTGGCACAGTTCTGCTGCAGGGTACAGGGCAC
    ACGTCCCCGAGGAGGAAGAGACGACCGGACCGGTGTCAAGACGACGTCCCATGTCCCGTG
 20  Q  G  L  L  F  S  T  L  L  L  A  G  L  A  Q  F  C  C  R  V  Q  G  T

171 TGGACCATTAGATACAACACCTGAAGGAAG
    ACCTGGTAATCTATGTTGTGGACTTCCTTC
 43  G  P  L  D  T  T  P  E  G  R

201 GCCTGGGAGAAGTGTCAGATGCCACCTGAGCGTAAACAGTTTTGTCACTGGCCTGCAAATGCCCTGCAGCAG
    CGGACCCTCTTCACAGTCTACGTGGAGTCGCATTTGTCAAAACAGTGACCGGGACGTTTACGGGACGTCGTC
 53  P  G  E  V  S  D  A  P  Q  R  K  Q  F  C  H  W  P  C  K  C  P  Q  Q

271 AAGCCCCGTTGCCCTCCTGGAGTGAGCCTG
    TTCGGGGCAACGGGAGGACCTCACTCGGAC
 76  K  P  R  C  P  P  G  V  S  L

301 GTGAGAGATGGCTGTGGATGCTGTAAAATCTGTGCCAAGCAACCAGGGGAAATCTGCAATGAAGCTGACC
    CACTCTCTACCGACACCTACGACATTTTAGACACGGTTCGTTGGTCCCCTTTAGACGTTACTTCGACTGG
 86  V  R  D  G  C  G  C  C  K  I  C  A  K  Q  P  G  E  I  C  N  E  A  D  L

371 TCTGTGACCCACACAAAGGGCTGTATTGTG
    AGACACTGGGTGTGTTTCCCGACATAACAC
110  C  D  P  H  K  G  L  Y  C  D

401 ACTACTCAGTAGACAGGCCTAGGTACGAGACTGGAGTGTGCATACCTTGTAGCTGTGGGTGCGAGTT
    TGATGAGTCATCTGTCCGGATCCATGCTCTGACCTCACACGTATGGAACATGACACCCACGCTCAA
120  Y  S  V  D  R  P  R  Y  E  T  G  V  C  A  Y  L  V  A  V  G  C  E  F

471 CAACCAGGTACATTATCATAATGGCCAAGT
    GTTGGTCCATGTAATAGTATTACCGGTTCA
143  N  Q  V  H  Y  H  N  G  Q  V
```

FIG._6A

```
501  GTTTCAGCCCAACCCCTGTTCAGCTGCCTCTGTGTGAGTGGGGCCATTGGATGCACACCTCTGTTCATA
     CAAAGTCGGGTTGGGGAACAAGTCGACGGAGACACACTCACCCGGTAACCTACGTGTGGAGACAAGTAT
153   F  Q  P  N  P  L  F  S  C  L  C  V  S  G  A  I  G  C  T  P  L  F  I

571  CCAAAGCTGGCTGGCCAGTCACTGCTCTGGA
     GGTTTCGACCGACCGTCAGTGACGAGACCT
176   P  K  L  A  G  S  H  C  S  G

601  GCTAAAGGTGGAAAGAAGTCTGATCAGTCAGATGTCAAACTGTAGCCTGGAACCATTACTACAGCAGCTTTCAACAA
     CGATTTCCACCTTTCTTCAGACTAGTCAGTTGACATGGACCTTGGTAATGATGTCGTCGAAAGTTGTT
186   A  K  G  G  K  K  S  D  Q  S  N  C  S  L  E  P  L  L  Q  Q  L  S  T  S

671  GCTACAAAACAATGCCAGCTTATAGAGATC
     CGATGTTTTGTTACGGTCGAATATCTCTAG
210   Y  K  T  M  P  A  Y  R  D  L

701  TCCCACTTATTTGGAAAAAAATGTCTGTGCAAGCAACAAAATGACTCCCTGCTCCAGAACATGTGG
     AGGGTGAATAAACCTTTTTTTTACAGACACGTTCGTTGTTTTACCTGAGGGACGAGGTCTTGTACCC
220   P  L  I  W  K  K  C  L  V  Q  A  T  K  W  T  P  C  S  R  T  C  G

771  GATGGGAATATCTAACAGGGTGACCAATGA
     CTACCCTTATAGATTGTCCCACTGGTTACT
243   M  G  I  S  N  R  V  T  N  E

801  AAACAGCAACTGTGAAATGAGAAAAGAGAAAAGACTGTGTTACATTCAGCCTTGCGACAGCAATATATTA
     TTTGTCGTTGACACTTTACTCTTTTCTCTTTTCTGACAATGTAAGTCGGAACGCTGTCGTTATATAAT
253   N  S  N  C  E  M  R  K  E  K  R  L  C  Y  I  Q  P  C  D  S  N  I  L

871  AAGACAATAAAGATTCCAAAGGAAAAACA
     TTCTGTTATTTCTAAGGGTTTCCTTTTTGT
276   K  T  I  K  I  P  K  G  K  T

901  TGCCAACTACTTTTGTCTCCAAACTCTCAAAGCTGAAAAATTTGTCTTTTTCTGGATGCTCAAGTACTCAGAGTT
     ACGGTTGATGAAAGGTTGAGAGGTTTCGACTTTTTAAACAGAAAAAGACCTACGAGTTCATGAGTCTCAA
286   C  Q  P  T  F  Q  L  S  K  A  E  K  F  V  F  S  G  C  S  S  T  Q  S  Y

971  ACAAACCCACTTTTGTGGAATATGCTTGG
     TGTTTGGGTGAAAACACCTTATACGAACC
310   K  P  T  F  C  G  I  C  L  D
```

*FIG._6B*

```
1001  ATAAGAGATGCTGTATCCCTAATAAGTCTAAAAATGATTACTATTCAATTTGATTGCCCAAATGAGGGGTC
      TATTCTCTACGACATAGGGATTATTCAGATTTTACTAATGATAAGTTAAACTAACGGGTTTACTCCCCAG
320    K  R  C  C  I  P  N  K  S  K  M  I  T  I  Q  F  D  C  P  N  E  G  S

1071  ATTTAAATGGAAGATGCTGTGACGTTAATC
      TAAATTTACCTTCTACGACACTAATGTAG
343    F  K  W  K  M  L  W  I  T  S

1101  TTGTGTGTGTCAGAGAAACTGCAGAGAACCTGGAGATATATTTTCTGAGCTTCAAGATTCTGTAAAACCAA
      AACACACACAGTCTCTTTGACGTCTCTTGGACCTCTATATAAAGACTCGAAGTTCTAAGACATTTTGGTT
353    C  V  C  Q  R  N  C  R  E  P  G  D  I  F  S  E  L  K  I  L  Q

1171  GCAAATGGGGGAAAAGTTAGTCAATCCTGT
      CGTTTACCCCCTTTTCAATCAGTTAGGACA

1201  CATANAATAAAAAATTAGTGAGTATAAAATGGTGGCAAATCTACTTGTTTAAAACAGTATGAATGCCT
      GTATNTTATTTTTTAATCACTCATATTTTACCACCGTTTAGATGAACAAATTTTGTCATATACTTACGGA

1271  ATTCTCAGATCACTACATTTAAGGCATTAG
      TAAGAGTCTAGTGATGTAAATTCCGTAATC

1301  AAACTTTTAAAAAGTTANCTTAAAAATATACATAA
      TTTGAAAATTTTTCAATNGAATTTTTATATGTATT
```

```
  1  CACGGTCCCAGGCGACAATGCAGGGGCTCCTCTCTGCTTGCTGGCCTGGCACAGTTCTGCT
     GTGCCAGGGTCGCTGTTACGTCCCCGACTGGACCTGGTAATCTAT
  1                M  Q  G  L  F  S  T  L  L  L  A  G  L  A  Q  F  C  C

71  GCAGGGTACAGGGCACTGGACATTAGATA
     CGTCCCCATGTCCCGTGACCTGGTAATCTAT
 20      R  V  Q  G  T  G  P  L  D  T

101  CAACACCCTGAAGGAAGGCCTGGAGACCTCTTCCGGAGTCTCTCACAGTGTCAGATGCACCTCAGCGTCTAAACAGTTTTGTCACTGGCCCTG
     GTTGTGGGACTTCCTTCCGGACCTCTGGAGAAGGCCTCAGAGTGTCACAGTCTACGTGGAGTCGCATTGTCAAAACAGTGACCGGGAC
 30      T  P  E  G  R  P  G  E  V  S  D  A  P  Q  R  K  Q  F  C  H  W  P  C

171  CAAATGCCCTCAGCAGAAGCCCCGTTGCCC
     GTTTACGGGAGTCGTCTTCGGGGCAACGGG
 53      K  C  P  Q  Q  K  P  R  C  P

201  TCCTGGAGTGAGCCTGGTGAGAGATGGCTGTGGATGCTGTAAAATCTGTGCCAAGCAACCAGGGGAAATC
     AGGACCTCACTCGGACCACTCTCTACGACATCCTACGACATTTTAGACACGGTTCGTTGGTCCCCTTTAG
 63      P  G  V  S  L  V  R  D  G  C  G  C  C  K  I  C  A  K  Q  P  G  E  I

271  TGCAATGAAGCTGACCTCTGTGACCCACAC
     ACGTTACTTCGACTGGAGACACTGGGTGTG
 86      C  N  E  A  D  L  C  D  P  H

301  AAAGGGCTGTATTGTGACTACTCAGTAGACAGGCCTAGGTACGAGACTGGAGTGTGTGCATACCTTGTAG
     TTTCCCGACATAACACTGATGAGTCATCTGTCCGGATCCATGCTCTGACCTCACACGTATGGAACATC
 96      K  G  L  Y  C  D  Y  S  V  D  R  P  R  Y  E  T  G  V  C  A  Y  L  V  A

371  CTGTTGGGTGCGAGTTCAACCAGGTACATT
     GACAACCACGCTCAAGTTGGTCCATGTAA
120      V  G  C  E  F  N  Q  V  H  Y

401  ATCATAATGGCCAACTGTTTCAGCCCCAACCCCTTGTTCAGCTGCCTCTGTGTGAGTGGGGCCATTGGATG
     TAGTATTACCGGTTGACAAGTCGGGTTGGGGAACAAGTCGACGGAGACACACTCACCCCGGTAACCTAC
130      H  N  G  Q  V  F  Q  P  N  P  L  F  S  C  L  C  V  S  G  A  I  G  C

471  CACACCCTCTGTTCATACCAAAGCTGGCTGG
     GTGTGGAGACAAGTATGGTTTCGACCGACC
153      T  P  L  F  I  P  K  L  A  G
```

```
501  CAGTCACTGCTCTGGAGCTAAAGGTGAAAGAAGTCTGATCAGTCAAACTGTAGCCTGGAACCATTACTA
     GTCAGTGACGAGACCTCGATTTCCACCTTTCTTCAGACTAGTCAGTTGACATTCGGACCTTGGTAATGAT
163   S  H  C  S  G  A  K  G  G  K  K  S  D  Q  S  N  C  S  L  E  P  L  L

571  CAGCAGCTTTCAACAAGCTACAAAACAATG
     GTCGTCGAAAGTTGTTCGATGTTTTGTTAC
186   Q  Q  L  S  T  S  Y  K  T  M

601  CCAGCTTATAGAAATCTCCCACTTATTTGGAAAAAAAAATGTCTTGTGCAAGCAACAAAATGGACTCCCT
     GGTCGAATATCTTTAGAGGGTGAATAAACCTTTTTTTTTACAGAACACGTTCGTTGTTTTACCTGAGGGA
196   P  A  Y  R  N  L  P  L  I  W  K  K  K  C  L  V  Q  A  T  K  W  T  P  C

671  GCTCCAGAACATGTGGGATGGGAATATCTA
     CGAGGTCTTGTACACCCTACCCTTATAGAT
220   S  R  T  C  G  M  G  I  S  N

701  ACAGGGTGACCAATGAAAACAGCAACTGTGAAATGAGAAAAGAGAAAAGACTGTGTTACATTCAGCCTG
     TGTCCCACTGGTTACTTTTGTCGTTGACACTTTACTCTTTTCTCTTTTCTGACACAATGTAAGTCGGAAC
230   R  V  T  N  E  N  S  N  C  E  M  R  K  E  K  R  L  C  Y  I  Q  P  C

771  CGACAGCAATATATTAAAGACAATAAAGAT
     GCTGTCGTTATATAATTTCTGTTATTTCTA
253   D  S  N  I  L  K  T  I  K  I

801  TCCCAAAGGAAAAAACATGCCAACTCTCCAAACTCTCCAAAGCTGAAAAATTTGTCTTTTCTGGATGC
     AGGGTTCCTTTTTTGTACGGTTGAGAGGTTTGAGAGGTTTCGACTTTTTAAACAGAAAAGACCTACG
263   P  K  G  K  T  C  Q  P  T  F  Q  L  S  K  A  E  R  F  V  F  S  G  C

871  TCAAGTACTCAGAGTTACAAACCCACTTTT
     AGTTCATGAGTCTCAATGTTTGGGTGAAAA
286   S  S  T  Q  S  Y  K  P  T  F
```

*FIG._7B*

```
901  TGTGGAATATGCTTGGATAAGAGAGATGCTGTATCCCTAATAAGTCTAAAATGATTACTATTCAATTTGATT
     ACACCTTATGCGAACCTATTCTCTACGACATAGGGATTATTCAGATTTTACTAATAAGTTGATAAACTAA
296   C  G  I  C  L  D  K  R  C  C  I  P  N  K  S  K  M  I  T  I  Q  F  D  C

971  GCCCAAATGAGGGGTCATTTAAAATGAAGA
     CGGGTTTACTCCCCAGTAAATTTACCTTCT
320   P  N  E  G  S  F  K  W  K  M

1001 TGCTGTGGATTACATCTGTGTGTCAGAGAAACTGCAGAGAACCTGGAGATATATTTCTGAGCTCAA
     ACGACACCTAATGTAGACACACAGTCTCTTGACCTCTATATAAAGACTCGAGTT
330   L  W  I  T  S  C  V  C  Q  R  N  C  R  E  P  G  D  I  F  S  E  L  K

1071 GATTCTGTAAAACCAAGCAAATGGGGAAA
     CTAAGACATTTGGTTCGTTTACCCCCTTT
353   I  L  Q

1101 AGTTAGTCAATCCTGTCATATAATAAAATTAGTGAGTAAAAAAAATTAGTGAGTAAAAAAAAAAAAAAAA
     TCAATCAGTTAGGACAGTATATTATTTTTTAATCACTCATTTTTTTTTTTTTTTTTTTTTTTTTTT

1171 AAAAAAAAAAAAAAAAAAAAAAAAAAGAAAAAAAA
     TTTTTTTTTTTTTTTTTTTTTTCTTTT

1201 AAAAAAAAAAA
     TTTTTTTTTTT
```

FIG.—7C

```
mouse.wisp-1    1  MRWLL LPWTLAAVAVLRVGNI LATALSPT PTTMT FTPAPLE ETT TRPE FCK
human.wisp-1    1  MRWF LPWTLAAVTAAAASTV LATALSPA PTTMD FTPAPLED TSS RPQ FCK mouse.wisp-1   51  WPCECPQS PPRCPLGVSLITDGCECCK ICAQQLGDNCTEAA ICDPHRGLY
human.wisp-1   51  WPCECPPS PPRCPLGVSLITDGCECCK MCAQQLGDNCTEAA ICDPHRGLY mouse.wisp-1  101  CDYSGDRPRYAIGVCAQVVGVGCVLDGVRYT NGES FQPNCR YNCTCIDGT
human.wisp-1  101  CDYSGDRPRYAIGVCAQVVGVGCVLDGVRY NGQS FQPNCK YNCTCIDGA mouse.wisp-1  151  VGCTPLCL SPR PPRLWCR QPRHVR VPG QCCEQWVCDD DAR RPQT ALL DT
human.wisp-1  151  VGCTPLCL RVR PPRLWCP HPRVS IPG HCCEQWVCE DDAK RPR KTAP RDT mouse.wisp-1  201  RAFAAS GAV EQRYE NCIAYTSPWSPCST TCGLGI STRISNVNAR CWPEQE
human.wisp-1  201  GAF DAV GEV EAWHRN CIAYTSPWSPCST SCGLGI STRISNVNAQ CWPEQE mouse.wisp-1  251  SRLCNLRPCDVDI QLH IKAGKKCLAVYQPE EAT NFTLAGCV STR TY RPKY
human.wisp-1  251  SRLCNLRPCDVDI HTL IKAGKKCLAVYQPEASM NFTLAGCI STR SY QPKY mouse.wisp-1  301  CGVCT DNRCCIPYKSKTI SVDF QCPE GPG FSRQVLWINAC FCNLSCRNPN
human.wisp-1  301  CGVCM DNRCCIPYKSKTI DVS FQCPD GLG FSRQVLWINAC FCNLSCRNPN mouse.wisp-1  351  DIFADLESYPDF EEIAN
human.wisp-1  351  DIFADLESYPDF SEIAN
```

FIG._8

```
mouse.wisp-2   1   M R G N P L   I H L L A   I S F L C   I L S M V Y S   Q L C P A P C A   C P W T   P P Q C P P   G V P L V L D G C
human.wisp-2   1   M R G T P K T H L L A F S L L C L L S K V R T Q L C P T P C T C P W P P P R C P L G V P L V L D G C mouse.wisp-2  51   G C C R V C A R R L G E S   C D   H L H V C D P   S Q G L V C Q P G A G P S   G R G A V C L F E E D D G S C
human.wisp-2  51   G C C R V C A R R L G E P C D Q L H V C D A S Q G L V C Q P G A G P G G R G A L C L L A E D D S S C mouse.wisp-2 101   E V N G R R Y L D G E T F   K P N C R V L C R C D D G G F T C L P L C S E D V R L P S W D C P R P R R
human.wisp-2 101   E V N G R L Y R E G E T F Q P H C S I R C E D G G F T C V P L C S E D V R L P S W D C P H P R R mouse.wisp-2 151   I Q V P G R C C P E W V C D Q A V M Q P A I Q P S S A Q G H Q L S A L V T P A S A D G P C P N W S T
human.wisp-2 151   V E V L G K C C P E W V C G Q G G - G L G T Q P L P A Q G P F S G L V S S L P P G V C P E W S T mouse.wisp-2 201   A W G P C S T T C G L Q I A T R V S N Q N R F C Q L E I Q R R L C L S R P C L A S R S H G S W N S A
human.wisp-2 200   A W G P C S T T C G L G M A T R V S N Q N R F C R L E T Q R R L C L S R P C P P S R G R S P Q N S A mouse.wisp-2 251   F
human.wisp-2 250   F
```

FIG._9

```
                          10        20        30        40        50
hWISP-3.DNA56350   MNKRRLLYPSGWLHGPSDMQGLLFSTLLLAGLAQFCCRVQGTGPLDTTPE
                                     ******************************* hWISP-3.DNA58800                    MQGLLFSTLLLAGLAQFCCRVQGTGPLDTTPE
                                             10        20        30

60        70        80        90       100
hWISP-3.DNA56350   GRPGEVSDAPQRKQFCHWPCKCPQQKPRCPPGVSLVRDGCGCCKICAKQP
                   **************************************************
hWISP-3.DNA58800   GRPGEVSDAPQRKQFCHWPCKCPQQKPRCPPGVSLVRDGCGCCKICAKQP
                          40        50        60        70        80

110       120       130       140       150
hWISP-3.DNA56350   GEICNEADLCDPHKGLYCDYSVDRPRYETGVCAYLVAVGCEFNQVHYHNG
                   **************************************************
hWISP-3.DNA58800   GEICNEADLCDPHKGLYCDYSVDRPRYETGVCAYLVAVGCEFNQVHYHNG
                          90       100       110       120       130

160       170       180       190       200
hWISP-3.DNA56350   QVFQPNPLFSCLCVSGAIGCTPLFIPKLAGSHCSGAKGGKKSDQSNCSLE
                   **************************************************
hWISP-3.DNA58800   QVFQPNPLFSCLCVSGAIGCTPLFIPKLAGSHCSGAKGGKKSDQSNCSLE
                         140       150       160       170       180

210       220       230       240       250
hWISP-3.DNA56350   PLLQQLSTSYKTMPAYRDLPLIWKKKCLVQATKWTPCSRTCGMGISNRVT
                   ********************.*****************************
hWISP-3.DNA58800   PLLQQLSTSYKTMPAYRNLPLIWKKKCLVQATKWTPCSRTCGMGISNRVT
                         190       200       210       220       230

260       270       280       290       300
hWISP-3.DNA56350   NENSNCEMRKEKRLCYIQPCDSNILKTIKIPKGKTCQPTFQLSKAEKFVF
                   **************************************************
hWISP-3.DNA58800   NENSNCEMRKEKRLCYIQPCDSNILKTIKIPKGKTCQPTFQLSKAEKFVF
                         240       250       260       270       280

310       320       330       340       350
hWISP-3.DNA56350   SGCSSTQSYKPTFCGICLDKRCCIPNKSKMITIQFDCPNEGSFKWKMLWI
                   **************************************************
hWISP-3.DNA58800   SGCSSTQSYKPTFCGICLDKRCCIPNKSKMITIQFDCPNEGSFKWKMLWI
                         290       300       310       320       330

360       370
hWISP-3.DNA56350   TSCVCQRNCREPGDIFSELKIL
                   **********************
hWISP-3.DNA58800   TSCVCQRNCREPGDIFSELKIL
                         340       350
```

*FIG._10*

```
hWISP-3.DNA56350   GTGGGGTTTGCAGAGGAGACAGGGGAGCTTTGTGTACCCGGAGCAATGAA
                           10        20        30        40        50 huWISP-1                                                                     A
                                                                             * hWISP-3.DNA56350   CAAGCGGCGACTTCTCTACCCCTCAGGGTGGCTCCACGGTCCCAGCGACA
                           60        70        80        90       100

10        20        30        40
huWISP-1           TGAGGTGGTTCCTGCCCTGGAC---GCTGGCAGCAGTGACAGCAGCAGCC
                    ** * ** ****  **  **   ***   ** *      ***       *
hWISP-3.DNA56350   TGCAGGGGCTCCTCTTCTCCACTCTTCTGCTTGCTGGCCTGGCACAGTTC
                          110       120       130       140       150

50        60        70        80        90
huWISP-1           GCCAGCACCGTCCTGGCCACGGCCCTCTCTCCAGCCCCTACGACCATGGA
                    * ***  ** * ** *** *           ***     *** **    **
hWISP-3.DNA56350   TGCTGCAGGGTACAGGGCACTG------GACCATTAGATACAACACCTGA
                          160       170             180       190

100       110       120       130       140
huWISP-1           CTTTACTCCAGCTCCACTGGAGGACACCTCCTCACGCCCCCAATTCTGCA
                     *  ** *     *  **   **   *   *       **   ** ** **
hWISP-3.DNA56350   AGGAAGGCCTGGAGAAGTGTCAGATGCACCTCAGCGTAAACAGTTTTGTC
                          200       210       220       230       240

150       160       170       180       190
huWISP-1           AGTGGCCATGTGAGTGCCCGCCATCCCCACCCCGCTGCCCGCTGGGGGTC
                    * ***** **  *  ***** *              ***** ***** *  ** **
hWISP-3.DNA56350   ACTGGCCCTGCAAATGCCCTCAGCAGAAGCCCCGTTGCCCTCCTGGAGTG
                          250       260       270       280       290

200       210       220       230       240
huWISP-1           AGCCTCATCACAGATGGCTGTGAGTGCTGTAAGATGTGCGCTCAGCAGCT
                   *****   *  * ********** *  ********  **  **  **   **** *
hWISP-3.DNA56350   AGCCTGGTGAGAGATGGCTGTGGATGCTGTAAAATCTGTGCCAAGCAACC
                          300       310       320       330       340

250       260       270       280       290
huWISP-1           TGGGGACAACTGCACGGAGGCTGCCATCTGTGACCCCCACCGGGGCCTCT
                   *****  * *****  ** ****   **  **********   **   ** ** *
hWISP-3.DNA56350   AGGGGAAATCTGCAATGAAGCTGACCTCTGTGACCCACACAAAGGGCTGT
                          350       360       370       380       390

300       310       320       330       340
huWISP-1           ACTGTGACTACAGCGGGGACCGCCCGAGGTACGCAATAGGAGTGTGTGCA
                    * ********  *   *** * **  ******  *  **********
hWISP-3.DNA56350   ATTGTGACTACTCAGTAGACAGGCCTAGGTACGAGACTGGAGTGTGTGCA
                          400       410       420       430       440

350       360       370       380       390
huWISP-1           CAGGTGGTCGGTGTGGGCTGCGTCCTGGATGGGGTGCGCTACAACAACGG
                    * * ** *** ** ****    *  *    ***  **  *  ** * **
hWISP-3.DNA56350   TACCTTGTAGCTGTTGGGTGCGAGTTCAACCAGGTACATTATCATAATGG
                          450       460       470       480       490
```

FIG._11A

```
                      400        410        420        430        440
huWISP-1              CCAGTCCTTCCAGCCTAACTGCAAGTACAACTGCACGTGCATCGACGGCG
                      ***   ** ***** ***  *  ** ** ****   **  *    ** *
hWISP-3.DNA56350      CCAAGTGTTTCAGCCCAACCCCTTGTTCAGCTGCCTCTGTGTGAGTGGGG
                      500        510        520        530        540

450        460        470        480        490
huWISP-1              CGGTGGGCTGCACACCACTGTGCCTCCGAGTGCGCCCCCCGCGTCTCTGG
                      *  *  ** ********  ****  *  * **       *     ****
hWISP-3.DNA56350      CCATTGGATGCACACCTCTGTTCATACCAAAGC---------TGGCTGG
                      550        560        570                  580

500        510        520        530        540
huWISP-1              TGCCCCCACCCGCGGCGCGTGAGC-ATACCTGGCCACTGCTGTGAGCAGT
                      **   *   * **   ****  **    ***  *  * *** ****
hWISP-3.DNA56350      ------CAGTCACTGCTCTGGAGCTAAAGGTGGAAAGAAGTCTGATCAGT
                              590        600        610        620

550        560        570        580        590
huWISP-1              GGGTATGTGAGGACGACGCCAAGAGGCCACGCAAGACCGCACCCCGTGAC
                      ***  **     *  *** *   * **   ** * *    ** *   **
hWISP-3.DNA56350      CAAACTGT-AGCCTGGAACCATTA--CTACAGCAGCTTTCAACAAGCTAC
                       630        640        650         660        670

600        610        620        630        640
huWISP-1              ACAGGAGCCTTCGATGCTGTGGGTGAGGTGGAGGCATGGCACAGGAACTG
                      *  *   *  ** *  * *  *  * *      *** * *  ** ** **
hWISP-3.DNA56350      AAAACAATGCCAGCTTATAGAGATCTCCCACTTATTTGGAAAAAAAAATG
                       680        690        700        710        720

650        660        670        680        690
huWISP-1              CATAGCCTACACAAGCCCCTGGAGCCCTTGCTCCACCAGCTGCGGCCTGG
                      * *   *    ***  **** ** ******  *  ** **     ***
hWISP-3.DNA56350      TCTTGTGCAAGCAACAAAATGGACTCCCTGCTCCAGAACATGTGGGATGG
                       730        740        750        760        770

700        710        720        730        740
huWISP-1              GGGTCTCCACTCGGATCTCCAATGTTAACGCCCAGTGCTGGCCTGAGCAA
                      *  *  ** *       ******  ***  *   *   **         **
hWISP-3.DNA56350      GAATATCTAACAGGGTGACCAATGAAAACAGCAACTGTGAAATGAGAAAA
                       780        790        800        810        820

750        760        770        780        790
huWISP-1              GAGAGCCGCCTCTGCAACTTGCGGCCATGCGATGTGGACATCCATACACT
                      ****   *  **  **  ** * ***  *****   **  *  **    *
hWISP-3.DNA56350      GAGAAAAGACTGTGTTACATTCAGCCTTGCGACAGCAATATATTAAAGAC
                       830        840        850        860        870

800        810        820        830        840
huWISP-1              CATTAAG------GCAGGGAAGAAGTGTCTGGCTGTGTACCAGCCAGAGG
                      ** ***        *** ** *  ** **     **  * *** *
hWISP-3.DNA56350      AATAAAGATTCCCAAAGGAAAAACATGCCAACCTACTTTCCAACTCTCCA
                       880        890        900        910        920

850        860        870        880        890
huWISP-1              CATCCATGAACTTCACACTTGCGGGCTGCATCAGCACACGCTCCTATCAA
                      * *    ** **       ** * ***   ** ** **  *    ** **
hWISP-3.DNA56350      AAGCTGAAAAATTTGTCTTTTCTGGATGCTCAAGTACTCAGAGTTACAAA
                       930        940        950        960        970
```

FIG._11B

```
                          900       910       920       930       940
huWISP-1         CCCAAGTACTGTGGAGTTTGCATGGACAATAGGTGCTGCATCCCCTACAA
                 ****  *  ****** *  *** **** **  ** *****  *****   *  **
hWISP-3.DNA56350 CCCACTTTTTGTGGAATATGCTTGGATAAGAGATGCTGTATCCCTAATAA
                          980       990      1000      1010      1020

950       960       970       980       990
huWISP-1         GTCTAAGACTATCGACGTGTCCTTCCAGTGTCCTGATGGGCTTGGCTTCT
                 ****** *  **       *    **  *  ** **    ***  *        **
hWISP-3.DNA56350 GTCTAAAATGATTACTATTCAATTTGATTGCCCAAATGAGGGGTCATTTA
                         1030      1040      1050      1060      1070

1000      1010      1020      1030      1040
huWISP-1         CCCGCCAGGTCCTATGGATTAATGCCTGCTTCTGTAACCTGAGCTGTAGG
                    *   **  *  **  *******      *  **    *  ***  *     *  *** **
hWISP-3.DNA56350 AATGGAAGATGCTGTGGATTACATCTTGTGTGTGTCAGAGAAACTGCAGA
                         1080      1090      1100      1110      1120

1050      1060      1070      1080      1090
huWISP-1         AATCCCAATGACATCTTTGCTGACTTGGAATCCTACCCTGACTTCTCAGA
                  *  **       **  **  ***  ****    *    *          **       ** *
hWISP-3.DNA56350 GAACCTGGAGATATATTTTCTGAGCTCAAGATTCTGTAAAACCAAGCAAA
                         1130      1140      1150      1160      1170

1100
huWISP-1         AATTGCCAAC
                   *   **
hWISP-3.DNA56350 TGGGGGAAAAGTTAGTCAATCCTGTCATANAATAAAAAAATTAGTGAGTA
                         1180      1190      1200      1210      1220 hWISP-3.DNA56350 TAAAATGGTGGCAAATCTACTTTGTTTAAAACAGTATGAATGCCTATTCT
                         1230      1240      1250      1260      1270 hWISP-3.DNA56350 CAGATCACTACATTTAAGGCATTAGAAACTTTTAAAAAGTTANCTTAAAA
                         1280      1290      1300      1310      1320 hWISP-3.DNA56350 ATATACATAA
                         1330
```

FIG._11C

```
                        10        20        30        40
hWISP-3.DNA56350   MNKRRLLYPSGWLHGPSDMQGLLFSTL-LLAGLAQFCCRVQGTGPLDTTP
                       *  .* **  ...  *         . .*  **
huWISP-1                                  MRWFLPWTLAAVTAAAASTVLATALSPAPTTM
                                              10        20        30

50        60        70        80        90
hWISP-3.DNA56350   EGRPGEVSDAPQRKQFCHWPCKCPQQKPRCPPGVSLVRDGCGCCKICAKQ
                    .  *.. *..  * *** *** **  **** ****. *** ***.**.*
huWISP-1           DFTPAPLEDTSSRPQFCKWPCECPPSPPRCPLGVSLITDGCECCKMCAQQ
                       40        50        60        70        80

100       110       120       130       140
hWISP-3.DNA56350   PGEICNEADLCDPHKGLYCDYSVDRPRYETGVCAYLVAVGCEFNQVHYHN
                   *.  *  ** .****.******* *****  **** ..*.***  .*.*.*
huWISP-1           LGDNCTEAAICDPHRGLYCDYSGDRPRYAIGVCAQVVGVGCVLDGVRYNN
                       90       100       110       120       130

150       160       170       180       190
hWISP-3.DNA56350   GQVFQPNPLFSCLCVSGAIGCTPL-FIPKLAGSHCSGAK----GGKKSDQ
                   ** ****  ..* *. **.*****  . . .     *. ..       * .*
huWISP-1           GQSFQPNCKYNCTCIDGAVGCTPLCLRVRPPRLWCPHPRRVSIPGHCCEQ
                       140       150       160       170       180

200       210       220       230       240
hWISP-3.DNA56350   SNCSLEPLLQQLSTSYKTMPAYRDLPLI--WKKKCLVQATKWTPCSRTCG
                    *   ..   . ... .   *. .     * ..*.   .* .*** .**
huWISP-1           WVCEDDAKRPRKTAP-RDTGAFDAVGEVEAWHRNCIAYTSPWSPCSTSCG
                       190       200       210       220       230

250       260       270       280       290
hWISP-3.DNA56350   MGISNRVTNENSNCEMRKEKRLCYIQPCDSNILKTIKIPKGKTCQPTFQL
                   .*.* *..* *..*    .* ***  .***  .*   **  ** *  . *
huWISP-1           LGVSTRISNVNAQCWPEQESRLCNLRPCDVDIHTLIK--AGKKCLAVYQP
                       240       250       260       270

300       310       320       330       340
hWISP-3.DNA56350   SKAEKFVFSGCSSTQSYKPTFCGICLDKRCCIPNKSKMITIQFDCPNEGS
                     .*  ..**  **.**.* .**.*.*.***** ***  *  .*.**.  .
huWISP-1           EASMNFTLAGCISTRSYQPKYCGVCMDNRCCIPYKSKTIDVSFQCPDGLG
                     280       290       300       310       320

350       360       370
hWISP-3.DNA56350   FKWKMLWITSCVCQRNCREPGDIFSELKIL
                   *  ...***  .*  *. .**.*  ***..*
huWISP-1           FSRQVLWINACFCNLSCRNPNDIFADLESYPDFSEIAN
                     330       340       350       360
```

*FIG. 12*

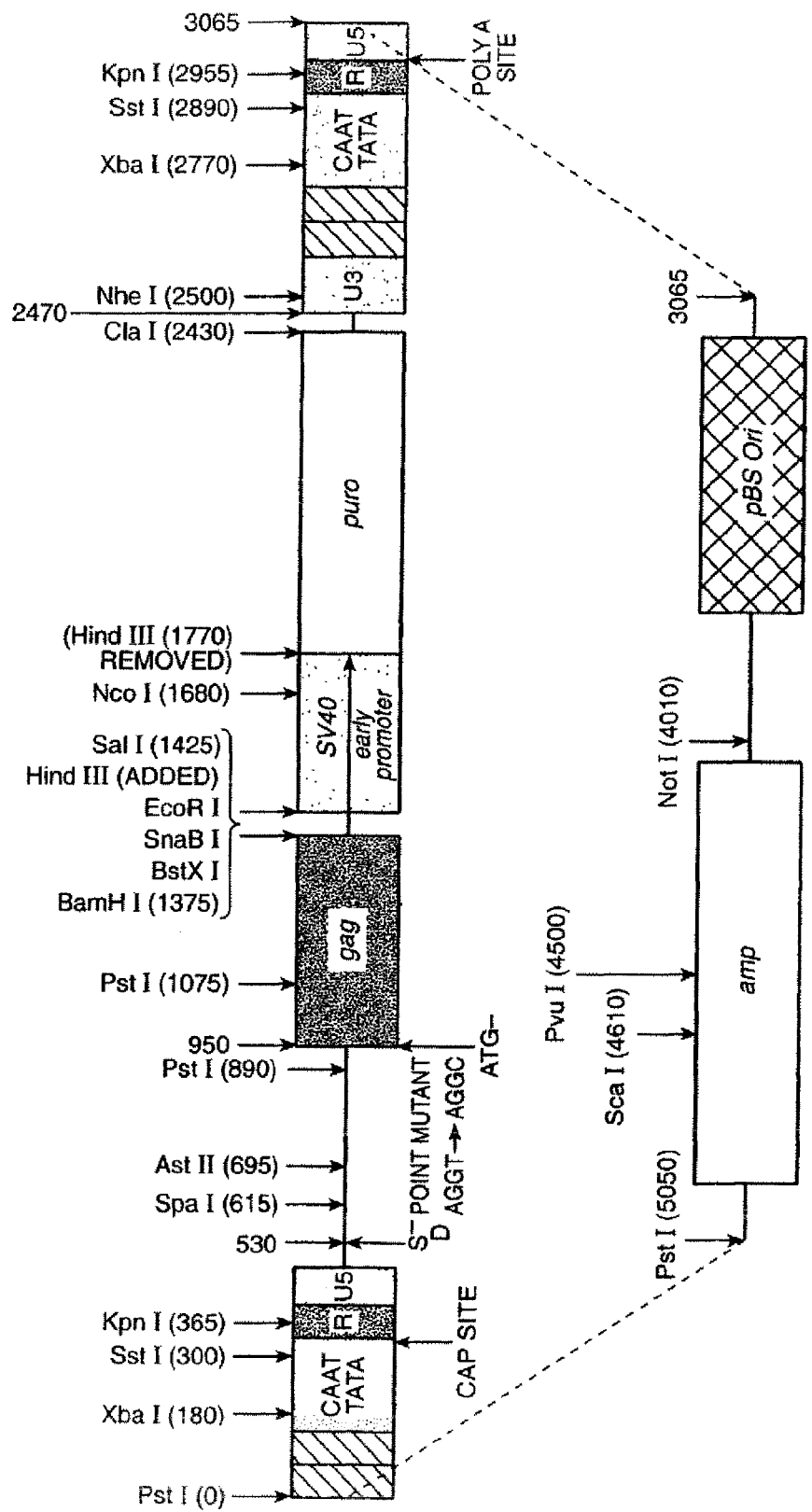
FIG._13

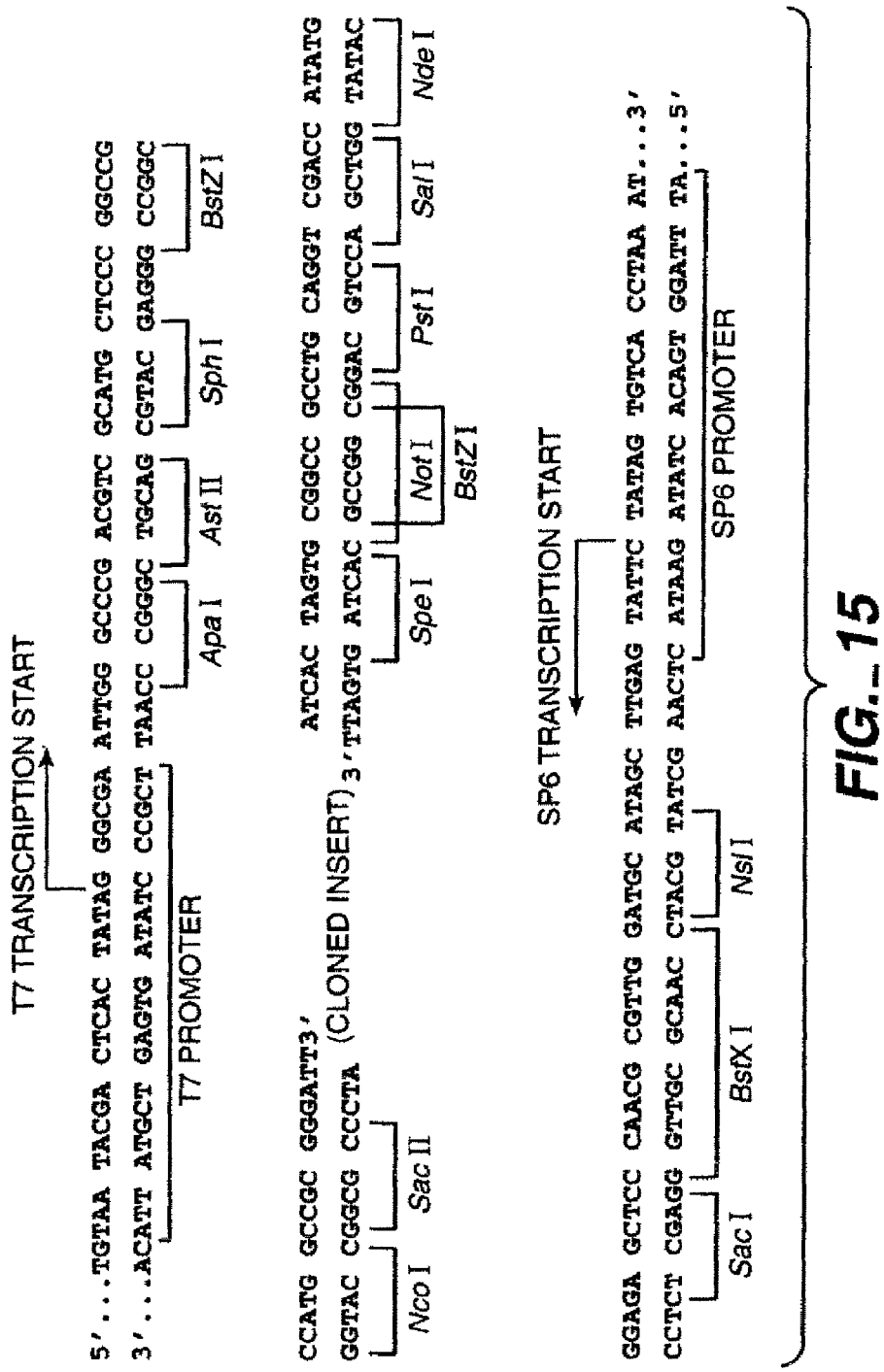
FIG._15

```
TTCGAGCTCGCCCGACATTGATTATTGACTAGAGTCGATCACCGGTTATTAATAGTAATC
AATTACGGGGTCATAGTTCATAGCCCATATATGGAGTTCCGCGTTACATAACTTACGGTA
AATGGCCCGCCTGGCTGACCGCCCAACGACCCCCGCCCATTGACGTCAATAATGACGTAT
GTTCCCATAGTAACGCCAATAGGGACTTTCCATTGACGTCAATGGGTGGAGTATTTACGG
TAAACTGCCCACTTGGCAGTACATCAAGTGTATCATATGCCAAGTACGCCCCCTATTGAC
GTCAATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTTGG
CAGTACATCAATGGGCGTGGATAGCGGTTTGACTCACGGGGATTTCCAAGTCTCCACCCC
ATTGACGTCAATGGGAGTTTGTTTTGGCACCAAAATCAACGGGACTTTCCAAAATGTCGT
AACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGAC
CTGGGCCCGGCCGAGGCCGCCTCGGCCTCTGAGCTATTCCAGAAGTAGTGAGGAGGCTTT
TTTGGAGGCCTAGGCTTTTGCAAAAAGCTAGCTTATCCGGCCGGGAACGGTGCATTGGAA
CGCGGATTCCCCGTGCCAAGAGT
><splice donor>
GACGTAAGTACCGCCTATAGAGCGACTAGTCCACC
><PUR>
ATGACCGAGTACAAGCCCACGGTGCGCCTCGCCACCCGCGACGACGTCCCGCGGGCCGTA
CGCACCCTCGCCGCCGCGTTCGCCGACTACCCCGCCACGCGCCACACCGTAGACCCGGAC
CGCCACATCGAGCGGGTCACCGAGCTGCAAGAACTCTTCCTCACGCGCGTCGGGCTCGAC
ATCGGCAAGGTGTGGGTCGCGGACGACGGCGCCGCGGTGGCGGTCTGGACCACGCCGGAG
AGCGTCGAAGCGGGGGCGGTGTTCGCCGAGATCGGCCCGCGCATGGCCGAGTTGAGCGGT
TCCCGGCTGGCCGCGCAGCAACAGATGGAAGGCCTCCTGGCGCCGCACCGGCCCAAGGAG
CCCGCGTGGTTCCTGGCCACCGTCGGCGTCTCGCCCGACCACCAGGGCAAGGGTCTGGGC
AGCGCCGTCGTGCTCCCCGGAGTGGAGGCGGCCGAGCGCGCCGGGGTGCCCGCCTTCCTG
GAGACCTCCGCGCCCCGCAACCTCCCCTTCTACGAGCGGCTCGGCTTCACCGTCACCGCC
GACGTCGAGTGCCCGAAGGACCGCGCGACCTGGTGCATGACCCGCAAGCCCGGTGCCAAC
><DHFR ATG>
ATGGTTCGACCATTGAACTGCATCGTCGCCGTGTCCCAAAATATGGGGATTGGCAAGAAC
GGAGACCTACCCTGCCCTCCGCTCAGGAACGCGTTCAAGTACTTCCAAAGAATGACCACA
ACCTCTTCAGTGGAAGGTAAACAGAATCTGGTGATTATGGGTAGGAAAACCTGGTTCTCC
ATTCCTGAGAAGAATCGACCTTTAAAGGACAGAATTAATATAGTTCTCAGTAGAGAACTC
AAAGAACCACCACGAGGAGCTCATTTTCTTGCCAAAAGTTTGGATGATGCCTTAAGACTT
ATTGAACAACCGGAATTGGCAAGTAAAGTAGACATGGTTTGGATAGTCGGAGGCAGTTCT
GTTTACCAGGAAGCCATGAATCAACCAGGCCACCTTAGACTCTTTGTGACAAGGATCATG
CAGGAATTTGAAAGTGACACGTTTTTCCCAGAAATTGATTTGGGGAAATATAAACCTCTC
CCAGAATACCCAGGCGTCCTCTCTGAGGTCCAGGAGGAAAAAGGCATCAAGTATAAGTTT
GAAGTCTACGAGAAGAAAGACTAA
><End DHFR>
CGTTAACTGCTCCCCTCCTAAAGCTATGCATTTTTATAAGACCATGGGACTTTTGCTGGC
TTTAGATCCCCTTGGCTTCGTTAGAACGCAGCTACAATTAATACATAACCTTATGTATCA
TACACATACGATTTAGGTGACACTATAGATAACATCCACTTTGCCTTTCTCTCCACAGGT
GTCCACTCCCAGGTCCAACTGCACCTCGGTTCTATCGATTGAATTCCCCGGGGATCCTCT
AGAGTCGACCTGCAGAAGCTTCGATGGCCGCCATGGCCCAACTTGTTTATTGCAGCTTAT
AATGGTTACAAATAAAGCAATAGCATCACAAATTTCACAAATAAAGCATTTTTTTCACTG
CATTCTAGTTGTGGTTTGTCCAAACTCATCAATGTATCTTATCATGTCTGGATCGATCGG
<sv40 origin>
GAATTAATTCGGCGCAGCACCATGGCCTGAAATAACCTCTGAAAGAGGAACTTGGTTA
<Kpn-SAR-Kpn insert here>
GGTACCGACTAGTCGCGTTACATAACTTACGGTAAATGGCCCGCCTGGCTGACCGCCCAA
```

FIG._16A

```
CGACCCCCGCCCATTGACGTCAATAATGACGTATGTTCCCATAGTAACGCCAATAGGGAC
TTTCCATTGACGTCAATGGGTGGAGTATTTACGGTAAACTGCCCACTTGGCAGTACATCA
AGTGTATCATATGCCAAGTACGCCCCCTATTGACGTCAATGACGGTAAATGGCCCGCCTG
GCATTATGCCCAGTACATGACCTTATGGGACTTTCCTACTTGGCAGTACATCTACGTATT
AGTCATCGCTATTACCATGGTGATGCGGTTTTGGCAGTACATCAATGGGCGTGGATAGCG
GTTTGACTCACGGGGATTTCCAAGTCTCCACCCCATTGACGTCAATGGGAGTTTGTTTTG
ACTAGTAGCAAGGTCGCCACGCACAAGATCAATATTAACAATCAGTCATCTCTCTTTAGC
AATAAAAAGGTGAAAAATTACATTTTAAAAATGACACCATAGACGATGTATGAAAATAAT
CTACTTGGAAATAAATCTAGGCAAAGAAGTGCAAGACTGTTACCCAGAAAACTTACAAAT
TGTAAATGAGAGGTTAGTGAAGATTTAAATGAATGAAGATCTAAATAAACTTATAAATTG
TGAGAGAAATTAATGAATGTCTAAGTTAATGCAGAAACGGAGAGACATACTATATTCATG
AACTAAAAGACTTAATATTGTGAAGGTATACTTTCTTTTCACATAAATTTGTAGTCAATA
TGTTCACCCCAAAAAAGCTGTTTGTTAACTTGTCAACCTCATTTCAAAATGTATATAGAA
AGCCCAAAGACAATAACAAAAATATTCTTGTAGAACAAAATGGGAAGAATGTTCCACTA
AATATCAAGATTTAGAGCAAAGCATGAGATGTGTGGGATAGACAGTGAGGCTGATAAAA
TAGAGTAGAGCTCAGAAACAGACCCATTGATATATGTAAGTGACCTATGAAAAAAATATG
GCATTTTACAATGGGAAAATGATGATCTTTTTCTTTTTAGAAAAACAGGGAAATATATT
TATATGTAAAAAATAAAAGGGAACCCATATGTCATACCATACACACAAAAAAATTCCAGT
GAATTATAAGTCTAAATGGAGAAGGCAAAACTTTAAATCTTTTAGAAAATAATATAGAAG
CATGCCATCATGACTTCAGTGTAGAGAAAAATTTCTTATGACTCAAAGTCCTAACCACAA
AGAAAAGATTGTTAATTAGATTGCATGAATATTAAGACTTATTTTTAAAATTAAAAAACC
ATTAAGAAAAGTCAGGCCATAGAATGACAGAAAATATTTGCAACACCCCAGTAAAGAGAA
TTGTAATATGCAGATTATAAAAAGAAGTCTTACAAATCAGTAAAAAATAAAACTAGACAA
AAATTTGAACAGATGAAAGAGAAACTCTAAATAATCATTACACATGAGAAACTCAATCTC
AGAAATCAGAGAACTATCATTGCATATACACTAAATTAGAGAAATATTAAAAGGCTAAGT
AACATCTGTGGCAATATTGATGGTATATAACCTTGATATGATGTGATGAGAACAGTACTT
TACCCCATGGGCTTCCTCCCCAAACCCTTACCCCAGTATAAATCATGACAAATATACTTT
AAAAACCATTACCCTATATCTAACCAGTACTCCTCAAAACTGTCAAGGTCATCAAAAATA
AGAAAAGTCTGAGGAACTGTCAAAACTAAGAGGAACCCAAGGAGACATGAGAATTATATG
TAATGTGGCATTCTGAATGAGATCCCAGAACAGAAAAAGAACAGTAGCTAAAAAACTAAT
GAAATATAAATAAAGTTTGAACTTTAGTTTTTTTTAAAAAAGAGTAGCATTAACACGGCA
AAGTCATTTTCATATTTTTCTTGAACATTAAGTACAAGTCTATAATTAAAAATTTTTTAA
ATGTAGTCTGGAACATTGCCAGAAACAGAAGTACAGCAGCTATCTGTGCTGTCGCCTAAC
TATCCATAGCTGATTGGTCTAAAATGAGATACATCAACGCTCCTCCATGTTTTTGTTTT
CTTTTTAAATGAAAAACTTTATTTTTTAAGAGGAGTTTCAGGTTCATAGCAAAATTGAGA
GGAAGGTACATTCAAGCTGAGGAAGTTTTCCTCTATTCCTAGTTTACTGAGAGATTGCAT
CATGAATGGGTGTTAAATTTTGTCAAATGCTTTTCTGTGTCTATCAATATGACCATGTG
ATTTTCTTCTTTAACCTGTTGATGGGACAAATTACGTTAATTGATTTCAAACGTTGAAC
CACCCTTACATATCTGGAATAAATTCTACTTGGTTGTGGTGTATATTTTTTGATACATTC
TTGGATTCTTTTTGCTAATATTTTGTTGAAAATGTTTGTATCTTTGTTCATGAGAGATAT
TGGTCTGTTGTTTTCTTTTCTTGTAATGTCATTTTCTAGTTCCGGTATTAAGGTAATGCT
GGCCTAGTTGAATGATTTAGGAAGTATTCCCTCTGCTTCTGTCTTCTGAGGTACCGCGGC
CGCCCGTCGTTTTAC
```

FIG._16B

<start pUC118>
<linearization linker inserted into HpaI site>
AACGTCGTGACTGGGAAAACCCTGGCGTTACCCAACTTAATCGCCTTGCAGCACATCCCC
CTTTCGCCAGCTGGCGTAATAGCGAAGAGGCCCGCACCGATCGCCCTTCCCAACAGTTGC
GCAGCCTGAATGGCGAATGGC
<start M13>
GCCTGATGCGGTATTTTCTCCTTACGCATCTGTGCGGTATTTCACACCGCATACGTCAAA
GCAACCATAGTACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCCCTTC
CTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTTGGGTGATGGTTC
ACGTAGTGGGCCATCGCCCTGATAGACGGTTTTTCGCCCTTTGACGTTGGAGTCCACGTT
CTTTAATAGTGGACTCTTGTTCCAAACTGGAACAACACTCAACCCTATCTCGGGCTATTC
TTTTGATTTATAAGGGATTTTGCCGATTTCGGCCTATTGGTTAAAAAATGAGCTGATTTA
ACAAAAATTTAACGCGAATTTTAACAAAATATTAACGTTTACAATTTTATGGTGCACTCT
CAGTACAATCTGCTCTGATGCCGCATAGTTAAGCCAGCCCCGACACCCGCCAACACCCGC
TGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAG
<                Hinc II (2271) to GTCATC>
<                Pst I (1973) to CTGCTG>
<                Acc I (183) delete 6 bp>
<Arbitrarily change EcoRI (1) to GAATAC>
<pUCx 83.11.25 sequence not fully known>
ACGAAAGGGCCTCGTGATACGCCTATTTTTATAGGTTAATGTCATGATAATAATGGTTTC
TTAGACGTCAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAATA
ATATTGAAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGC
TGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCT
ATGTGGCGCGGTATTATCCCGTATTGACGCCGGGCAAGAGCAACTCGGTCGCCGCATACA
CTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAA
CTTACTTCTGACAACGATCGGAGGACCGAAGGAGCTAACCGCTTTTTTGCACAACATGGG
GGATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTGG
CGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAAGAT
CCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTTC

FIG._16C

```
GTGCACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGTC
AGTGAGCGAGGAAGCG
<Sap-SAR-Sap insert here>
GAAGAGCCCGCGGGCAAGGTCGCCACGCACAAGATCAATATTAACAATCAGTCATCTCTC
TTTAGCAATAAAAAGGTGAAAAATTACATTTTAAAAATGACACCATAGACGATGTATGAA
AATAATCTACTTGGAAATAAATCTAGGCAAAGAAGTGCAAGACTGTTACCCAGAAAACTT
ACAAATTGTAAATGAGAGGTTAGTGAAGATTTA

```
AAGCTTTACTCGTAAAGCGAGTTGAAGGATCATATTTAGTTGCGTTTATGAGATAAGATT
GAAAGCACGTGTAAA
><start ORF504 (PTP)>
ATGTTTCCCGCGCGTTGGCACAACTATTTACAATGCGGCCAAGTTATAAAAGATTCTAAT
CTGATATGTTTTAAAACACCTTTGCGGCCCGAGTTGTTTGCGTACGTGACTAGCGAAGAA
GATGTGTGGACCGCAGAACAGATAGTAAAACAAAACCCTAGTATTGGAGCAATAATCGAT
TTAACCAACACGTCTAAATATTATGATGGTGTGCATTTTTTGCGGGCGGGCCTGTTATAC
AAAAAAATTCAAGTACCTGGCCAGACTTTGCCGCCTGAAAGCATAGTTCAAGAATTTATT
GACACGGTAAAAGAATTTACAGAAAAGTGTCCCGGCATGTTGGTGGGCGTGCACTGCACA
CACGGTATTAATCGCACCGGTTACATGGTGTGCAGATATTTAATGCACACCCTGGGTATT
GCGCCGCAGGAAGCCATAGATAGATTCGAAAAAGCCAGAGGTCACAAAATTGAAAGACAA
AATTACGTTCAAGATTTATTAATTTAATTAATATTATTTGCATTCTTTAACAAATACTTT
ATCCTATTTTCAAATTGTTGCGCTTCTTCCAGCGAACCAAAACTATGCTTCGCTTGCTCC
GTTTAGCTTGTAGCCGATCAGTGGCGTTGTTCCAATCGACGGTAGGATTAGGCCGGATAT
TCTCCACCACAATGTTGGCAACGTTGATGTTACGTTTATGCTTTTGGTTTTCCACGTACG
TCTTTTGGCCGGTAATAGCCGTAAACGTAGTGCCGTCGCGCGTCACGCACAACACCGGAT
GTTTGCGCTTGTCCGCGGGGTATTGAACCGCGCGATCCGACAAATCCACCACTTTGGCAA
CTAAATCGGTGACCTGCGCGTCTTTTTTCTGCATTATTTCGTCTTTCTTTTGCATGGTTT
CCTGGAAGCCGGTGTACATGCGGTTTAGATCAGTCATGACGCGCGTGACCTGCAAATCTT
TGGCCTCGATCTGCTTGTCCTTGATGGCAACGATGCGTTCAATAAACTCTTGTTTTTTAA
CAAGTTCCTCGGTTTTTTGCGCCACCACCGCTTGCAGCGCGTTTGTGTGCTCGGTGAATG
TCGCAATCAGCTTAGTCACCAACTGTTTGCTCTCCTCCTCCCGTTGTTTGATCGCGGGAT
CGTACTTGCCGGTGCAGAGCACTTGAGGAATTACTTCTTCTAAAAGCCATTCTTGTAATT
CTATGGCGTAAGGCAATTTGGACTTCATAATCAGCTGAATCACGCCGGATTTAGTAATGA
GCACTGTATGCGGCTGCAAATACAGCGGGTCGCCCCTTTTCACGACGCTGTTAGAGGTAG
GGCCCCCATTTTGGATGGTCTGCTCAAATAACGATTTGTATTTATTGTCTACATGAACAC
GTATAGCTTTATCACAAACTGTATATTTTAAACTGTTAGCGACGTCCTTGGCCACGAACC
GGACCTGTTGGTCGCGCTCTAGCACGTACCGCAGGTTGAACGTATCTTCTCCAAATTTAA
ATTCTCCAATTTTAACGCGAGCCA
><start ORF984 (ORF2)>
TTTTGATACACGTGTGTCGATTTTGCAACAACTATTGTTTTTTAACGCAAACTAAACTTA
TTGTGGTAAGCAATAATTAAATATGGGGAACATGCGCCGCTACAACACTCGTCGTTATG
AACGCAGACGGCGCCGGTCTCGGCGCAAGCGGCTAAAACGTGTTGCGCGTTCAACGCGGC
AAACATCGCAAAAGCCAATAGTACAGTTTTGATTTGCA
><start conotoxin>
TATTAACGGCGATTTTTAAATTATCTTATTTAATAAAT

```
ATGGCGAATGCATCGTATAACGTGTGGAGTCCGCTCATTAGAGCGTCATGTTTAGACAAG
AAAGCTACATATTTAATTGATCCCGATGATTTTATTGATAAATTGACCCTAACTCCATAC
ACGGTATTCTACAATGGCGGGGTTTTGGTCAAAATTTCCGGACTGCGATTGTACATGCTG
TTAACGGCTCCGCCCACTATTAATGAAATTAAAAATTCCAATTTTAAAAAACGCAGCAAG
AGAAACATTTGTATGAAAGAATGCGTAGAAGGAAAGAAAAATGTCGTCGACATGCTGAAC
AACAAGATTAATATGCCTCCGTGTATAAAAAAATATTGAACGATTTGAAAGAAAACAAT
GTACCGCGCGGCGGTATGTACAGGAAGAGGTTTATACTAAACTGTTACATTGCAAACGTG
GTTTCGTGTGCCAAGTGTGAAAACCGATGTTTAATCAAGGCTCTGACGCATTTCTACAAC
CACGACTCCAAGTGTGTGGGTGAAGTCATGCATCTTTTAATCAAATCCCAAGATGTGTAT
AAACCACCAAACTGCCAAAAAATGAAAACTGTCGACAAGCTCTGTCCGTTTGCTGGCAAC
TGCAAGGGTCTCAATCCTATTTGTAATTATTGAATAATAAAACAATTATAAATGCTAAAT
TTGTTTTTTTATTAACGATACAAACCAAACGCAACAAGAACATTTGTAGTATTATCTATAA
TTGAAAACGCGTAGTTATAATCGCTGAGGTAATATTTAAAATCATTTTCAAATGATTCAC
AGTTAATTTGCGACAATATAATTTTATTTTCACATAAACTAGACGCCTTGTCGTCTTCTT
CTTCGTATTCCTTCTCTTTTTCATTTTTCTCCTCATAAAAATTAACATAGTTATTATCGT
ATCCATATATGTATCTATCGTATAGAGTAAATTTTTTGTTGTCATAAATATATATGTCTT
TTTTAATGGGGTGTATAGTACCGCTGCGCATAGTTTTTCTGTAATTTACAACAGTGCTAT
TTTCTGGTAGTTCTTCGGAGTGTGTTGCTTTAATTATTAAATTTATATAATCAATGAATT
TGGGATCGTCGGTTTTGTACAATATGTTGCCGGCATAGTACGCAGCTTCTTCTAGTTCAA
TTACACCATTTTTTAGCAGCACCGGATTAACATAACTTTCCAAAATGTTGTACGAACCGT
TAAACAAAAACAGTTCACCTCCCTTTTCTATACTATTGTCTGCGAGCAGTTGTTTGTTGT
TAAAAATAACAGCCA
><start ORF603>
TTGTAATGAGACGCACAAACTAATATCACAAACTGGAAATGTCTATCAATATATAGTTGC
TGATATCATGGAGATAATTAAAATGATAACCATCTCGCAAATAAA
><start of polh transcription>
TAAGTATTTTACTGTTTTCGTAACAGTTTTGTAATAAAAAAAACCTATAAAT
><mutated polh start codon>
ATTCCGGATTATTCATACCGTCCCACCATCGGGCGC
><start polylinker >
GGATCCGCGGCCGCGAATTCTAAACCACCATGGCTAGCAGGCCT
><start of IgG>
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAAGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAA
><end of IgG>
TGACATAGGG
><untranslated His tag>
CATCATCATCATCATCATCATCATTAATTCTAGACTAGTCTGCAGATC
><end polylinker>
T
```

FIG._17B

><polh coding sequences>
GATCCTTTCCTGGGACCCGGCAAGAACCAAAAACTCACTCTCTTCAAGGAAATCCGTAAT
GTTAAACCCGACACGATGAAGCTTGTCGTTGGATGGAAAGGAAAAGAGTTCTACAGGGAA
ACTTGGACCCGCTTCATGGAAGACAGCTTCCCCATTGTTAACGACCAAGAAGTGATGGAT
GTTTTCCTTGTTGTCAACATGCGTCCCACTAGACCCAACCGTTGTTACAAATTCCTGGCC
CAACACGCTCTGCGTTGCGACCCCGACTATGTACCTCATGACGTGATTAGGATCGTCGAG
CCTTCATGGGTGGGCAGCAACAACGAGTACCGCATCAGCCTGGCTAAGAAGGGCGGCGGC
TGCCCAATAATGAACCTTCACTCTGAGTACACCAACTCGTTCGAACAGTTCATCGATCGT
GTCATCTGGGAGAACTTCTACAAGCCCATCGTTTACATCGGTACCGACTCTGCTGAAGAG
GAGGAAATTCTCCTTGAAGTTTCCCTGGTGTTCAAAGTAAAGGAGTTTGCACCAGACGCA
CCTCTGTTCACTGGTCCGGCGTATTAAAACACGATACATTGTTATTAGTACATTTATTAA
GCGCTAGATTCTGTGCGTTGTTGATTTACAGACAATTGTTGTACGTATTTTAATAATTCA
TTAAATTTATAATCTTTAGGGTGGTATGTTAGAGCGAAAATCAAATGATTTTCAGCGTCT
TTATATCTGAATTTAAATATTAAATCCTCAATAGATTTGTAAAATAGGTTTCGATTAGTT
TCAAACAAGGGTTGTTTTTCCGAACCGATGGCTGGACTATCTAATGGATTTTCGCTCAAC
GCCACAAAACTTGCCAAATCTTGTAGCAGCAATCTAGCTTTGTCGATATTCGTTTGTGTT
TTGTTTTGTAATAAAGGTTCGACGTCGTTCAAAATATTATGCGCTTTTGTATTTCTTTCA
TCACTGTCGTTAGTGTACAATTGACTCGACGTAAACACGTTAAATAAAGCTTGGACATAT
TTAACATCGGGCGTGTTAGCTTTATTAGGCCGATTATCGTCGTCGTCCCAACCCTCGTCG
TTAGAAGTTGCTTCCGAAGACGATTTTGCCATAGCCACACGACGCCTATTAATTGTGTCG
GCTAACACGTCCGCGATCAAATTTGTAGTTGAGCTTTTTGGAATTATTTCTGATTGCGGG
CGTTTTTGGGCGGGTTTCAATCTAACTGTGCCCGATTTTAATTCAGACAACACGTTAGAA
AGCGATGGTGCAGGCGGTGGTAACATTTCAGACGGCAAATCTACTAATGGCGGCGGTGGT
GGAGCTGATGATAAATCTACCATCGGTGGAGGCGCAGGCGGGGCTGGCGGCGGAGGCGGA
GGCGGAGGTGGTGGCGGTGATGCAGACGGCGGTTTAGGCTCAAATGTCTCTTTAGGCAAC
ACAGTCGGCACCTCAACTATTGTACTGGTTTCGGGCGCCGTTTTGGTTTGACCGGTCTG
AGACGAGTGCGATTTTTTCGTTTCTAATAGCTTCCAACAATTGTTGTCTGTCGTCTAAA
GGTGCAGCGGGTTGAGGTTCCGTCGGCATTGGTGGAGCGGGCGGCAATTCAGACATCGAT
GGTGGTGGTGGTGGTGGAGGCGCTGGAATGTTAGGCACGGGAGAAGGTGGTGGCGGCGGT
GCCGCCGGTATAATTTGTTCTGGTTTAGTTTGTTCGCGCACGATTGTGGGCACCGGCGCA
GGCGCCGCTGGCTGCACAACGGAAGGTCGTCTGCTTCGAGGCAGCGCTTGGGGTGGTGGC
AATTCAATATTATAATTGGAATACAAATCGTAAAAATCTGCTATAAGCATTGTAATTTCG
CTATCGTTTACCGTGCCGATATTTAACAACCGCTCAATGTAAGCAATTGTATTGTAAAGA
GATTGTCTCAAGCTCCGCACGCCGATAACAAGCCTTTTCATTTTTACTACAGCATTGTAG
TGGCGAGACACTTCGCTGTCGTCGACGTACATGTATGCTTTGTTGTCAAAAACGTCGTTG
GCAAGCTTTAAAATATTTAAAAGAACATCTCTGTTCAGCACCACTGTGTTGTCGTAAATG
TTGTTTTTGATAATTTGCGCTTCCGCAGTATCGACACGTTCAAAAAATTGATGCGCATCA
ATTTTGTTGTTCCTATTATTGAATAAATAAGATTGTACAGATTCATATCTACGATTCGTC
><start ORF588>
A
><start ORF1629>
TGGCCACCACAAATGCTACGCTGCAAACGCTGGTACAATTTTACGAAAACTGCAAAAACG
TCAAAACTCGGTATAAAATAATCAACGGGCGCTTTGGCAAAATATCTATTTTATCGCACA
AGCCCACTAGCAAATTGTATTTGCAGAAAACAATTTCGGCGCACAATTTTAACGCTGACG
AAATAAAAGTTCACCAGTTAATGAGCGACCACCCAAATTTTATAAAAATCTATTTTAATC
ACGGTTCCATCAACAACCAAGTGATCGTGATGGACTACATTGACTGTCCCGATTTATTTG
AAACACTACAAATTAAAGGCGAGCTTTCGTACCAACTTGTTAGCAATATTATTAGACAGC
TGTGTGAAGCGCTCAACGATTTGCACAAGCACAATTTCATACACAACGACATAAAACTCG
AAAATGTCTTATATTTCGAAGCACTTGATCGCGTGTATGTTTGCGATTACGGATTGTGCA
AACACGAAAACTCACTTAGCGTGCACGACGGCACGTTGGAGTATTTTAGTCCGGAAAAAA
TTCGACACACAACTATGCACGTTTCGTTTGACTGGTACGCGGCGTGTTAACATACAAGTT
GCTAACCGGCGG

FIG._17C

><end of polh locus fragment>
TTCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTG
><border ColE1 origin>
GGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGT
GGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTT ><border ColE1 origin>
AAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAA
CCAGCCAGCCGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAG
CGTTTCTGGGTGAGCAAAAACAGGAAGGCAAAATGCCGCAAAAAAGGGAATAAGGGCGAC
ACGGAAATGTTGAATACTCA
><Start Amp>
TACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAA
AAGTGCCACCTGACGTCTAAGAAACCATTATTATCATGACATTAACCTATAAAAATAGGC
GTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCC
GTCAGGGCGCGTCAGCGGGTGTTGGCGGGTGTCGGGCTGGCTTAACTATGCGGCATCAG
AGCAGATTGTACTGAGAGTGCACCATATATGCGGTGTGAAATACCGCACAGATGCGTAAG
GAGAAAATACCGCATCAGGCGCCATTCGCCATTCAGGCTGCGCAACTGTTGGGAAGGGCG
ATCGGTGCGGGCCTCTTCGCTATTACGCCAGCTGGCGAAAGGGGGATGTGCTGCAAGGCG
ATTAAGTTGGGTAACGCCAGGGTTTTCCCAGTCACGACGTTGTAAAACGACGGCCAGTGC
C

*FIG._17D*

AAGCTTTACTCGTAAAGCGAGTTGAAGGATCATATTTAGTTGCGTTTATGAGATAAGATT
GAAAGCACGTGTAAA
><start ORF504 (PTP)>
ATGTTTCCCGCGCGTTGGCACAACTATTTACAATGCGGCCAAGTTATAAAAGATTCTAAT
CTGATATGTTTTAAAACACCTTTGCGGCCCGAGTTGTTTGCGTACGTGACTAGCGAAGAA
GATGTGTGGACCGCAGAACAGATAGTAAAACAAAACCCTAGTATTGGAGCAATAATCGAT
TTAACCAACACGTCTAAATATTATGATGGTGTGCATTTTTTGCGGGCGGGCCTGTTATAC
AAAAAAATTCAAGTACCTGGCCAGACTTTGCCGCCTGAAAGCATAGTTCAAGAATTTATT
GACACGGTAAAAGAATTTACAGAAAAGTGTCCCGGCATGTTGGTGGGCGTGCACTGCACA
CACGGTATTAATCGCACCGGTTACATGGTGTGCAGATATTTAATGCACACCCTGGGTATT
GCGCCGCAGGAAGCCATAGATAGATTCGAAAAAGCCAGAGGTCACAAAATTGAAAGACAA
AATTACGTTCAAGATTTATTAATTTAATTAATATTATTTGCATTCTTTAACAAATACTTT
ATCCTATTTTCAAATTGTTGCGCTTCTTCCAGCGAACCAAAACTATGCTTCGCTTGCTCC
GTTTAGCTTGTAGCCGATCAGTGGCGTTGTTCCAATCGACGGTAGGATTAGGCCGGATAT
TCTCCACCACAATGTTGGCAACGTTGATGTTACGTTTATGCTTTTGGTTTTCCACGTACG
TCTTTTGGCCGGTAATAGCCGTAAACGTAGTGCCGTCGCGCGTCACGCACAACACCGGAT
GTTTGCGCTTGTCCGCGGGGTATTGAACCGCGCGATCCGACAAATCCACCACTTTGGCAA
CTAAATCGGTGACCTGCGCGTCTTTTTTCTGCATTATTTCGTCTTTCTTTTGCATGGTTT
CCTGGAAGCCGGTGTACATGCGGTTTAGATCAGTCATGACGCGCGTGACCTGCAAATCTT
TGGCCTCGATCTGCTTGTCCTTGATGGCAACGATGCGTTCAATAAACTCTTGTTTTTTAA
CAAGTTCCTCGGTTTTTGCGCCACCACCGCTTGCAGCGCGTTTGTGTGCTCGGTGAATG
TCGCAATCAGCTTAGTCACCAACTGTTTGCTCTCCTCCTCCCGTTGTTTGATCGCGGGAT
CGTACTTGCCGGTGCAGAGCACTTGAGGAATTACTTCTTCTAAAAGCCATTCTTGTAATT CTATGGCGTAAGGCAATTTGGACTTCATAATCAGCTGAATCACGCCGGATTTAGTAATGA
GCACTGTATGCGGCTGCAAATACAGCGGGTCGCCCCTTTTCACGACGCTGTTAGAGGTAG
GGCCCCCATTTTGGATGGTCTGCTCAAATAACGATTTGTATTTATTGTCTACATGAACAC
GTATAGCTTTATCACAAACTGTATATTTTAAACTGTTAGCGACGTCCTTGGCCACGAACC
GGACCTGTTGGTCGCGCTCTAGCACGTACCGCAGGTTGAACGTATCTTCTCCAAATTTAA
ATTCTCCAATTTTAACGCGAGCCA
><start ORF984 (ORF2)>
TTTTGATACACGTGTGTCGATTTTGCAACAACTATTGTTTTTTAACGCAAACTAAACTTA
TTGTGGTAAGCAATAATTAAATATGGGGAACATGCGCCGCTACAACACTCGTCGTTATG
AACGCAGACGGCGCCGGTCTCGGCGCAAGCGGCTAAAACGTGTTGCGCGTTCAACGCGGC
AAACATCGCAAAAGCCAATAGTACAGTTTTGATTTGCA
><start conotoxin>
TATTAACGGCGATTTTTTAAATTATCTTATTTAATAAATAGTTATGACGCCTACAACTCC
CCGCCCGCGTTGACTCGCTGCACCTCGAGCAGTTCGTTGACGCCTTCCTCCGTGTGGCCG
AACACGTCGAGCGGGTGGTCGATGACCAGCGGCGTGCCGCACGCGACGCACAAGTATCTG
TACACCGAATGATCGTCGGGCGAAGGCACGTCGGCCTCCAAGTGGCAATATTGGCAAATT
CGAAAATATATACAGTTGGGTTGTTTGCGCATATCTATCGTGGCGTTGGGCATGTACGTC
CGAACGTTGATTTGCATGCAAGCCGAAATTAAATCATTGCGATTAGTGCGATTAAAACGT
TGTACATCCTCGCTTTTAATCATGCCGTCGATTAAATCGCGCAATCGAGTCAAGTGATCA
AAGTGTGGAATAATGTTTTCTTTGTATTCCCGAGTCAAGCGCAGCGCGTATTTTAACAAA
CTAGCCATCTTGTAAGTTAGTTTCA

FIG._18A

><start ORF453>
TTTAATGCAACTTTATCCAATAATATATT
><start ORF327>
ATGTATCGCACGTCAAGAATTAACAATGCGCCCGTTGTCGCATCTCAACACGACTATGAT
AGAGATCAAATAAAGCGCGAATTAAATAGCTTGCGACGCAACGTGCACGATCTGTGCACG
CGTTCCGGCACGAGCTTTGATTGTAATAAGTTTTTACGAAGCGATGACATGACCCCCGTA
GTGACAACGATCACGCCCAAAAGAACTGCCGACTACAAAATTACCGAGTATGTCGGTGAC
GTTAAAACTATTAAGCCATCCAATCGACCGTTAGTCGAATCAGGACCGCTGGTGCGAGAA
GCCGCGAAGT
><start ORF630>
ATGGCGAATGCATCGTATAACGTGTGGAGTCCGCTCATTAGAGCGTCATGTTTAGACAAG
AAAGCTACATATTTAATTGATCCCGATGATTTTATTGATAAATTGACCCTAACTCCATAC
ACGGTATTCTACAATGGCGGGGTTTTGGTCAAAATTTCCGGACTGCGATTGTACATGCTG
TTAACGGCTCCGCCCACTATTAATGAAATTAAAAATTCCAATTTTAAAAAACGCAGCAAG
AGAAACATTTGTATGAAAGAATGCGTAGAAGGAAAGAAAAATGTCGTCGACATGCTGAAC
AACAAGATTAATATGCCTCCGTGTATAAAAAAAATATTGAACGATTTGAAAGAAAACAAT
GTACCGCGCGGCGGTATGTACAGGAAGAGGTTTATACTAAACTGTTACATTGCAAACGTG
GTTTCGTGTGCCAAGTGTGAAAACCGATGTTAATCAAGGCTCTGACGCATTTCTACAAC
CACGACTCCAAGTGTGTGGGTGAAGTCATGCATCTTTTAATCAAATCCCAAGATGTGTAT
AAACCACCAAACTGCCAAAAAATGAAAACTGTCGACAAGCTCTGTCCGTTTGCTGGCAAC
TGCAAGGGTCTCAATCCTATTTGTAATTATTGAATAATAAAACAATTATAAATGCTAAAT
TTGTTTTTTATTAACGATACAAACCAAACGCAACAAGAACATTTGTAGTATTATCTATAA
TTGAAAACGCGTAGTTATAATCGCTGAGGTAATATTTAAAATCATTTTCAAATGATTCAC
AGTTAATTTGCGACAATATAATTTTATTTTCACATAAACTAGACGCCTTGTCGTCTTCTT
CTTCGTATTCCTTCTCTTTTTCATTTTTCTCCTCATAAAAATTAACATAGTTATTATCGT
ATCCATATATGTATCTATCGTATAGAGTAAATTTTTGTTGTCATAAATATATATGTCTT
TTTTAATGGGGTGTATAGTACCGCTGCGCATAGTTTTTCTGTAATTTACAACAGTGCTAT
TTTCTGGTAGTTCTTCGGAGTGTGTTGCTTTAATTATTAAATTTATATAATCAATGAATT
TGGGATCGTCGGTTTTGTACAATATGTTGCCGGCATAGTACGCAGCTTCTTCTAGTTCAA
TTACACCATTTTTTAGCAGCACCGGATTAACATAACTTTCCAAAATGTTGTACGAACCGT
TAAACAAAAACAGTTCACCTCCCTTTTCTATACTATTGTCTGCGAGCAGTTGTTTGTTGT
TAAAAATAACAGCCA
><start ORF603>
TTGTAATGAGACGCACAAACTAATATCACAAACTGGAAATGTCTATCAATATATAGTTGC
TGATATCATGGAGATAATTAAAATGATAACCATCTCGCAAATAAA
><start of polh transcription>
TAAGTATTTTACTGTTTTCGTAACAGTTTTGTAATAAAAAAACCTATAAAT
><mutated polh start codon>
ATTCCGGATTATTCATACCGTCCCACCATCGGGCGC
><start polylinker >
GGATCCGCGGCCGCGAATTCTAAACCACCATGGGCAGCTGCCCGGG
><His tag>
CATCATCATCATCATCATCATCATTAATTCTAGACTAGTCTGCAGATC
><end polylinker>
T

FIG._18B

><polh coding sequences>
GATCCTTTCCTGGGACCCGGCAAGAACCAAAAACTCACTCTCTTCAAGGAAATCCGTAAT
GTTAAACCCGACACGATGAAGCTTGTCGTTGGATGGAAAGGAAAAGAGTTCTACAGGGAA
ACTTGGACCCGCTTCATGGAAGACAGCTTCCCCATTGTTAACGACCAAGAAGTGATGGAT
GTTTTCCTTGTTGTCAACATGCGTCCCACTAGACCCAACCGTTGTTACAAATTCCTGGCC
CAACACGCTCTGCGTTGCGACCCCGACTATGTACCTCATGACGTGATTAGGATCGTCGAG
CCTTCATGGGTGGGCAGCAACAACGAGTACCGCATCAGCCTGGCTAAGAAGGGCGGCGGC
TGCCCAATAATGAACCTTCACTCTGAGTACACCAACTCGTTCGAACAGTTCATCGATCGT
GTCATCTGGGAGAACTTCTACAAGCCCATCGTTTACATCGGTACCGACTCTGCTGAAGAG
GAGGAAATTCTCCTTGAAGTTTCCCTGGTGTTCAAAGTAAAGGAGTTTGCACCAGACGCA
CCTCTGTTCACTGGTCCGGCGTATTAAAACACGATACATTGTTATTAGTACATTTATTAA
GCGCTAGATTCTGTGCGTTGTTGATTTACAGACAATTGTTGTACGTATTTAATAATTCA
TTAAATTTATAATCTTTAGGGTGGTATGTTAGAGCGAAAATCAAATGATTTTCAGCGTCT
TTATATCTGAATTTAAATATTAAATCCTCAATAGATTTGTAAAATAGGTTTCGATTAGTT
TCAAACAAGGGTTGTTTTTCCGAACCGATGGCTGGACTATCTAATGGATTTTCGCTCAAC
GCCACAAAACTTGCCAAATCTTGTAGCAGCAATCTAGCTTTGTCGATATTCGTTTGTGTT
TTGTTTTGTAATAAAGGTTCGACGTCGTTCAAAATATTATGCGCTTTTGTATTTCTTTCA
TCACTGTCGTTAGTGTACAATTGACTCGACGTAAACACGTTAAATAAAGCTTGGACATAT
TTAACATCGGGCGTGTTAGCTTTATTAGGCCGATTATCGTCGTCGTCCCAACCCTCGTCG
TTAGAAGTTGCTTCCGAAGACGATTTTGCCATAGCCACACGACGCCTATTAATTGTGTCG
GCTAACACGTCCGCGATCAAATTTGTAGTTGAGCTTTTTGGAATTATTTCTGATTGCGGG
CGTTTTTGGGCGGGTTTCAATCTAACTGTGCCCGATTTTAATTCAGACAACACGTTAGAA
AGCGATGGTGCAGGCGGTGGTAACATTTCAGACGGCAAATCTACTAATGGCGGCGGTGGT
GGAGCTGATGATAAATCTACCATCGGTGGAGGCGCAGGCGGGGCTGGCGGCGGAGGCGGA
GGCGGAGGTGGTGGCGGTGATGCAGACGGCGGTTTAGGCTCAAATGTCTCTTTAGGCAAC
ACAGTCGGCACCTCAACTATTGTACTGGTTTCGGGCGCCGTTTTTGGTTTGACCGGTCTG
AGACGAGTGCGATTTTTTTCGTTTCTAATAGCTTCCAACAATTGTTGTCTGTCGTCTAAA
GGTGCAGCGGGTTGAGGTTCCGTCGGCATTGGTGGAGCGGGCGGCAATTCAGACATCGAT
GGTGGTGGTGGTGGTGGAGGCGCTGGAATGTTAGGCACGGGAGAAGGTGGTGGCGGCGGT
GCCGCCGGTATAATTTGTTCTGGTTTAGTTTGTTCGCGCACGATTGTGGGCACCGGCGCA
GGCGCCGCTGGCTGCACAACGGAAGGTCGTCTGCTTCGAGGCAGCGCTTGGGGTGGTGGC
AATTCAATATTATAATTGGAATACAAATCGTAAAAATCTGCTATAAGCATTGTAATTTCG
CTATCGTTTACCGTGCCGATATTTAACAACCGCTCAATGTAAGCAATTGTATTGTAAAGA
GATTGTCTCAAGCTCCGCACGCCGATAACAAGCCTTTTCATTTTTACTACAGCATTGTAG
TGGCGAGACACTTCGCTGTCGTCGACGTACATGTATGCTTTGTTGTCAAAAACGTCGTTG
GCAAGCTTTAAAATATTTAAAAGAACATCTCTGTTCAGCACCACTGTGTTGTCGTAAATG
TTGTTTTTGATAATTTGCGCTTCCGCAGTATCGACACGTTCAAAAAATTGATGCGCATCA
ATTTGTTGTTCCTATTATTGAATAAATAAGATTGTACAGATTCATATCTACGATTCGTC
><start ORF588>
A
><start ORF1629>
TGGCCACCACAAATGCTACGCTGCAAACGCTGGTACAATTTTACGAAAACTGCAAAAACG
TCAAAACTCGGTATAAAATAATCAACGGGCGCTTTGGCAAAATATCTATTTTATCGCACA
AGCCCACTAGCAAATTGTATTTGCAGAAAACAATTTCGGCGCACAATTTTAACGCTGACG
AAATAAAAGTTCACCAGTTAATGAGCGACCACCCAAATTTTATAAAAATCTATTTTAATC
ACGGTTCCATCAACAACCAAGTGATCGTGATGGACTACATTGACTGTCCCGATTTATTTG
AAACACTACAAATTAAAGGCGAGCTTTCGTACCAACTTGTTAGCAATATTATTAGACAGC
TGTGTGAAGCGCTCAACGATTTGCACAAGCACAATTTCATACACAACGACATAAAACTCG
AAAATGTCTTATATTTCGAAGCACTTGATCGCGTGTATGTTTGCGATTACGGATTGTGCA

FIG._18C

```
AACACGAAAACTCACTTAGCGTGCACGACGGCACGTTGGAGTATTTTAGTCCGGAAAAAA
TTCGACACACAACTATGCACGTTTCGTTTGACTGGTACGCGGCGTGTTAACATACAAGTT
GCTAACCGGCGG
><end of polh locus fragment>
TTCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTG
><border ColE1 origin>
GGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGT
GGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTT
><border ColE1 origin>
AAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAA
CCAGCCAGCCGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAG
CGTTTCTGGGTGAGCAAAAACAGGAAGGCAAAATGCCGCAAAAAAGGGAATAAGGGCGAC
ACGGAAATGTTGAATACTCA
><Start Amp>
TACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAA
AAGTGCCACCTGACGTCTAAGAAACCATTATTATCATGACATTAACCTATAAAAATAGGC
GTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCC
GTCAGGGCGCGTCAGCGGGTGTTGGCGGGTGTCGGGCTGGCTTAACTATGCGGCATCAG
AGCAGATTGTACTGAGAGTGCACCATATATGCGGTGTGAAATACCGCACAGATGCGTAAG
GAGAAAATACCGCATCAGGCGCCATTCGCCATTCAGGCTGCGCAACTGTTGGGAAGGGCG
ATCGGTGCGGGCCTCTTCGCTATTACGCCAGCTGGCGAAAGGGGGATGTGCTGCAAGGCG
ATTAAGTTGGGTAACGCCAGGGTTTTCCCAGTCACGACGTTGTAAAACGACGGCCAGTGC
C
```

FIG._18D

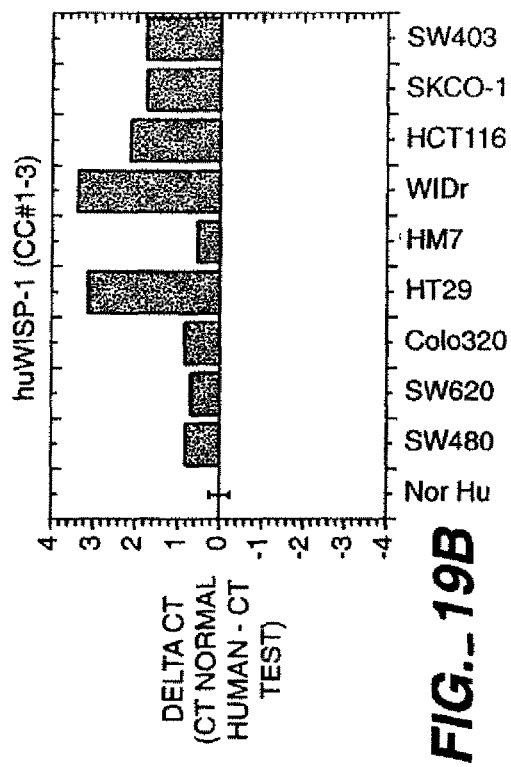
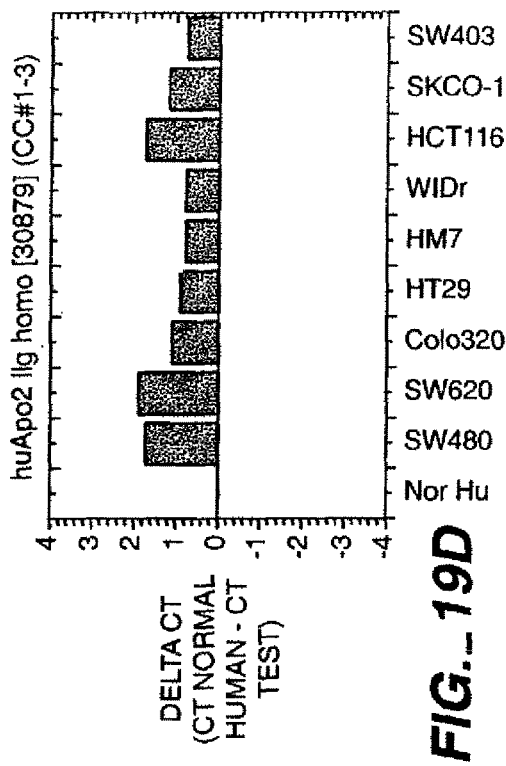
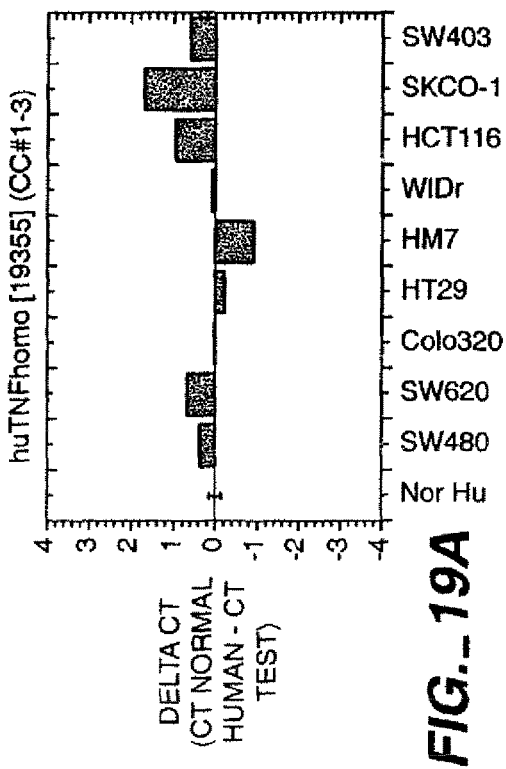
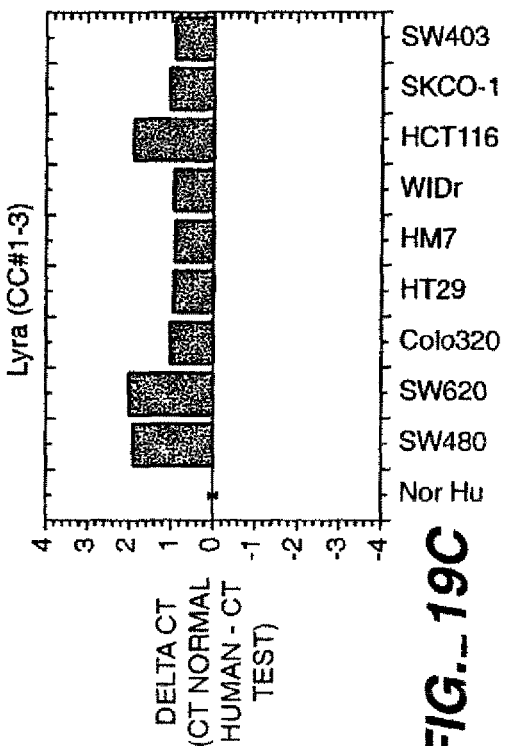
FIG._19A, FIG._19B, FIG._19C, FIG._19D

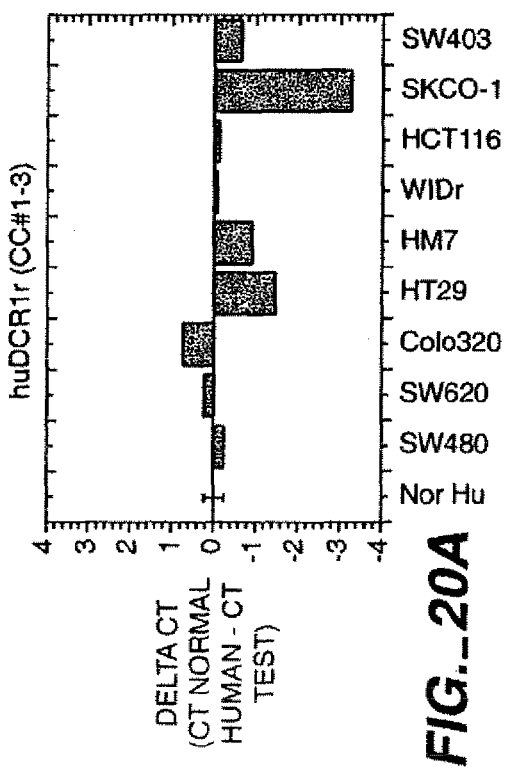
FIG._20A
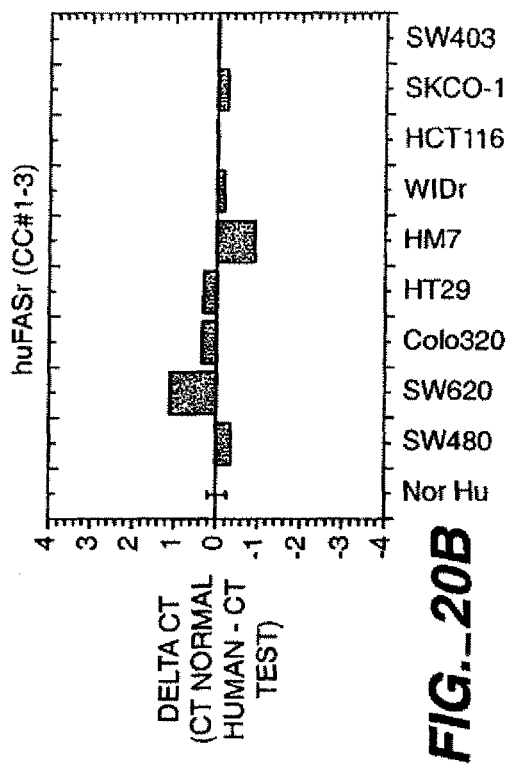
FIG._20B
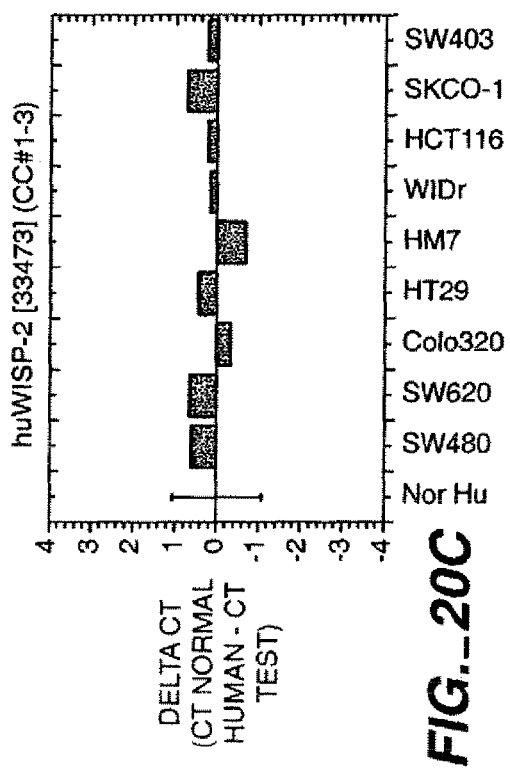
FIG._20C
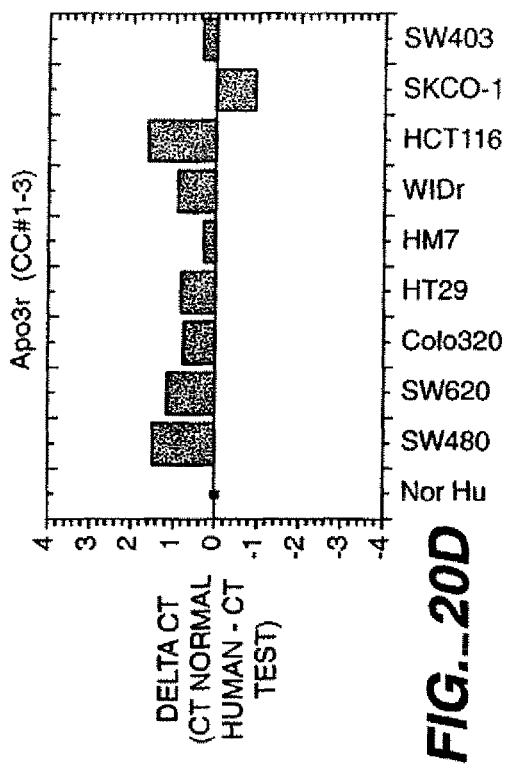
FIG._20D

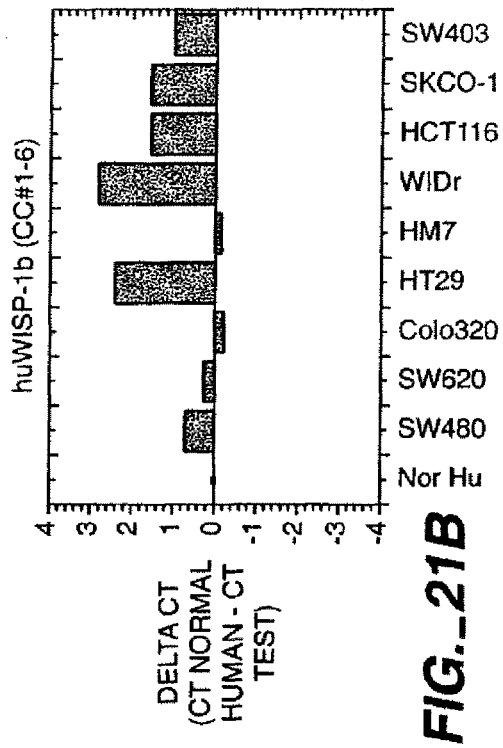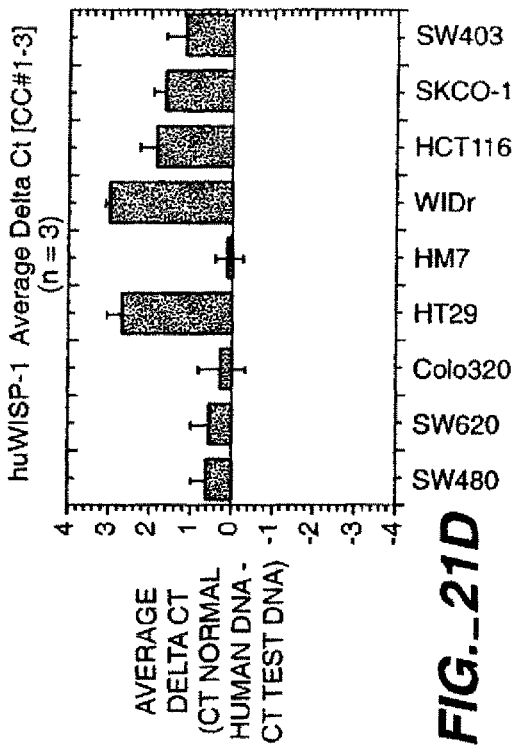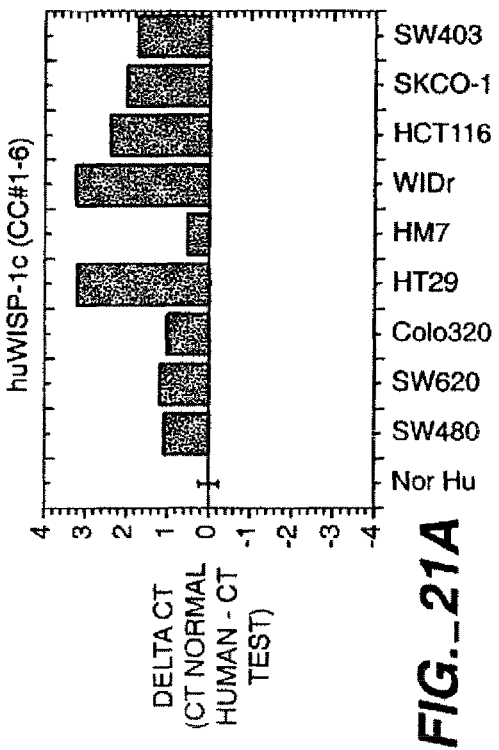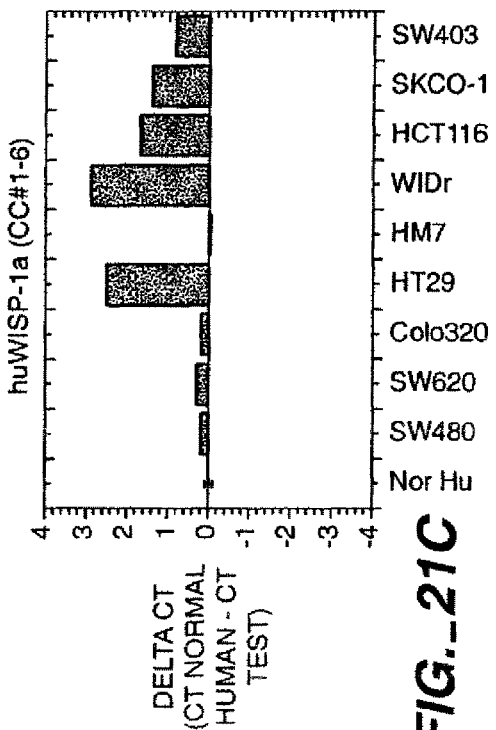
FIG._21A  FIG._21B  FIG._21C  FIG._21D

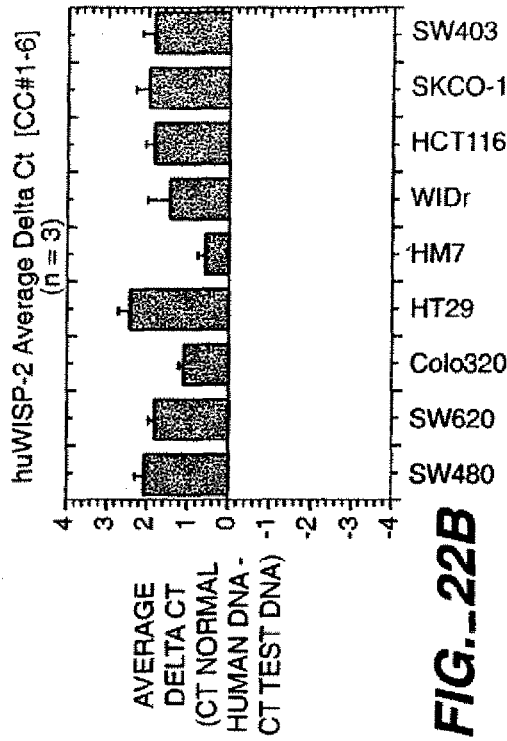
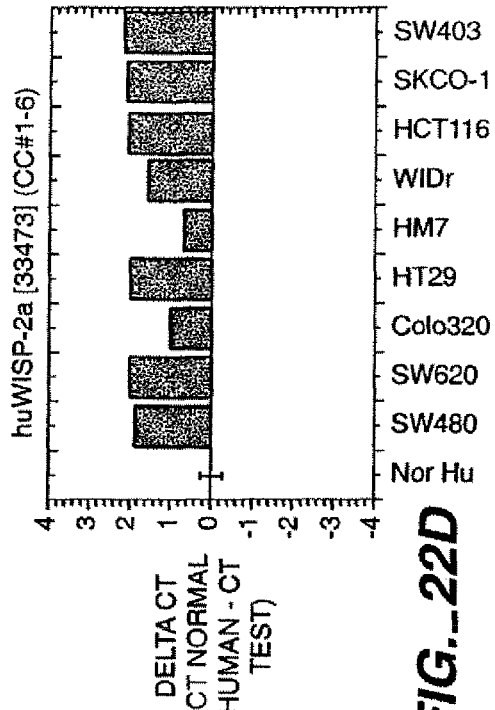
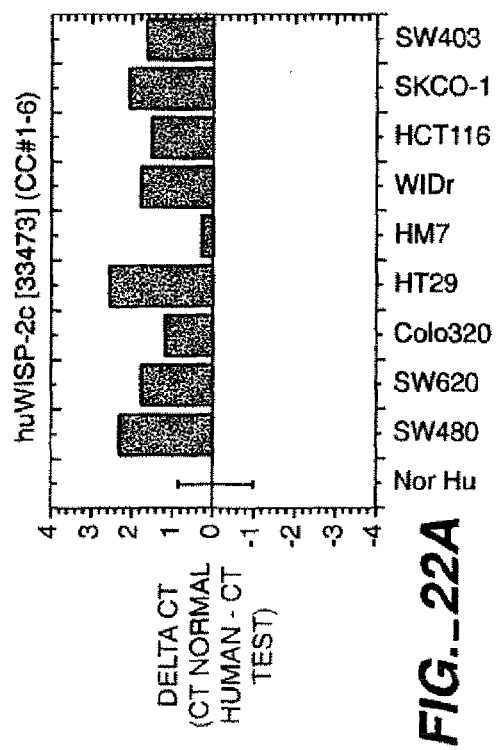
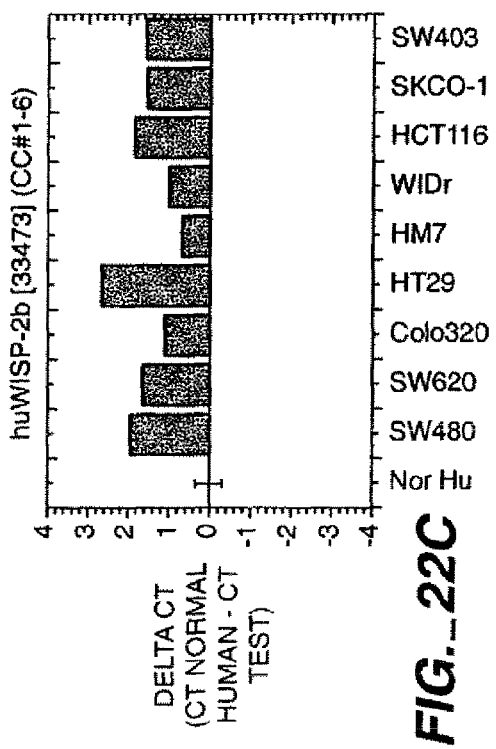
FIG._22A  FIG._22B  FIG._22C  FIG._22D

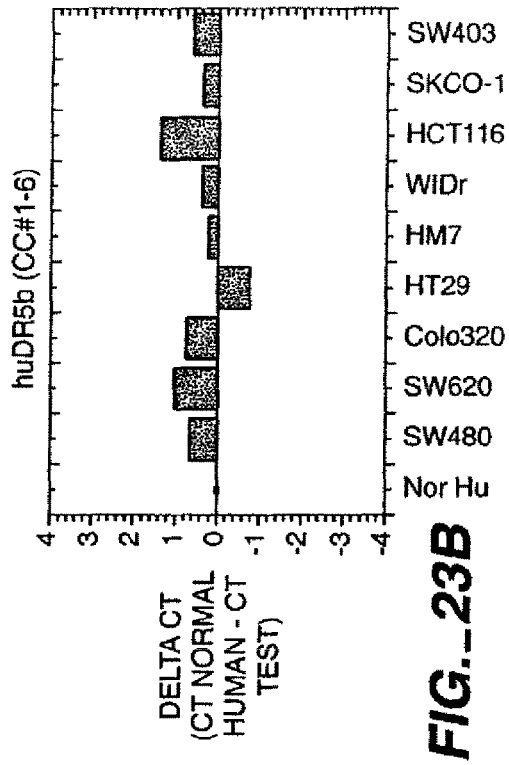
FIG._23B
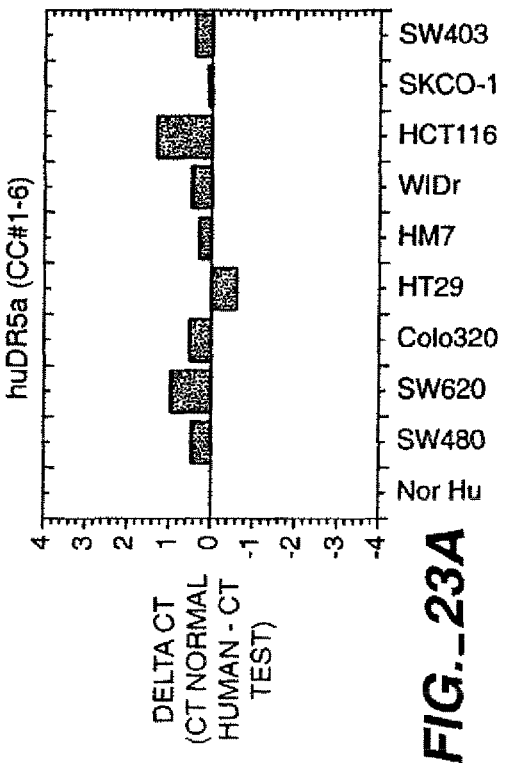
FIG._23A
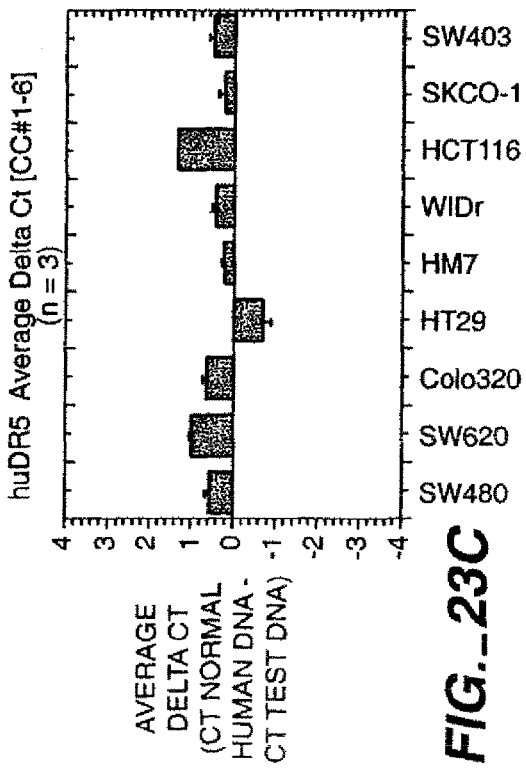
FIG._23C

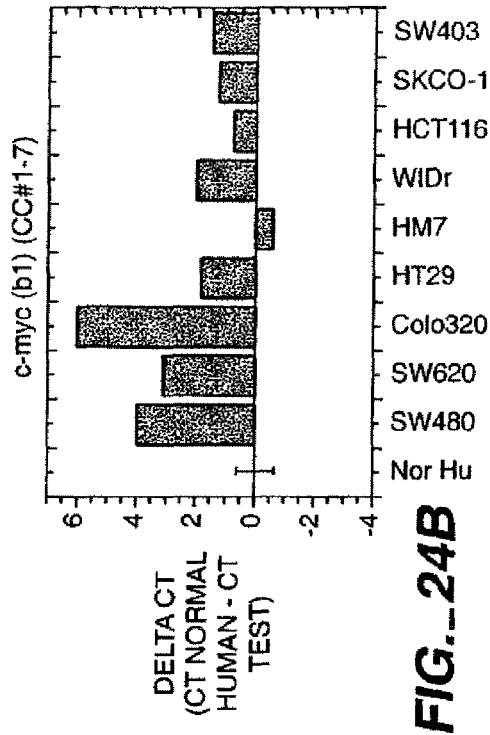
FIG._24A
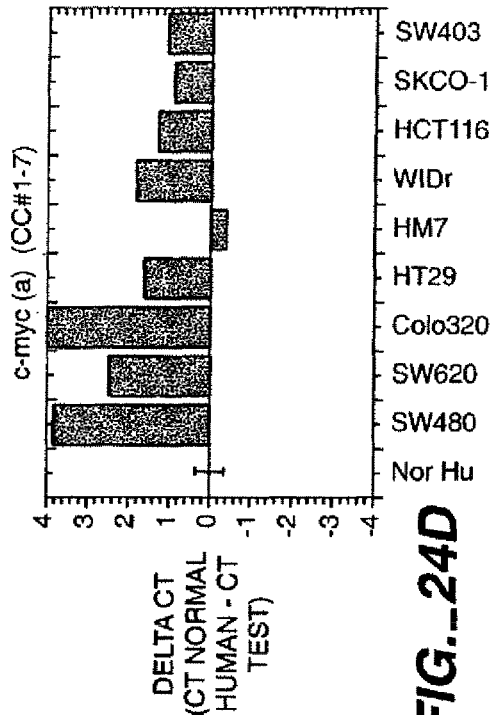
FIG._24B
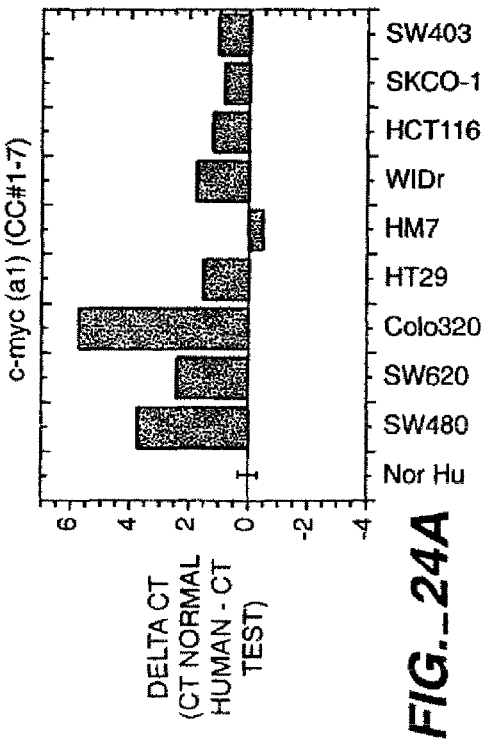
FIG._24C
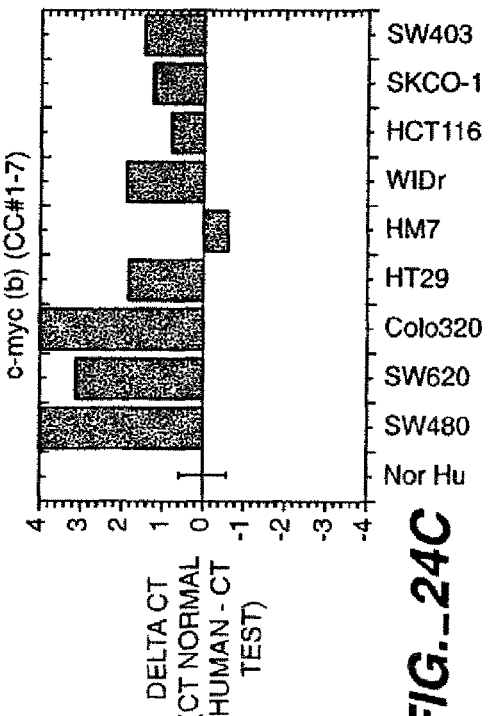
FIG._24D

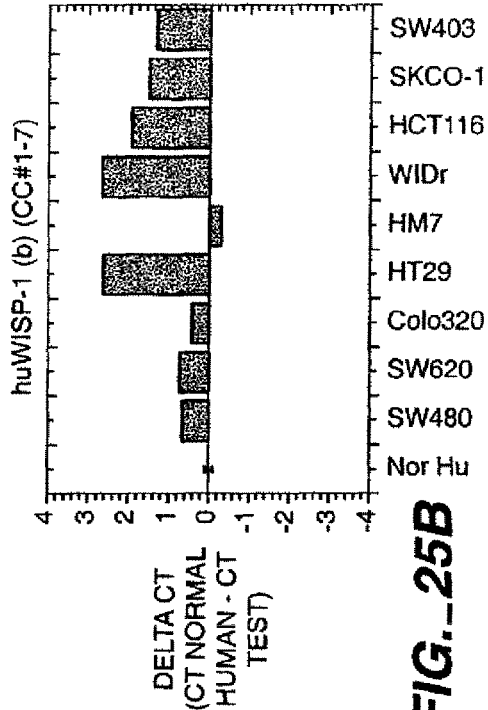
FIG._25B
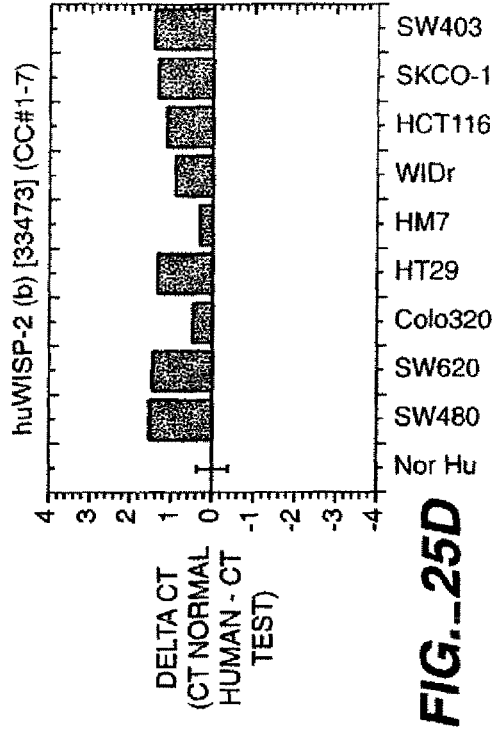
FIG._25D
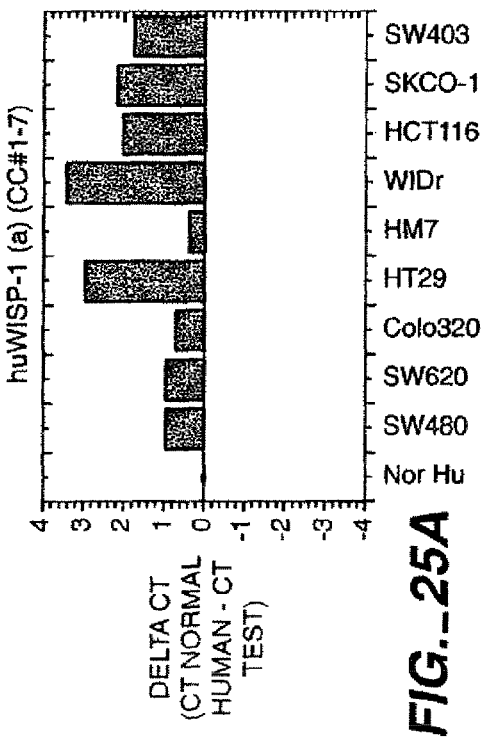
FIG._25A
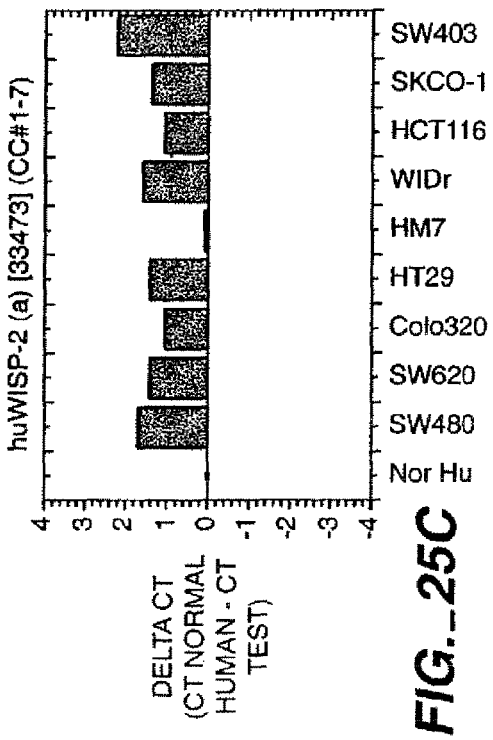
FIG._25C

5'-GCCAGTCTGGGCCCAGCTCCCCCGAGAGGTGGTCGGATCCTCTGGGCTGCTCGGTCGATG
CCTGTGCCACTGACGTCCAGGCATGAGGTGGTTCCTGCCCTGGACGCTGGCAGCAGTGAC
AGCAGCAGCCGCCAGCACCGTCCTGGCCACGGCCCTCTCTCCAGCCCCTACGACCATGGA
CTTTACCCCAGCTCCACTGGAGGACACCTCCTCACGCCCCAATTCTGCAAGTGGCCATG
TGAGTGCCCGCCATCCCCACCCCGCTGCCCGCTGGGGGTCAGCCTCATCACAGATGGCTG
TGAGTGCTGTAAGATGTGCGCTCAGCAGCTTGGGGACAACTGCACGGAGGCTGCCATCTG
TGACCCCCACCGGGGCCTCTACTGTGACTACAGCGGGACCGCCCGAGAGGTGGTCGGTG
TGGGCTGCGTCCTGGATGGGGTGCGCTACAACAACGGCCAGTCCTTCCAGCCTAACTGCA
AGTACAACTGCACGTGCATCGACGGCGCGGTGGGCTGCACACCACTGTGCCTCCGAGTGC
GCCCCCCGCGTCTCTGGTGCCCCCACCCGCGGCGCGTGAGCATACCTGGCCACTGCTGTG
AGCAGTGGGTATGTGAGGACGACGCCAAGAGGCCACGCAAGACCGCACCCGTGACACAG
GAGCCTTCGATGCTGTGGGTGAGGTGGAGGCATGGCACAGGAACTGCATAGCCTACACAA
GCCCCTGGAGCCCTTGCTCCACCAGCTGCGGCCTGGGGGTCTCCACTCGGATCTCCAATG
TTAACGCCCAGTGCTGGCCTGAGCAAGAGAGCCGCCTCTGCAACTTGCGGCCATGCGATG
TGGACATCCATACACTCATTAAGGCAGGGAAGAAGTGTCTGGCTGTGTACCAGCCAGAGG
CATCCATGAACTTCACACTTGCGGGCTGCATCAGCACACGCTCCTATCAACCCAAGTACT
GTGGAGTTTGCATGGACAATAGGTGCTGCATCCCCTACAAGTCTAAGACTATCGACGTGT
CCTTCCAGTGTCCTGATGGGCTTGGCTTCTCCCGCCAGGTCCTATGGATTAATGCCTGCT
TCTGTAACCTGAGCTGTAGGAATCCCAATGACATCTTTGCTGACTTGGAATCCTACCCTG
ACTTCTCAGAAATTGCCAACTAGGCAGGCACAAATCTTGGGTCTTGGGGACTAACCCAAT
GCCTGTGAAGCAGTCAGCCCTTATGGCCAATAACTTTTCACCAATGAGCCTTAGTTACCC
TGATCTGGACCCTTGGCCTCCATTTCTGTCTCTAACCATTCAAATGACGCCTGATGGTGC
TGCTCAGGCCCATGCTATGAGTTTTCTCCTTGATATCATTCAGCATCTACTCTAAAGAAA
AATGCCTGTCTCTAGCTGTTCTG

FIG._26

5'-TTTAATTAAACCCCCAAGGGCTGCGGAAGGAGCATATCTGGTGCTCCTGATGGGCCGGCC
AGTCTGGGCCCAGCTCCCCCGAGAGGTGGTCGGATCCTCTGGGCTGCTCGGTCGATGCCT
GTGCCACTGACGTCCAGGCATGAGGTGGTTCCTGCCCTGGACGCTGGCAGCAGTGACAGC
AGCAGCCGCCAGCACCGTCCTGGCCACGGCCCTCTCTCCAGCCCCTACGACCATGGACTT
TACCCCAGCTCCACTGGAGGACACCTCCTCACGCCCCAATTCTGCAAGTGGCCATGTGA
GTGCCCGCCATCCCCACCCCGCTGCCCGCTGGGGGTCAGCCTCATCACAGATGGCTGTGA
GTGCTGTAAGATGTGCGCTCAGCAGCTTGGGGACAACTGCACGGAGGCTGCCATCTGTGA
CCCCACCGGGGCCTCTACTGTGACTACAGCGGGACCGCCCGAGGTACGCAATAGGAGT
GTGTGCACGCAGGGAAGAAGTGTCTGGCTGTGTACCAGCCAGAGGCATCCATGAACTTCA
CACTTGCGGGCTGCATCAGCACACGCTCCTATCAACCCAAGTACTGTGGAGTTTGCATGG
ACAACAGGTGCTGCATCCCCTACAAGTCTAAGACTATCGACGTGTCCTTCCAGTGTCCTG
ATGGGCTTGGCTTCTCCCGCCAGGTCCTATGGA

FIG._27

5'-CAGAATTTGAACTGGGATCCACCTGTCTCTAAAGATGGGTTTCCTCCCATGCTTCCACAC
TGCCTCTCTTGATCAGAAACATACAAGGAGCTGAGAACATGTCCTCCACTCCCTGGGTAC
CTTTGCTGGTTAGAAGCCAACTTGCTGTCCTGTGGGAGGTACAGCCAATTTCTGTGTTC
CTCTGAGTTCTGGGGACCGCAGACCTTAGTGTGGTGAAAGTGAGCGTTGGGGGCTGGTGG
GAGCTGTAGATTCATGCAGATTCTGTTCCCCACACACAGATGCTGTGGGTGAGGTGGAGG
CATGGCACAGGAACTGCATAGCCTACACAAGCCCTGGAGCCCTTGCTCCACCAGCTGCG
GCCTGGGGGTCTCCACTCGGATCTCCAATGTTAACGCCCAGTGCTGGCCTGAGCAAGAGA
GCCGCCTCTGCAACTTGCGGCCATGCGATGTGGACATCCATACACTCATTAAGGCAGGGA
AGAAGTGTCTGGCTGTGTACCAGCCAGAGGCATCCATGAACTTCACACTTGCGGGCTGCA
TCAGCACACGCTCCTATCAACCCAAGTACTGTGGAGTTTGCATGGACAATAGGTGCTGCA
TCCCCTACAAGTCTAAGACTATCGACGTGTCCTTCCAGTGTCCTGATGGGCTTGGCTTCT
CCCGCCAGGTCGTATGGATTAAT

FIG._28

5'-GTCTGGGCCCAGCTCCCCCGAGAGGTGGTCGGATCCTCTGGGCTGCTCGGTCGATGCCTG
TGCCACTGACGTCCAGGCATGAGGTGGTTCCTGCCCTGGACGCTGGCAGCAGTGACAGCA
GCAGCCGCCAGCACCGTCCTGGCCACGGCCCTCTCTCCAGCCCCTACGACCATGGACTTT
ACCCCAGCTCCACTGGAGGACACCTCCTCACGCCCCAATTCTGCAAGTGGCCATGTGAG
TGCCCGCCATCCCCACCCCGCTGCCCGCTGGGGGTCAGCCTCATCACAGATGGCTGTGAG
TGCTGTAAGATGTGCGCTCAGCAGCTTGGGGACAACTGCACGGAGGCTGCCATCTGTGAC
CCCCACCGGGGCCTCTACTGTGACTACAGCGGGGACCGCCCGAGGTACGCAATAGGAGTG
TGTGCACGCAGGGAAGAAGTGTCTGGCTGTGTACCAGCCAGAGGCATCCATGAACTTCAC
ACTTGCGGGCTGCATCAGCACACGCTCCTATCAACCCAAGTACTGTGGAGTTTGCATGGA
CAACAGGTGCTGCATCCCCTACAAGTCTAAGACTATCGACGTGTCCTTCCAGTGTCCTGA
TGGGCTTGGCTTCTCCCGCCAGGTCCTATGGATTAATGCCTGCTTCTGTAACCTGAGCTG
TAGGAATCCCAATGACATCTTTGCTGACTTGGAATCCTACCCTGACTTCTCAGAAATTGC
CAACTAGGCAGGCACAAATCTTGGGTCTTGGGGACTAACCCAATGCCTGTGAAGCAGTCA
GCCCTTATGGCCAATAACTTTTCACCAATGAGCCTTAGTTACCCTGATCTGGACCCTTGG
CCTCCATTTCTGTCTCTAACCATTCAAATGACGCCTGATGGTGCTGCTCAGGCCCATGCT
ATGAGTTTTCTCCTTGATATCATTCAGCATCTACTCTAAAGAAAAATGCCTGTCTCTAGC
TGTTCTGGACTACACCCAAGCCTGATCCAGCCTTTCCAAGTCACTAGAAGTCCTGCTGGA
TCTTGCCTAAATCCCAAGAAATGGAATCAGGTAGACTTTTAATATCACTAATTTCTTCTT
TAGATGCCAAACCACAAGACTCTTTGGGTCCATTCAGATGAATAGATGGAATTTGGAACA
ATAGAATAATCTATTATTTGGAGCCTGCCAAGAGGTACTGTAATGGGTAATTCTGACGTC
AG

FIG._29

5'-CAGAACAGCTAGAGACAGGCATTTTTCTTTAGAGTAGATGCTGAATGATATCAAGGAGAA
AACTCATAGCATGGGCCTGAGCAGCACCATCAGGCGTCATTTGAATGGTTAGAGACAGAA
ATGGAGGCCAAGGGTCCAGATCAGGGTAACTAAGGCTCATTGGTGAAAAGTTATTGGCCA
TAAGGGCTGACTGCTTCACAGGCATTGGGTTAGTCCCCAAGACCCAAGATTTGTGCCTGC
CTAGTTGGCAATTTCTGAGAAGTCAGGGTAGGATTCCAAGTCAGCAAAGATGTCATTGGG
ATTCCTACAGCTCAGGTTACAGAAGCAGGCATTAATCCATAGGACCTGGCGGGAGAAGCC
AAGCCCATCAGGACACTGGAAGGACACGTCGATAGTCTTAGACTTGTAGGGGATGCAGCA
CCTATTGTCCATGCAAACTCCACAGTACTTGGGTTGATAGGAGCGTGTGCTGATGCAGCC
CGCAAGTGTGAAGTTCATGGATGCCTCTGGCTGGTACACAGCCAGACACTTCTTCCCTGC
CTTAATGAGTGTATGGATGTCCACATCGCATGGCCGCAAGTTGCAGAGGCGGCTCTCTTG
CTCAGGCCAGCACTGGGCGTTAACATTGGAGATCCGAGTGGAGACCCCCAGGCCGCAGCT
GGTGGAGCAAGGGCTCCAGGGGCTTGTGTAGGCTATGCAGTTCCTGTGCCATGCCTCCAC
CTCACCCACAGCATCTGTGTGTGGGGAACAGAATCTGCATGAATCTACAGCTCCCACCAG
CCCCCAACGCTCACTTTCACCACACTAAGGTCTGCGGTCCCCAGAACTCAGAGGAACACA
GAAATTGGCTGTACCTCCCCACAGGACAGCAAGTTGGCTTCTAACCAGCAAAGGTACCCA
GGGAGTGGAGGACATGTTCTCAGCTCCTTGTATGTTTCTGATCAAGAGAGGCAGTGTGGA
AGCATGGAGGAAACCCATCTTTAGAGACAGGTGGATCCCAGTTCAAATTCTGCTCTACC
ACCTACAAGCTGTGTGATCTTAGATAACCCACCCTGGGCCTGTCTCCCCATTAGAACAAT
AACACCTGCCTGTGCGGCTGGCAACACAATAATAAGGGCCTAGATTTTTACTGAGTATGC
ATCAATCATCCTTGCTAAGTGCTGGGAATGGGACTTTTTTTTT

*FIG._30*

5'-CCTGATCTGGACCCTTGGCCTCCAATTCTGTCTGTAACCATTCAAATGACGCCTGGTGGT
GCTGCTCAGGCCCATAGCAAGGTTCAGCCTGGTTAAGTCCAAGCTGAATTAGCGGCCGCG
TCGACAGTAGGAGTGTGTGCACATGCTGTGGGTGAGGTGGAGGCATGGCACAGGAACTGC
ATAGCCTACACAAGCCCCTGGAGCCCTTGCTCCACCAGCTGCGGCCTGGGGGTCTCCACT
CGGATCTCCAATGTTAACGCCCAGTGCTGGCCTGAGCAAGAGAGCCGCCTCTGCAACTTG
CGGCCATGCGATGTGGACATCCATACACTCATTAAGGCAGGGAAGAAGTGTCTGGCTGTG
TACCAGCCAGAGGCATCCATGAACTTCACACTTGCGGGCTGCATCAGCACACGCTCCTAT
CAACCCAAGTACTGTGGAGTTTGCATGGACAATAGGTGCTGCATCCCCTACAAGTCTAAG
ACTATCGACGTGTCCTTCCAGTGTCCTGATGGGCTTGGCTTCTCCCGCCAGGTCCTATGG
ATTAAT

*FIG._31*

5'-GGCCCAGCTCCCCCGAGAGGTGGTCGGATCCTCTGGGCTGCTCGGTCGATGCCTGTGCCA
CTGACGTCCAGGCATGAGGTGGTTCCTGCCCTGGACGCTGGCAGCAGTGACAGCAGCAGC
CGCCAGCACCGTCCTGGCCACGGCCCTCTCTCCAGCCCCTACGACCATGGACTTTACCCC
AGCTCCACTGGAGGACACCTCCTCACGCCCCAATTCTGCAAGTGGCCATGTGAGTGCCC
GCCATCCCCACCCCGCTGCCCGCTGGGGGTCAGCCTCATCACAGATGGCTGTGAGTGCTG
TAAGATGTGCGCTCAGCAGCTTGGGGACAACTGCACGGAGGCTGCCATCTGTGACCCCCA
CCGGGGCCTCTACTGTGACTACAGCGGGGACCGCCCGAGAGGTGGTCGGTGTGGGCTGCG
TCCTGGATGGGGTGCGCTACAACAACGGCCAGTCCTTCCAGCCTAACTGCAAGTACAACT
GCACGTGCATCGACGGCGCGGTGGGCTGCACACCACTGTGCCTCCGAGTGCGCCCCCGC
GTCTCTGGTGCCCCCACCCGCGGCGCGTGAGCATACCTGGCCACTGCTGTGAGCAGTGGA
TATGTGAGGACGACGCCAAGAGGCCACGCAAGACCGCACCCCGTGACACAGGAGCCTTCG
ATGCCAGAAGCGCCCGCTCCCTCAGAGATGTGACAACCAAAATCATCTCCAGACCTTTCC
AAATACACCCTAGGAGACAAAATTGCTCGGTGGAGAAGCAGTCCTGTGAGGACAGGAGGA
GGCGTGGAGGAAAGCTTTGTCCCCAGCAGCCCCAGGGAAGCAAGGCAGCTCTCCCACCAC
CACCTCCCCAGGAGGGCCACACGAGGGTCACGGGGGGAGCAGGGAGGCGGAAGCTGTCTG
CCATTGTGTCTGGCCCAGTGACCCTGTTCTGACCGAGCACAAGCGGAGCCCCTGCCTAGC
CGAGATGCTGTGGGTGAGGTGGAGGCATGGCACAGGAACTGCATAGCCTACACAAGCCCC
TGGAGCCCTTGCTCCACCAGCTGCGGCCTGGGGGTCTCCACTCGGATCTCCAATGTTAAC
GCCCAGTGCTGGCCTGAGCAA

FIG._32

WISP POLYPEPTIDES AND NUCLEIC ACIDS ENCODING SAME

RELATED APPLICATIONS

This is a continuation application of U.S. patent application Ser. No. 12/648,425, filed Dec. 29, 2009 now abandoned, which is a continuation application of U.S. patent application Ser. No. 11/488,375, filed on Jul. 17, 2006, now abandoned, which is a divisional application of U.S. patent application Ser. No. 10/112,267, filed on Mar. 27, 2002, now U.S. Pat. No. 7,101,850, which is a divisional application of U.S. patent application Ser. No. 09/182,145, filed on Oct. 29, 1998, now U.S. Pat. No. 6,387,657, which claims priority to U.S. Provisional Patent Application Ser. No. 60/063,704, filed Oct. 29, 1997, and to U.S. Provisional Patent Application Ser. No. 60/081,695, filed on Apr. 14, 1998, and to U.S. Provisional Patent Application Ser. No. 60/073,612, filed Feb. 4, 1998, the entire disclosures of which applications are hereby incorporated by reference.

GOVERNMENT LICENSE RIGHTS

This invention was made with government support under grant no. 5P01 CA41086, awarded by the National Institutes of Health, National Cancer Institute. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 31, 2012, is named GNE157US.txt and is 242,134 bytes in size.

FIELD OF THE INVENTION

The present invention relates generally to the identification and isolation of novel DNA and to the recombinant production of novel polypeptides having homology to connective tissue growth factor, designated herein as Wnt-1-Induced Secreted Proteins (WISPs).

BACKGROUND OF THE INVENTION

Malignant tumors (cancers) are the second leading cause of death in the United States, after heart disease. Boring et al., *CA Cancer J. Clin.*, 43:7 (1993).

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers.

The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype. Hunter, *Cell*, 64:1129 (1991); Bishop, *Cell*, 64:235-248 (1991).

A well-known mechanism of gene (e.g., oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome. Alitalo et al., *Adv. Cancer Res.*, 47:235-281 (1986). It is believed that the overexpression of the gene parallels gene amplification, i.e., is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor ($p185^{HER2}$; HER2) related to the epidermal growth factor receptor (EGFR), is overexpressed in about 25% to 30% of human breast cancer. Slamon et al., *Science*, 235:177-182 (1987); Slamon et al., *Science*, 244:707-712 (1989). It has been reported that gene amplification of a protooncogen is an event typically involved in the more malignant forms of cancer, and could act as a predictor of clinical outcome. Schwab et al., *Genes Chromosomes Cancer*, 1:181-193 (1990); Alitalo et al., supra. Thus, erbB2 overexpression is commonly regarded as a predictor of a poor prognosis, especially in patients with primary disease that involves axillary lymph nodes (Slamon et al., (1987) and (1989), supra; Ravdin and Chamness, *Gene*, 159:19-27 (1995); and Hynes and Stern, *Biochim Biophys Acta*, 1198:165-184 (1994)), and has been linked to sensitivity and/or resistance to hormone therapy and chemotherapeutic regimens, including CMF (cyclophosphamide, methotrexate, and fluoruracil) and anthracyclines. Baselga et al., *Oncology*, 11(3 Suppl 1):43-48 (1997). However, despite the association of erbB2 overexpression with poor prognosis, the odds of HER2-positive patients responding clinically to treatment with taxanes were greater than three times those of HER2-negative patients. Baselga et al., supra. A recombinant humanized anti-ErbB2 (anti-HER2) monoclonal antibody (a humanized version of the murine anti-ErbB2 antibody 4D5, referred to as rhuMAb HER2 or HERCEPTIN®) has been clinically active in patients with ErbB2-overexpressing metastatic breast cancers that had received extensive prior anticancer therapy. Baselga et al., *J. Clin. Oncol.*, 14:737-744 (1996).

Cytokines have been implicated in the pathogenesis of a number of brain diseases in which neurological dysfunction has been attributed to a change in amino acid neurotransmitter metabolism. In particular, members of the transforming growth factor-β (TGF-β) family have been implicated. TGF peptides are small polypeptides that were first identified by their ability to induce proliferation and transformation in noncancerous cells in culture. Although initially defined as a growth factor, TGF-β also inhibits proliferation of epithelial, endothelial, lymphoid, and hematopoietic cells. This cytokine is thought to play an important role in regulating the duration of the inflammatory response, allowing the healing process to proceed. It is also a potent immunomodulator, which has many pleiotrophic effects, including regulating many other cytokines.

The TGF-β superfamily includes bone morphogenetic proteins (BMP-2, BMP-4, BMP-5, BMP-6, BMP-7), activins A & B, decapentaplegic (dpp), 60A, OP-2, dorsalin, growth differentiation factors (GDFs), nodal, MIS, Inhibin-∀, TGF-β1, TGF-β2, TGF-β3, TGF-β5, and glial-derived neurotrophic factor (GDNF). Atrisano, et al., *J. Biochemica et Biophysica Acta*, 1222:71-80 (1994), of particular interest are the growth differentiation factors, for as their name implies, these factors are implicated in the differentiation of cells.

Connective tissue growth factor (CTGF) is a growth factor induced in fibroblasts by many factors, including TGF-β, and is essential for the ability of TGF-β to induce anchorage-independent growth (AIG), a property of transformed cells. CTGF was discovered in an attempt to identify the type of plateletderived growth factor (PDGF) dimers present in the growth media of cultured endothelial cells, and is related immunologically and biologically to PDGF. See U.S. Pat. No. 5,408,040. CTGF also is mitogenic and chemotactic for cells, and hence growth factors in this family are believed to play a role in the normal development, growth, and repair of human tissue.

Seven proteins related to CTGF, including the chicken ortholog for Cyr61, CEF10, human, mouse, and *Xenopus laevis* CTGF, and human, chicken, and *Xenopus laevis* Nov have been isolated, cloned, sequenced, and characterized as belonging to the CTGF gene family. Oemar and Luescher, *Arterioscler. Thromb. Vasc. Biol.*, 17:1483-1489 (1997). The gene encoding Cyr61 has been found to promote angiogenesis, tumor growth, and vascularization. Babic et al., *Proc. Natl. Acad. Sci. USA*, 95:6355-6360 (1998). The nov gene is expressed in the kidney essentially at the embryonic stage, and alterations of nov expression, relative to the normal kidney, have been detected in both avian nephroblastomas and human Wilms' tumors. Martinerie et al., *Oncogene*, 9:2729-2732 (1994). Wt1 downregulates human nov expression, which downregulation might represent a key element in normal and tumoral nephrogenesis. Martinerie et al., *Oncogene*, 12:1479-1492 (1996). It has recently been proposed that the CTGF, nov, and cyr61 genes, which encode secreted proteins that contain conserved sequences and IGFBP motifs in their N-termini and bind IGFs with low affinity, represent more members of the IGFBP superfamily, along with the low-affinity mac25/IGFBP-7 (Yamanaka et al., *J. Biol. Chem.*, 272:30729-30734 (1997)) and the high-affinity IGFBPs 1-6. CTGF under this proposal would be designated IGFBP-8. Kim et al., *Proc. Natl., Acad. Sci. USA*, 94:12981-12986 (1997).

Recently, a protein was found in the mouse designated ELM1 that is expressed in low metastatic cells. Hashimoto et al., *J. Exp. Med.*, 187:289-296 (1998). The elm1 gene, a mouse homologue of WISP-1 disclosed below, is another member of the CTGF, Cyr61/Cef10, and neuroblastoma over-expressed-gene family and suppresses in vivo tumor growth and metastasis of K-1735 murine melanoma cells. Another recent article on rCop-1, the rat orthologue of WISP-2 described below describes the loss of expression of this gene after cell transformation. Zhang et al., *Mol. Cell. Biol.*, 18:6131-6141 (1998).

CTGF family members (with the exception of nov) are immediate early growth-responsive genes that are thought to regulate cell proliferation, differentiation, embryogenesis, and wound healing. Sequence homology among members of the CTGF gene family is high; however, functions of these proteins in vitro range from growth stimulatory (i.e., human CTGF) to growth inhibitory (i.e., chicken Nov and also possibly hCTGF). Further, some molecules homologous to CTGF are indicated to be useful in the prevention of desmoplasia, the formation of highly cellular, excessive connective tissue stroma associated with some cancers, and fibrotic lesions associated with various skin disorders such as scleroderma, keloid, eosinophilic fasciitis, nodular fasciitis, and Dupuytren's contracture. Moreover, CTGF expression has recently been demonstrated in the fibrous stoma of mammary tumors, suggesting cancer stroma formation involves the induction of similar fibroproliferative growth factors as wound repair. Human CTGF is also expressed at very high levels in advanced atherosclerotic lesions, but not in normal arteries, suggesting it may play a role in atherosclerosis. Oemar and Luescher, supra. Therefore, molecules homologous to CTGF are of importance.

Extracellular and membrane-bound proteins play important roles in the formation, differentiation, and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones), which are, in turn, received and interpreted by diverse cell receptors or membrane-bound proteins. These secreted polypeptides or signaling molecules normally pass through the cellular secretory pathway to reach their site of action in the extracellular environment, usually at a membrane-bound receptor protein.

Secreted proteins have various industrial applications, including use as pharmaceuticals, diagnostics, biosensors, and bioreactors. In fact, most protein drugs available at present, such as thrombolytic agents, interferons, interleukins, erythropoietins, colony stimulating factors, and various other cytokines, are secreted proteins. Their receptors, which are membrane-bound proteins, also have potential as therapeutic or diagnostic agents. Receptor immunoadhesins, for instance, can be employed as therapeutic agents to block receptor-ligand interaction. Membrane-bound proteins can also be employed for screening of potential peptide or small molecule inhibitors of the relevant receptor/ligand interaction. Such membrane-bound proteins and cell receptors include, but are not limited to, cytokine receptors, receptor kinases, receptor phosphatases, receptors involved in cell-cell interactions, and cellular adhesin molecules like selectins and integrins. Transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Efforts are being undertaken by both industry and academia to identify new, native secreted and membrane-bound receptor proteins, particularly those having homology to CTGF. Many efforts are focused on the screening of mammalian recombinant DNA libraries to identify the coding sequences for novel secreted and membrane-bound receptor proteins. Examples of screening methods and techniques are described in the literature. See, for example, Klein et al., *Proc. Natl. Acad. Sci.*, 93:7108-7113 (1996); and U.S. Pat. No. 5,536,637.

Wnts are encoded by a large gene family whose members have been found in round worms, insects, cartilaginous fish, and vertebrates. Holland et al., *Dev. Suppl.*, 125-133 (1994). Wnts are thought to function in a variety of developmental and physiological processes since many diverse species have multiple conserved Wnt genes. McMahon, *Trends Genet.*, 8:236-242 (1992); Nusse and Varmus, *Cell*, 69:1073-1087

(1992). Wnt genes encode secreted glycoproteins that are thought to function as paracrine or autocrine signals active in several primitive cell types. McMahon, supra (1992); Nusse and Varmus, supra (1992). The Wnt growth factor family includes more than ten genes identified in the mouse (Wnt-1, -2, -3A, -3B, -4, -5A, -5B, -6, -7A, -7B, -8A, -8B, -10B, -11, -12, and -13) (see, e.g., Gavin et al., *Genes Dev.*, 4:2319-2332 (1990); Lee et al., *Proc. Natl. Acad. Sci. USA*, 92:2268-2272 (1995); Christiansen et-al., *Mech. Dev.*, 51:341-350 (1995)) and at least nine genes identified in the human (Wnt-1, -2, -3, -5A, -7A, -7B, -8B, -10B, and -11) by cDNA cloning. See, e.g., Vant Veer et al., *Mol. Cell. Biol.*, 4:2532-2534 (1984).

The Wnt-1 proto-oncogene (int-1) was originally identified from mammary tumors induced by mouse mammary tumor virus (MMTV) due to an insertion of viral DNA sequence. Nusse and Varmus, *Cell*, 31:99-109 (1982). In adult mice, the expression level of Wnt-1 mRNA is detected only in the testis during later stages of sperm development. Wnt-1 protein is about 42 KDa and contains an aminoterminal hydrophobic region, which may function as a signal sequence for secretion (Nusse and Varmus, supra, 1992). The expression of WnL-2/irp is detected in mouse fetal and adult tissues and its distribution does not overlap with the expression pattern for Wnt-1. Wnt-3 is associated with mouse mammary tumorigenesis. The expression of Wnt-3 in Mouse embryos is detected in the neural tubes and in the limb buds. Wnt-5a transcripts are detected in the developing fore- and hind limbs at 9.5 through 14.5 days and highest levels are concentrated in apical ectoderm at the distal tip of limbs. Nusse and Varmus, supra (1992). Recently, a Wnt growth factor, termed Wnt-x, was described (WO95/17416) along with the detection of Wnt-x expression in bone tissues and in bone-derived cells. Also described was the role of Wnt-x in the maintenance of mature osteoblasts and the use of the Wnt-x growth factor as a therapeutic agent or in the development of other therapeutic agents to treat bone-related diseases.

Wnts may play a role in local cell signaling. Biochemical studies have shown that much of the secreted Wnt protein can be found associated with the cell surface or extracellular matrix rather than freely diffusible in the medium. Papkoff and Schryver, *Mol. Cell. Biol.*, 10:2723-2730 (1990); Bradley and Brown, *EMBO J.*, 9:1569-1575 (1990).

Studies of mutations in Wnt genes have indicated a role for Wnts in growth control and tissue patterning. In *Drosophila*, wingless (wg) encodes a Wnt-related gene (Rijsewik et al., *Cell*, 50:649-657 (1987)) and wg mutations alter the pattern of embryonic ectoderm, neurogenesis, and imaginal disc outgrowth. Morata and Lawrence, *Dev. Biol.*, 56:227-240 (1977); Baker, *Dev. Biol.*, 125:96-108 (1988); Klingensmith and Nusse, *Dev. Biol.*, 166:396-414 (1994). In *Caenorhabditis elegans*, lin-44 encodes a Wnt homolog which is required for asymmetric cell divisions. Herman and Horvitz, *Development*, 120:1035-1047 (1994). Knock-out mutations in mice have shown Wnts to be essential for brain development (McMahon and Bradley, *Cell*, 62:1073-1085 (1990); Thomas and Cappechi, *Nature*, 346:847-850 (1990)), and the outgrowth of embryonic primordia for kidney (Stark et al., *Nature*, 372: 679-683 (1994)), tail bud (Takada et al., *Genes Dev.*, 8:174-189 (1994)), and limb bud. Parr and McMahon, *Nature*, 374: 350-353 (1995) Overexpression of Wnts in the mammary gland can result in mammary hyperplasia (McMahon, supra (1992); Nusse and Varmus, supra (1992)), and precocious alveolar development. Bradbury et al., *Dev. Biol.*, 170:553-563 (1995).

Wnt-5a and Wnt-5b are expressed in the posterior and lateral mesoderm and the extraembryonic mesoderm of the day 7-8 murine embryo. Gavin et al., supra (1990). These embryonic domains contribute to the AGM region and yolk sac tissues from which multipotent hematopoietic precursors and HSCs are derived. Dzierzak and Medvinsky, *Trends Genet.*, 11:359-366 (1995); Zon et al., in Gluckman and Coulombel, ed., Colloque, *INSERM*, 235:17-22 (1995), presented at the Joint International Workshop on Foetal and Neonatal Hematopoiesis and Mechanism of Bone Marrow Failure, Paris France, Apr. 3-6, 1995; Kanatsu and Nishikawa, *Development*, 122:823-830 (1996). Wnt-5a, Wnt-10b, and other Wnts have been detected in limb buds, indicating possible roles in the development and patterning of the early bone microenvironment as shown for Wnt-7b. Gavin et al., supra (1990); Christiansen et al., *Mech. Devel.*, 51:341-350 (1995); Parr and McMahon, supra (1995).

The Wnt/Wg signal transduction pathway plays an important role in the biological development of the organism and has been implicated in several human cancers. This pathway also includes the tumor suppressor gene, APC. Mutations in the APC gene are associated with the development of sporadic and inherited forms of human colorectal cancer. The Wnt/Wg signal leads to the accumulation of beta-catenin/Armadillo in the cell, resulting in the formation of a bipartite transcription complex consisting of beta-catenin and a member of the lymphoid enhancer binding factor/T cell factor (LEF/TCF)HMG box transcription factor family. This complex translocates to the nucleus where it can activate expression of genes downstream of the Wnt/Wg signal, such as the engrailed and Ultrabithorax genes in *Drosophila*. The downstream target genes of Wnt-1 signaling in vertebrates that presumably function in tumorigenesis, however, are currently unknown.

For a most recent review on Wnt, see Cadigan and Nusse, *Genes & Dev.*, 11:3286-3305 (1997).

There is a need to elucidate the further members of the above families, including cell-surface molecules that may be tumor-specific antigens or proteins that serve a regulatory function in initiating the Wnt pathway of tumorigenesis. These would also include downstream components of the Wnt signaling pathway that are important to the transformed phenotype and the development of cancer.

SUMMARY OF THE INVENTION

Several putative Wnt-1-induced genes have been identified at the mRNA level in a high-throughput cDNA substraction experiment. Thus, applicants have identified novel cDNA clones (WISP1, WISP2, and WISP3) that encode novel polypeptides of the WISP family, designated as WISP-1, WISP-2, and WISP-3, respectively. This class of polypeptides was formerly referred to as Wnt-1-induced Gene (WIG) polypeptides, with WISP-1 and WISP-2 formerly designated as WIG-1 and WIG-2, respectively. One of the cDNA clones encodes a novel polypeptide, human WISP-2, having homology to CTGF, wherein the polypeptide is designated in the present application as "human WISP-2" or "PR0261". The WISP-1 and WISP-3 molecules also have homology to CTGF.

In one embodiment, this invention provides isolated nucleic acid comprising DNA having at least about 600 nucleotides and at least about a 75% sequence identity to (a) a DNA molecule encoding a human WISP-1 polypeptide comprising the sequence of amino acids 23 to 367 of FIGS. 3A-3C (SEQ ID NO:3), or (b) the complement of the DNA molecule of (a). Preferably, this nucleic acid has at least one WISP biological activity. In a more preferred embodiment, this nucleic acid has at least about a 95% sequence identity to (a) a DNA molecule encoding a human WISP-1 polypeptide comprising the sequence of amino acids 23 to 367 of FIGS. 3A-3C (SEQ ID NO:3), or (b) the complement of the DNA molecule of (a).

More preferred is the nucleic acid comprising DNA encoding a human WISP-1 polypeptide having amino acid residues 23 to 367 of FIGS. 3A-3C (SEQ ID NO:3), or DNA encoding a human WISP-1 polypeptide having amino acid residues 1 to 367 of FIGS. 3A-3C (SEQ ID NO:4), or the complement of either of the encoding DNAs. Further preferred is this nucleic acid comprising DNA encoding a human WISP-1 polypeptide having amino acid residues 23 to 367 or 1 to 367 of FIGS. 3A-3C except for an isoleucine residue at position 184 rather than a valine residue or a serine residue at position 202 rather than an alanine residue (SEQ ID NOS:5-8, respectively). Further preferred also is this nucleic acid comprising DNA encoding a human WISP-1 polypeptide having amino acid residues 23 to 367 or 1 to 367 of FIGS. 3A-3C except for an isoleucine residue at position 184 rather than a valine residue and a serine residue at position 202 rather than an alanine residue (SEQ ID NOS:21-22, respectively).

Also preferred is this nucleic acid comprising DNA encoding a mouse WISP-1 polypeptide having amino acid residues 23 to 367 of FIGS. 1A-1B (SEQ ID NO:11), or DNA encoding a mouse WISP-1 polypeptide having amino acid residues 1 to 367 of FIGS. 1A-1B (SEQ ID NO:12), or the complement of either of the encoding DNAs.

Also provided by this invention is isolated nucleic acid comprising DNA having at least about 600 nucleotides and at least about a 85% sequence identity to (a) a DNA molecule encoding a mouse WISP-1 polypeptide comprising the sequence of amino acids 23 to 367 of FIGS. 1A-1B (SEQ ID NO:11), or (b) the complement of the DNA molecule of (a). Preferably, this nucleic acid has at least one WISP biological activity. More preferably, this nucleic acid comprises DNA having at least about a 95% sequence identity to (a) a DNA molecule encoding a mouse WISP-1 polypeptide comprising the sequence of amino acids 23 to 367 of FIGS. 1A-1B (SEQ ID NO:11), or (b) the complement of the DNA molecule of (a).

In another preferred embodiment, the invention provides an isolated nucleic acid comprising DNA having at least about 600 nucleotides and at least about a 75% sequence identity to (a) a DNA molecule encoding the same full-length polypeptide encoded by the human WISP-1 polypeptide cDNA in ATCC Deposit No. 209533 (pRK5E.h.WISP-1.568.38), or (b) the complement of the DNA molecule of (a). This nucleic acid preferably comprises DNA having at least about 600 nucleotides and at least about a 95% sequence identity to (a) a DNA molecule encoding the same full-length polypeptide encoded by the human WISP-1 polypeptide cDNA in ATCC Deposit No. 209533 (pRK5E.h.WISP-1.568.38), or (b) the complement of the DNA molecule of (a).

In another aspect, the invention provides a process for producing a WISP-1 polypeptide comprising culturing a host cell comprising the above nucleic acid under conditions suitable for expression of the WISP-1 polypeptide and recovering the WISP-1 polypeptide from the cell culture. Additionally provided is an isolated WISP-1 polypeptide encoded by the above nucleic acid, including where the polypeptide is human WISP-1 or mouse WISP-1.

In another embodiment, the invention provides isolated nucleic acid comprising SEQ ID NO:23, 24, 25, 26, 27, 28, or 29, and an isolated WISP-1 polypeptide encoded by such a nucleic acid.

Also provided by this invention is an isolated nucleic acid having at least about 600 nucleotides and produced by hybridizing a test DNA molecule under stringent conditions with (a) a DNA molecule encoding a human WISP-1 polypeptide comprising the sequence of amino acids 23 to 367 of FIGS. 3A-3C (SEQ ID NO:3), or (b) the complement of the DNA molecule of (a), and, if the test DNA molecule has at least about a 75% sequence identity to (a) or (b), isolating the test DNA molecule.

Further provided is a polypeptide produced by (i) hybridizing a test DNA molecule under stringent conditions with (a) a DNA molecule encoding a human WISP-1 polypeptide comprising the sequence of amino acids 23 to 367 of FIGS. 3A-3C (SEQ ID NO:3), or (b) the complement of the DNA molecule of (a), and if the test DNA molecule has at least about a 75% sequence identity to (a) or (b), (ii) culturing a host cell comprising the test DNA molecule under conditions suitable for expression of the polypeptide, and (iii) recovering the polypeptide from the cell culture.

In another aspect, the invention provides isolated nucleic acid comprising DNA having at least about an 80% sequence identity to (a) a DNA molecule encoding a human WISP-2 polypeptide comprising the sequence of amino acids 24 to 250 of FIGS. 4A-4B (SEQ ID NO:15), or (b) the complement of the DNA molecule of (a). Preferably, this nucleic acid has at least one WISP biological activity. Also, preferably this nucleic acid comprises DNA having at least about a 95% sequence identity to (a) a DNA molecule encoding a human WISP-2 polypeptide comprising the sequence of amino acids 24 to 250 of FIGS. 4A-4B (SEQ ID NO:15), or (b) the complement of the DNA molecule of (a) In another preferred embodiment, this nucleic acid comprises DNA encoding a human WISP-2 polypeptide having amino acid residues 24 to 250 of FIGS. 4A-4B (SEQ ID NO:15), or DNA encoding a human WISP-2 polypeptide having amino acid residues 1 to 250 of FIGS. 4A-4B (SEQ ID NO:16), or a complement of either of the encoding DNAs.

In another aspect, the invention provides isolated nucleic acid comprising DNA having at least about an 80% sequence identity to (a) a DNA molecule encoding a human WISP-2 polypeptide comprising the sequence of amino acids 1 to 250 of FIGS. 4A-4B (SEQ ID NO:16), or (b) the complement of the DNA molecule of (a).

In another aspect, the invention provides isolated nucleic acid comprising DNA having at least about 500 nucleotides and at least about an 80% sequence identity to (a) a DNA molecule encoding a mouse WISP-2 polypeptide comprising the sequence of amino acids 24 to 251 of FIGS. 2A-2B (SEQ ID NO:19), or (b) the complement of the DNA molecule of (a). In a preferred embodiment, this nucleic acid comprises DNA having at least about a 95% sequence identity to (a) a DNA molecule encoding a mouse WISP-2 polypeptide comprising the sequence of amino acids 24 to 251 of FIGS. 2A-2B (SEQ ID NO:19), or (b) the complement of the DNA molecule of (a). More preferably, the nucleic acid comprises DNA encoding a mouse WISP-2 polypeptide having amino acid residues 24 to 251 of FIGS. 2A-2B (SEQ ID NO:19), or DNA encoding a mouse WISP-2 polypeptide having amino acid residues 1 to 251 of FIGS. 2A-2B (SEQ ID NO:20), or the complement of either of these encoding DNAs.

In a further aspect, the invention provides isolated nucleic acid comprising DNA having at least about 500 nucleotides and at least about an 80% sequence identity to (a) a DNA molecule encoding a mouse WISP-2 polypeptide comprising the sequence of amino acids 1 to 251 of FIGS. 2A-2B (SEQ ID NO:20), or (b) the complement of the DNA molecule of (a).

In yet another aspect, the invention provides an isolated nucleic acid comprising DNA having at least about 400 nucleotides and at least about a 75% sequence identity to (a) a DNA molecule encoding the same full-length polypeptide encoded by the human WISP-2 polypeptide cDNA in ATCC Deposit No. 209391 (DNA33473), or (b) the complement of the DNA molecule of (a). Preferably, this nucleic acid comprises DNA having at least about a 95% sequence identity to (a) a DNA molecule encoding the same full-length polypeptide encoded by the human WISP-2 polypeptide cDNA in ATCC Deposit No. 209391 (DNA33473), or (b) the complement of the DNA molecule of (a).

In another embodiment, this invention provides an isolated nucleic acid comprising the nucleotide sequence of the full-length coding sequence of clone UNQ228 (DNA33473) deposited under accession number ATCC 209391.

In another aspect, the invention provides a process for producing a WISP-2 polypeptide comprising culturing a host cell comprising the above nucleic acid under conditions suitable for expression of the WISP-2 polypeptide and recovering the WISP-2 polypeptide from the cell culture. Additionally provided is a WISP-2 polypeptide encoded by the isolated nucleic acid, including where the polypeptide is human WISP-2 or mouse WISP-2. In a specific embodiment of this, the invention provides isolated native-sequence human WISP-2 polypeptide comprising amino acid residues 1 to 250 of FIGS. 4A-4B (SEQ ID NO:16) or comprising amino acid residues 24 to 250 of FIGS. 4A-4B (SEQ ID NO:15).

In a further embodiment, the invention provides an isolated nucleic acid having at least about 400 nucleotides and produced by hybridizing a test DNA molecule under stringent conditions with (a) a DNA molecule encoding a human WISP-2 polypeptide comprising the sequence of amino acids 24 to 250 of FIGS. 4A-4B (SEQ ID NO:15), or (b) the complement of the DNA molecule of (a), and, if the test DNA molecule has at least about a 75% sequence identity to (a) or (b), isolating the test DNA molecule.

In a still further embodiment, the invention provides a polypeptide produced by (i) hybridizing a test DNA molecule under stringent conditions with (a) a DNA molecule encoding a human WISP-2 polypeptide comprising the sequence of amino acids 24 to 250 of FIGS. 4A-4B (SEQ ID NO:15), or (b) the complement of the DNA molecule of (a), and if the test DNA molecule has at least about a 75% sequence identity to (a) or (b), (ii) culturing a host cell comprising the test DNA molecule under conditions suitable for expression of the polypeptide, and (iii) recovering the polypeptide from the cell culture.

In yet another embodiment, the invention provides isolated nucleic acid comprising DNA having a 100% sequence identity in more than about 500 nucleotides to (a) a DNA molecule encoding a human WISP-3 polypeptide comprising the sequence of amino acids 34 to 372 of FIGS. 6A-6C (SEQ ID NO:32), or (b) the complement of the DNA molecule of (a). Preferably, this nucleic acid has at least one WISP biological activity. Preferably, this nucleic acid comprises DNA encoding a human WISP-3 polypeptide having amino acid residues 34 to 372 of FIGS. 6A-6C (SEQ ID NO:32) or amino acids 1 to 372 of FIGS. 6A-6C (SEQ ID NO:33), or the complement thereof.

In a still further, embodiment, the invention provides an isolated nucleic acid comprising DNA having a 100% sequence identity in more than about 500 nucleotides to (a) a DNA molecule encoding the same full-length polypeptide encoded by the human WISP-3 polypeptide cDNA in ATCC Deposit No. 209706 (DNA56350-1176-2), or (b) the complement of the DNA molecule of (a). A still further aspect of the invention involves a process for producing a WISP-3 polypeptide comprising culturing a host cell comprising WISP-3-encoding nucleic acid under conditions suitable for expression of the WISP-3 polypeptide and recovering the WISP-3 polypeptide from the cell culture.

Further provided is an isolated WISP-3 polypeptide encoded by the WISP-3-encoding nucleic acid. Preferably, this polypeptide is human WISP-3.

In another embodiment, the invention provides an isolated nucleic acid produced by hybridizing a test DNA molecule under stringent conditions with (a) a DNA molecule encoding a human WISP-3 polypeptide comprising the sequence of amino acids 34 to 372 of FIGS. 6A-6C (SEQ ID NO:32), or (b) the complement of the DNA molecule of (a), and, if the test DNA molecule has a 100% sequence identity to (a) or (b) in more than about 500 nucleotides, isolating the test DNA molecule.

Also provided is a polypeptide produced by (i) hybridizing a test DNA molecule under stringent conditions with (a) a DNA molecule encoding a human WISP-3 polypeptide comprising the sequence of amino acids 34 to 372 of FIGS. 6A-6C (SEQ ID NO:32), or (b) the complement of the DNA molecule of (a), and if the test DNA molecule has a 100% sequence identity to (a) or (b) in more than about 500 nucleotides, (ii) culturing a host cell comprising the test DNA molecule under conditions suitable for expression of the polypeptide, and (iii) recovering the polypeptide from the cell culture.

In yet another embodiment, the invention provides isolated nucleic acid comprising DNA having a 100% sequence identity in more than about 400 nucleotides to (a) a DNA molecule encoding a human WISP-3 polypeptide comprising the sequence of amino acids 16 to 355 of FIGS. 7A-7C (SEQ ID NO:36), or (b) the complement of the DNA molecule of (a). Preferably, this nucleic acid has at least one WISP biological activity. Preferably, this nucleic acid comprises DNA encoding a human WISP-3 polypeptide having amino acid residues 16 to 355 of FIGS. 7A-7C (SEQ ID NO:36), or amino acid residues 1 to 355 of FIGS. 7A-7C (SEQ ID NO:37) or the complement thereof.

In a still further embodiment, the invention provides an isolated nucleic acid comprising DNA having a 100% sequence identity in more than about 400 nucleotides to (a) a DNA molecule encoding the same full-length polypeptide encoded by the human WISP-3 polypeptide cDNA in ATCC Deposit No. 209707 (DNA58800-1176-2), or (b) the complement of the DNA molecule of (a).

A still further aspect of the invention involves a process for producing a WISP-3 polypeptide of FIG. 7A-7C comprising culturing a host cell comprising WISP-3-encoding nucleic acid under conditions suitable for expression of the WISP-3 polypeptide and recovering the WISP-3 polypeptide from the cell culture.

Further provided is an isolated WISP-3 polypeptide of FIG. 7A-7C encoded by the WISP-3-encoding nucleic acid. Preferably, this polypeptide is human WISP-3.

In another embodiment, the invention provides an isolated nucleic acid produced by hybridizing a test DNA molecule under stringent conditions with (a) a DNA molecule encoding a human WISP-3 polypeptide comprising the sequence of amino acids 16 to 355 of FIGS. 7A-7C (SEQ ID NO:36), or (b) the complement of the DNA molecule of (a), and, if the test DNA molecule has a 100% sequence identity to (a) or (b) in more than about 400 nucleotides, isolating the test DNA molecule.

Also provided is a polypeptide produced by (i) hybridizing a test DNA molecule under stringent conditions with (a) a DNA molecule encoding a human WISP-3 polypeptide comprising the sequence of amino acids 16 to 355 of FIGS. 7A-7C (SEQ ID NO:36), or (b) the complement of the DNA molecule of (a), and if the test DNA molecule has a 100% sequence identity to (a) or (b) in more than about 400 nucleotides, (ii) culturing a host cell comprising the test DNA molecule under conditions suitable for expression of the polypeptide, and (iii) recovering the polypeptide from the cell culture.

Preferably the complements of the DNA molecules herein remain stably bound to the primary sequence under at least moderate, and optionally, under high stringency conditions.

Also provided are vectors comprising the above nucleic acids, host cells comprising the vector, preferably wherein the cell is a Chinese hamster ovary (CHO) cell, an E. coli cell, a baculovirus-infected cell, or a yeast cell.

Additionally provided are a chimeric molecule comprising one of the above polypeptides or an inactivated variant thereof, fused to a heterologous amino acid sequence, wherein the heterologous amino acid sequence may be, for example, an epitope tag sequence, a polyamino acid such as poly-histidine, or an immunoglobulin constant region (Fc). Also provided is an antibody which specifically binds to one of the above polypeptides, wherein the antibody can be a monoclonal antibody.

Further provided are a composition comprising one of the above polypeptides and a carrier therefor, and a composition comprising an antagonist to one of the polypeptides and a carrier therefor. In one such embodiment, the invention provides a composition comprising a WISP-1, WISP-2, or WISP-3 polypeptide and a pharmaceutically acceptable carrier. Preferably, the polypeptide is a human polypeptide. Also, preferably, these compositions may also comprise a chemotherapeutic agent or growth-inhibitory agent.

In another aspect, the invention provides a pharmaceutical product comprising:
(a) the composition comprising WISP-1, WISP-2, or WISP-3 polypeptide and a pharmaceutically acceptable carrier;
(b) a container containing said composition; and
(c) a label affixed to said container, or a package insert included in said pharmaceutical product referring to the use of said WISP-1, WISP-2, or WISP-3 polypeptide in the treatment of a WISP-related disorder.

In yet another embodiment, the invention provides a method for treating a WISP-related disorder in a mammal comprising administering to the mammal an effective amount of any of the above compositions, including the composition of a WISP-1, WISP-2, or WISP-3 polypeptide in a pharmaceutically acceptable carrier, and including the composition of an antagonist to a WISP-1, WISP-2, or WISP-3 polypeptide in a pharmaceutically acceptable carrier. Preferably, the disorder is a malignant disorder or arteriosclerosis. More preferably, the malignant disorder is breast cancer, ovarian cancer, colon cancer, or melanoma. Also, preferably the mammal is human. In another preferred embodiment, the WISP-1, WISP-2, or WISP-3 polypeptide is administered in combination with a chemotherapeutic agent, a growth inhibitory agent, or a cytotoxic agent.

In another embodiment, the invention supplies a process for diagnosing a disease or a susceptibility to a disease related to a mutation in a nucleic acid sequence encoding a WISP-1. WISP-2. or WISP-3 polypeptide comprising:
(a) isolating a nucleic acid sequence encoding a WISP-1, WISP-2, or WISP-3 polypeptide from a sample derived from a host; and
(b) determining a mutation in the nucleic acid sequence encoding a WISP-1, WISP-2, or WISP-3 polypeptide.

In another embodiment, the invention provides a method of diagnosing a WISP-related disorder in a mammal comprising detecting the level of expression of a gene encoding a WISP-1, WISP-2, or WISP-3 polypeptide (a) in a test sample of tissue cells obtained from the mammal, and (b) in a control sample of known normal tissue cells of the same cell type, wherein a higher or lower expression level in the test sample indicates the presence of a WISP-related dysfunction in the mammal from which the test tissue cells were obtained. Preferably, such a disorder is a type of cancer and a higher expression level in the test sample indicates the presence of a tumor in the mammal.

In a still further embodiment, the invention provides an isolated antibody binding a WISP-1, WISP-2, or WISP-3 polypeptide. Preferably, the antibody induces death of a cell overexpressing a WISP-1, WISP-2, or WISP-3 polypeptide, more preferably a cancer cell. Also preferred is an antibody that binds to a human WISP-1, WISP-2, or WISP-3 polypeptide, and is a human or humanized antibody. More preferred is a monoclonal antibody, still more preferred, a monoclonal antibody that has complementary-determining regions and constant immunoglobulin regions, and in other embodiments is an antibody fragment, a single-chain antibody, or an anti-idiotypic antibody. In addition, the antibody is suitably labeled with a detectable label or immobilized on a solid support.

Also provided is a composition comprising an antibody to a WISP-1, WISP-2, or WISP-3 polypeptide in admixture with a pharmaceutically acceptable carrier. Preferably, the antibody is to a human WISP-1, WISP-2, or WISP-3 polypeptide, and is a human or humanized antibody, most preferably a monoclonal antibody against human WISP-1. Further, the composition may comprise a growth-inhibitory amount of said antibody.

In another embodiment, the invention provides a method for treating cancer in a mammal comprising administering to the mammal an effective amount of the above antibody composition. In a preferred aspect of this method, the cancer is colon cancer, the antibody is against human WISP-1 and is a humanized or human monoclonal antibody, and the mammal is human.

In another aspect, the invention provides a method for treating a WISPrelated disorder in a mammal comprising administering to the mammal an effective amount of a composition comprising an antagonist to a WISP-1, WISP-2, or WISP-3 polypeptide in a pharmaceutically acceptable carrier.

In a further aspect, the invention provides a method for inhibiting the growth of tumor cells comprising exposing a cell that overexpresses a Wnt-1-induced gene to an effective amount of an antagonist that inhibits the expression or activity of a WISP-1, WISP-2, or WISP-3 polypeptide.

A further aspect entails a method for inhibiting the growth of tumor cells comprising exposing said cells to an effective amount of the composition with the growth-inhibiting amount of an anti-WISP-1, anti-WISP-2, or anti-WISP-3 antibody in admixture with the carrier.

In a preferred aspect of this method, the tumor cells are colon cancer cells, the antibody is against human WISP-1 and is a humanized or human monoclonal antibody, and the mammal is human.

Also provided herein is a kit comprising one of the above WISP polypeptides or WISP antagonists, such as anti-WISP antibodies, and instructions for using the polypeptide or antagonist to detect or treat a WISP-related disorder, such as cancer induced by Wnt, one such preferred kit is a cancer diagnostic kit comprising an anti-WISP-1, anti-WISP-2, or anti-WISP-3 antibody and a carrier in suitable packaging.

Preferably, this kit further comprises instructions for using said antibody to detect the WISP-1, WISP-2, or WISP-3 polypeptide.

Also provided is a method for inducing cell death comprising exposing a cell which is induced by Wnt to an effective amount of one of the above WISP polypeptides or WISP antagonists, such as anti-WISP antibodies. Preferably, such cell is a cancer cell. More preferably, the cell is in a mammal, more preferably a human. In addition, an effective amount of another chemotherapeutic antibody is used in the exposure of the cell, such as an anti-ErbB2 antibody. Further, optionally the method comprises exposing the cell to a chemotherapeutic agent, a growth-inhibitory agent, or radiation. Optionally, the cell is exposed to the growth-inhibitory agent prior to exposure to the antibody.

In a further aspect, the invention provides an article of manufacture, comprising:
a container;
a label on the container; and
a composition comprising an active agent contained within the container; wherein the composition is effective for inducing cell death or inhibiting the growth of tumor cells, the label on the container indicates that the composition can be used for treating conditions characterized by overinduction of Wnt or a WISP-related disorder or by overexpression of a WISP-1, WISP-2, or WISP-3 polypeptide, and the active agent in the composition is an antagonist to one of the polypeptides, that is, an agent that inhibits the expression and/or activity of the WISP-1, WISP-2, or WISP-3 polypeptide. Preferably, the active agent in such article of manufacture is an anti-WISP-1, anti-WISP-2, or anti-WISP-3 antibody, and the label on the container indicates that the composition can be used for treating a WISP-related disorder.

In another embodiment, the invention provides a process for identifying agonists to a WISP-1, WISP-2, or WISP-3 polypeptide comprising:
(a) contacting cells and a compound to be screened under conditions suitable for the stimulation of cell proliferation by the polypeptide; and
(b) measuring the proliferation of the cells to determine if the compound is an effective agonist.

Additionally, the invention provides an agonist to a WISP-1, WISP-2, or WISP-3 polypeptide identified by the above process.

Further, the invention provides a method for identifying a compound that inhibits the expression or activity of a WISP-1, WISP-2, or WISP-3 polypeptide, comprising contacting a candidate compound with a WISP-1, WISP-2, or WISP-3 polypeptide under conditions and for a time sufficient to allow the compound and polypeptide to interact. In a preferred embodiment, this method comprises the steps of:
(a) contacting cells and a compound to be screened in the presence of the WISP-1, WISP-2, or WISP-3 polypeptide under conditions suitable for the stimulation of cell proliferation by polypeptide; and
(b) measuring the proliferation of the cells to determine if the compound is an effective antagonist.

Further, a compound identified by this method is provided.

In another aspect, this invention provides a compound that inhibits the expression or activity of a WISP-1, WISP-2, or WISP-3 polypeptide.

In another embodiment, the invention provides a method for determining the presence of a WISP-1, WISP-2, or WISP-3 polypeptide comprising exposing a cell suspected of containing the WISP-1, WISP-2, or WISP-3 polypeptide to an anti-WISP-1, anti-WISP-2, or anti-WISP-3 antibody and determining binding of said antibody to said cell.

In another preferred embodiment, the invention provides a method of diagnosing a WISP-related disorder in a mammal comprising (a) contacting an anti-WISP-1, anti-WISP-2, or anti-WISP-3 antibody with a test sample of tissue cells obtained from the mammal, and (b) detecting the formation of a complex between the anti-WISP-1, anti-WISP-2. or anti-WISP-3 antibody and the WISP-1, WISP-2, or WISP-3 polypeptide in the test sample. Preferably, said test sample is obtained from an individual suspected to have neoplastic cell growth or proliferation. Also, preferably the antibody is labeled with a detectable label and/or is immobilized on a solid support.

BRIEF DESCRIPTION OF THE DRAWINGS

FIGS. 1A-1B show the derived amino acid sequence of a native-sequence mouse WISP-1 protein from amino acids 1 to 367 (SEQ ID NO:12) and the nucleotide sequence (and complementary sequence) encoding the protein (SEQ ID NOS:9 and 10, respectively). There is a 1104-bp coding region and 584 bp of 3' untranslated region. In the Figure, amino acids 1 through 22 form a putative signal sequence, amino acids 23 through 367 are the putative mature protein (SEQ ID NO:11), with amino acids 86 to 88, 143 to 145, 284 to 286, and 343 to 345 being potential glycosylation sites. Potential protein kinase C phosphorylation sites are at amino acids 43-45, 159-161, 235-237, 292-294, 295-297, and 345-347. Potential casein kinase II phosphorylation sites are at amino acids 44-47, 131-134, 145-148, and 358-361. Potential N-myristoylation sites are at amino acids 18-23, 72-77, 127-132, 149-154, 231-236, and 289-294. A potential amidation site, is at amino acids 269-272. A potential prokaryotic membrane lipoprotein lipid attachment site is at amino acids 113-123. A potential von Willebrand C1 domain is at amino acids 130-146. A potential thrombospondin 1 domain is at amino acids 223-237. A potential CT module is at amino acids 301-312. A potential IGF binding protein consensus site is at amino acids 72-80.

FIGS. 2A-2B show the derived amino acid sequence of a native-sequence mouse WISP-2 protein from amino acids 1 to 251 (SEQ ID NO:20) and the nucleotide sequence (and complementary sequence) encoding the protein (SEQ ID NOS:17 and 18, respectively) from a clone 1367.3. There are 756 bp of coding nucleotides and 722 bp of 31 untranslated region. In the Figure, amino acids 1 through 23 form a putative signal sequence; amino acids 24 through 251 are the putative mature protein (SEQ ID NO:19). A potential N-glycosylation site is at amino acids 197-200. A potential glycosaminoglycan attachment site is at amino acids 85-88. Potential protein kinase C phosphorylation sites are at amino acids 85-87 and 112-114. Potential N-myristoylation sites are at amino acids 49-54, 81-86, 126-131, 210-215, and 245-250. A potential amidation site is at amino acids 103-106. A potential phospholipase A2 aspartic acid active site is at amino acids 120-130. A potential IGF binding protein consensus signature is at amino acids 49-64. A potential von Willebrand C1 domain is at amino acids 107-123. A potential thrombospondin 1 domain is at amino acids 202-216. A potential IGF binding protein consensus site is at amino acids 49-57.

FIGS. 3A-3C show the derived amino acid sequence of a native-sequence human WISP-1 protein from amino acids 1 to 367 (SEQ ID NO:4) and the nucleotide sequence (and complementary sequence) encoding the protein (SEQ ID NOS:1 and 2, respectively). There are 1104 bp of coding region in this human clone 568.38, and 1638 bp of 3' untranslated region. In the Figure, amino acids 1 through 22 form a putative signal sequence, amino acids 23 through 367 are the putative mature protein (SEQ ID NO:3), with amino acids 85 to 87, 143 to 145, 284 to 286, and 343 to 345 being potential glycosylation sites. A potential cAMP- and cGMP-dependent protein kinase phosphorylation site is from amino acids 171 to 174; potential protein kinase C phosphorylation sites are at amino acids 43-45, 235-237, 292-294, and 345-347. Potential casein kinase II phosphorylation sites are at amino acids 30-33, 145-148, and 358-361. Potential N-myristoylation sites are at amino acids 72-77, 127-132, 149-154, 201-206, 231-236, 289-294, and 327-332. A potential amidation site is at amino acids 269-272. A potential prokaryotic membrane lipoprotein lipid attachment site is at amino acids 113-123. A potential von Willebrand C1 domain is at amino acids 130-146. A potential thrombospondin I domain is at amino acids 223-237. A potential CT (C-Terminal) module is at amino acids 301-312. A potential IGF binding protein consensus site is at amino acids 72-80.

FIGS. 4A-4B show the derived amino acid sequence of a native-sequence human WISP-2 protein from amino acids 1 to 250 (SEQ ID NO:16) and the nucleotide sequence (and complementary sequence) encoding the protein (SEQ ID NOS:13 and 14, respectively). The coding region is 753 bp and the 3' untranslated region is 519 bp. The putative signal sequence is from amino acid residues 1 through 23 and the putative mature region is from 24 through 250 (SEQ ID NO:15). The clone designated herein as "UNQ228" and/or "DNA33473-seqmin" (SEQ ID NO:38) begins at nucleotide 34 of SEQ ID NO:13. Potential protein kinase C phosphorylation sites are at amino acids 4-6, 118-120, and 227-229. A potential casein-kinase II phosphorylation site is at amino acids 98-101. A potential N-myristoylation site is at amino acids 3-8, 49-54, 81-86, 85-90, 126-131, 164-169, 166-171, 167-172, 183-188, and 209-214. A potential IGF binding protein consensus signature is at amino acids 49-64. A potential von Willebrand C1 domain is at amino acids 107-123. A potential thrombospondin 1 domain is at amino acids 2.01-215. A potential IGF binding protein consensus site is at amino acids 49-57.

FIG. 5 shows a 841-bp consensus nucleotide sequence designated "DNA30843" (SEQ ID NO:39) derived from the nucleotide sequences of twenty different expressed sequence tags from Incyte. When aligned with the other sequences, DNA30843 has 3 gaps. It has 441 bp orf (+I). DNA30843 was used to design probes for isolation of human WISP-2.

FIGS. 6A-6C show the derived amino acid sequence of a native-sequence human WISP-3 protein from amino acids 1 to 372 (SEQ ID NO:33) and the nucleotide sequence (and complementary sequence) encoding the protein (SEQ ID NOS:30 and 31, respectively). In the Figure, amino acids 1 through 33 form a putative signal sequence, amino acids 34 through 372 are the putative mature protein (SEQ ID NO:32), with amino acids 196 to 198 and 326 to 328 being potential glycosylation sites. Potential protein kinase C phosphorylation sites are at amino acids 209-211, 246-248, 277-279, 308-310, and 342-344. Potential casein kinase II phosphorylation sites are at amino acids 47-50, 254-257, and 293-296. Potential N-myristoylation sites are at amino acids 21-26, 89-94, 139-144, 166-171, 180-185, 185-190, 188-193, 242-247, and 302-307. A potential amidation site is at amino acids 188-191. Potential prokaryotic membrane lipoprotein lipid attachment sites are at amino acids 130-140 and 160-170. A potential IGF binding protein signature site is at amino acids 89-104. A potential IGF binding protein site (less stringent than prosite's) is at amino acids 89-97.

FIGS. 7A-7C show the derived amino acid sequence of a native-sequence human WISP-3 protein from amino acids 1 to 355 (SEQ ID NO:37) and the nucleotide sequence (and complementary sequence) encoding the protein (SEQ ID NOS:34 and 35, respectively). This protein is believed to be a splice variant of the nucleotide sequence shown in FIG. 6 with a shorter 5' end. In the Figure, amino acids 1 through 15 form a putative signal sequence, amino acids 16 through 355 are the putative mature protein (SEQ ID NO:36), with amino acids 178 to 180 and 308 to 310 being potential glycosylation sites. Potential protein kinase C phosphorylation sites are at amino acids 191-193, 228-230, 259-261, 290-292, and 324-326. Potential casein kinase II phosphorylation sites are at amino acids 29-32, 236-239, and 275-278. Potential N-myristoylation sites are at amino acids 3-8, 71-76, 121-126, 148-153, 162-167, 167-172, 170-175, 224-229, and 284-289. A potential amidation site is at amino acids 170-173. Potential prokaryotic membrane lipoprotein lipid attachment sites are at amino acids 112-122 and 142-152. A potential IGF binding protein signature site is at amino acids 71-87. A potential IGF binding protein site (less stringent than prosite's) is at amino acids 71-79.

FIG. 8 shows an alignment of the full-length amino acid sequences of the human and mouse WISP-1 (SEQ ID NOS:4 and 12, respectively).

FIG. 9 shows an alignment of the full-length amino acid sequences of the human and mouse WISP-2 (SEQ ID NOS:16 and 20, respectively).

FIG. 10 shows an alignment of the amino acid sequences of the two clones of human WISP-3 (SEQ ID NOS:33 and 37, respectively).

FIG. 11A-11C show an alignment of the nucleotide sequences of human WISP-1 (nucleotides 89-1188 of SEQ ID NO:1) and the human WISP-3 (SEQ ID NO:30).

FIG. 12 shows an alignment of the amino acid sequences of human WISP-1 (SEQ ID NO:4) and the human WISP-3 (SEQ ID NO:33).

FIG. 13 shows a map of the vector pBabe puro (5.1 kb) used to transform cells for purposes of differential expression. The vector includes both unique restriction sites and multiple restriction sites. It is shown here in modified form for Wnt-1 cloning wherein the HindIII site after the SV40 promoter in the original pBabe puro vector has been removed and a HindIII site added to the multiple cloning site of the original pBabe puro vector. Wnt-1 is cloned from EcoRI-HindIII in the multiple cloning site. Constructs derived from this vector are selected in ampicillin (100 μg/ml) and the cells infected in culture are selected in 1.0-2.5 μg/ml puromycin.

FIG. 15 shows the cloning site region of the plasmid pGEM-T used to clone all of the WISP sequences herein (SEQ ID NOS:51 and 52 for 5' and 3' sequences, respectively).

FIGS. 16A-16D show the sequence (SEQ ID NO:53) of a plasmid that is used to prepare an expression plasmid for expression of mouse WISP-1 in mammalian cells, the latter being designated pRK5.CMV.puro-dhfR.mWISP-1.6H is.

FIGS. 17A-17D show the sequence (SEQ ID NO:54) of plasmid pb.PH.IgG, which is used to prepare an expression plasmid for expression of mouse WISP-1 DNA in baculovirus-infected insect cells.

FIGS. 18A-18D show the sequence (SEQ ID NO:55) of plasmid pbPH.His.c, which is used to prepare an expression plasmid for expression of mouse WISP-1 DNA in baculovirus-infected insect cells, the latter being designated pbPH.mu.568.8his.baculo.

FIGS. 19A-19D show graphs of the delta CT in nine colon cancer cell lines and DNA from the blood of ten normal human donors (Nor Hu) as control, for human TNF, human WISP-1. Lyra, and human Apo2 ligand, respectively, using the ABI Prism 7700™ Sequence Detection System procedure for testing genomic amplification.

FIGS. 20A-20D show graphs of the delta CT in nine colon cancer cell lines and Nor Hu as control, for human DCR1, huFAS, human WISP-2, and Apo3, respectively, using the ABI Prism 7700™ Sequence Detection System procedure for testing genomic amplification.

FIGS. 21A-21D show graphs of the delta CT in nine colon cancer cell lines and Nor Hu as control, for three different runs of human WISP-1 (designated in the figure as huWISP-1c, -1b, and -1a) and the average of these three runs of human WISP-1, respectively, using the ABI Prism 7700™ Sequence Detect-Ion System procedure for testing genomic amplification.

FIGS. 22A-22D show graphs of the delta CT in nine colon cancer cell lines and Nor Hu as control, for three different runs of human WISP-2 (designated in the figure as huWISP-2c, -2b, and -2a; FIGS. 22A, C, and D, respectively) and the average of these three runs of human WISP-2 (FIG. 22B), using the ABI Prism 7700™ Sequence Detection System procedure for testing genomic amplification.

FIGS. 23A-23C show graphs of the delta CT in nine colon cancer cell lines and Nor Hu as control, for two different runs of human DR5 (DR5a and DR5b) and the average of these two runs of DR5, respectively, using the ABI Prism 7700™, Sequence Detection System procedure for testing genomic amplification.

FIGS. 24A-24D show graphs of the delta CT in nine colon cancer cell lines and Nor Hu as control, for four different runs of c-myc (c-myc(a1), c-myc(b1), c-myc (b), and c-myc (a)), respectively, using the ABI Prism 7700™ Sequence Detection System procedure for testing genomic amplification.

FIGS. 25A-25D show graphs of the delta CT in nine colon cancer cell lines and Nor Hu as control, for two different runs of human WISP-1 (designated in the figure as huWISP-1(a) and huWISP-1(b)) and for two different runs of human WISP-2 (designated in the figure as huWISP-2(a) and huWISP-2(b)), respectively, using the ABI Prism 7700™ Sequence Detection System procedure for testing genomic amplification.

FIG. 26 shows the sequence (SEQ ID NO:23) of clone 568.13, a potential splice variant of human WISP-1 obtained by screening with a probe derived from clone 568.15A, which is the initial clone isolated from a human lung library in the process to obtain full-length human WISP-1 DNA.

FIG. 27 shows the sequence (SEQ ID NO:24) of clone 568.1A, a potential human WISP-1 splice variant, 51 end only, obtained by screening with a probe derived from clone 568.15A.

FIG. 28 shows the sequence (SEQ ID NO:25) of clone 568.39, a potential human WISP-1 splice variant, 5' end only, obtained by screening with a probe derived from clone 568.15A.

FIG. 29 shows the sequence (SEQ ID NO:26) of clone 568.4A, a potential human WISP-1 splice variant obtained by screening with a probe derived from clone 568.15A.

FIG. 30 shows the sequence (SEQ ID NO:27) of clone 568.5A, a potential human WISP-1 splice variant, 51 end only, obtained by screening with a probe derived from clone 568.15A.

FIG. 31 shows the sequence (SEQ ID NO:28) of clone 568.6B, a potential human WISP-1 splice variant, 5' end only, obtained by screening with a probe derived from clone 568.15A.

FIG. 32 shows the sequence (SEQ ID NO:29) of clone 568.7, a potential human WISP-1 splice variant, 51 end only, obtained by screening with a probe derived from clone 568.15A.

DETAILED DESCRIPTION OF THE PREFERRED EMBODIMENTS

I. Definitions

Figure 14:
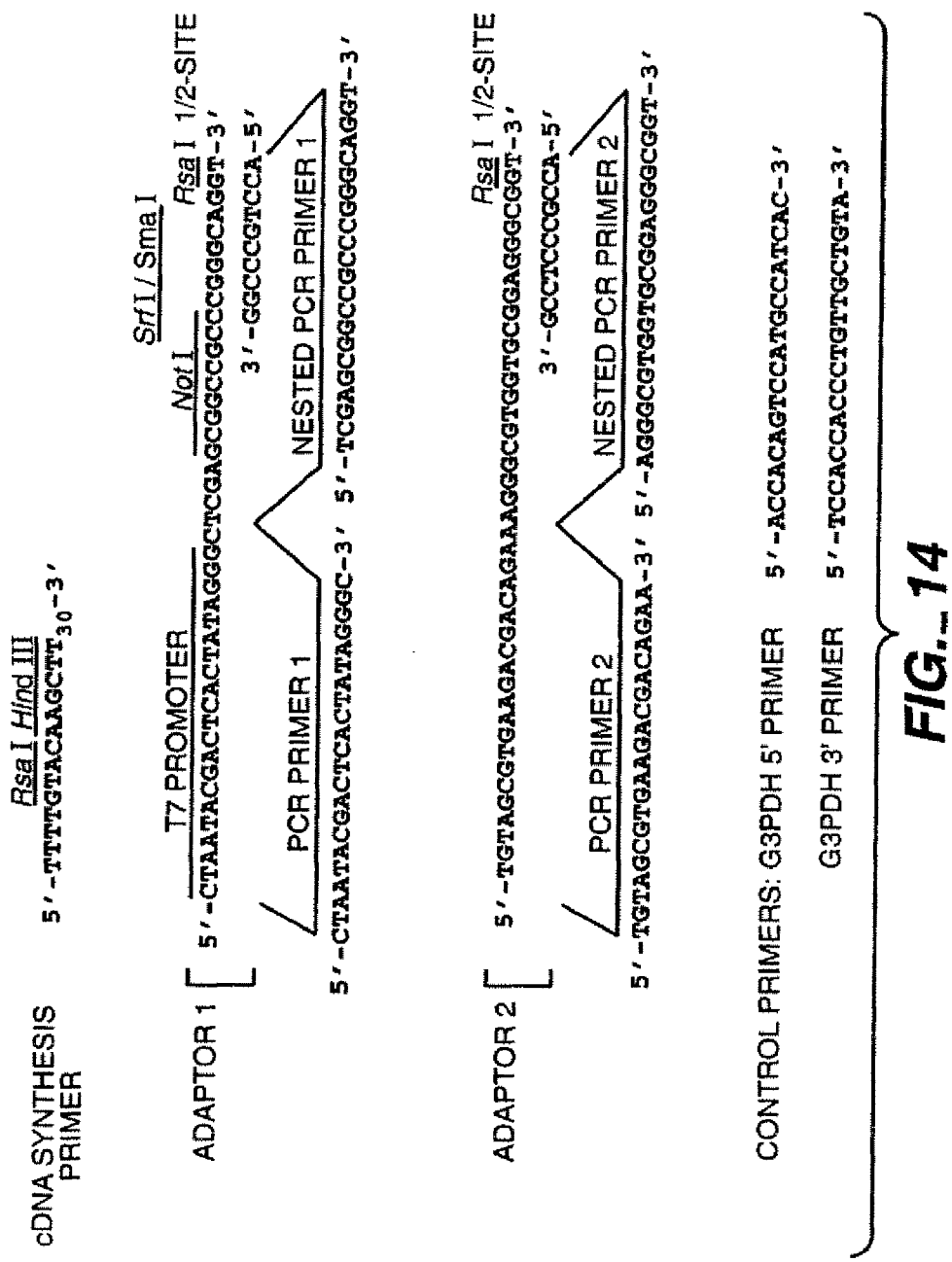
FIG. 14 shows the sequences of the PCR-Select@ cDNA synthesis primer (SEQ ID NO:40), adaptors 1 and 2 (SEQ ID NOS:41 and 42, respectively) and complementary sequences for the adaptors (SEQ ID NOS:43 and 44, respectively), PCR primer 1 (SEQ ID NO:45), PCR primer 2 (SEQ ID NO:46), nested PCR primer 1 (SEQ ID NO:47), nested PCR primer 2 (SEQ ID NO:48), control primer G3PDH 51 primer (SEQ ID NO:49), and control primer G3PDH 3' primer (SEQ ID NO:50) used for suppression subtractive hybridization for identifying WISP clones. When the adaptors are ligated to RsaI-digested cDNA, the RsaI site is restored.

The term "WISP polypeptide" refers to the family of native-sequence human and mouse WISP proteins and variants described herein whose genes are induced at least by Wnt-1. This term includes WISP-1, WISP-2, and WISP-3.

The terms "WISP-1 polypeptide", "WISP-1 homologue" and grammatical variants thereof, as used herein, encompass native-sequence WISP-1 protein and variants (which are further defined herein). The WISP-1 polypeptide may be isolated from a variety of sources, such as from human tissue types or from another source, or prepared by recombinant or synthetic methods, or by any combination of these and similar techniques.

The terms "WISP-2 polypeptide", "WISP-2 homologue", "PR0261", and "PR0261 polypeptide" and grammatical variants thereof, as used herein, encompass native-sequence WISP-2 protein and variants (which are further defined herein). The WISP-2 polypeptide may be isolated from a variety of sources, such as from human tissue types or from another source, or prepared by recombinant or synthetic methods, or by any combination of these and similar techniques.

The terms "WISP-3 polypeptide", "WISP-3 homologue", and grammatical variants thereof, as used herein, encompass native-sequence WISP-3 protein and variants (which are further defined herein) The WISP-3 polypeptide may be isolated from a variety of sources, such as from human tissue types or from another source, or prepared by recombinant or synthetic methods, or by any combination of these and similar techniques.

A "native-sequence WISP-1 polypeptide" comprises a polypeptide having the same amino acid sequence as a WISP-1 polypeptide derived from nature. Such native-sequence WISP-1 polypeptides can be isolated from nature or can be produced by recombinant or synthetic means. The term "native-sequence WISP-1 polypeptide" specifically encompasses naturally occurring truncated or secreted forms of a WISP-1 polypeptide disclosed herein, naturally occurring variant forms (e.g., alternatively spliced forms or splice variants), and naturally occurring allelic variants of a WISP-1 polypeptide. In one embodiment of the invention, the native-sequence WISP-1 polypeptide is a mature or full-length native-sequence human WISP-1 polypeptide comprising amino acids 23 to 367 of FIGS. 3A-3C (SEQ ID NO: 3) or amino acids 1 to 367 of FIGS. 3A-3C (SEQ ID NO: 4), respectively, with or without the N-terminal methionine.

In another embodiment of the invention, the native-sequence WISP-1 polypeptide is the full-length or mature native-sequence human WISP-1 polypeptide comprising amino acids 23 to 367 or 1 to 367 of FIGS. 3A-3C wherein the valine residue at position 184 or the alanine residue at position 202 has/have been changed to an isoleucine or serine residue, respectively (SEQ ID NOS: 5-8), with or without the N-terminal methionine. In another embodiment of the invention, the native-sequence WISP-1 polypeptide is the full-length or mature native-sequence human WISP-1 polypeptide comprising amino acids 23 to 367 or 1 to 367 of FIGS. 3A-3C wherein the valine residue at position 184 and the alanine residue at position 202 has/have been changed to an isoleucine or serine residue, respectively (SEQ ID NOS: 21 and 22, respectively), with or without the N-terminal methionine. In another embodiment of the invention, the native sequence WISP-1 polypeptide is a mature or full-length native-sequence mouse WISP-1 polypeptide comprising amino acids 23 to 367 of FIGS. 1A-1B (SEQ ID NO: 11), or amino acids 1 to 367 of FIGS. 1A-1B (SEQ ID NO: 12), respectively, with or without the N-terminal methionine.

In another embodiment of the invention, the native-sequence WISP-1 polypeptide is one which is encoded by a nucleotide sequence comprising one of the human WISP-1 splice or other native-sequence variants, including SEQ ID NOS:23, 24, 25, 26, 27, 28, or 29, with or without an N-terminal methionine.

A "native-sequence WISP-2 polypeptide" or a "native-sequence PRO261 polypeptide" comprises a polypeptide having the same amino acid sequence as a WISP-2 polypeptide derived from nature. Such native-sequence WISP-2 polypeptides can be isolated from nature or can be produced by recombinant or synthetic means. The term "native-sequence WISP-2 polypeptide" specifically encompasses naturally occurring truncated or secreted forms of a WISP-2 polypeptide disclosed herein, naturally occurring variant forms (e.g., alternatively spliced forms or splice variants), and naturally occurring allelic variants of a WISP-2 polypeptide. In one embodiment of the invention, the native-sequence WISP-2 polypeptide is a mature or full-length native-sequence human WISP2 polypeptide comprising amino acids 1-24 up to 250 of FIGS. 4A-4B (SEQ ID NOS:15, 16, and 56-77), including amino acids 24 to 250 and amino acids 1 to 250 of FIGS. 4A-4B (SEQ ID NOS:15 and 16, respectively), with or without the N-terminal methionine. In another embodiment of the invention, the native-sequence WISP-2 polypeptide is a mature or full-length native-sequence mouse WISP-2 polypeptide comprising amino acids 1-24 up to 251 of FIGS. 2A-2B (SEQ ID NOS:19, 20, and 78-99), including amino acids 24 to 251 and amino acids 1 to 251 of FIGS. 2A-2B (SEQ ID NOS:19 and 20, respectively), with or without the N-terminal methionine.

A "native-sequence WISP-3 polypeptide" comprises a polypeptide having the same amino acid sequence as a WISP-3 polypeptide derived from nature. Such native-sequence WISP-3 polypeptides can be isolated from nature or can be produced by recombinant or synthetic means. The term "native-sequence WISP-3 polypeptide" specifically encompasses naturally occurring truncated or other forms of a WISP-3 polypeptide disclosed herein, naturally occurring variant forms (e.g., alternatively spliced forms or splice variants), and naturally occurring allelic variants of a WISP-3 polypeptide. In one embodiment of the invention, the native-sequence WISP-3 polypeptide is a mature or full-length, native-sequence human WISP-3 polypeptide comprising amino acids 34 to 372 of FIGS. 6A-6C (SEQ ID NO:32) or amino acids 1 to 372 of FIGS. 6A-6C (SEQ ID NO:33), respectively, with or without the N-terminal methionine. In another embodiment of the invention, the native-sequence WISP-3 polypeptide is a mature or full-length, native-sequence human WISP-3 polypeptide comprising amino acids 16 to 355 of FIGS. 7A-7C (SEQ ID NO:36) or amino acids 1 to 355 of FIGS. 7A-7C (SEQ ID NO:37) respectively, with or without the N-terminal methionine.

The term "WISP-1 variant" means an active WISP-1 polypeptide as defined below having at least about 80%, preferably at least about 85%, more preferably at least about 90%, most preferably at least about 95% amino acid sequence identity with human mature WISP-1 having the deduced amino acid sequence shown in FIGS. 3A-3C (SEQ ID NO: 3), and/or with human full-length WISP-1 having the deduced amino acid sequence shown in FIGS. 3A-3C (SEQ ID NO: 4), and/or with mouse mature WISP-1 having the deduced amino acid sequence shown in FIG. 1A-1B (SEQ ID NO: 11), and/or with mouse full-length WISP-1 having the deduced amino acid sequence shown in FIG. 1A-1B (SEQ ID NO: 12). Such variants include, for example, WISP-1 polypeptides wherein one or more amino acid residues are added to, or deleted from, the N- or C-terminus of the full-length or mature sequences of FIGS. 3A-3C and 1A-1B (SEQ ID NOS:4, 3, 12, and 11, respectively), including variants from other species, but excludes a native-sequence WISP-1 polypeptide.

The term "WISP-2 variant" or "PRO261 variant" means an active WISP-2 polypeptide as defined below having at least about 80%, preferably at least about 85%, more preferably at least about 90%, most preferably at least about 95% amino acid sequence identity with human mature WISP-2 having the putative deduced amino acid sequence shown in FIG. 4A-AB (SEQ ID NO:15), and/or with human full-length WISP-2 having the deduced amino acid sequence shown in FIG. 4A-4B (SEQ ID NO:16), and/or with mouse mature WISP-2 having the putative deduced amino acid sequence shown in FIG. 2A-2B (SEQ ID NO:19), and/or with mouse full-length WISP-2 having the deduced amino acid sequence shown in FIG. 2A-2B (SEQ ID NO:20).

Such variants include, for instance, WISP-2 polypeptides wherein one or more amino acid residues are added to, or deleted from, the N- or C-terminus of the full-length and putative mature sequences of FIGS. 4A-4B and 2A-2B (SEQ ID NOS:16, 15, 20, and 19, respectively), including variants from other species, but excludes a native-sequence WISP-2 polypeptide.

The term "WISP-3 variant" means an active WISP-3 polypeptide as defined below having at least about 80%, preferably at least about 85%, more preferably at least about 90%, most preferably at least about 95% amino acid sequence identity with human mature WISP-3 having the deduced amino acid sequence shown in FIGS. 6A-6C (SEQ ID NO:32), and/or with human full-length WISP-3 having the deduced amino acid sequence shown in FIGS. 6A-6C (SEQ ID NO:33), and/or with human mature WISP-3 having the deduced amino acid sequence shown in FIGS. 7A-7C (SEQ ID NO:36), or with human full-length WISP-3 having the deduced amino acid sequence shown in FIGS. 7A-7C (SEQ ID NO:37). Such variants include, for instance, WISP-3 polypeptides wherein one or more amino acid residues are added to, or deleted from, the N- or C-terminus of the full-length or mature sequences of FIGS. 6A-6C and 7A-7C (SEQ ID NOS:32, 33, 36, and 37, respectively), including variants from other species, but excludes a native-sequence WISP-3 polypeptide.

"Percent (%) amino acid sequence identity" with respect to the WISP sequences identified herein is defined as the percentage of amino acid residues in a candidate sequence that are identical with the amino acid residues in a WISP polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN, or Megalign (DNASTAR™) software. Those skilled in the art can determine appropriate parameters for measuring alignment, including any algorithms needed to achieve maximal alignment over the full length of the sequences being compared.

"Percent (%) nucleic acid sequence identity" with respect to the coding region of the WISP sequences identified herein, including UNQ228 (DNA34387-seq min) sequence, and the coding region therein, is defined as the percentage of nucleotides in a candidate sequence that are identical with the nucleotides in the coding region of the WISP sequence of interest, e.g., in the UNQ228 (DNA34387-seq min) sequence (SEQ ID NO:38) or coding region therein (SEQ ID NO:16), after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared.

"Stringent conditions" are those that (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1%; bovine serum albumin/ 0.1% Ficoll/0.1% polyvinylpyrrolidone/50 mM sodium phosphate buffer at pH 6.5 with 750 mM sodium chloride, 75 mm sodium citrate at 420 C; (3) employ 50% formamide, 5×SSC (0.75 M NaCl, 0.075 M sodium citrate), δ 0 mM sodium phosphate (pH 6.8) 0.1% sodium pyrophosphate, 5×Denhardt's Is solution, sonicated salmon sperm DNA (50 µg/ml), 0.1% SDS, and 10% dextran sulfate at 42° C., with washes at 420 C in 0.2×SSC and 0.1% SDS; or (4) employ a buffer of 109. dextran sulfate, 2×SSC (sodium chloride/sodium citrate), and 50% formamide at 55° C., followed by a high-stringency wash consisting of 0.1×SSC containing EDTA at 55° C.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and percent SDS) less stringent than described above. An example of moderately stringent conditions is a condition such as overnight incubation at 370 C in a solution comprising: 20% formamide, 5×SSC (150 mM NaCl, is mm trisodium citrate), So mM sodium phosphate (pH 7.6), 5×Denhardt's solution, lot dextran sulfate, and 20 mg/mL denatured sheared salmon sperm DNA, followed by washing the filters in 1×SSC at about 37-50° C. The skilled artisan will recognize how to adjust the temperature, ionic strength, etc., as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the WISP natural environment will not be present. Ordinarily, however, isolated polypeptide will be prepared by at least one purification step. An "isolated" nucleic acid encoding a WISP polypeptide or "isolated" DNA33473 or "isolated" PR0261 polypeptide-encoding nucleic acid molecule is a nucleic acid molecule that is identified and separated from at least one contaminant nucleic acid molecule with which it is ordinarily associated in the natural source of the respective nucleic acid. Isolated DNA33473 or an isolated WISP-encoding nucleic acid molecule is other than in the form or setting in which it is found in nature. An isolated WISP-encoding or DNA33473 nucleic acid molecule therefore is distinguished from the WISP-encoding or DNA33473 nucleic acid molecule, respectively, as it exists in natural cells. However, an isolated WISP-encoding or DNA33473 nucleic acid molecule includes a nucleic acid molecule contained in cells that ordinarily express WISP-encoding DNA or DNA33473, respectively, where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptides; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-WISP polypeptide, such as anti-PR0261, monoclonal antibodies (including agonist, antagonist, and neutralizing antibodies), and anti-WISP polypeptide, such as anti-PR0261, and antibody compositions with polyepitopic specificity. The term "monoclonal antibody" as used herein refers to an antibody obtained from a population of substantially homogeneous antibodies, i.e., the individual antibodies comprising the population are identical except for possible naturally occurring mutations that may be present in minor amounts.

"Active" or "activity" or "WISP biological activity", for purposes herein, describes form(s) of a WISP polypeptide, such as PRO261, including its variants, or its antagonists, which retain the biologic and/or immunologic activities of a native or naturally occurring (native-sequence) WISP polypeptide, such as PRO261, or its antagonist. Preferred "activities" for a WISP polypeptide or its antagonist include the ability to inhibit proliferation of tumor cells or to stimulate proliferation of normal cells and to treat arteriosclerosis, including atherosclerosis, as well as to induce wound repair and hematopoiesis, prevent desmoplasia, prevent fibrotic lesions associated with skin disorders such as scleroderma, keloid, eosinophilic fasciitis, nodular fasciitis, and Dupuytren's contracture, to treat bone-related diseases such as osteoporosis, to regulate anabolism including promotion of growth, to treat immune disorders, to treat Wilms' tumor and kidney-related disorders, to treat testis-related disorders, to treat lung-related disorders, and to treat cardiac disorders.

An "antagonist" of a WISP polypeptide is a molecule that inhibits an activity of a WISP polypeptide. Preferred antagonists are those which interfere with or block an undesirable biological activity of a WISP polypeptide, such as where a WISP polypeptide might act to stimulate cancer cells and the antagonist would serve to inhibit the growth of those cells. In some cases, such as with WISP-1, WISP-2, and WISP-3, the antagonist may be useful to inhibit the binding of a WISP polypeptide to an IGF. Such molecules include anti-bodies and small molecules that have such inhibitory capability, as well as WISP polypeptide variants of, and receptors for, WISP polypeptide (if available) or portions thereof that bind to WISP. For example, antagonists can be derived from receptors of WISP-1, WISP-2, and WISP-3 using the predicted family of receptors for WISPs-1, -2, and -3 (the CTGF receptors). Thus, the receptor can be expression cloned from the family; then a soluble form of the receptor is made by identifying the extracellular domain and excising the transmembrane domain therefrom. The soluble form of the receptor can then be used as an antagonist, or the receptor can be used to screen for small molecules that would antagonize WISP polypeptide activity.

Alternatively, using the murine sequences shown in FIGS. 1A-1B and 2A-2B (SEQ ID NOS:11, 12, 19, and 20, respectively) or the human sequences shown in FIGS. 3A-3C, 4A-4B, (SEQ ID NOS:3, 4, 15, and 16, respectively), 6A-6C, and 7A-7C, variants of native WISP-1, WISP-2, or WISP-3, are made that act as antagonists. Using knowledge from the CTGF receptor family, the receptor binding sites of WISP-1, WISP-2, and WISP-3 polypeptides can be determined by binding studies and one of them eliminated by standard techniques (deletion or radical substitution) so that the molecule acts as an antagonist.

Antagonist activity can be determined by several means, including standard assays for induction of cell death such as that described herein, e.g., $^3$H-thymidine proliferation assays, or other mitogenic assays, such as an assay measuring the capability of the candidate antagonist of inducing EGF-potentiated anchorage independent growth of target cell lines (Volckaert et al., Gene, 15:215-223 (1981)) and/or growth inhibition of neoplastic cell lines. Roberts et al., Proc. Natl. Acad. Sci. USA, 82:119-123 (1985). Anchorage-independent growth refers to the ability of WISP polypeptide-treated, or TGF-β-treated and EGF-treated non-neoplastic target cells to form colonies in soft agar, a characteristic ascribed to transformation of the cells. In this assay, the candidate is incubated together with an equimolar amount of a WISP polypeptide otherwise detectable in the EGF-potentiated anchorage-independent target cell growth assay, and the culture observed for failure to induce anchorage independent growth. In addition, an antagonist may be an IGF such as IGF-I or a peptide mimic of IGF-I or a receptor to IGF or a receptor to an IGFBP.

"Treatment" refers to both therapeutic treatment and prophylactic or preventative measures. Those in need of treatment include those already with the disorder or condition as well as those in which the disorder or condition is to be prevented.

"Mammal" for purposes of treatment refers to any animal classified as a mammal, including humans, domestic, and farm animals, and zoo, sports, or pet animals, such as dogs, horses, cats, sheep, pigs, cows, etc. Preferably, the mammal is human.

A "disorder" or "WISP-related disorder" is any condition that would benefit from treatment with the WISP polypeptides or WISP antagonists herein. This includes chronic and acute disorders, as well as those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal, and blastocoelic disorders; hematopoiesis-related disorders; tissue-growth disorders; skin disorders; desmoplasia, fibrotic lesions; kidney disorders; bone-related disorders; trauma such as burns, incisions, and other wounds; catabolic states; testicular-related disorders; and inflammatory, angiogenic, and immunologic disorders, including arteriosclerosis. A "Wnt-related disorder" is one caused at least by the upregulation of the Wnt gene pathway, including Wnt-1 and Wnt-4, but preferably Wnt-1, and may include cancer.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The preferred cancers for treatment herein are breast, colon, lung, and melanoma.

The term "cytotoxic agent" as used herein refers to a substance that inhibits or prevents the function of cells and/or causes destruction of cells. The term is intended to include radioactive isotopes (e.g., $^{131}$I, $^{125}$I, $^{90}$Y, and $^{186}$Re), chemotherapeutic agents, and toxins such as enzymatically active toxins of bacterial, fungal, plant, or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

A "growth-inhibitory agent" when used herein refers to a compound or composition which inhibits growth of a cell, such as an Wnt-overexpressing cancer cell, either in vitro or in vivo. Thus, the growth-inhibitory agent is one which significantly reduces the percentage of malignant cells in S phase. Examples of growth-inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The 4D5 antibody (and functional equivalents thereof) can also be employed for this purpose if the cancer involves ErbB2-overexpressing cancer cells. See, e.g., WO 92/22653.

"Northern analysis" or "Northern blot" is a method used to identify RNA sequences that hybridize to a known probe such as an oligonucleotide, DNA fragment, cDNA or fragment thereof or RNA fragment. The probe is labeled with a radioisotope such as $^{32}p$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra.

The technique of "polymerase chain reaction." or "PCR." as used herein generally refers to a procedure wherein minute amounts of a specific piece of nucleic acid. RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed—, these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.,* 51:263 (1987): Erlich, ed. *PCR Technology*. (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

II. Compositions and Methods of the Invention

A. Full-Length WISP Polypeptide

The present invention provides newly-identified and isolated nucleotide sequences encoding a polypeptide referred to in the present application as a WISP polypeptide, including a WISP-1, WISP-2, or WISP-3 polypeptide. In particular, cDNAs have been identified and isolated encoding novel murine and human WISP-1 and WISP-2, and human WISP-3 splice variants as disclosed in further detail in the Examples below.

Using BLAST and FastA sequence alignment computer programs, it was found that the coding sequences of mouse and human WISP-1 and -2, as well as the two coding sequences of human WISP-3 disclosed herein, show significant homology to DNA sequences disclosed in the GenBank database, including those published by Adams et al., *Nature*, 377:3-174 (1995).

Further, using BLAST and FastA sequence alignment computer programs, it was found that various portions of the coding sequences of mouse and human WISP-1 and WISP-2 show significant homology to CTGF, cef-10, Cyr61, and/or Nov protein. In this regard, mouse WISP-1 is 47% homologous to mouse CTGF and 46% homologous to human CTGF, mouse WISP-2 is 46% homologous to chick cef-10 protein precursor and 42% homologous to human Cyr61 protein, human WISP-1 is 47% homologous to mouse CTGF and 48% homologous to human CTGF, and human WISP-2 is 48% homologous to mouse CTGF, 49% homologous to human CTGF precursor, 46% homologous to mouse Nov protein homolog precursor, 49% homologous to human CTGF, and 48% homologous to mouse CTGF precursor. Further, apparently the amino acid sequences of mouse WISP-1 and mouse ELM1 (Hashimoto et al., supra) are identical, and the amino acid sequences of human WISP-1 and mouse ELM1 are 84% identical.

Since these factors have also been correlated with IGFBPs, it is presently believed that the WISP-1 and WISP-2 polypeptides disclosed in the present application are newly identified members of the CTGF or IGFBP family and possess activity relating to development of normal, injured, and cancerous cells and tissue. More specifically, WISP-1 and WISP-2 may be involved in breast cancer, lung cancer, melanoma, and colon cancer, as well as in wound repair. Further, they may be involved in atherosclerosis.

Further, using BLAST and FastA sequence alignment computer programs, it was found that various portions of the coding sequences of the two splice variants of human WISP-3 show significant homology to mouse ELM1 and CTGF proteins. In this regard, both splice variants of WISP-3 are 45% homologous to mouse ELM1 and 42% homologous to mouse and human CTGF and its precursor, with the longer variant of FIG. 6 being 43% homologous to *Xenopus* CTGF and the shorter variant of FIG. 7 being 42% homologous to *Xenopus* CTGF.

B. WISP Polypeptide Variants

In addition to the full-length native-sequence WISP polypeptides described herein, it is contemplated that variants of these sequences can be prepared. WISP variants can be prepared by introducing appropriate nucleotide changes into the WISP-encoding DNA, or by synthesis of the desired variant WISP polypeptides. Those skilled in the art will appreciate that amino acid changes may alter posttranslational processes of the WISP polypeptide, such as changing the number or position of glycosylation sites or altering the membrane-anchoring characteristics, if the native WISP polypeptide is membrane bound.

Variations in the native full-length WISP sequences, or in various domains of the WISP polypeptides described herein, can be made, for example, using any of the techniques and guidelines for conservative and non-conservative mutations set forth, for instance, in U.S. Pat. No. 5,364,934. Variations may be a substitution, deletion, or insertion of one or more codons encoding the WISP polypeptide that results in a change in the amino acid sequence as compared with the native-sequence WISP polypeptide. Optionally the variation is by substitution of at least one amino acid with any other amino acid in any portion of the WISP polypeptide. Guidance in determining which amino acid residue may be inserted, substituted, or deleted without adversely affecting the desired activity may be found by comparing the sequence of the WISP polypeptide with that of homologous known CTGF protein molecules, in the case of WISP-1, WISP-2, and WISP-3, and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to about 5 amino acids. The variation allowed may be determined by systematically making insertions, deletions, or substitutions of amino acids in the sequence and testing the resulting variants for activity in in vitro assays for gene upregulation or downregulation and in transgenic or knockout animals.

The variations can be made on the cloned DNA to produce the WISP DNA or WISP polypeptide variant DNA using methods known in the art such as oligonucleotide-mediated (site-directed) mutagenesis (Carter et al., *Nucl. Acids Res.,* 13:4331 (1986); Zoller et al., *Nucl. Acids Res.,* 10:6487 (1987)), cassette mutagenesis (Wells et al., *Gene,* 34:315- (1985)), alanine scanning, PCR mutagenesis, restriction selection mutagenesis (Wells et al., *Philos. Trans. R. Soc. London SerA,* 317:415 (1986)), or other known techniques.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions. T. E. Creighton, *Proteins: Structure and Molecular Properties* (W.H. Freeman & Co., San Francisco, 1983); Chothia, *J. Mol. Biol.,* 150:1 (1976). If alanine substitution does not yield adequate amounts of variant, an isoteric amino acid can be used.

Further deletional variants of the full-length WISP polypeptide include variants from which the N-terminal signal peptide, if any (such as, for example, those putatively identified as amino acids 1 to 22 for WISP-1, 1 to 23 for WISP2, 1-33 for the WISP-3 of FIGS. 6 and 1-15 for the WISP-3 of FIG. 7), and/or the initiating methionine has been deleted.

C. Modifications of the WISP Polypeptide

Covalent modifications of the WISP polypeptides are included within the scope of this invention. One type of covalent modification includes reacting targeted amino acid residues of a WISP polypeptide with an organic derivatizing agent that is capable of reacting with selected side chains or the N- or C-terminal residues. Derivatization with bifunctional agents is useful, for instance, for crosslinking a WISP polypeptide to a water-insoluble support matrix or surface for use in the method for purifying anti-WISP antibodies, and viceversa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane, and agents such as methyl-3-((p-azidophenyl) dithio)propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the V-amino groups of lysine, arginine, and histidine side chains (Creighton, supra, pp. 79-86), acetylation of the N-terminal amine, and amidation of any C-terminal carboxyl group.

Another type of covalent modification of the WISP polypeptide included within the scope of this invention comprises altering the native glycosylation pattern of the polypeptide. "Altering the native glycosylation pattern" is intended for purposes herein to mean deleting one or more carbohydrate moieties found in the native sequence (either by deleting the underlying glycosylation site or by removing the glycosylation moieties by chemical and/or enzymatic means) and/or adding one or more glycosylation sites that are not present in the native sequence. In addition, the phrase includes qualitative changes in the glycosylation of the native proteins, involving a change in the nature and proportion of the various sugar residues present.

Addition of glycosylation sites to the WISP polypeptide herein may be accomplished by altering the amino acid sequence. The alteration may be made, for example, by the addition of, or substitution by, one or more serine or threonine residues to the native sequence (for O-linked glycosylation sites). The amino acid sequence may optionally be altered through changes at the DNA level, particularly by mutating the DNA encoding the WISP polypeptide at preselected bases such that codons are generated that will translate into the desired amino acids. The DNA mutation(s) may be made using methods described above.

Another means of increasing the number of carbohydrate moieties on the WISP polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the WISP polypeptide may be accomplished chemically or enzymatically or by mutational substitution of codons encoding amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exoglycosidases as described by Thotakura et al., *Meth. Enzymol.,* 138:350 (1987).

Another type of covalent modification comprises linking the WISP polypeptide to one of a variety of nonproteinaceous polymers, e.g., polyethylene glycol, polypropylene glycol, or polyoxyalkylenes, in the manner set forth, e.g., in U.S. Pat. No. 4,640,835; 4,496,689; 4,301,144; 4,670,417; 4,791,192 or 4,179,337.

The WISP polypeptide of the present invention may also be modified in a way to form a chimeric molecule comprising a WISP polypeptide, or a fragment thereof, fused to a heterologous polypeptide or amino acid sequence. In one embodiment, such a chimeric molecule comprises a fusion of the WISP polypeptide with a tag polypeptide which provides an epitope to which an anti-tag antibody can selectively bind. The epitope tag is generally placed at the amino- or carboxyl-terminus of a native or variant WISP molecule. The presence of such epitope-tagged forms can be detected using an antibody against the tag polypeptide. Also, provision of the epitope tag enables the WISP polypeptides to be readily purified by affinity purification using an anti-tag antibody or another type of affinity matrix that binds to the epitope tag. In an alternative embodiment, the chimeric molecule may comprise a fusion of the WISP polypeptides, or fragments thereof, with an immunoglobulin or a particular region of an immunoglobulin. For a bivalent form of the chimeric molecule, such a fusion could be to the Fc region of an Ig, such as an IgG molecule.

Various tag polypeptides and their respective antibodies are well known in the art. Examples include poly-histidine (poly-His) or poly-histidine-glycine (poly-His-Gly) tags; the flu HA tag polypeptide and its antibody 12CA5 (Field et al., *Mol. Cell. Biol.,* 8:2159-2165 (1988)); the c-myc tag and the 8F9, 3C7, 6E10r G4, B7, and 9E10 antibodies thereto (Evan et al., *Molecular and Cellular Biology,* 5:3610-3616 (1985)); and the Herpes Simplex virus glycoprotein D (gD) tag and its antibody. Paborsky et al., *Protein Engineering,* 2 (6):547-553 (1990). Other tag polypeptides include the Flag-peptide (Hopp et al., *BioTechnology,* 6:1204-1210 (1988)); the KT3 epitope peptide (Martin et al., *Science,* 255:192-194 (1992)); an a-tubulin epitope peptide (Skinner et al., *J. Biol. Chem.,* 266:15163-15166 (1991)); and the T7 gene 10 protein peptide tag. Lutz-Freyermuth et al., *Proc. Natl. Acad. Sci. USA,* 87:6393-6397 (1990).

D. Preparation of WISP Polypeptide

The description below relates primarily to production of WISP polypeptides by culturing cells transformed or transfected with a vector containing at least DNA encoding the mature or full-length sequences of human or mouse WISP-1 (SEQ ID NOS:3, 4, 11, or 12, respectively), or containing at least DNA encoding the mature or full-length sequences of human or mouse WISP-2 (SEQ ID NOS:15, 16, 19, or 20, respectively), or containing at least DNA encoding the mature or full-length sequences of human WISP-3 of FIG. 6A-6C (SEQ ID NOS:32 or 33, respectively), or containing at least DNA encoding the mature or full-length sequences of human WISP-3 of FIG. 7A-7C (SEQ ID NOS:36 or 37, respectively).

It is, of course, contemplated that alternative methods, which are well known in the art, may be employed to prepare WISP polypeptides. For instance, the WISP polypeptide sequence, or portions thereof, may be produced by direct peptide synthesis using solid-phase techniques. See, e.g., Stewart et al., Solid-Phase Peptide Synthesis (W.H. Freeman Co.: San Francisco, Calif., 1969); Merrifield, *J. Am. Chem. Soc.,* 85:2149-2154 (1963). In vitro protein synthesis may be performed using manual techniques or by automation. Automated synthesis may be accomplished, for instance, using an Applied Biosystems peptide synthesizer (Foster City, Calif.) in accordance with manufacturer's instructions, various portions of WISP polypeptides may be chemically synthesized separately and combined using chemical or enzymatic methods to produce a full-length WISP polypeptide.

1. Isolation of DNA Encoding WISP Polypeptide

DNA encoding a WISP polypeptide may be obtained from a cDNA library prepared from tissue believed to possess the mRNA for WISP polypeptide and to express it at a detectable level. Accordingly, DNA encoding human WISP polypeptide can be conveniently obtained from a cDNA library prepared from human tissue, such as a human fetal liver library or as otherwise described in the Examples. The gene encoding WISP polypeptide may also be obtained from a genomic library or by oligonucleotide synthesis.

A still alternative method of cloning WISP polypeptide is suppressive subtractive hybridization, which is a method for generating differentially regulated or tissue-specific cDNA probes and libraries. This is described, for example, in Diatchenko et al. *Proc. Natl. Acad. Sci. USA,* 93:6025-6030 (1996). The procedure is based primarily on a technique called suppression, PCR and combines normalization and subtraction in a single procedure, The normalization step equalizes the abundance of cDNAs within the target population and the subtraction step excludes the common sequences between the target and driver populations.

Libraries can be screened with probes (such as antibodies to a WISP polypeptide or oligonucleotides of at least about 20-80 bases) designed to identify the gene of interest or the protein encoded by it. Screening the cDNA or genomic library with the selected probe may be conducted using standard procedures, such as described in Sambrook et al., supra. An alternative means to isolate the gene encoding WISP polypeptide is to use PCR methodology. Sambrook et al., supra; Dieffenbach et al., *PCR Primer: A Laboratory Manual* (New York: Cold Spring Harbor Laboratory Press, 1995).

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 3-P-labeled ATP, biotinylation, or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having polypeptide-coding sequence may be obtained by screening selected cDNA or genomic libraries using the deduced amino acid sequences disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for WISP polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, CaPO-4 and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system trans format ions have been described in U.S. Pat. No. 4,399,216. Transformations into yeast are typically carried out according to the method of Van Solingen et al., *J. Bact.*, 130:946 (19-77) and Hsiao et al., *Proc. Natl. Acad. Sci.* (*USA*), 76:3829 (1979) However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., *Methods in Enzymology*, 185:527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989). *Pseudomonas* such as *P. aeruginosa*, and *Streptomyces*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635). These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W311G may be modified to effect a genetic mutation in the genes encoding proteins endogamous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (AT-CC 55,244), which has the complete genotype tonA ptr3 phoA E1.5 (argF-lac)169 degP ompT kan$^r$; *E. coli* W3110 strain 37D6, which has the complete genotype tonA ptr3 phoA ELS (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors containing nucleic acid encoding WISP polypeptide. *Saccharomyces cerevisiae* is a commonly used lower eukaryotic host microorganism. However, a number of other genera, species, and strains are commonly available and useful herein, such as *Schizosaccharomyces pombe* (Beach and Nurse, *Nature*, 290:140 (1981); EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 (1988) *Candida; Trichoderma reesia* (EP 244, 234); *Neurospora crassa* (Case et al., *Proc. Natl. Acad. Sci. USA*, 76:5259-5263 (1979)); *Schwanniomyces* such as *Schwanniomyces occidentalis* (EP 394, 538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 (1983); Tilburn et al., *Gene*, 26:205-221 (1983); Yelton et al., *Proc. Natl. Acad. Sci. USA*, 81:1470-1474 (1984)) and *A. niger* Kelly and Hynes, *EMBO J.*, 4:475-479 (1985). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated WISP are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture (Graham et al., *J. Gen Virol.*, 36:59 (1977)); Chinese hamster ovary cells/– DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the desired WISP polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired WISP polypeptide may be produced recombinantly not only directly, but also as a fusion polypeptide with a heterologous polypeptide, which may be a signal sequence, if the WISP polypeptide is conducive to being secreted, or other polypeptide having a specific cleavage site at the N-terminus of the mature or full-length protein or polypeptide. In general, the signal sequence may be a component of the vector, or it may be a part of the DNA encoding the WISP polypeptide that is inserted into the vector. The signal sequence may be a prokaryotic signal sequence such as, for example, the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* a-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders, and including signals from WISP polypeptides.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 u plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding WISP polypeptide, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7. Stinchcomb et al., *Nature,* 282:39 (1979); Kingsman et al., *Gene,* 7:141 (1979); Tschemper et al., *Gene,* 10:157 (1980). The trp1 gene provides a selection marker for a mutant strain of yeast lacking the ability to grow in tryptophan, for example, ATCC No. 44076 or PEP4-1. Jones, *Genetics,* 85:12 (1977).

Expression and cloning vectors usually contain a promoter operably linked to the nucleic acid sequence encoding WISP polypeptide to direct mRNA synthesis. Promoters recognized by a variety of potential host cells are well known. Promoters suitable for use with prokaryotic hosts include the B-lactamase and lactose promoter systems (Chang et al., *Nature,* 275:615 (1978); Goeddel et al., *Nature,* 281:544 (1979)), alkaline phosphatase, a tryptophan (trp) promoter system (Goeddel, *Nucleic Acids Res.,* 8:4057 (1980); EP 36,776), and hybrid promoters such as the tac promoter, deBoer et al., *Proc. Natl. Acad. Sci. USA,* 80:21-25 (1983). Promoters for use in bacterial systems also will contain a Shine-Dalgarno (S.D.) sequence operably linked to the DNA encoding the WISP polypeptide.

Examples of suitable promoting sequences for use with yeast hosts include the promoters for 3-phosphoglycerate kinase (Hitzeman et al., *J. Biol. Chem.,* 255:2073 (1980)) or other glycolytic enzymes (Hess et al., *J. Adv. Enzyme Rea.,* 7:149 (1968); Holland, *Biochemistry,* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

WISP transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus, and Simian Virus 40 (SV40); from heterologous mammalian promoters, e.g., the actin promoter or an immunoglobulin promoter; and from heat-shock promoters, provided such promoters are compatible with the host cell systems.

Transcription of a DNA encoding a WISP polypeptide by higher eukaryotes may be increased by inserting an enhancer' sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma, enhancer on the late side of the replication origin, and adenovirus enhancers. The enhancer may be spliced into the vector at a position 5' or 3' to the sequence coding for a WISP polypeptide, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding WISP polypeptide.

Still other methods, vectors, and host cells suitable for adaptation to the synthesis of WISP polypeptides in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence WISP polypeptide 'or against a synthetic peptide based on the DNA sequences provided herein or against exogenous sequence fused to DNA encoding WISP polypeptide and encoding a specific antibody epitope.

5. Purification of Polypeptide

Forms of WISP polypeptide may be recovered from culture medium or from host cell lysates. If membrane-bound, it can be released from the membrane using a suitable detergent solution (e.g., Triton-X 100) or by enzymatic cleavage. Cells employed in expression of WISP polypeptides can be disrupted by various physical or chemical means, such as freeze-thaw cycling, sonication, mechanical disruption, or cell lysing agents.

It may be desired to purify WISP polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; protein A SEPHAROSE™ columns to remove contaminants such as IgG; and metal chelating columns to bind epitope-tagged forms of the WISP polypeptide. Various methods of protein purification may be employed, and such methods are known in the art and described, for example, in Deutscher, *Methods in Enzymology*, 182 (1990); and Scopes, *Protein Purification: Principles and Practice* (Springer-Veriag: New York, 1982).

In one specific example of purification, either a poly-His tag or the Fc portion of human IgG is added to the C-terminal coding region of the cDNA for WISP-1, WISP-2, or WISP-3 before expression. The conditioned media from the transfected cells are harvested by centrifugation to remove the cells and filtered. For the poly-His-tagged constructs, the protein may be purified using a Ni-NTA column. After loading, the column may be washed with additional equilibration buffer and the protein eluted with equilibration buffer containing 0.25 M imidazole. The highly purified protein may then be desalted into a storage buffer if desired.

Immunoadhesin (Fc-containing) constructs of the WISP-1, WISP-2, and WISP-3 proteins may be purified from the conditioned media by pumping them onto a 5-ml Protein A column which had been equilibrated in a phosphate buffer. After loading, the column may be washed extensively with equilibration buffer before elution with citric acid. The eluted protein may be immediately neutralized by collecting 1-ml fractions into tubes containing TRIS buffer. The highly purified protein may be subsequently desalted into storage buffer as described above for the poly-His-tagged proteins. The homogeneity of the protein may be assessed by SDS polyacrylamide gels and by N-terminal amino acid sequencing by Edman degradation.

The purification step(s) selected will depend, for example, on the nature of the production process used and the particular WISP polypeptide produced.

E. Uses for WISP Polypeptide and Its Nucleic Acid

Nucleotide sequences (or their complement) encoding WISP polypeptides have various applications in the art of molecular biology, including uses as hybridization probes, in chromosome and gene mapping, and in the generation of anti-sense RNA and DNA. Nucleic acid encoding WISP polypeptide will also be useful for the preparation of WISP polypeptides by the recombinant techniques described herein.

The full-length nucleotide sequences for mouse or human WTSP-1 or WISP-2 (SEQ ID NOS: 9, 1, 17, and 13, respectively), or portions thereof, or the full-length nucleotide sequences for human WISP-3 of FIG. 6 (SEQ ID NO:30) or for WISP-3 of FIG. 7 (SEQ ID NO:34) may be used as hybridization probes for a cDNA library to isolate or detect the full-length gene encoding the WISP polypeptide of interest or to isolate or detect still other genes (for instance, those encoding naturally occurring variants of WISP polypeptide, other WISP polypeptide family members, or WISP polypeptides from other species) which have a desired sequence identity to the WISP polypeptide sequences disclosed in FIGS. 1, 2, 3A and 3B, 4, 6A and 6B, and 7A and 7B (SEQ ID NOS: 3, 4, 11, 12, 15, 16, 19, 20, 32, 33, 36, or 37). For example, such procedures as in situ hybridization, Northern and Southern blotting, and PCR analysis may be used to determine whether DNA and/or RNA encoding a different WISP is present in the cell type(s) being evaluated. Optionally, the length of the probes will be about 20 to about 50 bases. For example, the hybridization probes may be derived from the UNQ228 (DNA33473-seq min) nucleotide sequence (SEQ ID NO:38) or the full-length human WISP-2 nucleotide sequence (SEQ ID NO:13) as shown in FIG. 4 or from genomic sequences including promoters, enhancer elements, and introns of DNA encoding native-sequence WISP polypeptide.

By way of example, a screening method will comprise isolating the coding region of the WISP gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of any of the genes encoding WISP polypeptides of the present invention can be used to screen libraries of human cDNA, genomic DNA, or mRNA to determine to which members of such libraries the probe hybridizes. Hybridization techniques are described in further detail in the Examples below.

The probes may also be employed in PCR techniques to generate a pool of sequences for identification of closely related WISP sequences.

Nucleotide sequences encoding a WISP polypeptide can also be used to construct hybridization probes for mapping the gene which encodes that WISP polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries. If the amplification of a given gene is functionally relevant, then that gene should be amplified more than neighboring genomic regions which are not important for tumor survival. To test this, the gene can be mapped to a particular chromosome, e.g. by radiation-hybrid analysis. The amplification level is then determined at the location identified, and at neighboring genomic region. Selective or preferential amplification at the genomic region to which to gene has been mapped is consistent with the possibility that the gene amplification observed promotes tumor growth or survival. Chromosome mapping includes both framework and epicenter mapping. For further details see e.g., Stewart et al., *Genome Research* 7, 422-433 (1997)

Nucleic acid encoding a WISP polypeptide may be used as a diagnostic tc-determine the extent and rate of the expression of the DNA encoding the WISP polypeptide in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

Nucleic acids which encode WISP polypeptides or any of their modified forms can also be used to generate either transgenic animals or "knock-out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a WISP polypeptide can be used to clone genomic DNA encoding the WISP polypeptide in accordance with established techniques and the genomic sequences used to generate transgenic animals that contain cells which express DNA encoding the WISP polypeptide.

Methods for generating transgenic animals, particularly animals such as mice or rats, have become conventional in the art and are described, for example, in U.S. Pat. Nos. 4,736, 866 and 4,870,009 and WO 97/38086. Typically, particular cells would be targeted for WISP transgene incorporation with tissue-specific enhancers. Transgenic animals that include a copy of a transgene encoding the WISP polypeptide introduced to the germ line of the animal at an embryonic stage can be used to examine the effect of increased expression of DNA encoding the WISP polypeptide. Such animals can be used as tester animals for reagents thought to confer protection from, for example, pathological conditions associated with its overexpression. In accordance with this facet of the invention, an animal is treated with the Teagent and a reduced incidence of the pathological condition, compared to untreated animals bearing the transgene, would indicate a potential therapeutic intervention for the pathological condition.

Alternatively, non-human homologues of WISP polypeptides can be used to construct a WISP polypeptide "knock-out" animal which has a defective or altered gene encoding a WISP polypeptide as a result of homologous recombination between the endogenous gene encoding the WISP polypeptide and altered genomic DNA encoding the WISP polypeptide introduced into an embryonic cell of the animal. For example, cDNA encoding the WISP polypeptide can be used to clone genomic DNA encoding the WISP polypeptide in accordance with established techniques. A portion of the genomic DNA encoding the WISP polypeptide can be deleted or replaced with another gene, such as a gene encoding a selectable marker which can be used to monitor integration. Typically, several kilobases of unaltered flanking DNA (both at the 5' and 3' ends) are included in the vector. See e.g., Thomas and Capecchi, *Cell,* 51:503 (1987) for a description of homologous recombination vectors. The vector is introduced into an embryonic stem cell line (e.g., by electroporation) and cells in which the introduced DNA has homologously recombined with the endogenous DNA are selected. See e.g., Li et al., *Cell,* 69:915 (1992). The selected cells are then injected into a blastocyst of an animal (e.g., a mouse or rat) to form aggregation chimeras. See e.g., Bradley, in *Teratocarcinomas and Embryonic Stem Cells: A Practical Approach*, E. J. Robertson, ed. (IRL, Oxford, 1987). pp. 113-152. A chimeric embryo can then be implanted into a suitable pseudopregnant female foster animal and the embryo brought to term to create a "knock-out" animal. Progeny harboring the homologously recombined DNA in their germ cells can be identified by standard techniques and used to breed animals in which all cells of the animal contain the homologously recombined DNA. Knockout animals can be characterized, for instance, by their ability to defend against certain pathological conditions and by their development of pathological conditions due to absence of the WISP polypeptide.

In particular, assays in which CTGF, IGFBPs, and other members of the CTGF superfamily and other growth factors are usually used are preferably performed with the WISP-1 and WISP-2 polypeptides. For example, an assay to determine whether TGF-β induces the WISP polypeptide, indicating a role in cancer, may be performed as known in the art, as well as assays involving induction of cell death and $^3$H-thymidine proliferation assays. Mitogenic and tissue growth assays are also performed with the WISP polypeptide as set forth above. The results are applied accordingly.

The WISP polypeptides of the present invention may also be used to induce the formation of anti-WISP polypeptide antibodies, which are identified by routine screening as detailed below.

In addition to their uses above, the WISP-1, WISP-2, and WISP-3 polypeptides of the present invention are useful as the basis for assays of IGF activity. Importantly, since such an assay measures a physiologically significant binding event, i.e., that of an IGF to its IGFBP, triggering a detectable change (such as phosphorylation, cleavage, chemical modification, etc.). It is unlikely to be both more sensitive and more accurate than immunoassays, which detect the physiologically non-significant binding of an IGF to anti-WISP polypeptide antibody. Although more sensitive and accurate than antibodies, the WISP-1, WISP-2, and WISP-3 molecules of the invention can be used to assay IGF (such as IGF-I or IGF-II) levels in a sample in the same ways in which antibodies are used.

For diagnostic purposes, the WISP-1, WISP-2, or WISP-3 polypeptide can be used in accordance with immunoassay technology. Examples of immunoassays are provided by Wide at pages 199-206 of *Radioimmune Assay Method*, Kirkham and Huner, ed. E & S. Livingstone. Edinburgh. 1970.

Thus, in one embodiment. WISP-1, WISP-2, and WISP-3 polypeptides can be detectably labeled and incubated with a test sample containing IGF molecules (such as biological fluids, e.g. serum, sputum, urine, etc.), and the amount of WISP-1, WISP-2, or WISP-3 molecule bound to the sample ascertained.

Immobilization of reagents is required for certain assay methods. Immobilization entails separating the WISP-1, WISP-2, or WISP-3 polypeptide from any analyte that remains free in solution. This conventionally is accomplished by either insolubilizing the WISP-1, WISP-2, or WISP-3 polypeptide before the assay procedure, as by adsorption to-a-water-insoluble matrix or surface (Bennich et al . . . U.S. Pat. No. 3,720,760), by covalent coupling (for example, using glutaraldehyde cross-linking), or by insolubilizing the molecule afterward. e.g. by immunoprecipitation.

The foregoing are merely exemplary diagnostic assays for IGF. Other methods now or hereafter developed for the determination of these analytes are included within the scope hereof.

WISP-1, WISP-2, and WISP-3 polypeptides are also useful in radioimmunoassays to measure !GFs such as IGF-I or IGF-II. Such a radioimmunoassay would be conducted as described in the literature using the naturally purified or recombinant WISP-1, WISP-2 or WISP-3 as the WISP element.

In addition, WISP polypeptides are useful for screening for compounds that bind to them as defined above. Preferably, these compounds are small molecules such as organic or peptide molecules that exhibit one or more of the desired activities. Screening assays of this kind are conventional in the art, and any such screening procedure may be employed, whereby the test sample is contacted with the WISP polypeptide herein and the extent of binding and biological activity of the bound molecule are determined.

More specifically, this invention encompasses methods of screening compounds to identify those that mimic the WISP polypeptide (agonists) or prevent the effect of the WISP polypeptide (antagonists). Screening assays for antagonist drug candidates are designed to identify compounds that bind or complex with the WISP polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a WISP polypeptide encoded by a nucleic acid identified herein under conditions and for a time sufficient to allow these two components to interact.

In binding assays, the interaction is binding and the complex formed can be isolated or detected in the reaction mixture. In a particular embodiment, the WISP polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the WISP polypeptide and drying. Alternatively, an immobilized antibody, e.g., a monoclonal antibody, specific for the WISP polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular WISP polypeptide encoded by a gene identified herein, its interaction with that polypeptide can be assayed by methods well known for detecting protein-protein interactions. Such assays include traditional approaches, such as, e.g., cross-linking co-immunoprecipitation, and co-purification through gradients or chromatographic columns. In addition, protein-protein interactions can be monitored by using a yeast-based genetic system described by Fields and co-workers (Fields and Song, *Nature* (London), 340: 245-246 (1989); Chien et al., *Proc. Natl. Acad. Sci. USA,* 88: 9578-9582 (1991)) as disclosed by Chevray and Nathans, *Proc. Natl. Acad. Sci. USA,* 89: 5789-5~93 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a WISP polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

If the WISP polypeptide has the ability to stimulate the proliferation of endothelial cells in the presence of the co-mitogen ConA, then one example of a screening method takes advantage of this ability. Specifically, in the proliferation assay, human umbilical vein endothelial cells are obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the compound to be screened are added and after incubation at 37° C., cultures are pulsed with $^{3-}$H-thymidine and harvested onto glass fiber filters (phD; Cambridge Technology, Watertown, Mass.). Mean $^{3-}$(H)-thymidine incorporation (cpm) of triplicate cultures is determined using a liquid scintillation counter (Beckman Instruments, Irvine, Calif.). Significant $^{3-}$(H) thymidine incorporation indicates stimulation of endothelial cell proliferation.

To assay for antagonists, the assay described above is performed; however, in this assay the WISP polypeptide is added along with the compound to be screened and the ability of the compound to inhibit $^{3-}$(H)-thymidine incorporation in the presence of the WISP polypeptide indicates that the compound is an antagonist to the WISP polypeptide. Alternatively, antagonists may be detected by combining the WISP polypeptide and a potential antagonist with membrane-bound WISP polypeptide receptors or recombinant receptors under appropriate conditions for a competitive inhibition assay. The WISP polypeptide can be labeled, such as by radioactivity, such that the number of WISP polypeptide molecules bound to the receptor can be used to determine the effectiveness of the por-ential antagonist. The gene encoding the receptor can be identified by numerous methods known to those of skill in the art, for example, ligand panning and FACS sorting. Coligan et al., *Current Protocols in Immun.,* 1 (2): Chapter 5 (1991). Preferably, expression cloning is employed wherein polyadenylated RNA is prepared from a cell responsive to the WISP polypeptide and a cDNA library created from this RNA is divided into pools and used to transfect COS cells or other cells that are not responsive to the WISP polypeptide. Transfected cells that are grown on glass slides are exposed to labeled WISP polypeptide. The WISP polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled WISP polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled WISP polypeptide in the presence of the candidate compound. The ability of the compound to enhance or block this interaction could then be measured.

The compositions useful in the treatment of WISP-related disorders include, without limitation, antibodies, small organic and inorganic molecules, peptides, phosphopeptides, antisense and ribozyme molecules, triple-helix molecules, etc—, that inhibit the expression and/or activity of the target gene product.

More specific examples of potential antagonists include an oligonucleotide that binds to the WISP polypeptide, (poly) peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the WISP polypeptide that recognizes the receptor but imparts no effect, thereby competitively inhibiting the action of the WISP polypeptide.

Another potential WISP polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to D13A or RNA. For example, the 5' coding portion of the polynucleotide sequence, which encodes the mature WISP polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6: 3073 (1979); Cooney et al., *Science,* 241: 456 (1988); Dervan et al., *Science,* 251: 1360 (1991)), thereby preventing transcription and the production of the WISP polypeptide. The antisense RNA oligonucleotide hybridizes to the mRNA in vivo and blocks translation of "he mRNA molecule into the WISP polypeptide (anti-sense,—Okano, *Neurochem.,* 56: 560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the WISP polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the WISP polypeptide, thereby blocking the normal biological activity of the WISP polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4: 469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

WISP-1, WISP-2, and WISP-3 polypeptides are additionally useful in of Irinity purification of an 1GF that binds to WISP-1. WISP-2, or WISP-3 (such as, for example. IGF-I) and in purifying antibodies thereto. The WISP-1, WISP-2, or WISP-3 is typically coupled to an immobilized resin such as Affi-Gel 10™ (Bio-Rad. Richmond, Calif.) or other such resins (support matrices) by means well known in the art. The resin is equilibrated in a buffer (such as one containing 150 mM NaCl. 20 mM HEPES, pH 7.4 supplemented to contain 20% glycerol and 0.5% NP-40) and the preparation to be purified is placed in contact with the resin, whereby the molecules are selectively adsorbed to the WISP-1, WISP-2, or WISP-3 on the resin.

The resin is then sequentially washed with suitable buffers to remove non-adsorbed material, including unwanted contaminants, from the mixture to be purified, using, e.g. 150 mM NaCl. 20 mM HEPES, pH 7.4, containing 0.5% NP-40: 150 mM NaCl, 20 mM HEPES, pH 7.4 containing 0.5 M NaCl and 0.1% NP-40: 150 mM NaCl. 20 mM HEPES, pH 7.4 containing 0.1% deoxycholate: 150 mM NaCl. 20 mM HEPES, pH 7.4 containing 0.1% NP-40: and a solution of 0.1% NP-40.20% glycerol and 50 mM glycine, pH 3. The resin is then treated so as to elute the 1GF using a buffer that will break the bond between the 1GF and WISP-1, WISP-2, or WISP-3 (using. e.g. 50 mM glycine, pH 3. 0.1% NP-40.20% glycerol, and 100 mM NaCl).

It is contemplated that the WISP polypeptides of the present invention may be used to treat various conditions, including those characterized by overexpression and/or activation of at least the Wnt pathway. Further, since the WISP-1, WISP-2, and WISP-3 molecules respond to hormone-expressed breast cancer in mice and are abnormally expressed in human cancer, and are over-amplified in various colon cancer cell lines, they are useful in diagnosing cancer, for example, as a marker for increased susceptibility to cancer or for having cancer. Exemplary conditions or disorders to be treated with the WISP polypeptides include benign or malignant tumors (e.g., renal, liver, kidney, bladder, testicular, breast, gastric, ovarian, colorectal, prostate, pancreatic, lung, esophageal, vulval, thyroid, hepatic carcinomas; sarcomas; glioblastomas; and various head and neck tumors); leukemias and lymphoid malignancies; other disorders such as neuronal, glial, astrocytal, hypothalamic, and other glandular, macrophagal, epithelial, stromal, and blastocoelic disorders; cardiac disorders; renal disorders; catabolic disorders; bone-related disorders such as osteoporosis; and inflammatory, angiogenic, and immunologic disorders, such as arteriosclerosis; as well as connective tissue disorders, including wound healing.

The WISP polypeptides of the invention are administered to a mammal, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Intravenous or subcutaneous administration of the polypeptide is preferred.

Therapeutic formulations of the WISP polypeptide are prepared for storage by mixing the polypeptide having the desired degree of purity with optional pharmaceutically acceptable carriers, excipients, or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or polyethylene glycol (PEG).

Other therapeutic regimens may be combined with the administration of the WISP polypeptides of the instant invention. For example, the patient to be treated with the polypeptides disclosed herein may also receive radiation therapy if the disorder is cancer. Alternatively, or in addition, a chemotherapeutic agent may be administered to the patient with cancer. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede or follow administration of the polypeptide or m6y be given simultaneously therewith. The polypeptide may be combined with an anti-oestrogeri compound such as tamoxifen or an anti-progesterone such as onapristone (see, EP 616812) in dosages known for such molecules.

It may be desirable also to co-administer with the WISP polypeptide (or anti-WISP polypeptide) antibodies against other tumor-associated antigens, such as antibodies which bind to HER-2, EGFR, ErbB2, ErbB3, ErbB4, or vascular endothelial factor (VEGF). Alternatively, or in addition, two or more different anti-cancer antibodies, such as anti-ErbB2 antibodies, may be co-administered to the patient with the WISP polypeptide (or anti-WISP polypeptide antibody). Sometimes, it may be beneficial also to administer one or more cytokines to the patient.

In a preferred embodiment, the WISP polypeptide is co-administered with a growth-inhibitory agent to the cancer patient. For example, the growth-inhibitory agent may be administered first, followed by the WISP polypeptide. However, simultaneous administration or administration of the WISP polypeptide first is also contemplated. Suitable dosages for the growth-inhibitory agent are those presently used and may be lowered due to the combined action (synergy) of the growth-inhibitory agent and polypeptide. The antibodies, cytotoxic agents, cytokines, or growth-inhibitory agents are suitably present in combination in amounts that are effective for the purpose intended.

The active ingredients may also be entrapped in microcapsules prepared, for example, by coacervation techniques or by interfacial polymerization, for example, hydroxymethyl cellulose or gelatin microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences,* 16th edition, Osol, A. Ed. (1980), supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene7vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For the prevention or treatment of disease or disorder, the appropriate dosage of WISP polypeptide will depend on the type of disorder to be treated, as defined above, the severity and course of the disorder, whether the polypeptide is administered for preventive or therapeutic purposes, previous therapy, the patient's clinical history and response to the polypeptide, the route of administration, the condition of the patient, and the discretion of the attending physician. The polypeptide is suitably administered to the patient at one time or over a series of treatments.

Depending on the type and severity of the disease, about 1 µg/kg to 15 mg/kg (e.g., 0.1-20 mg/kg) of WISP polypeptide is an initial candidate dosage for administration to the patient, whether, for example, by one or more separate administrations, or by continuous infusion. A typical daily dosage might range from about 1 pg/kg to 100 mg/kg or more, depending on the factors mentioned above. For repeated administrations over several days or longer, depending on the condition, the treatment is sustained until a desired suppression of svmproms of the disorder occurs. However, other dosage regimens may be useful. The progress of this therapy is easily monitored by conventional techniques and assays. In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). The active agent in the composition is the WISP polypeptide. The label on, or associated with, the container indicates that the composition is used for treating the condition or disorder of choice. The article of manufacture may further comprise a second container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

F. Anti-WISP Polypeptide Antibodies

The present invention further provides anti-WISP polypeptide antibodies. Exemplary antibodies include polyclonal, monoclonal, humanized, bispecific, and heteroconjugate antibodies.

1. Polyclonal Antibodies

The anti-WISP polypeptide antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the WISP polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-WISP polypeptide antibodies may, alternatively, be monoclonal antibodies. Monoclonal antibodies may be prepared using hybridoma methods, such as those described by Kohler and Milstein, *Nature,* 256: 4 95 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the WISP polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as PEG, to form a hybridoma cell. Goding, *Monoclonal Antibodies: Principles and Practice* (Academic Press: New York, 1986) pp. 59-103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif., and the American Type Culture Collection, Manassas, Va. Human myeloma and mouse-human heteromyeloma cell lines also have been described for the production of human monoclonal antibodies. Kozbor, *J. Immunol.,* 133:3001 (1984); Brodeur et al., *Monoclonal Antibody Production Techniques and Applications* (Marcel Dekker, Inc.: New York, 1987) pp. 51-63.

The culture medium in which the hybridoma cells are cultured can then be assayed for the presence of monoclonal antibodies directed against a WISP polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107: 220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, CHO cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA*, 81: 6851-6855 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

3. Humanized Antibodies

The anti-WISP antibodies of the invention may further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity-determining region (CDR) of the recipient are replaced by residues from a CDR of a non-human species (donor antibody) such as mouse, rat, or rabbit having the desired specificity, affinity, anj capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an Fc, typically that of a human immunoglobulin. Jones et al., *Nature*, 321:522-525 (1986); Riechmann et al., *Nature*, 332: 323-329 (1988); Presta, *Curr. Op. Struct. Biol.*, 2:593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produce a using various techniques known in the art, including phage-display libraries. Hoogenboom and Winter, *J. Mol. Biol.*, 227:381 (1991); Marks et al., *J. Mol. Biol.*, 222:581 (1991). The techniques of Cole et al. and Boerner et al. are also available for the preparation of human monoclonal antibodies. Cole et al., *Monoclonal Antibodies and Cancer Therapy*, Alan R. Liss, p. 7? (1985); Boerner et al., *J. Immunol.*, 147(1):86-95 (1991).

4. Bispecific Antibodies

Bispecific antibodies are monoclonal, preferably human or humanized, antibodies that have binding specificities for at least two different antigens. In the present case, one of the binding specificities is for a WISP polypeptide; the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions, it is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121-210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection. WO 91/00360; WO 92/200373; EP 03089. It is contemplated that the antibodies may be prepared in vitro using known methods in synthetic protein chemistry, including those involving cross-linking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-WISP Polypeptide Antibodies

The antibodies of the invention may be used as affinity purification agents. In this process, the antibodies are immobilized on a solid phase such a SEPHADEX™ resin or filter paper, using methods well known in the art. The immobilized antibody is contacted with a sample containing the WISP polypeptide (or fragment thereof) to be purified, and thereafter the support is washed with a suitable solvent that will remove substantially all the material in the sample except the WISP protein, which is bound to the immobilized antibody. Finally, the support is washed with another suitable solvent, such as glycine buffer, pH 5.0, that will release the WISP polypeptide from the antibody.

Anti-WISP polypeptide antibodies may also be useful in diagnostic assays for WISP polypeptide, e.g., detecting its expression in specific cells, tissues, or serum. Thus, the antibodies may be used in the diagnosis of human malignancies (see, for example, U.S. Pat. No. 5,183,884).

For diagnostic applications, the antibody typically will be labeled with a detectable moiety. Numerous labels are available which can be preferably grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2. Coligen et al., Ed., (Wiley-Interscience: New York, 1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin, and Texas Red are available. The fluorescent labels can be conjugated to the antibody using the techniques disclosed in *Current Protocols in Immunology*, supra, Coligen, ed., for example. Fluorescence can be quantified using a fluorimeter.

(c) Various enzyme-substrate labels are available, and U.S. Pat. No. 4,275,149 provides a review of some of these. The enzyme preferably catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucoge-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., *Methods for the Preparation of Enzyme-Antibody Conjugates for use in Enzyme Immunoassay, in Methods in Enzym.*, Vol. 73, Langone and Van Vunakis, eds. (New York: Academic Press, 1981), pp. 147-166.

Examples of enzyme-substrate combinations include:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (4-methylumbelliferyl-β-D-galactosidase).

Numerous other enzyme-substrate combinations are available to those skilled in the art. For a general review of these, see, for example, U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-WISP polypeptide antibody need not be labeled, and the presence thereof can be detected using a labeled antibody which binds to the anti-WISP polypeptide antibody.

The antibodies of the present invention may be employed in any known assay method, such as competitive binding assays, direct and indirect sandwich assays, and immunoprecipitation assays. Zola, *Monoclonal Antibodies: A Manual of Techniques* (New York: CRC Press, Inc., 1987), pp. 147-158.

Competitive binding assays rely on the ability of a labeled standard to compete with the test sample analyte for binding with a limited amount of antibody. The amount of WISP protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of bincting to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Preferably, the antibody is labeled with a radionuclide (such as $^{111}$In, $^{99}$Tc, $^{14}$C, $^{131}$I, $^{125}$I, $^{3}$H, $^{32}$P or $^{32}$S) so that the tumor can be localized using immunoscintiography.

Additionally, anti-WISP polypeptide antibodies may be useful as antagonists to WISP polypeptide functions where WISP polypeptide is upregulated in cancer cells or stimulates their prolilferation or is upregulated in atheroscierotie-tissue. Hence, for example, the anti-WISP polypeptide antibodies may by themselves or with a chemotherapeutic agent or other cancer treatment or drug such as anti-HER-2 antibodies be effective in treating certain forms of cancer such as breast cancer, colon cancer, lung cancer, and melanoma. Further uses for the antibodies include inhibiting the binding of a WISP polypeptide to its receptor, if applicable, or to an IGF, if applicable. For therapeutic use, the antibodies can be used in the formulations, schedules, routes, and doses indicated above under uses for the WISP polypeptides. In addition, anti-WISP polypeptide antibody may be administered into the lymph as well as the blood stream.

As a matter of convenience, the anti-WISP antibody of the present invention can be provided as an article of manufacture such as a kit. An article of manufacture containing a WISP polypeptide or antagonists thereof useful for the diagnosis or treatment of the disorders described above comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle).

The active agent in the composition is the WISP polypeptide or an agonist or antagonist thereto. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above. A kit format generally is a packaged combination of reagents in predetermined amounts with instructions for performing the diagnostic or treatment assay.

If the active agent is an antibody that is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer), and the like. The relative amounts of the various reagents may be varied widely to provide for concentrations in solution of the reagents which substantially maximize the sensitivity of the assay. Particularly, the reagents may be provided as dry powders, usually lyophilized, including excipients which on dissolution will provide a reagent solution having the appropriate concentration.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Blvd., Manassas, Va.

Example 1

Isolation of cDNA Clones Encoding Mouse WISP-1

Several putative WISP genes have been identified at the m RNA level in a high-throughput PCR-select cDNA substraction experiment carried out using a mouse mammary cell line (C57MG), which has been transformed by a Wnt-1 retroviral vector and compared with the parental cell line. The WISP family disclosed herein, including the mouse WISP-1 gene, was induced only in the transformed cell line C57MGWnt-1.

1. Suppression Subtractive Hybridization

Mouse WISP-1 was isolated independently by Wnt-1 differential screening using suppression subtractive hybridization (SSH), as described by Diatchenko et al., *Proc. Natl. Acad. Sci. USA*, 93: 6025-6030 (1996). SSH was carried out using the PCR-SELECT®R cDNA Subtraction Kit (Clontech Laboratories, Inc.) according to the manufacturer's protocol. Driver double-stranded (ds) cDNA was synthesized from 2 micrograms of polyA+ RNA isolated from a mouse mammary cell line (C57MG), obtainable from a mouse breast cancer myoepithelial cell line. This cell line is described in Brown et al., *Cell*, 46: 1001-1009 (1986); Olson and Papkoff, *Cell Growth and Differentiation*, 5: 197-206 (1994); Wong et al., *Mol. Cell. Biol.*, 14: 6278-6286 (1994); and Jue et al., *Mol. Cell. Biol.*, 12: 321-328 (1992), and is responsive to Wnt-1 but not to Wnt-4. Tester ds cDNA was synthesized from 2 micrograms of polyA+ RNA isolated from a transformed version of C57MG, called C57MG/wnt-1.

The C57MG/wnt-1 mouse mammary derivative cell line was prepared by first transforming the parent line with a Wnt-1 retroviral vector, pBabe Puro (5.1 kb). This vector has a 5' LTR, packaging elements, a multiple cloning site, the puromycin-resistance gene driven off the SV40 promoter, a 3' LTR, and the bacterial elements for replication and ampicillin selection. The vector was modified slightly for Wnt-1 cloning by removing the HindIII site after the SV40 promoter and adding a HindIII site to the multiple cloning site. Wnt-1 is cloned from EcoRI-HindIII in the multiple cloning site. FIG. 13 shows a map of the vector.

The transformed derivative cells were grown up in a conventional fashion, and the final cell population was selected in DMEM+10% FCS with 2.5 µg/ml puromycin to stabilize the expression vector.

PCR was performed using the Clontech kit, including the cDNA synthesis primer (SEQ ID NO:40), adaptors 1 and 2 (SEQ ID NOS:41 and 42, respectively) and complementary sequences for the adaptors (SEQ ID NOS: 43 and 44, respectively), PCR primer 1 (SEQ ID NO:45), PCR primer 2 (SEQ ID NO:46), nested PCR primer 1 (SEQ ID NO:47), nested PCR primer 2 (SEQ ID NO:48), control primer G3PDH5' primer (SEQ ID NO:49), and control primer G3PDH3' primer (SEQ ID NO:50), shown in FIG. 14.

Products generated from the secondary PCR reaction were inserted into the cloning site region of pGEM-T vector (Promega), shown in FIG. 15 (SEQ ID NOS: 51 and 52 for 5' and 3' sequences, respectively). Plasmid DNAs were prepared using the WIZARD MINIPREP™ Kit (Promega). DNA sequencing of the subcloned PCR fragments was performed manually by the chain termination reaction (SEQUENASE 2.0™ Kit, Pharmacia). Nucleic acid homology searches were performed using the BLAST program noted above.

A total of 1384 clones were sequenced out of greater than 5000 tound. A total of 1996 DNA templates were prepared. A program was used to trim the vector off, and a different program used to cluster the clones into two or more identical clones or with an overlap of 50 bases the same. Then a BLAST was performed of a representative clone from the cluster. Primers were designed for RT-PCR to see if the clones were differentially expressed.

2. Semi-Quantitative RT-PCR

One of the clones was clone 568 having 71 bp, which was identified as encoding mouse WISP-1. There were six clones in this cluster. The nucleotide sequence and putative amino acid sequence of full-length mouse WISP-1 are shown in FIGS. 1A-1B (SEQ ID NOS: 9 and 12, respectively). RT-PCR primers were designed for confirming differential expression, screening for full-length mouse clone, and screening for the human clone. These primers were 568.PCR.top1 (nucleotides 909-932 of the full-length nucleotide sequence encoding mouse WISP-1 (SEQ ID NO:9) of FIGS. 1A-1B) and 568.PCR.bot1 (nucleotides 955-978 of the full-length complementary nucleotide sequence encoding mouse WISP-1.(SEQ ID NO:10) of FIGS. 1A-1B), which are as follows:

```
                                    (SEQ ID NO: 100)
568.PCR.top1: 5'-CCAGCCAGAGGAGGCCACGAAC (SEQ ID NO: 101)
568.PCR.bot1: 3'-TGTGCGTGGATGGCTGGGTTCATG
```

For the RT-PCR procedure, cell lines were grown to subconfluence before extracting the RNA. Total RNA was extracted using Stat-60™ (TEL-TEST™ B) per manufacturer's instructions. First-strand cDNA was prepared from 0.1 μg-3 μg of total RNA with the SUPERSCRIPT™ RT kit (Gibco, BRL). PCR amplification of 5 μl of first-strand cDNA was performed in a 50-μl PCR reaction. The above primers were used to amplify first-strand cDNA. As controls, primers corresponding to nucleotide positions 707-729 (sense; 5'-GTGGCCCATGCTCTGGCAGAGGG (SEQ ID NO: 102)) or 836-859 (sense; 5'-GACTGGAGCAAGGTCGTC-CTCGCC (SEQ ID NO: 103)) and 1048-1071 (anti-sense; 5'-GCACCACCCACAAGGAAGCCATCC (SEQ ID NO: 104)) of human triosephosphate isomerase (huTPI) (Maquat et al., *J. Biol. Chem.*, 260: 3748-3753 (1985); Brown et al., *Mol. Cell. Biol.*, 5: 1694-1706 (1985)) were used to amplify first-strand cDNA. For mouse triosephosphate isomerase, primers corresponding to nucleotide positions 433-456 (sense; 51-GACGAAAGGGAAGCCGGCATCACC (SEQ ID NO: 105)) or 457-480 bp (sense; 51-GAGAAGGTCGT-GTTCGAGCAAACC (SEQ ID NO: 106)) and 577-600 bp (antisense; 51-CTTCTCGTGTACTTCCTGTGCCTG (SEQ ID NO:107)) or 694-717 bp (antisense; 5'-CACGT-CAGCTGGCGTTGCCAGCTC (SEQ ID NO:108)) were used for amplification.

Briefly, 4 μCi of ($^{32}$P-)CTP (3000 Ci/mmol) was added to each reaction with 2.5 U of TAKARA EX TAQ™ (PanVera, Madison, Wis.) and 0.2 μM of each dNTP. The reactions were amplified in a 480 PCR THERMOCYCLER™ (Perkin Elmer) using the following conditions: 94° C. for 1 min., 62° C. for 30 sec., 72° C. for 1 min, for 18-25 cycles. 5 μl of PCR products were electrophoresed on a 6% polyacrylamide gel. The gel was exposed to film. Densitometry measurements were obtained using ALPHA EASE VERSION 3.3 a™ software (Alpha Innotech Corporation) to quantitate the WISP- or TPI-specific gene products.

3. Northern Blot Analysis

Adult multiple-tissue Northern blots (Clontech) and the Northern blot of the C57MG parent and C57MG/Wnt-1 derivative polyA+ RNA (2 μg/lane) were hybridized with a 70-bp mouse WISP-1 probe (amino acids 278 through 300 of FIG. 1A-1B; QPEEATNFTLAGCVSTRTYRPKY; SEQ ID NO:109) generated using the primers 568.PCR.top1 and 568.per.bot1 noted above. The membranes were washed in 0.1×SSC at 55-65° C. and exposed for autoradiography. Blots were rehybridized with a 75-bp synthetic probe from the human actin gene. See Godowski et al., *Proc. Natl. Acad. Sci. USA*, 86: 8083-8087 (1989) for a method for making a probe with overlapping oligos, which is how the actin probe was prepared.

4. cDNA Library Screening

Clones encoding the full-length mouse WISP-1 were isolated by screening a XgtlO oligodT primed mouse embryo library (Clontech) with the primers 568.PCR.top1 and 568.PCR.bot1 noted above. The inserts of 13 of these clones were subcloned into pBLUESCRIPT™ IISK+ and their DNA sequences determined by dideoxy DNA sequencing on both strands.

5. Results

The recently described technique of SSH combines a high subtraction efficiency with an equalized representation of differentially expressed sequences. This method is based on specific PCR reactions that permit exponential amplification of cDNAs which differ in abundance, whereas amplification of sequences of identical abundance in two populations is suppressed. The SSH technique was used herein to isolate genes expressed in a mouse mammary myoepithelial cell transformed with Wnt-1 whose expression is reduced or absent in the parental myoepithelial cell. The polyA RNA extracted from both types of cells was used to synthesize tester and driver cDNAs. The degree of subtraction efficiency was monitored by Southern blot analysis of unsubtracted and subtracted PCR products using a β-actin probe. No β-actin mRNA was apparent in the subtracted PCR products, confirming the efficiency of the subtraction.

The subtracted cDNA library was subcloned into a pGEM-T vector for further analysis. A random sample of 1996 clones was sequenced from the transformed colonies obtained. To determine if the clones obtained were differentially expressed, PCR primers were designed for selected clones and semi-quantitative RT-PCR and Northern analyses were performed using mRNA from the mouse mammary cell line and its derivative. It was found that expression of Wnt-1 in C57MG cells leads to elongated cell morphology and loss of contact inhibition.

One clone (m568.19A) of those that fulfilled the criteria for differential expression was found to encode full-length mouse WISP-1. By both RT-PCR analysis and Northern analysis, it was found that this clone provided an about three-fold induction in the Wnt-1 cell line over the parent cell line.

The cDNA sequence of this clone and deduced amino acid sequence of full-length mouse WISP-1 are shown in FIGS.

1A-1B (SEQ ID NOS:9 and 12, respectively) The sequence alignment of human and mouse WISP-1 (SEQ ID NOS:4 and 12, respectively) is shown in FIG. 8. In situ analysis of the clone is presented below, along with thymidine incorporation assay and angiostatic assay results.

This clone was placed in pRK5E, an *E. coli*-derived cloning vector having a human cytomegalovirus intermediate early gene promoter, an SV40 origin and polyA site, an sp6 transcription initiation site, a human immunoglobulin splice acceptor, and XhoI/NotI cDNA cloning sites. It is a progeny of pRK5D that has an added ScaI site. Holmes et al., *Science*, 253:1278-1280 (1991). Upon transformation into JM109 cells, the plasmid rendered the cells ampicillin resistant. Upon digestion with XbaI and BamHI, a 1140-bp fragment was obtained, and the mouse insert size was 1122 base pairs, from the ATG to the stop codon, including a 3' tag of six histidines.

Example 2

Isolation of a cDNA Clone Encoding Mouse WISP-2

The cDNA for mouse WISP-2 was isolated independently by Wnt-1 differential screening using the procedure described in Example 1. The initial clone isolated was 318 bp in length and was designated clone 1367. There were four clones in this cluster. The clone was sequenced as described above and RT-PCR primers were designed as follows:
1367.per.top1: nucleotides 1604-1627 of FIGS. 2A-2B:

```
3'-GGTGTGAAGACCGTCCGGTCCCGG    (SEQ ID NO: 110)
``` and
1367.per.bot1: nucleotides 1438-1461 of FIGS. 2A-2B:

```
5'-GTGT(3CCTTTCCTGATCTGAGAAC   (SEQ ID NO: 111)
```

After RT-PCR and Northern blot procedures were carried out as described in Example 1 to confirm differential expression, a five-fold induction in the Wnt-1 cell line was observed.

Clones encoding full-length mouse WISP-2 were isolated from RNA library 211:

C57MG/Wnt-1. mRNA for construction of this library was isolated from the C57MG/Wnt-1 cell line described in Example 1. The RNA was used to generate an oligo-dT-primed cDNA library in the cloning vector pRK5E using reagents and protocols from Life Technologies, Gaithersburg, Md. (SUPERSCRIPT PLASMID SYSTEM™).

In this procedure, the double-stranded cDNA was primed with oligo dT containing a NotI site, linked with blunt-to-SalI hemikinased adaptors, cleaved with NotI, sized to greater than 1000 bp appropriately by gel electrophoresis, and cloned in a defined orientation into the XhoI/NotI-cleaved pRK5E vector. The library was screened by colony hybridization with a probe 1367.50mer.1 of bases 1463-1512 of FIGS. 2A-2B:
3'-GGGACGGGCCGACCCTTCTTAAAAGAC-CCTTGTACTTCTCTACCTTAGTG (SEQ ID NO:112). The full-length mouse WISP-2 clone was obtained, designated clone 1367.3.

The cDNA for mouse WISP-2, like the mouse WISP-1 molecule, encodes a novel secreted protein that belongs to the CTGF family and has the mouse homologue of SST DNA33473 of Example 4. (The alignment of human and mouse WISP-2 (SEQ ID NOS: 16 and 20, respectively) is shown in FIG. 9.) The mouse WISP-2 gene is 38% identical in sequence to mouse wisp-1, disclosed in Example 1, but lacks the C-terminal 95 amino acids thought to be involved in dimerization and receptor binding. Mouse WISP-2 was highly expressed in the lung. In-situ analysis of the clone is noted below. The nucleotide sequence and putative amino acid sequence of full-length mouse WISP-2 are shown in FIGS. 2A-2B (SEQ ID NOS:17 and 20, respectively). The putative signal sequence is from amino acid positions 1 to 23 of SEQ ID:20.

The clone was inserted into pRK5E, described above. Upon transformation of JM109 cells, the plasmid rendered the cells ampicillin resistant, Upon digestion with BamHI and NotI, a 1770-bp fragment was obtained, having a mouse insert of 756 bp from ATG to the stop codon.

Example 3

Isolation of a cDNA Clone Encoding Human WISP-1

To isolate the full-length human clone corresponding to m568.19A (mouse WISP-1), a human lung cDNA library (Clontech), treated with the SUPERSCRIPT™ kit using the pRKSE vector as described above, was screened with a 70-bp probe at low stringency (20% formamide, 1×SSC, 55° C. wash). The probe had the sequence from nucleotides 909-978 of the full-length mouse WISP-1 nucleotide sequence of FIGS. 1A-1B, i.e., the sequence:

```
                                    (SEQ ID NO: 113)
51-CCAGCCAGAGGAGGCCACGAACTTCACTCTCGCAGGCTGTGTCAG

CACACGCACCTACCGACCCAAGTAC
```

Only one clone was identified, hL.568.15A. The insert to this clone was subcloned into pBLUESCRIPT™ IISK+ and its DNA sequence determined by dideoxy DNA sequencing on both strands. This clone was found to be missing about 280 amino acids. Hence, a new probe (hu.568.50mer.1) was designed from clone 15A having the nucleotides 750-799 of the full-length human WISP-1 nucleotide sequence shown in FIGS. 3A and 3B, i.e.,

```
                                    (SEQ ID NO: 114)
51-GCCCCTGGAGCCCTTGCTCCACCAGCTGCGGCCTGGGGGTCTCCA

CTCGG
```

This probe was used to screen a human fetal kidney cDNA library (Clontech) treated with the SUPERSCRIPT™ kit using the pRK5E vector as described above, by colony hybridization. A number of clones were obtained by screening this human fetal kidney cDNA library (clones without the A or B designation) or by screening a human fetal kidney λgt10 library (clones with the A or B designation) using the same probes described above. The inserts of these clones were subcloned into pBLUESCRIPT™ IISK+ and their DNA sequences determined by dideoxy DNA sequencing on both strands.

Two of these clones, designated as 568.1A and 568.4A, have their respective sequences (SEQ ID NOS:24 and 26) shown in FIGS. 27 and 29. These clones are missing the von Willebrand C1 domain, the variable domain, and the thrombospondin 1 domain, and have a frameshift, other clones, designated as 568.13, 568.39, 568.5A, 568.6B, and 568.7 (SEQ ID NOS:23, 25, 27, 28, and 29, respectively; FIGS. 26, 28, and 30-32, respectively), were obtained that lack one or more domains and/or short amino-acid stretches (e.g., an 8-amino-acid deletion) or contain additional short amino-acid stretches and may contain introns or alternative splice variants.

Two clones sharing a significant amount of sequence with the full-length clone 568.38 were identified: 568.23 and 568.35. Human clone 568.38 encoded the full-length human WISP-1. The nucleotide sequence and putative amino acid sequence for clone 568.38 are shown in FIGS. 3A-3C (SEQ ID NOS:1 and 4, respectively). The aligning sequences of clones 568.38 and 568.35 differ from the corresponding aligning sequences of clones 568.15A and 568.23 in that the respective sequences of the latter two clones have an isoleucine residue at amino acid position 184 of FIGS. 3A-3C, whereas the respective corresponding sequences of clones 568.38 and 568.35 have a valine residue at this position. Further, the aligning sequences of clones 568.35 and 568.38 differ from each other in that the sequence of clone 568.35 has a serine residue at amino acid position 202 of FIGS. 3A-3C, whereas the corresponding sequence of clone 568.38 has an alanine residue at this position.

The human WISP-1 polypeptide, by homology searching, is also found to be a member of the CTGF family. The clone was placed in a pRK5E plasmid as described above and deposited with the ATCC. Upon transformation into JM109 cells, the plasmid rendered the cells ampicillin resistant. Digestion with ClaI and EcoRV yielded a 1435-bp fragment with an insert size of 1104 basepairs from ATG to the stop codon.

In situ hybridization of human WISP-1 was performed, with the results given below. Northern analysis of human WISP-1 showed high expression in adult heart tissue and ovary tissue, and in fetal kidney tissue. Also presented below are thymidine incorporation assay, gene amplification assay, and angiostatic assay results.

The chromosomal location of the human WISP genes was determined by radiation hybrid mapping using the Stanford G3™ and the MIT Genebridge 4 Radiation Hybrid™ panels. WISP-1 resides at approximately 3.48 cR from the meiotic marker AFM259xc5 (LOD score 16.31) on the Genebridge map. This places WISP-1 in band 8q24.1 to 8q24.3, roughly four megabases distal to c-myc located at chromosome band 8q24.12-8q24.13. Takahashi et al., *Cytogenet. Cell Genet.*, 57: 109-111 (1991). c-myc is a region that is a recurrent site of amplification in non-small cell lung carcinoma.

Example 4

Isolation of a cDNA Clone Encoding Human PRO261 (Designated Herein as Human WISP-2)

The extracellular domain (ECD) sequences (including the secretion signal, if any) of from about 950 known secreted proteins from the SWISS-PROT™ public protein database were used to search expressed sequence tag (EST) databases. The EST databases included public EST databases (e.g., GenBank) and a proprietary EST DNA database (LIFESEQ™, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6-frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.: http://bozeman.mbt.washington.edu/phrap.docs/phrap.html).

A consensus DNA sequence was assembled relative to other EST sequences using phrap. The EST sequences used (from Incyte) were Nos. 2633736, 2118874, 360014, 2316216, 1985573, 2599326, 1544634, 2659601, 1319684, 783649, 627240, 1962606, 2369125, 939761, 1666205, 692911, 984510, 1985843, 2104709, and 2120142. This consensus sequence is herein designated DNA30843 (see FIG. 5). Based on the DNA30843 consensus sequence, oligonucleotides were synthesized: 1) to identify by PCR a cDNA library that contained the sequence of interest, and 2) for use as probes to isolate a clone of the full-length coding sequence for PRO261 (human WISP-2). A pair of PCR primers, forward and reverse, were synthesized having the respective sequences:

```
5'-AAAGGTGCGTACCCAGCTGTGCC      (SEQ ID NO: 115)
and

3'-TCCAGTCGGCAGAAGCGGTTCTGG.    (SEQ ID NO: 116)
```

Additionally, a synthetic oligonucleotide hybridization probe was constructed from the consensus DNA30843 sequence, which probe has the sequence:

```
                                  (SEQ ID NO: 117)
5'-CCTGGTGCTGGATGGCTGTGGCTGCTGCCGGGTATGTGCACGGCG

GCTGGG.
```

For screening several libraries for a source of a full-length clone, DNA from the libraries was screened by PCR amplification, as per Ausubel et al., *Current Protocols in Molecular Biology* (Green Publishing Associates and Wiley Interscience, N.Y., 1989), with the PCR primer pair identified above. A positive library was then screened by colony hybridization to isolate clones encoding PRO261 (human WISP-2) using the probe oligonucleotide and one of the PCR primers.

RNA for construction of the cDNA libraries was isolated from human fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt-to-SalT-hemikinased adaptors, cleaved with NotI, sized appropriately by gel electrophoresis, and cloned in a defined orientation into a suitable cloning vector (such as pRK5B or pRK5D; pRK5B is a precursor of pRK5D that does not contain the SfiI site; see Holmes et al., *Science*, 253:1278-1280 (1991)) in the unique XhoI and NotI sites.

DNA sequencing of the clones isolated as described above gave the DNA sequence for PRO261 (herein designated as UNQ228 (DNA33473-seq min); SEQ ID NO:38), which begins at nucleotide 34 of SEQ ID NO:13 (FIG. 4A-4B) and the derived amino acid sequence for PRO261 (SEQ ID NO:16).

The entire nucleotide sequence encoding human WISP-2 is shown in FIGS. 4A-4B (SEQ ID NO:13). This sequence contains a single open reading frame with an apparent translational initiation site at nucleotide positions 22-24 of SEQ ID NO:13 and ending at the stop codon after nucleotide 770 of SEQ ID NO:13 (FIGS. 4A-4B). The predicted polypeptide precursor is 250 amino acids long (FIGS. 4A-4B). The putative signal sequence spans from amino acid positions 1' to 23 of SEQ ID NO:16. Clone UNQ228 (DNA33473-seq min) has been deposited with ATCC and is assigned ATCC deposit no. 209391.

Analysis of the amino acid sequence of the full-length PR0261 polypeptide suggests that portions of it possess significant homology to CTGF, thereby indicating that PR0261 is a novel growth factor.

The entire nucleotide sequence encoding human WISP-3 from this clone is shown in FIGS. 6A-6C (SEQ ID NO:30) This sequence contains a single open reading frame with an apparent translational initiation site at nucleotide positions 46-48 of SEQ ID NO:30 and ending at the stop codon after nucleotide 1161 of SEQ ID NO:30 (FIGS. 6A-6C). The predicted polypeptide precursor is 372 amino acids long (FIGS. 6A-6C). The putative signal sequence is from amino acid positions 1 to 33 of SEQ ID NO:33. Clone UNQ462 (DNA56350-1176-2) has been deposited with ATCC and is assigned ATCC deposit no. 209706.

Example 5

Isolation of cDNA Clones Encoding Human WISP-3

In this example, the gene encoding WISP-3 was cloned twice essentially in parallel. First, it was determined whether the databases described above contained any new members of the WISP family. Two EST homologies to the WISPs were found and both were cloned. Full-length clones were isolated corresponding to each of these EST homologies. The efforts resulted in two full-length clones of the same gene (the original EST homologies had been from distinct regions of the same gene). The first clone obtained was designated as DNA56350 and the second as DNA58800.

DNA56350

Based on the sequence of INCYTE 3208053, a virtual DNA 48917 was obtained and oligonucleotides were synthesized for use as probes to isolate a clone of the full-length coding sequence for PRO956 (human WISP-3). A pair of PCR primers, forward and reverse, were synthesized having the sequences:

5'-GTCTTGTGCAAGCAACAAAATGGACTCC    (SEQ ID NO: 118)

3'-GACACAATGTAAGTCGGAACGCTGTCG    (SEQ ID NO: 119)

Additionally, a synthetic oligonucleotide hybridization probe was constructed from the INCYTE sequence, which probe has the sequence:

(SEQ ID NO: 120)
5'-GCTCCAGAACATGTGGGATGGGAATATCTAACAGGGTGACCAATG

AAAAC

A human fetal kidney library primed with oligo dT containing a XhoI-NotI size cut greater than 3700 kb was screened for a source of a full-length clone by PCR amplification with the PCR primer pair identified above. The positive library was then used to isolate clones encoding PRO956 (human WISP-3) using the probe oligonucleotide and one of the PCR primers.

DNA sequencing of the clone isolated as described above gave the DNA sequence for PR0956 (herein designated as UNQ462 (SEQ ID NO:30), and the derived amino acid sequence for PR0956 (SEQ ID NO:33).

The entire nucleotide sequence encoding human WISP-3 from this clone is shown in FIG. 6 (SEQ ID NO:30). This sequence contains a single open reading frame with an apparent translational initiation site at nucleotide positions 46-48 of SEQ ID NO:30 and ending at the stop codon after nucleotide 1161 of SEQ ID NO:30 (FIG. 6). The predicted polypeptide precursor is 372 amino acids long (FIG. 6). The putative signal sequence is from amino acid positions 1 to 33 of SEQ ID NO:33. Clone UNQ462 (DNA56350-1176-2) has been deposited with ATCC and is assigned ATCC deposit no. 209706.

Analysis of the amino acid sequence of the full-length PRO956 polypeptide suggests that portions of it possess significant homology to CTGF, thereby indicating that PRO956 is a novel growth factor. This clone has an additional methionine just 5' of the first methionine in this clone. The amino acid sequence of this clone is 42% homologous to that of human WISP-1, and 32% r homologous to that of human WISP-2.

In situ hybridization of human WISP-3 is shown below. Using the mapping techniques set forth above, it was found that human WISP-3 was localized to chromosome 6q22-6q23 and was linked to the marker AFM211ze5 with a LOD score of 1000. WISP-3 is approximately 18 megabases proximal to CTGF and 23 megabases proximal to the human cellular oncogene MYB, which are also located at 6q22-6q23. Martinerie et al., *Oncogene,* 7: 2529-2534 (1992); Meese et al., *Genes Chromosomes Cancer,* 1: 88-94 (1989).

The clone was inserted into pRK5E, described above. Upon transformation of JM109 cells, the plasmid rendered the cells ampicillin resistant. Upon digestion with BamHI and NotI, a fragment was obtained having a human insert from ATG to the stop codon as indicated in FIG. 6.

DNA58800

Based on the sequence of HS142L7, a virtual DNA 56506 was obtained and oligonucleotides were synthesized for use as probes to isolate a clone of the full-length coding sequence for PRO790 (human WISP-3). To this end, a pair of PCR primers, forward and reverse, were synthesized having the sequences:

5'-CCTGGAGTGAGCCTGGTGAGAGA    (SEQ ID NO: 121)

3'-ACACTGGGTGTGTTTCCCGACATAACA    (SEQ ID NO: 122)

Additionally, a synthetic oligonucleotide hybridization probe was constructed from the HS142L7 sequence, which probe has the sequence:

(SEQ ID NO: 123)
5'-TGGTTGCTTGGCACAGATTTTACAGCATCCACAGCCATCTCTCA

A human bone marrow library primed with oligo dT containing a XhoI-NotI size cut of 1-3 kb was screened for a source of a full-length clone by PCR amplification with the PCR primer pair identified above. The positive library was then used to isolate clones encoding PRO790 (human WISP-3) using the probe oligonucleotide and one of the PCR primers.

DNA sequencing of the clone isolated as described above gave the DNA sequence for PRO790 (SEQ ID NO:34), and the derived amino acid sequence for PRO790 (SEQ ID NO:37).

The entire nucleotide sequence encoding human WISP-3 from this clone is shown in FIGS. 7A-7C (SEQ ID NO:34). This sequence contains a single open reading frame with an apparent translational initiation site at nucleotide positions 16-18 of SEQ ID NO:34 and ending at the stop codon after nucleotide 1077 of SEQ ID NO:34 (FIGS. 7A-7C). The predicted polypeptide precursor is 355 amino acids long (FIGS. 7A-7C). The putative signal sequence spans from amino acid positions 1 to 15 of SEQ ID NO:37. This clone DNA58800-1176-2 has been deposited with ATCC and is assigned ATCC deposit no. 209707.

Analysis of the amino acid sequence of the full-length PRO790 polypeptide suggests that portions of it possess significant homology to CTGF, thereby indicating that, like PRO956 which is a splice variant thereof, PRO790 is a novel growth factor.

In situ hybridization of human WISP-3 is shown below.

The clone was inserted into pRK5E, described above. Upon transformation of JM109 cells, the plasmid rendered the cells ampicillin resistant. Upon digestion with BamHI and NotI, a fragment was obtained having a human insert from ATG to the stop codon as indicated in FIGS. 7A-7C.

Example 6

Use of WISP-Encoding DNA as a Hybridization Probe

The following method describes use of a nucleotide sequence encoding a WISP polypeptide as a hybridization probe.

DNA comprising the coding sequence of full-length or mature human WISP-1 (as shown in FIGS. 3A-3C, SEQ ID NOS:4 or 3, respectively), or full-length or mature mouse WISP-1 (as shown in FIGS. 1A-1B, SEQ ID NOS:12 or 11, respectively), or of full-length or putative mature human WISP-2 (as shown in FIG. 4A-4B, SEQ ID NOS:16 or 15, respectively), or full-length or putative mature mouse WISP-2 (as shown in FIGS. 2A-2B, SEQ ID NOS:20 or 19, respectively) is employed as a probe to screen for homologous DNAs (such as those encoding naturally occurring variants of these particular WISP proteins in human tissue cDNA libraries or human tissue genomic libraries.

Hybridization and washing of filters containing either library DNAs is performed under the following high-stringency conditions. Hybridization of radiolabeled WISP-polypeptide-derived probe (such as UNQ228 (DNA33473-seq min)-derived probe) to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding a full-length, native-sequence WISP polypeptide can then be identified using standard techniques known in the art.

Example 7

Expression of WISP Polypeptide in E. coli

This example illustrates preparation of an unglycosylated form of WISP polypeptide by recombinant expression in E. coli.

The DNA sequence encoding WISP polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2: 95 (1977)) which contains genes for ampicillin and tetracycline resistance. The vector is digested with restriction enzyme and dephosphorylated. The PCR-amplified sequences are then ligated into the vector. The vector will preferably include sequences which encode an antibiotic-resistance gene, a trp promoter, a polyhis leader (including the first six STII codons, polyhis sequence, and enterokinase cleavage site), the WISP-coding region, lambda transcriptional terminator, and an argU gene.

The ligation mixture is then used to transform a selected E. coli strain using the methods described in Sambrook et al., supra. Transformants are identified by their ability to grow on LB plates, and antibiotic-resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger-scale culture. The cells are then grown to a desired optical density, during which the expression promoter is turned on.

After the cells are cultured for several more hours, the cells can be harvested by centrifugation. The cell pellet obtained by the centrifugation can be solubilized using various agents known in the art, and the WISP polypeptide can then be purified using a metal-chelating column under conditions that allow tight binding of the protein.

Example 8

Expression of WISP Polypeptide in Mammalian Cells

This example illustrates preparation of a potentially glycosylated form of WISI-polypeptide by recombinant expression in mammalian cells.

The vector, pRK5E, was employed as the expression vector. The appropriate DNA encoding WISP polypeptide was ligated into pRK5E with selected restriction enzymes to allow insertion of the DNA for WISP polypeptide using ligation methods as described in Sambrook et al., supra. The resulting vectors were pRK5E.h.WIG-1.568.38, pRK5E.m.WIG-1.568.6his, pRK5E-m.WIG-2.1367.3, plasmid encoding human WISP-2, DNA56350-1176-2, and DNA58800-1176-2, all deposited at the ATCC. These vectors are conveniently referred to collectively as pRK5E.WISP in the general description below.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 αg pRK5E.WISP DNA is mixed with about 1 pg DNA encoding the VA RNA gene (Thimmappaya et al., Cell, 31:543 (1982)) and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in phosphate-buffered saline (PBS) is added for 30 seconds. The 293 cells are then washed with serum-free medium, fresh medium is added, and the cells are incubated for about 5 days.

Approximately 24 hours after the transfections, the culture medium is removed and replaced with culture medium (alone) or culture medium containing 200 μCi/ml $^{35}$S-cysteine and 200 μCi/M1 $^{35}$S-methionine. After a 12-hour incubation, the conditioned medium is collected, concentrated on a spin filter, and loaded onto a 15% SDS gel. The processed gel may be dried and exposed to film for a selected period of time to reveal the presence of the WISP polypeptide. The cultures containing transfected cells may undergo further incubation (in serum-free medium) and the medium is tested in selected bioassays.

In an alternative technique, the WISP polypeptide may be introduced into 293 cells transiently using the dextran sulfate method described by Somparyrac et al., *Proc. Natl. Acad. Sci.* 12:7575 (1981). 293 cells are grown to maximal density in a spinner flask and 700 pg pRK5E.WISP DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin, and 0.1 μg/ml bovine transferrin. After about four days, the conditioned media are centrifuged and filtered to remove cells and debris. The sample containing expressed WISP polypeptide can then be concentrated and purified by any selected method, such as dialysis and/or column chromatography.

In another embodiment, the WISP polypeptide can be expressed in CHO cells. The pRK5E.WISP can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of the WISP polypeptide, the culture medium may be replaced with serum-free medium. Preferably, the cultures are incubated for about 6 days, and then the conditioned medium is harvested. The medium containing the expressed WISP polypeptide can then be concentrated and purified by any selected method.

Epitope-tagged WISP polypeptide may also be expressed in host CHO cells. The WISP polypeptide may be subcloned out of the pRK5 vector. Suva et al., *Science*, 237: 893-896 (1987); EP 307,247 published Mar. 15, 1989. The subclone insert can undergo PCR to fuse in-frame with a selected epitope tag such as a poly-his tag into a baculovirus expression vector. The poly-his-tagged WISP polypeptide insert can then be subcloned into a SV40-driven vector containing a selection marker such as DHFR for selection of stable clones. Finally, the CHO cells can be transfected (as described above) with the SV40-driven vector. Labeling may be performed, as described above, to verify expression. The culture medium containing the expressed poly-His-tagged WISP can then be concentrated and purified by any selected method, such as by $Ni^{2+}$-chelate affinity chromatography.

In particular, mouse WISP-1 cDNA for insertion into mammalian expression vectors was created via PCR using clone m568.19A (see above) pure phage DNA as template and using as primers m.568.per.top4 (5'-TGACTTCCAG-GCATGAGGTGGCTCCTG; SEQ ID NO:124) and m.568.per.bot3 (5'-ATTGGCAATCTCTTCGAAGT-CAGGGTAAGATTCC; SEQ ID NO:125) for the 6-his version, or m.568.per.top4 (SEQ ID NO:124) and 568.per.bot5, which has a 3'-terminal XbaI site (5'-GGTACGTCTAGAC-TAATTGGCAATCTCTTCGAAGTCAGGG; SEQ ID NO:126) for the non-his version. The insert integrity was confirmed by sequencing and analyzed. The PCR was run using Pfu polymerase and the conditions were:

| | temp. | time |
|---|---|---|
| denaturation | 94° C. | 1 min |
| annealing | 62° C. | 30 sec |
| extension | 72° C. | 1.5 min | of cycles: 25

For transient expression in 293 cells analyzed by Western blot, the above inserts were ligated into the pRK5 vector referred to above at the BamHI/XbaI site using the BOE-HRINGER MANNHEIM™ rapid ligation kit. The resulting plasmids were designated pRK5.mu.WISP-1.6his and pRK5.mu.WISP-1, nohis for the His-tagged and non-His-tagged inserts, respectively. Then the 293 cells were plated and allowed to reach approximately 85% confluency overnight (37° C./5% $CO_2$). The plated cells were transfected with plasmid DNA pRK5.mu.WISP-1.6his or pRK5.mu.WISP-1.nohis by using lipofectamine (Gibco BRL) at a 4.5:1 lipid:DNA ratio.

Transfection efficiency (>70% usually) was monitored using a GFP expression plasmid (pGREEN LANTERN™ from Gibco BRL). Approximately 5 hours post-transfection, the medium was changed to fresh SF media (50:50 with 1×L-Glu and 1×P/S) for protein production. The conditioned media was—allowed to accumulate for specified amounts of time (depending on the experiment) before harvesting.

The medium was harvested and concentrated in the presence of 1 mM PMSF using the CENTRICON-10™ concentrator. The concentrated, conditioned media (usually 1.5 ml) was then bound to $Ni^{++}$NTA agarose beads (Qiagen) for 2 hours (for the His-tagged version only). Protein was eluted from the beads by boiling for 10 minutes in 2×SDS loading buffer (Novex) with or without beta-mercaptoethanol for reduced vs. non-reduced protein, respectively.

The protein was visualized by SDS-PAGE using 4-20% gradient TRIS-glycine gels, 10-wells, 1 mm thickness (Novex). Gels ran at 125 volts (constant) for 95 minutes. Western transfer was achieved using a NOVEX™ transfer apparatus to PVDF membranes (Novex) at 200 mA (constant) for 45 minutes. The blots were blocked for a minimum of 1 hour at room temperature in blocking buffer (PBS+TWEEN-20™ (0.5%), 5% dry milk, and 3% goat serum). Blots were incubated in primary antibody (for His-tagged protein: INVITROGEN™ anti-his (C-terminal)-HRP-conjugated antibody or for the non-His version: polyclonal anti-murine WISP-1 antibody prepared as described below) at a 1:2000 dilution in fresh blocking buffer for 1 hour at room temperature. The non-His-tagged protein blots were incubated in secondary antibody (PIERCE™ goat anti-rabbit IgG(H+L) HRP conjugated) diluted 1:2000 in fresh blocking buffer. The blots were incubated in chemiluminescent substrate (ECL™ from Amersham or SUPERSIGNAL™ from Pierce) for 1 minute before exposing to film.

For transient expression analyzed by antibody staining, 293 cells were cultured, plated, and transfected as described above. The cells were fixed to culture dishes for 2 minutes in 1:1 methanol:acetone solution. Fixed cells were then incubated in primary antibody (for His-tagged protein: INVITROGEN™ anti-his (C-term)-HRP-conjugated antibody or for the non-His version: polyclonal anti-murine WISP-1 antibody prepared as described below) diluted 1:1000 in PBS with 10% fetal bovine serum for 2 hours. The non-His-tagged protein blots were then incubated in secondary antibody (PIERCE™ goat anti-rabbit IgG(H+L) HRP conjugated) diluted 1:150 in PBS with 10% fetal bovine serum for 1 hour. T h P incubation was in color reagent substrate for HRP for up to 1 hour (1.0% O-dianisidine-saturated ETOH, 0.01% hydrogen peroxide in PBS).

For stable expression of mouse WISP-1 in mammalian cells, the starting vector employed was pRK5.CMV.puro-dhfR, the sequence of which is shown in FIGS. 16A-16D. This vector has two SAR sequences cloned into KpnI, SapI sites of the SVIDS, splice-donor vector, and has the pSVI backbone with the pRK5 cloning linker (pSV15) and the intron made from pSVI.WTSD.D by adding a linearization linker ML) into the Hpa1site. The sequence is edited to include changes in vector puc118 backbone derived from the sequence of pRK5 and includes a four-base insertion after MCS characteristic of the SVI vector.

The above inserts were ligated into pRK5.CMV.puro-dhfR at the BamHI/XbaI site using the BOEHRINGER MANNHEIM™ rapid ligation kit, producing pRK5.CMV.puro-dhfR.mu.WISP-1.6his or pRK5. CMV. puro-dhfR.mu.WISP-1, nohis. This construct allows for stable selection of expressing cells using either puromycin (2 µg/ml in 293 cells or 10 µg/ml in CHO-DP12 cells) or the DHFR deletion in the CHO-DP12 line, which allows for subsequent amplification in methotrexate. Isolated colonies representative of stably transfected cells were picked, —cultured under selective pressure, and analyzed by antibody staining or Western blot as described above.

Example 9

Expression of WISP Polypeptide in Yeast

The following method describes recombinant expression of a WISP polypeptide in yeast.

First, yeast expression vectors are constructed for intracellular production or secretion of a WISP polypeptide from the ADH2/GAPDH promoter. DNA encoding a WISP polypeptide and the promoter is inserted into suitable restriction enzyme sites in the selected plasmid to direct intracellular expression. For secretion, DNA encoding a WISP polypeptide can be cloned into the selected plasmid, together with DNA encoding the ADH2/GAPDH promoter, a native WISP signal peptide or other mammalian signal peptide or yeast alpha-factor or invertase secretory signal/leader sequence, and linker sequences (if needed) for expression.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant WISP polypeptide can subsequently be isolated and purified by removing the yeast cells from the fermentation medium by centrifugation and then concentrating the medium using selected cartridge filters. The concentrate containing the WISP polypeptide may further be purified using selected column chromatography resins.

Example 10

Expression of WISP Polypeptide in Baculovirus-Infected Insect Cells and Purification Thereof The following method describes recombinant expression of a WISP polypeptide in baculovirus-infected insect cells, and purification thereof.
General The sequence coding for WISP polypeptide is fused upstream of an epitope tag contained within a baculovirus expression vector. Such epitope tags include poly-His tags and immunoglobulin tags (like Fc regions of IgG). A variety of plasmids may be employed, including plasmids derived from commercially available plasmids such as pVL1393 (Novagen). Briefly, the sequence encoding WISP polypeptide or the desired portion of the coding sequence (such as the sequence encoding the mature protein if the protein is extracellular) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using lipofectin (commercially available from Gibco-BRL). After 4-5 days of incubation at 28° C., the released viruses are harvested and used for further amplifications, viral infection and protein expression are performed as described by O'Reilley et al., *Baculovirus Expression Vectors: A Laboratory Manual* (oxford: Oxford University Press, 1994).

Expressed poly-His-tagged WISP polypeptide can then be purified, for example, by $Ni^{2-}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL HEPES, pH 7.9; 12.5 mm $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8), and filtered through a 0.45 µm filter. A $Ni^{2-}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non-specifically bound protein. After reaching $A_{280}$ baseline again, the column is developed with a 0 to 500 mM imidazole gradient in the secondary wash buffer. One-mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged WISP polypeptide are pooled and dialyzed against loading buffer.

Alternatively, purification of the IgG-tagged (or Fc-tagged) WISP polypeptide can be performed using known chromatography techniques, including, for instance, Protein A or protein G column chromatography.
Specific
1. Expression In particular, mouse WISP-1 polypeptide was expressed in a baculovirus expression system similar to that described above using as the baculovirus transfer vector pb.PH.mu.568.9.1gG.baculo or pbPH.mu.568.8his.baculo. FIGS. 17A-17D show the sequence (SEQ ID NO:54) of plasmid pb.PH.IgG, which was used to prepare pb.PH.mu.568.9.1gG.baculo. FIGS. 18A-18D show the sequence (SEQ ID NO:55) of plasmid pbPH.His.c, which was used to prepare pbPH.mu.568.8his.baculo.

Both of these baculovirus transfer vectors are based on pVL1393 (Pharmingen), which has neither the His nor Fc tags. The pb.PH.IgG vector (FIG. 17) allows the expression of foreign proteins under control of the AcNPV polyhedrin promoter, which is active in the very late phase of virus infection. The foreign protein can be expressed as a C-terminal human IgG fusion protein. The His(b)-tag will not be translated as a result of the IgG stop coc'-.on just 51 of the His(8)-tag. The sequence encoding the foreign protein should Le inserted as a 3' blunt-ended fragment into the unique StuI preceeding the His-taq. In that case an additional proline residue will be added. The 5' site can be either BamHI, EcoRI, NotI, NcoI, and NheI.

The IgG vector was constructed by NdeI digestion of the pVL1393.IgG plasmid followed by Klenow treatment to fill in the sticky end site. This is followed by a NcoI digest and insertion into the pbBH.His.c x NcoI/SmaI-digested vector.

The sequence of pbPH.His.c shown in FIGS. 18A-18D contains the backbone sequence of the vector pVL1392, which contains approximately the EcoRIIXmaIII fragment of AcMNPV C-6, from position 0.0 to 5.7 mu. Possee et al., *Virology*, 185: 229-241 (1991). It allows the expression of foreign proteins under control of the *Autographa californica* nuclear polyhedrosis virus (AcNPV) polyhedrin gene promoter, which is active in the very late phase of virus infection.

The foreign protein can be expressed as a C-terminally His- or a IgG (Fc region only)-tagged protein. The sequence encoding the foreign protein should be inserted as a 31-blunt-ended fragment into the unique SmaI site preceding the His-tag or the SLuI site for IgG. In that case an additional glycine residue will be added for His tags and a proline will be added for IgG tags. The 5' site can be either BamHIf NotI, EcoRI, or NcoI. Bam HI was used for both.

The vectors were constructed by inserting a PCR insert into BamHIISmaI for the His vector and BamHIIStuj for the IgG vector. The PCR insert was made using 5'-phosphorylated primers as follows: m.568.per.top6 (5'-TTTCCCTTTG-GATCCTAAACCAACATGAGGTGGCTCCTGCCC; SEQ ID NO:127) and m.568.per.bot3 (SEQ ID NO:125), 5' phosphorylated. A twenty-cycle PCR reaction with Pfu polymerase enzyme was performed using the following conditions: 1 min at 95'C, 30 sec at 60'C, 3.5 min at 72'C. The PCR product was purified with QIAQUICK"' and digested with BamHI at 37'C for 1 hr. The digested PCR insert was ligated into the digested vector using a 1:3 ratio of insert to vector with 1 µl T4 DNA ligase (Bio Labs). ULTRA MAX™ DH5a FT competent cells, 100 µl, (Gibco BRL Cat #10643-013) were added to the ligation product, and the mixture was incubated on ice for 30 min, followed by a heat shock at 42'C for 45 sec. Individual colonies were picked and miniscreen DNA was prepared using QIA PREpT1 (Qiagen). Construct sequencing was performed using ABI Prism's dRHODAMINE DYE'" terminator cycle sequencing.

The plasmid pb. PH. IgG has a polylinker BamHI-NotI-EcoRI-Ncf-~)I-SrfI-StuI-(IgG Fc region only)-Stop-XbaI-SpeI-PsLI-BglII. The location of particular regions in this plasmid is as follows: Insertion of polylinker/foreign gene: 4129-4912 (BamHI-BglII), polh coding: 4913-5479, ORF 1629: 7134-4820; ORF 588 (PK1): 7133-7723; ColE1 origin of replication: -7973-8858, and ampicillin coding: 9779-8230. The plasmid pbPH.His.c has a polylinker BamH I-NotI-EcoRI-NcOI-SrfI-SmaI-(His 8)-Stop-XbaI-SpeI-PstI-BglII. The NcoI site of pbPH.His.c resides within a Kozak sequence. The location of particular regions in this plasmid is as follows: ORF 504 (PTP): 76-582, ORF 984 (ORF2): 1600-614, ORF 453 (ORF3): 2323-1868, conotoxin: 1818-1657, ORF 327 (ORF4): 2352-2681, ORF 630 (lef-2): 2662-3294, ORF 603: 3937-3332, ORF polh: 4093 (mutated codon ATG/'ATT), insertion of polylinker/foreign gene: 4129-4218 (BamHI-BglII), polh coding: 4224-4790, ORF 1629: 6445-4820, ORF 588 (PK1): 6444-7034, ColE1 origin of replication: 7284-8169, and ampicillin coding: 9090-8230.

The mouse WISP-1 cDNA disclosed herein was inserted into the vectors pbPH.His.c and pb.PH.IgG to produce the respective expression plasmids by creating a 3' blunt-ended fragment for cloning into the unique SmaI site preceding the His-tag or IgG-tag. An additional glycine residue was added to the His protein produced. An additional proline was added to the IgG protein. The 51 site of the cDNA insert was BamHI.

2. Purification

For purification purposes, either a poly-His tag or the Fc portion of human IgG was added to the C-terminal coding region of the cDNA before expression. The conditioned media from the transfected cells (0.5 to 2 L) was harvested by centrifugation to remove the cells and filtered through 0.22 micron filters. For the poly-His-tagged constructs, the protein was purified using a Ni*2-NTA column (Qiagen). Before purification, imidazole was added to the conditioned media to a concentration of 5 mM. The conditioned media was pumped onto a 6-ml Ni*2-NTA column equilibrated in 20 mM HEPES, pH 7.4, buffer containing 0.3 M NaCl and 5 mM imidazole at a flow rate of 4-5 ml/min at 4'C. After loading, the column was washed with additional equilibration buffer and the protein was eluted with equilibration buffer containing 0.25 M imidazole. The highly purified protein was subsequently desalted into a storage buffer containing 10 mM HEPES, 0.14 M NaCl, and 4% mannitol, pH 6.8, with a 25 ml G25 SUPERFINE™ (Pharmacia) column and stored at −80'C.

Immunoadhesin (Fc-containing) constructs of WISP-1 protein were purified from the conditioned media as follows. The conditioned media was pumped onto a 5-ml Protein A column (Pharmacia) which had been equilibrated in a 20 mm Na phosphate buffer, pH 6.8. After loading, the column was washed extensively with equilibration buffer before elution with 100 mM citric acid, pH 3.5. The eluted protein was immediately neutralized by collecting 1-ml fractions into tubes containing 275 uL of 1 M Tris, pH 9, buffer. The highly purified protein was subsequently desalted into storage buffer as described above for the poly-His-tagged proteins. The homogeneity of the protein was assessed by SDS polyacrylamide gels and by N-terminal amino acid sequencing by Edman degradation.

Example 11

Axis Duplication Assay

*Xenopus* embryos were injected with human WISP-2 mRNA into either a presumptive ventral or presumptive dorsal vegetal blastomere at the 8- to 16-cell stage to overexpress locally the encoded protein and assay for its developmental effects. The methods used are described in Sokol et al., *Cell*, 67: 741-752 (1991).

More specifically, for synthesis of capped RNA, human WISP-2 and mouse Wnt-1 cDNAs were cloned into the pGEMHE vector (gift of Dr. Todd Evans, AECOM) to prepare pGEMHE.hu.WISP-2.8H and pGEMHE.mu.Wnt-1, respectively. The constructs were linearized at the 3' end using the SphI restriction enzyme. Capped RNAs were synthesized using AMBION's T7 MESSAGEMACHINE™ RNA synthesis kit.

For obtaining mature oocytes, an adult female *Xenopus laevis* was injected with 200 I.U. pregnant mare serum 3 days before use. The night before the experiment, the female frog was injected with 800 I.U. of human chorionic gonadotropin. Fresh oocytes were squeezed from female frogs the next morning. In vitro fertilization of oocytes was performed by mixing oocytes with minced testes from a sacrificed male frog. Fertilized eggs were dejellied with 2% cysteine (pH 7.8) for 10 minutes. Dejellied eggs were washed once with distilled water and transferred to 0.1× Modified Barth's Solution (MBS) (Methods in Cell Bioloav, Volume 36, *Xenopus laevis*:

Practical uses in Cell and Molecular Biology, Kay and Peng, Eds (New York: Academic Press, 1991)) with 5% Ficoll. Eggs were lined on injection trays which contained 0.1×MBS with 5% Ficoll for injection. After injection, embryos were kept in 0.1×MBS in an 18'C incubator. Embryos were staged according to Nieuwkoop and Faber, Normal Table of *Xenopus laevis*: (Daudin)—(Amsterdam: North-Holland, 1967).

For animal cap assays, embryos were injected at the 2-cell stage with 1 ng of capped RNA, and animal caps were isolated at stage 8 and cultured in 1×MMR for another 24 hours for the RT-PCR assay. Total RNA was isolated from harvested animal caps using a RNEASy™ kit (Qiagen). RNA samples (approximately 1 μg) were reverse transcribed using random hexamer and GIBCO:BRL SUPERSCRIPT JIT' reverse transcriptase. The annealing temperature,_:~ for the PCR reactions was 550 C unless noted otherwise.

For axis duplication assays, embryos at the 8-cell stage were injected with 1 ng capped RNA at either the dorsal or ventral vegetal blastomere and incubated in 0.1×MBS for 72 hours.

The sequences of PCR primers used in this experiment were:

```
EF-1a.U:
5'-CAGATTGGTGCTGGATATGC        (SEQ ID NO: 128)

EF-1a.D:
5'-ACTGCCTTGATTACTCCTAC        (SEQ ID NO: 129)

noggin.U:
5'-AGTTGCAGATGTGGCTCT          (SEQ ID NO: 130)

noggin.D:
5'-AGTCCAAGAGTCTCAGCA          (SEQ ID NO: 131)

goosecoid.U:
5'-ACAACTGGAAGCACTGGA          (SEQ ID NO: 132)

goosecoid.D:
5'-TCTTATTCCAGAGGAACC          (SEQ ID NO: 133)

cardiac-actin.U:
5'-TCCCTGTACGCTTCTGGTCGTA      (SEQ ID NO: 134)

cardiac-actin.D:
5'-TCTCAAAGTCCAAAGCCACATA      (SEQ ID NO: 135)

NCAM.U:
5'-CACAGTTCCAGCAAATAC          (SEQ ID NO: 136)

NCAM.D:
5'-GGAATCAGGCGGTACAGT          (SEQ ID NO: 137)
```

It was found that human WISP-2 can partially induce axis duplication in this assay.

Example 12

Thymidine Incorporation Assay

In a ($^3$H)-thymidine incorporation assay, 19 different cell lines, including RAG (renal adenocarcinoma, mouse) and NRK-49F (normal kidney fibroblasts, rat) cells, identified in Table I below, were plated in 96-well plates at $3 \times 10^4$ in HGDMEM with 10% serum. Twenty four hours after plating, the medium was changed to HGDMEM with 0.2% serum before adding the test proteins. WISP proteins were added to a final concentration of approximately 3.6 ng/ul. Serial dilutions were made in a total volume of 70 μl/well of fresh media. After 18 hr incubation at 37° C., 5 μCi/ml ($^3$H)thymidine was added for 5 hrs. Medium was aspirated and cells were removed with 1× trypsin onto a GF/C filter using Packard's™ 96-well FILTERMATE 196™. The filters were dried and 40 μl of scintillation fluid was added for counting on a top count, microplate scintillation counter (Packard).

The results are shown in Table I:

TABLE I

IH-Thymidine Incorporation Assay Results

| Cell line | Type | ATCC No. | mWISP-1-IgG | hWISP-1-IgG | hWISP-2-IgG |
|---|---|---|---|---|---|
| HT-29 (human colon) | adenocarcinoma moderately well-differentiated | HTB-38 | No change | No change | |
| Wi-Dr (human colon) | adenocarcinoma | CCL-218 | No change | No change | |
| Calu-1 (human lung, | epidermoid carcinoma grade III, metastasis to pleura | HTB-54 | inhibits ~1.1x | inhibits ~1.2X | |
| Calu-6 (human lung) | anaplastic carcinoma, probably lung | HTB-56 | No change | stimulates ~1.4X | |
| SK-MES-1 (human lung) | squamous carcinoma, pleural effusion | HTB-58 | No change | No change | |
| A549 (human lung) | carcinoma | CCL-185 | inhibits-1.5x | inhibits ~1.7X | |
| H460 (human lung) | large cell carcinoma | HTB-177 | inhibits ~1.4X | inhibits ~1.3X | |
| SW900 (human lung) | squamous cell carcinoma | HTB-59 | no change | no change | |
| MRC5 (human lung) | normal diploid | CCL-171 | no change | no change | |

TABLE I-continued

IH-Thymidine Incorporation Assay Results

| Cell line | Type | ATCC No. | mWISP-1-IgG | hWISP-1-IgG | hWISP-2-IgG |
|---|---|---|---|---|---|
| IMR-90 (human lung) | normal diploid | CCL-186 | stimulates ~1.1x | stimulates ~1.5X | |
| Wnt-I C57 mg (mouse mammary gland) | myo-epithelial | | inhibits ~2x | | |
| MLg (mouse lung) | lung | | stimulates ~4X | | |
| LL/2 (mouse lung) | lung carcinoma | | | inhibits ~2x | |
| JC (mouse mammary gland) | carcinoma | | inhibits ~2x | inhibits ~3x | |
| N MuMG (mouse mammary gland) | normal | | stimulates ~2X | stimulates ~1.4X | |
| NRK-49F (rat kidney) | normal fibroblast | | stimulates ~3X | stimulates ~3.5x | |
| RAG (mouse kidney) | adenocarcinoma | | stimulates ~4.5X | stimulates ~3X | stimulates ~4X |
| NIH/3T3 (mouse embryo) | fibroblast | | stimulates ~3X | | |
| UCLA-P3 (human lung) | | | inhibits ~1.5x | inhibits ~2X | |

It is seen that WISP-1 and WISP-2 exhibit both stimulatory and inhibitory effects on proliferation of normal and tumor cells, depending on the cell line employed.

Example 13

Preparation of Antibodies that Bind Wisp Polypeptide

1. Polyclonal Antibodies

Polyclonal antisera were generated in female New Zealand White rabbits against murine WISP-1 and human WISP-2. The antigens used were proteins fused with hist-idine for murine WISP-1 and proteins fused with the Fc portion of IgG for human WISP-2. The same protocol was used for both proteins. Each protein was homogenized with Freund's complete adjuvant for the primary injection and with Freund's incomplete adjuvant for all subsequent boosts. For the primary immunization and the first boost, 3.3 µg per kg body weight was injected directly into the popliteal lymph nodes as described in Bennett et al., *J. Biol. Chem.*, 266: 23060-23067 (1991) and "Production of Antibodies by Inoculation into Lymph Nodes" by Morton Sigel et al. in *Methods in Enzymology*, Vol. 93 (New York: Academic Press, 1983). For all subsequent boosts, 3.3 µg per kg body weight was injected into subcutaneous and intramuscular sites. Injections were done every 3 weeks with bleeds taken on the following two weeks.

2. Monoclonal Antibodies

Techniques for producing monoclonal antibodies that can specifically bind a WISP polypeptide are known in the art and are described, for instance, in Goding, supra. Immunogens that may be employed include purified WISP polypeptide, fusion proteins containing WISP polypeptide, and cells expressing recombinant WISP polypeptide on the cell surface. Selection of the immunogen can be made by the skilled artisan without undue experimentation.

Mice, such as Balb/c, are immunized with the WISP immunogen emulsified in complete Freund's adjuvant and injected subcutaneously or intraperitoneally in an amount from 1 to 100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retroorbital bleeding for testing in ELISA assays to detect antibodies to WISP polypeptide.

After a suitable antibody titer has been detected, the animals "positive" for antibodies can be injected with a final intravenous injection of a WISP polypeptide. Three to four days later, the mice are sacrificed and the spleen cells are harvested. The spleen cells are then fused (using 35% PEG) to a selected murine myeloma cell line such as P3X63AgU.1, available from ATCC, No. CRL 1597, or x63-AgB.653 (Kearney et al., *J. Immunology*, 123: 1548 (1979)). The fusions generate hybridoma cells which can then be plated in 96-well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against a WISP polypeptide. Determination of "positive" hybridoma cells secreting the desired monoclonal antibodies against a WISP polypeptide is within the skill in the art.

The positive hybridoma cells can be injected intraperitoneally into syngeneic Balb/c mice to produce ascites containing the anti-WISP polypeptide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel-exclusion chromatography. Alternatively, affinity chromatography based upon binding of antibody to protein A or protein G can be employed.

Specifically, for each of the human WISP-1 antibodies, five female Balb-c mice were pre-bled and then injected via their hind foot pads with purified human WISP-1, tagged with the Fc portion of IgG and emulsified prior to injection in MPL-TDM adjuvant (Ribi Immunochemical Research, Hamilton, Mont.) in a 1:1 ratio of WISP antigen to adjuvant. The dosing schedule for the WISP-1 immunogen was as follows:

| Injection Date- | Dose/Site | Dose/Animal | Concentration |
| --- | --- | --- | --- |
| Day 16 of month 1 | 50 µl site | 100 µl/animal | 6 µg/animal |
| Day 12 of month 2 | 50 µl/site | 100 µl/animal | 6 µg/animal |
| Day 21 of month 2 | 50 µl/site | 100 µl/animal | 6 µg/animal |
| Day 28 of month 2 | 50 µl/site | 100 µl/animal | 2 µg/animal |
| Day 4 of month 3 | 50 µl/site | 100 µl/animal | 2 µg/animal |
| Day 11 of month 3 | 50 µl/site | 100 µl/animal | 2 µg/animal |
| Day 18 of month 3 | 50 µl/site | 100 µl/animal | 2 µg/animal |
| Day 25 of month 3 | 50 µl/site | 100 µl/animal | 2 µg/animal |

For WISP-1, the mice were bled on Day 10 of month 4. After the mice were bled, the monoclonal antibodies were made by harvesting their spleens and by fusion as indicated above, using as the murine myeloma cell line X63.AgB.653.

The five monoclonal antibodies generated to human.WISP-1 are:

| | |
| --- | --- |
| 10F2.2A7 | gamma2b/kappa |
| 10A9.2B1 | gamma2a/kappa |
| 8F7.1B1 | gamma1/kappa |
| 1H1.ID5 | gamma1/kappa |
| 2G7.2H4 | gamma 1/kappa |

For WISP-2 monoclonal antibodies the same regimen is employed except that purified human WISP-2 is used as immunogen in the above protocol rather than purified human WISP-1 and the dosing schedule for the WISP-2 immunogen is as follows:

| Injection Date- | Dose/Site | Dose/Animal | Concentration |
| --- | --- | --- | --- |
| Day 16 of month 1 | 50 µl/site | 100 µl/animal | 6 µg/animal |
| Day 21 of month 2 | 50 µl/site | 100 µl/animal | 1 µg/animal |
| Day 28 of month 2 | 50 µl/site | 100 µl/animal | 1 µg/animal |
| Day 4 of month 3 | 50 µl/site | 100 µl/animal | 1 µg/animal |
| Day 11 of month 3 | 50 µl/site | 100 µl/animal | 1 µg/animal |
| Day 18 of month 3 | 50 µl/site | 100 µl/animal | 1 µg/animal |
| Day 25 of month 3 | 50 µl/site | 100 µl/animal | 1 µg/animal |

Example 14

Uses of Antibodies that Bind WISP Polypeptide

1. Cell Lines

The established human breast tumor cells BT474 and MDA-MB-231 (which are available from ATCC) are grown in minimum essential medium (Gibco, Grand Island, N.Y.) supplemented with 10% heat-inactivated fetal bovine serum (FBS) (HyClone, Logan, Utah), sodium pyruvate, L-glutamine (2 mM), non-essential amino acids, and 2× vitamin solution and maintained at 37° C. in 5% $CO_2$. Zhang et al., *Invas. & Metas.*, 11:204-215 (1991); Price et al., *Cancer Res.*, 50:717-721 (1990).

2. Antibodies

Anti-WISP-1 or anti-WISP-2 monoclonal antibodies that may be prepared as described above are harvested with PBS containing 25 mM EDTA and used to immunize BALB/c mice. The mice are given injections i.p. of 107 cells in 0.5 ml PBS on weeks 0, 2f 5 and '7. The mice with antisera that immunoprecipitated 32p-labeled Wnt-1 are given i.p. injections of a wheatgerm agglutinin-SEPHAROSE™ (WGA)-purified Wnt membrane extract on weeks 9 and 13. This is followed by an i.v. injection of 0.1 ml of the Wnt-1 preparation, and the splenocytes are fused with mouse myeloma line X63-Ag8.653. Hybridoma supernatants are screened for Wnt-1 binding by ELISA and radioimmunoprecipitation. MOPC-21 (IgG1) (Cappell, Durham, N.C.) is used as an isotype-matched control.

Additionally, the anti-ErbB2 $IgG_1\kappa$ murine monoclonal antibodies 4D5 (ATCC CRL 10463 deposited May 24, 1990) and 7C2, specific for the extracellular domain of ErbB2, may be used with the above antibodies. They are produced as described in Fendly et al., *Cancer Research*, 50:1550-1558 (1990) and WO89/06692.

3. Analysis of Cell Cycle Status and Viability

Cells are simultaneously examined for viability and cell cycle status by flow cytometry on a FACSTAR PLUS™ (Becton Dickinson Immunocytometry Systems USA, San Jose, Calif.). Breast tumor cells are harvested by washing the monolayer with PBS, incubating cells in 0.05% trypsin and 0.53 mM EDTA (Gibco), and resuspending them in culture medium. The cells are washed twice with PBS containing 1% FBS and the pellet is incubated for 30 minutes on ice with 50 µl of 400 µM 7-aminoactinomycin D (7AAD) (Molecular Probes, Eugene, Oreg.), a vital dye which stains all permeable cells. Cells are then fixed with 1.0 ml of 0.5% paraformaldehyde in PBS and simultaneously permeabilized and stained for 16 hours at 4° C. with 220 µl of 10 µg/ml HOECHST 33342™ dye (also a DNA binding dye) containing 5% TWEEN 20™.

The data from $1\times10^4$ cells are collected and stored using LYSYS II™ software and analyzed using PAINT-A-GATE™ software (Becton Dickinson). Darzynkiewica et al., *Cytometry*, 13:795-808 (1992); Picker et al., *J. Immunol.*, 150:1105-1121 (1993). The viability and percentage of cells in each stage of the cell cycle are determined on gated single cells using 7AAD and Hoechst staining, respectively. (Cell doublets are excluded by pulse analysis of width vs. area of the Hoechst signal.) Cell numbers are determined using a hemocytometer.

4. DNA Synthesis (($^3$H)-Thymidine Incorporation Assay)

The assay was performed exactly as described in Example 12, except that the WISP polypeptides used as test proteins were replaced by the polyclonal antibodies generated in New Zealand White rabbits against murine WISP-1 and human WISP-2 described in Example 13, and not all the cell lines in Example 12 were tested. The results are shown in Table II:

TABLE II $^3$H-Thymidine Incorporation Assay Results

| Cell line | Type | ATCC No. | pAB.mWISP-1 | pAB.mWISP-2 |
|---|---|---|---|---|
| HT-29 (human colon) | adenocarcinoma moderately well-differentiated | HTB-38 | No change | No change |
| Wi-Dr (human colon) | adenocarcinoma | CCL-218 | No change | No change |
| N MuMG (mouse mammary gland) | normal | | stimulates ~3X | |
| NRK-49F (rat kidney) | normal fibroblast | | stimulates ~2X | |
| RAG (mouse kidney) | adenocarcinoma | | stimulates ~4.X | |
| NIH/3T3 (mouse embryo) | fibroblast | | stimulates ~2X | |

It is seen that the polyclonal antibodies to mouse WISP-1 and to human WISP-2 exhibited both stimulatory and inhibitory effects on proliferation of normal and tumor cells, depending on the cell line employed.

5. Affinity of Binding to Putative Receptor

Radioiodinated anti-WISP-1 and anti-WISP-2 antibodies are prepared by the IODOGEN™ method. Fracker et al., *Biochem. Biophys. Res. Comm.*, 80:849-857 (1978). Binding assays are performed using appropriate receptor-expressing cells (such as, for mouse anti-WISP antibodies, MLG, a mouse lung cell line available from the ATCC) cultured in 96-well tissue culture plates (Falcon, Becton Dickinson Labware, Lincoln Park, N.J.). The cells are trypsinized and seeded in wells of 96-well plates at a density of $10^4$ cells/well and allowed to adhere overnight. The monolayers are washed with cold culture medium supplemented with 0.1% sodium azide and then incubated in triplicate with 100 μl of serial dilutions of $^{125}$I-anti-WISP-1 or WISP-2 antibodies in cold culture medium containing 0.1% sodium azide for 4 hours on ice. Non-specific binding is estimated by the preincubation of each sample with a 100-fold molar excess of nonradioactive antibodies in a total volume of 100 Unbound radioactivity is removed by two washes with cold medium containing 0.1% sodium azide. The cell-associated radioactivity is detected in a gamma counter after solubilization of the cells with 150 μl of 0.1 M NaOH/well. The WISP-1 and WISP-2 binding constants ($K_d$) and anti-WISP antibody binding affinities are determined by Scatchard analysis.

It is expected that the antibodies against WISP-1 and WISP-2 will affect the growth of these cells.

Example 15

Further Uses of Antibodies that Bind WISP Polypeptide

1. WISP-1 and WISP-2

This example shows that the WISP-1 and WISP-2 genes are amplified in the genome of certain human lung, colon, and/or breast malignant tumors and/or cell lines. Amplification is associated with overexpression of the gene product, indicating that the WISP-1 and WISP-2 proteins are useful targets for therapeutic intervention in certain cancers such as colon, lung, breast, and other cancers. A therapeutic agent may take the form of antagonists of WISP molecules, for example, murine-human, chimeric, humanized, or human antibodies against WISP-1 and WISP-2, such as the antibodies prepared as described above.

The starting material for the screen was genomic DNA isolated from a variety of cancers. The DNA is quantitated precisely, e.g., fluorometrically. As a negative control, DNA was isolated from the cells of ten normal healthy individuals, pooled, and used as an assay control for the gene copy in healthy individuals.

The 5' nuclease assay (for example, TAQMAN™) and real-time quantitative PCR (for example, ABI PRIZM 7700™ Sequence Detection System™ (Perkin Elmer, Applied Biosystems Division, Foster City, Calif.)), were used to find genies potentially amplified in certain cancers. The results were used to determine whether the DNAs encoding WISP-1 and WISP-2 are over-represented in any of the primary lung or colon cancers or cancer cell lines or breast cancer cell lines that were screened. The primary lung cancers were obtained from individuals with tumors of the type and stage as indicated in Table III. An explanation of the abbreviations used for the designation of the primary tumors listed in Table III and the primary tumors and cell lines referred to throughout this example is given below:

Human lung carcinoma cell lines include A549 (SRCC768), Calu-1 (SRCC769), Calu-6 (SRCC770), H157 (SRCC771), H441 (SRCC772), H460 (SRCC773), SKMES-1 (SRCC774) and SW900 (SRCC775), all available from ATCC. Primary human lung tumor cells usually derive from adenocarcinomas, squamous cell carcinomas, large cell carcinomas, non-small cell carcinomas, small cell carcinomas, and broncho alveolar carcinomas, and include, for example, SRCC724 (squamous cell carcinoma abbreviated as "SqCCa"), SRCC725 (non-small cell carcinoma, abbreviated as "NSCCa"), SRCC726 (adenocarcinoma, abbreviated as "AdenoCa"), SRCC727 (adenocarcinoma), SRCC728 (squamous cell carcinoma), SRCC729 (adenocarcinoma), SRCC730 (adeno/squamous cell carcinoma), SRCC731 (adenocarcinoma), SRCC732 (squamous cell carcinoma), SRCC733 (adenocarcinoma), SRCC734 (adenocarcinoma), SRCC735 (broncho alveolar carcinoma, abbreviated as "BAC"), SRCC736 (squamous cell carcinoma), SRCC738 (squamous cell carcinoma), SRCC739 (squamous cell carcinoma), SRCC740 (squamous cell carcinoma), and SRCC740 (lung cell carcinoma, abbreviated as "LCCa").

Colon cancer cell lines include, for example, ATCC cell lines SW480 (adenocarcinoma, SRCC776), SW620 (lymph node metastasis of colon adenocarcinoma, SRCC777), COL0320 (adenocarcinoma, SRCC778), HT29 (adenocarcinoma, SRCC779), HM7 (carcinoma, SRCC780), CaWiDr (adenocarcinoma, srcc781), HCT116 (carcinoma, SRCC782), SKC01 (adenocarcinoma, SRCC~83), SW403 (adenocarcinoma, SRCC784), LS174T (carcinoma, SRCC785), and HM7 (a high mucin producing variant of ATCC colon adenocarcinoma cell line LS174T, obtained from Dr. Robert Warren, UCSF). Primary colon tumors include colon adenoocarcinomas designated CT2 (SRCC742), CT3 (SRCC743), CT8 (SRCC744), CT10 (SRCC~45), CT12 (SRCC746), CT14 (SRCC747), CT15 (SRCC748), CT17 (SRCC750), CT1 (SRCC751), CT4 (SRCC752), CT5 (SRCC753), CT6 (SRCC754), CT7 (SRCC755), CT9 (SRCC756), CT11 (SRCC757), CT18 (SRCC758), and DcR3, BACrev, BACfwd, T160, and T159.

Human breast carcinoma cell lines include, for example, HBL100 (SRCC759), MB435s (SRCC760), T47D (SRCC761), MB468 (SRCC762), MB175 (SRCC763), MB361 (SRCC764), BT20 (SRCC765), MCF7 (SRCC766), and SKBR3 (SRCC767).

The results are reported in delta (Δ) CT units. One unit corresponds to one PCR cycle or approximately a 2-fold amplification relative to normal, two units corresponds to 4-fold, 3 units to 8-fold amplification and so on. Quantitation was obtained using primers derived from the 3'-untranslated regions of the WISP-1 and WISP-2 cDNAs and a TAQ-MAN™ fluorescent probe corresponding to the respective intervening sequences. Using the 3' region tends to avoid crossing intron-exon boundaries in the genomic DNA, an essential requirement for accurate assessment of gene amplification using this method. The sequences for the primers and probes (forward, reverse, and probe) used for the WISP-1-encoding and WISP-2-encoding gene amplification were as follows:

```
WISP-1 Probe and primers:
hu.WISP1.TMP (probe)
5'-AGCCTTTCCAAGTCACTAGAAGTCCT,GCTGG(SEQ ID NO: 138)

hu.WISP1.TMF (forward primer)
5'-CTGGACTACACCCAAGCCTGA          (SEQ ID NO: 139)

hu.WISP1.TMR (reverse primer)
5'-CATTTCTTGGGATTTAGGCAAGA        (SEQ ID NO: 140)

WISP-2 probe and primers:
DNA33473.3utr-5 (forward primer)
5'-TCTAGCCCACTCCCTGCCT            (SEQ ID NO:141)

DNA33473.3utr-3 (reverse primer)
5'-GAAGTCGGAGAGAAAGCTCGC          (SEQ ID NO:142)

DNA33473.3utr-probe
5'-CACACACAGCCTATATCAAACAT'UCACACG (SEQ ID NO:143)
```

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI PRIM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-rime through fiber optics cables for all 96 wells, and detected at the CCD. The system includes software for running the instrument and for analyzing the data.

5'-Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

The results of the first run performed are shown in FIGS. 19A-D and 20A-D for WISP-1 and WISP-2, respectively, and controls. Note the pattern shown in FIG. 19B (marked huWISP-1). The standard deviation for two samples of normal human DNA is shown in the column marked Nor Hu. This was used as a quality control tool. If the standard deviation was unacceptably large, the entire run was repeated. The nine additional columns corresponded to the human colon cancer cell lines noted above. The delta CT's for HT29 and WIDr were >3, corresponding to an about 8-fold over-representation of the WISP-1 gene in these samples compared to the normal samples. Similarly, FIG. 19B suggests an about 4-fold amplification of WISP-1 in the HCT116, SKCo-1, and SW403 cell lines.

As a comparison, see FIG. 20B (mark~d huFASr). The generally small delta CT values indicate that this gene was not significantly amplified in any of the cell lines (the value of 1 for SW620 corresponding to 2-fold amplification is within the noise level for the assay)

The WISP-1 result was confirmed in three replicate reactions. See FIGS. 21A-D, 22A-D, and 23A-C. The pattern and delta CT values obtained were very similar in FIGS. 21A-C (marked huWISP-1c, huWISP-1b, and huWISP-1a, respectively). The result was essentially identical to that obtained in the first run. HT29 and WIDr showed the highest levels of WISP-1 amplification, while HCT116, SKCo-1, and SW403 cell lines showed somewhat lower levels of WISP-1 gene amplification. Two additional reactions from a third run were confirmatory. See FIGS. 25A and 25B.

The WISP-1 gene is located on chromosome 8, in the general vicinity of the myc gene, which is known to be amplified in some colon cancer cell lines. The pattern obtained using primers and probe for the myc gene, namely, hu.c-myc.tm.p 5'-CTTGAGACTGAAAGATTTAGCCAT-AATGTAAACTGCCT (SEQ ID NO:144)

hu.c-myc.tm.f 5'-CAAATGCAACCTCACAACCTTG (SEQ ID NO:145), and hu.c-myc.tm.r 5'-TTCTTTTATGCCCAAAGTCCAATT (SEQ ID NO:146), is consistent with a published report (*Cancer Research*, 57: 1769-1775 (1997)), tending to validate the 5' nuclease assay method, but is clearly different from that obtained for WISP-1. These data prove that the myc gene is not the target of the amplification detected using the primers and probes for WISP-1.

The data using primers and probes based on the WISP-2 DNA sequence suggest that this gene may be the target of low-level gene amplification in most of the cell 14 nes examined. See FIGS. 20C, 22A-D, and 25C and D. Hence, antibodies to both WISP-1 and WISP-2, particularly humanized antibodies, are expected to be of benefit in combating certain types of cancer such as colon cancer, similar to the humanized anti-HER-2 antibody in clinical use.

2. WISP-2

Description of Tumors and Cell Lines

Amplification using several different tumor types was performed for human WISP-2 (PR0261), as described below. Table III describes the stage, T stage, and N stage of various primary tumors which were used to screen the WISP-2 compound of the invention.

TABLE III

Primary Lung and Colon Tumor Profiles

| Primary Tumor | Stage | Other Stage | Dukes Stage | T Stage | N Stage |
|---|---|---|---|---|---|
| Human lung tumor SqCCA (SRCC724) [LT1] | IB | — | — | T1 | N1 |
| Human lung tumor NSCCa (SRCC725) [LT1a] | IA | — | — | T3 | N0 |
| Human lung tumor AdenoCa (SRCC726) (LT2) | IB | — | — | T2 | N0 |
| Human lung tumor AdenoCa (SRCC727) (LT3) | IB | — | — | T1 | N2 |
| Human lung tumor SqCCq (SRCC728) [LT4] | IIB | — | — | T2 | N0 |
| Human lung tumor AdenoCa (SRCC729) [LT6] | IV | — | — | T1 | N0 |
| Human lung tumor Aden/SqCCa (SRCC730) [LT7] | IB | — | — | T1 | N0 |
| Human lung tumor AdenoCa (SRCC731) [LT9] | IIB | — | — | T2 | N0 |
| Human lung tumor SqCCa (SRCC732) [LT10] | IA | — | — | T2 | N1 |
| Human lung tumor AdenoCa (SRCC733) [LT11] | IB | — | — | T1 | N1 |
| Human lung tumor AdenoCa (SRCC734) [LT12] | IIA | — | — | T2 | N0 |
| Human lung tumor BAC (SRCC735) [LT13] | IB | — | — | T2 | N0 |
| Human lung tumor SqCCa (SRCC736) [LT15] | IB | — | — | T2 | N0 |
| Human lung tumor SqCCa (SRCC737) [LT16] | IB | — | — | T2 | N0 |
| Human lung tumor SqCCa (SRCC738) [LT17) | IIB | — | — | T2 | N1 |
| Human lung tumor SqCCa (SRCC739) [LT18] | IB | — | — | T2 | N0 |
| Human lung tumor SqCCa (SRCC740) [LT19] | IB | — | — | T2 | N0 |
| Human lung tumor LCCa (SRCC741) [LT21] | IIB | — | — | T3 | N1 |
| Human colon AdenoCa (SRCC742) (CT2] | — | M1 | D | pT4 | N0 |
| Human colon AdenoCa (SRCC743) [CT3] | | — | B | pT3 | N0 |
| Human colon AdenoCa (SRCC 744) [CT8] | | | B | T3 | N0 |
| Human colon AdenoCa (SRCC745) [CT10] | | | A | pT2 | N0 |
| Human colon AdenoCa (SRCC746) [CT12] | | M0, R1 | B | T3 | N0 |
| Human colon AdenoCa (SRCC747) [CT14] | | pM0, R0 | B | pT3 | pN0 |
| Human colon AdenoCa (,(;RCC748) (CT15] | | M1, R2 | D | T4 | N2 |
| Human colon AdenoCa (SRCC749) [CT16] | | pM0 | B | pT3 | pN0 |
| Human colon AdenoCa (SRCC750) [CT17] | | | C1 | pT3 | pN1 |
| Human colon AdenoCa (SRCC751) [CT1] | | M0, R1 | B | pT3 | N0 |
| Human colon AdenoCa (SRCC752) (CT4] | | | B | pT3 | M0 |
| Human colon AdenoCa (SRCC753) (CT5] | | G2 | C1 | pT3 | pN0 |
| Human colon AdenoCa (SRCC754) [CT6] | | PM0, R0 | B | pT3 | pN0 |
| Human colon AdenoCa (SRCC755) [CT7] | | G1 | A | pT2 | pN0 |
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | M0, R0 | B | pT3 | pN0 |

DNA Preparation:

DNA was prepared from cultured cell lines, primary tumors, and normal human blood (controls and framework and epicenter mapping). The isolation was performed using purification kit #13362 (which includes 10 purification tips with a capacity of 400 pg genomic DNA each), buffer set #1960 and protease #19155 and #19101, all from Quiagen, according to the manufacturer's instructions and the description below.

Cell Culture Lysis:

Cells were washed and trypsinized at a concentration of $7.5 \times 10^8$ per tip and pelleted by centrifuging at 1000 rpm for 5 minutes at 4° C., followed by washing again with 112 volume of PBS recentrifugation. The pellets were washed a third time, and the suspended cells collected and washed 2× with PBS. The cells were then suspended into 10 mL PBS. Buffer C1 was equilibrated at 4° C. Protease #19155 (Quiagen) was diluted into 6.25 ml cold $ddH_2O$ to a final concentration of 20 mg/ml and equilibrated at 4° C. 10 mL of G2 Buffer was prepared by diluting RNAse A stock (Quiagen) (100 mg/ml) to a final concentration of 200 µg/ml.

Buffer C1 (10 mL, 4° C.) and ddH2O (40 mL, 4° C.), were then added to the 10 mL of cell suspension, mixed by inverting and incubated on ice for 10 minutes. The cell nuclei were pelleted by centrifuging in a BECKMAN™ swinging bucket rotor at 2500 rpm at 4° C. for 15 minutes. The supernatant was discarded and the nuclei were suspended with a vortex into 2 mL Buffer C1 (at 4° C.) and 6 mL ddH, —O, followed by a second 4° C. centrifugation at 2500 rpm for 15 minutes. The nuclei were then resuspended into the residual buffer using 200 µl per tip. G2 buffer (10 ml) was added to the suspended nuclei while gentle vortexing was applied. Upon completion of buffer addition, vigorous vortexing was applied for 30 seconds. Quiagen protease (200 pl, prepared as indicated above) was added and incubated at 50° C. for 60 minutes. The incubation and centrifugation were repeated until the lysates were clear (e.g., incubating an additional 30-60 minutes, pelleting at 3000×g for 10 min., 4° C.).

Solid Human Tumor Sample Preparation and Lysis:

Tumor samples were weighed and placed into 50-ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenized in 19 ml G2 buffer for 60 seconds using the large tip of the polytron in a laminar-flow TC hood to order to avoid inhalation of aerosols, and held at room temperature. Between samples, the polytron was cleaned by spinning at 2×30 seconds each in 2 L ddH$_2$O, followed by G2 buffer (50 ml) If tissue was still present on the generator tip, the apparatus was disassembled and cleaned.

Protease (Quiagen), prepared as indicated above, 1.0 ml, was added, followed by vortexing and incubation at 50° C. for 3 hours. The incubation and centrifugation were repeated until the lysates were clear (e.g., incubating additional 30-60 minutes, pelleting at 3000×g for 10 min., 4° C.).

Human Blood Preparation and Lysis:

Blood was drawn from healthy volunteers using standard infectious agent protocols and citrated into 10 ml samples per tip. Protease (Quiagen) was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50-ml conical tube, and 10 ml C1 buffer and 30 ml ddH$_2$O (both previously equilibrated to 4° C.) were added, and the components mixed by inverting and held on ice for 10 minutes. The nuclei were pelleted with a BECKMAN™ swinging bucket rotor at 2500 rpm, 4° C. for 15 minutes and the supernatant was discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer Using a 200-µl tip. G2 buffer (10 ml) was added to the suspended nuclei while gently vortexing, followed by vigorous vortexing for 30 seconds. Protease (Quiagen) was added (200 µl) and incubated at 50° C. for 60 minutes. The incubation and centrifugation were repeated until the lysates were clear (e.g., incubating an additional 30-60 minutes, pelleting at 3000×g for 10 min., 4° C.).

Purification of Cleared Lysates; Isolation of Genomic DNA:

Genomic DNA was, equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30-ml silanized, autoclaved 30-ml COREX™ tubes with 15-ml QF buffer (50° C.). Isopropanol (10.5 ml) was added to each sample, and the tubes were covered with paraffin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml. 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1-2 hours. Samples were held overnight at 4° C. as dissolution continued. The DNA solution was then transferred to 1.5-ml tubes with a 26-gauge needle on a tuberculin syringe. The transfer was repeated 5× in order to shear the DNA. Samples were then placed at 50° C. for 1-2 hours.

Quantitation of Genomic DNA and Preparation for Gene Amplification Assay:

The DNA levels in each tube were quantified by standard A260, A280 spectrophotometry on a 1:20 dilution (5 µl DNA+95 pl ddH$_2$O) using the 0.1-ml quartz cuvettes in the BECKMAN DU640™ spectrophotometer. A260/A280 ratios were in the range of 1.8-1.9. Each DNA sample was then diluted further to approximately 200 ng/ml in TE (pH 8.5). If the original material was highly concentrated (about 700 ng/µl), the material was placed at 50° C. for several hours until resuspended.

Fluorometric DNA quantitation was then performed on the diluted material (20-600 ng/ml) using the manufacturer's guidelines as modified below. This was accomplished by allowing a HOEFFER DYNA QUANT 200™ fluorometer to warm up for about 15 minutes. The HOECHST™ dye working solution (#H33258, 10 prepared within 12 hours of use) was diluted into 100 ml 1×THE buffer. A 2-ml cuvette was filled with the fluorometer solution, placed into the machine, and the machine was zeroed. pGEM 3Zf(+) (2 µl, lot #360851026) was added to 2 ml of fluorometer solution and calibrated at 200 units. A second 2 µl of pGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometrically-determined concentration was then used to dilute each sample to 10 ng/µl in ddH$_2$O. This was done simultaneously on all template samples for a single TAQMAN™ plate assay, and with enough material to run 500-1000 assays. The samples were tested in triplicate with both B-actin and GAPDH on a single plate with normal human DNA and no-template controls. The diluted samples were used, provided that the CT value of normal human DNA subtracted from test DNA was +/−1 CT. The diluted, lot-qualified genomic DNA was stored in 1.0-ml aliquots at −80° C. Aliquots which were subsequently to be used in the gene amplification assay were stored at 4° C. Each 1-ml aliquot is enough for 8-9 plates or 64 tests.

Framework Mapping and Epicenter Marking.

Human WISP-1 was reexamined with both framework and epicenter mapping. Selected tumors from the above initial screen were reexamined with both framework and epicenter mapping. Table IV indicates the chromosomal mapping of the framework markers that were used in the present example. The framework markers are located approximately every 20 megabases along Chromosome 8 and were used to control for aneuploidy.

TABLE IV

Framework Markers

| Map Position on Chromosome 8 | Stanford Human Genome Center Marker Name |
|---|---|
| H9 | EST-00040 |
| H59 | WI-961 |
| H121 | SHGC-11323 |
| H200 | SHGC-7433 |
| H256 | AFMa183zfl |

Table V describes the epicenter markers that were employed in association with WISP-1. These markers are located in close proximity to the gene for WISP-1 and are used to assess the amplification status of the region of chromosome 8 in which the gene for WISP-1 is located. The distance between individual markers is measured in centirays (cR), which is a radiation breakage unit approximately equal to a 1% chance of a breakage between two markers. One cR is very roughly equivalent to 20 kilobases. The marker SHGC-32958 is the marker found to be the closest to the location on chromosome 8 to which the gene encoding WISP-1 most closely maps.

TABLE V

Epicenter Markers

| Map Position on Chromosome 8 | Stanford Human Genome Center Marker Name | Distance to next Marker (cR) |
|---|---|---|
| H257 | AFMa248tel | 103(gap) |
| H259 | SHGC-36664 | 33 |
| H261 | AFM259xc5 | 63 |
| H266 | SHGC-32958 | 41 |
| H267 | AFMa175xcl | 19 |
| H268 | AFM337wg5 | 87 |
| H273 | SHGC-33759 | 71 |
| H274 | SHGC-32752 | 5 |
| H275 | WI-7711 | 21 |
| H277 | HGC-34940 | — |

The framework markers for human WISP-2 are located approximately every 20 megabases along Chromosome 20, and are used to control for aneuploidy. The markers are shown in Table VI.

TABLE VI

Framework Markers

| Map Position on Chromosome 20 | Stanford Human Genome Center Marker Name |
|---|---|
| T10 | SHGC-2797 |
| T48 | UT759 |
| T73 | AFMa339xf5 |
| T115 | SHGC-33922 |
| T159 | HGC-36268 |

The marker SHGC-33922 is the marker to which human WISP-2 DNA most closely maps. This marker is between the framework markers.

Framework analysis showed that all markers were u7p in tumors; thus, chromosome 20 was aneuploid in many tumors. Since the markers were up due to aneuploidy, epicenter analysis was not done for human WISP-2 gene.

The ΔCt values of the above described framework markers along Chromosome 8 relative for WISP-1 are indicated for selected tumors in Tables VII and VIII.

TABLE VII

Amplification of framework markers relative to Human WISP-1 DNA Framework Markers (Δct)

Probe/Delta CT

| Template | C-myc (SD) | WISP-1 (SD) | WISP-2 (SD) | H9 (SD) | H59 (SD) | H121 (SD) | H200 (SD) | H256 (SD) |
|---|---|---|---|---|---|---|---|---|
| Nor Hu | 0.00 | 0.00 | 0.00 | 0.00 | 0.00 | 0.00 | 0.00 | 0.00 |
| | (0.91) | (0.01) | (0.20) | (0.13) | (0.20) | (0.14) | (0.16) | (0.04) |
| SW480 | 1.86 | 0.84 | 1.92 | −1.18 | 1.01 | 0.17 | 0.165 | 0.81 |
| SW620 | 1.45 | 0.98 | 1.60 | 0.45 | 0.75 | 1.00 | 0.81 | 0.52 |
| Colo320 | 3.73 | 0.65 | 1.88 | 0.69 | 0.70 | 0.89 | 0.60 | 0.40 |
| HT29 | 0.83 | 2.67 | 2.20 | −1.13 | −0.40 | −0.55 | 1.00 | 2.42 |
| HM7 | −2.03 | 0.07 | −0.28 | −0.28 | 0.24 | −0.48 | 0.12 | −0.26 |
| WiDr | −0.13 | 2.91 | 1.67 | −0.20 | 0.95 | 0.07 | 1.43 | 2.55 |
| HCT116 | −0.57 | 1.82 | 1.04 | 1.24 | 1.56 | 0.84 | 1.76 | 1.53 |
| SKCO-1 | 0.19 | 1.68 | 0.97 | −0.30 | 0.32 | 0.12 | 1.39 | 1.63 |
| SW403 | −0.72 | 1.34 | 1.77 | 0.23 | 0.53 | 0.26 | 1.48 | 1.48 |
| Nor Hu | — | 0.00 | 0.00 | 0.00 | 0.00 | 0.00 | 0.00 | 0.00 |
| | | (0.18) | (1.02) | (0.08) | (0.13) | (0.01) | (0.16) | (0.37) |
| CT-2 | — | 0.65 | 0.44 | −0.25 | 0.11 | 0.07 | 0.13 | 0.95 |
| CT-3 | — | 0.90 | 0.95 | −0.27 | 0.05 | −0.10 | −0.11 | 0.32 |
| CT-8 | — | 0.47 | −0.34 | 0.07 | −0.20 | 0.00 | −0.04 | 0.07 |
| CT-10 | — | 0.76 | 0.50 | 0.23 | −0.36 | −0.08 | 0.17 | 0.70 |
| CT-12 | — | 1.30 | 2.14 | −0.70 | −0.45 | 0.24 | 0.47 | 1.75 |
| CT-14 | — | 1.17 | −0.48 | 0.05 | 0.18 | 0.31 | 0.23 | 1.5! |
| CT-15 | — | 0.22 | −0.13 | 0.13 | −0.48 | 0.29 | 0.11 | 0.59 |
| CT-16 | — | 0.26 | 0.10 | 0.00 | −0.15 | −0.23 | −0.09 | 0.95 |

TABLE VII-continued

Amplification of framework markers relative to Human WISP-1 DNA Framework Markers (Δct)

| | Probe/Delta CT | | | | | | | |
|---|---|---|---|---|---|---|---|---|
| Template | C-myc (SD) | WISP-1 (SD) | WISP-2 (SD) | H9 (SD) | H59 (SD) | H121 (SD) | H200 (SD) | H256 (SD) |
| CT-17 | — | 0.57 | −0.33 | 0.73 | −0.11 | −0.05 | −0.11 | 0.25 |
| Nor Hu | — | 0.00 | 0.00 | 0.00 | 0.00 | 0.00 | 0.00 | 0.00 |
| | | (0.45) | (1.07) | (0.04) | (0.21) | (0.18) | (0.03) | (0.18) |
| CT-1 | — | 0.64 | −0.37 | −0.36 | 0.19 | 0.68 | 0.01 | 0.66 |
| CT-4 | — | 0.15 | −0.23 | −1.00 | 0.24 | −0.11 | 0.30 | 0.14 |
| CT-5 | — | 0.86 | −1.23 | −0.60 | −0.25 | 0.22 | 0.51 | 0.62 |
| CT-6 | — | 0.03 | 0.39 | −0.24 | 0.61 | 0.70 | 0.01 | 0.19 |
| CT-7 | — | −0.20 | −1.36 | −0.76 | 0.00 | −0.09 | −0.13 | −0.16 |
| CT-9 | — | 0.30 | −0.54 | −0.50 | 0.29 | 0.54 | 0.11 | 0.18 |
| CT-11 | — | 0.48 | 0.14 | −0.89 | 0.34 | 0.82 | 0.17 | −0.06 |
| CT-18 | — | −0.20 | −1.37- | −0.52 | 0.32 | 0.66 | 0.08 | 0.12 |

TABLE VIII

Amplification of framework markers relative to Human WISP-1 DNA Framework Markers (δct)

| | Probe/Delta CT | | | | | |
|---|---|---|---|---|---|---|
| Template | WISP-2 (SD) | T10 (SD) | T48 (SD) | T73 (SD) | T115 (SD) | T159 (SD) |
| Nor Hu | 0.00 | 0.00 | 0.00 | 0.00 | 0.00 | 0.00 |
| | (0.05) | (0.16) | (0.09) | (0.21) | (3.22) | (0.09) |
| SW480 | 1.31 | 1.32 | 0.63 | 1.94 | −5.66 | 1.61. |
| SW620 | 1.32 | 2.02 | 1.42 | 1.06 | −10.95 | 1.48 |
| Colo320 | 0.43 | 1.35 | 1.37 | 0.61 | 0.30 | 1.37 |
| HT29 | 1.76 | 1.09 | −2.23 | 1.26 | −5.47 | 1.87 |
| HM7 | −0.32 | 0.32 | 0.38 | 0.41 | −6.3 | 0.48 |
| WiDr | 1.76 | 1.61 | −1.38 | 1.04 | −7.36 | 1.55 |
| HCT116 | 1.18 | 1.24 | 1.15 | 1.46 | −8.38 | 1.49 |
| SKCO-1 | 1.40 | 1.17 | 1.19 | 1.13 | −5.34 | 1.61 |
| SW403 | 1.92 | 2.24 | −17.23 | 1.38 | −3.66 | 2.12 |

Gene Amplification Assay Results:

The human WISP-2 (PR0261) compound of the invention was screened in the following primary tumors and the resulting ΔCt values are reported in Table IX.

TABLE IX

ΔCt values in lung and colon primary tumor models

| Primary Tumor | PR0261 |
|---|---|
| LT1 | 0.41 |
| LT1a | 1.08 |
| LT2 | 0.27 |
| LT3 | 0.98 |
| LT4 | 0.32 |
| LT6 | 0.45 |
| LT7 | 0.03 |
| LT9 | 0.18 |
| LT10 | 1.16 |
| LT11 | 0.67, 1.59, 0.63, 0.19, |
| LT12 | 0.80, 1.73, 1.08, 2.23 |
| LT13 | 1.02, 1.13, 1.01, 0.29 |
| LT15 | 0.97, 2.64, 0.56, 2.38 |
| LT16 | 0.80, 0.75, 0.82, 2.05 |
| LT17 | 1.67, 2.01, 1.43, 0.93 |
| LT18 | 1.22, 0.46, 0.15, −0.17 |
| LT19 | 0.76, 1.38, 1.39, 2.33 |
| LT21 | 0.04, 1.14, 0.48, 3.40 |
| CT2 | 1.66 |
| CT3 | 2.14 |
| CT8 | 0.55 |
| CT10 | 1.00 |
| CT12 | 0.34 |
| CT14 | 1.03 |
| CT15 | 0.67 |
| CT16 | 0.87 |
| CT17 | −0.19 |
| M | −0.06 |
| CT4 | 1.00 |
| CT5 | 1.07 |
| CT6 | −0.08 |
| CT7 | 0.15 |
| CT9 | 0.68 |
| CT11 | 0.59 |
| CT18 | 0.73 |
| A549 | — |
| Calu-1 | |
| Calu-6 | |
| H157 | |
| H441 | |
| H460 | |
| SKMES1 | |
| SW900 | — |
| SW480 | 0.62, 1.86, 1.90, 1.91, 1.20, 2.36, 1.57, 1.68, 1.68, 1.53, 1.36, 2.50 1.59, |
| SW620 | 0.66, 1.98, 1.65, 1.57, 1.85, 1.83, 1.63, 1.41, 1.61, 1.42, 1.24, 1.59, 1.52, |
| Colo320 | −0.33, 2.49, 0.66, 0.99, 0.48, 1.06, 0.91, 1.24, 0.72, 1.04, 0.33, 0.46, 0.2-- |
| HT29 | 0.46, 2.00, 1.95, 2.59, 1.61, 2.59, 2.58, 1.39, 1.49, 1.32 1.38, 1.40, |
| HM7 | −0.70, 0.54, 0.74, 0.67, −0.29, 0.66, 0.27, 0.-08, 0.64, 0.34, 0.09, 0.29, 0.21 |
| WiDr | 0.19, 1.84, 1.64, 1.58, 1.00, 0.91, 1.71, 0.87 1.44, 1.57, 0.93, |
| HCT116 | 0.25, 1.08, 1.29, 2.05, 1.04, 1.81, 2.01, 1.56, 1.29, 1.05, 1.07, 1.09, 0.96 |
| SKC01 | 0.73, 2.10, 1.99, 1.50, 1.33, 2.13, 1.00, 1.33, 1.33, 1.29 1.26, 1.19 |
| SW403 | 0.26, 2.15, 1.98, 1.52, 1.42, 1.67, 2.20, 2.19, 2.40, 1.40, 1.50, 1.291.43, |
| LS174T | 1.48 |
| HBL100 | 1.40 |
| MB435s | 1.43 |
| T47D | 0.38 |
| MB468 | −0.08 |
| MB175 | 0.23 |
| MB361 | 0.37 |
| BT20 | 1.66 |
| MCF7 | 0.53 |
| SKBR3 | 1.73 |

The ΔCt values for DNA33473 (PR0261; human WISP-2) in a variety of primary lung and colon tumors as well as lung tumor cell lines are reported in Table IX. A ΔCt value of >1 was typically used as the threshold value for amplification scoring, as this represents a doubling of the gene copy. Table IX indicates that significant amplification of DNA33474 occurred in: primary lung tumors LT1a, LT10, LT12, LT15, LT17 and LT19; (2) primary colon tumors CT2, CT3, CT14, and CT5; (3) colon tumor cell lines SW480, SW620, HT29, WiDr, HCT116, SKC01, SW403, and LS174T and (4) breast tumor cell lines HBL100, MB435s, BT20 and SKBR3.

The ΔCt and average ΔCt values for the primary lung tumors were the following: 1.08, 1.16, 1.17, 1.64, 1.50 and 1.47, respectively; those for the primary colon tumors were 1.16, 2.14, 1.03 and 1.07, respectively; those for the colon tumor cell lines were 1.67, 1.54, 1.73, 1.24, 1.32, 1.35, 1.65, and 1.48, respectively; and those for the breast tumor cell lines were 1.40, 1.43, 1.66, and 1.73, respectively.

For the lung tumors, this represents approximately a 2.1-, 2.2-, 2.2-, 3.1-, 2.8-, and 2.8-, respectively, fold increase in gene copy relative to normal tissue. For the colon tumors, this represents a 2.2-, 4.4-, 2.0-, and 2.1-, respectively, fold increase in gene copy relative to normal tissue. For the colon tumor cell lines, this represents a 3.2-, 2.9-, 3.3-, 2.4-, 2.5-, 2.5-, 3.1-, and 2.8-, respectively, fold increase in gene copy relative to normal tissue. For the breast tumor cell lines, this represents a 2.6-, 2.7-, 3.2-, and 3.3-, respectively, fold increase in gene copy relative to normal tissue. Because amplification of DNA33473 (PR0261) occurs in various tumors, it is likely associated with tumor formation or growth. As a result, antagonists (e.g., antibodies) directed against the protein encoded by DNA33473 (PR0261) would be expected to be useful in cancer therapy.

Example 16

In Situ Hybridization

In situ hybridization is a powerful and versatile technique for the detection and localization of nucleic acid sequences within cell or tissue preparations. It may be useful, for example, in identifying sites of gene expression, analyzing the tissue distribution of transcription, identifying and localizing viral infection, following changes in specific mRNA synthesis, and aiding in chromosome mapping.

In situ hybridization was performed following an optimized version of the protocol by Lu and Gillett, *Cell Vision* 1: 169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A ($^{33}$-P) UTP-labeled antisense riboprobe was generated from a PCR product and hybridized at 55° C. overnight. The slides were dipped in KODAK NTB2™ nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed-vacuum dried. To each tube containing dried $^{33}$P-UTP, the following ingredients were added:

2.0 µl 5× transcription buffer
1.0 µl DTT (100 mM)
2.0 µl NTP mix (2.5 mM: 10 µl each of 10 mM GTP, CTP & ATP+10 µl H$_2$0)
1.0 µl UTP (50 µM)
1.0 µl RNAsin
1.0 µl DNA template (1 µg)
1.0 µl H$_2$
1.0 µl RNA polymerase (for PCR products T3=AS, T7=S, usually)

The tubes were incubated at 37° C. for one hour. A total of 1.0 µl RQ1 DNase was added, followed by incubation at 37° C. for 15 minutes. A total of 90 µl TE (10 mM Tris pH 7.6/1 mM EDTA, pH 8.0) was added, and the mixture was pipetted onto DE81 paper. The remaining solution was loaded in a MICROCON-50™ ultrafiltration unit, and spun using program 10 (6 minutes). The filtration unit was inverted over a second tube and spun using program 2 (3 minutes). After the final recovery spin, a total of 100 µl TE was added. Then 1 µl of the final product was pipetted on DE81 paper and counted in 6 ml of BIOFLUOR II™.

The probe was run on a TBE/urea gel. A total of 1-3 µl of the probe or 5 µl of RNA Mrk III was added to 3 µl of loading buffer. After heating on a 95° C. heat block for three minutes, the gel was immediately placed on ice. The wells of gel were flushed, and the sample was loaded and run at 180-250 volts for 45 minutes. The gel was wrapped in plastic wrap (SARAN™ brand) and exposed to XAR film with an intensifying screen in a −70° C. freezer one hour to overnight.

$^{33}$P-Hybridization

A. Pretreatment of Frozen Sections

The slides were removed from the freezer, placed on aluminum trays, and thawed at room temperature for 5 minutes. The trays were placed in a 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml s.c. H$_2$O). After deproteination in 0.5 µg/ml proteinase K for 10 minutes at 37° C. (12.5 µl of 10 mg/ml stock in 250 ml prewarmed RNAse-free RNAse buffer), the sections were washed in 0.5×SSC for 10 minutes at room temperature. The sections were dehydrated in 70%, 95%, and 100% ethanol, 2 minutes each.

B. Pretreatment of Paraffin-Embedded Sections

The slides were deparaffinized, placed in s.c. H$_2$O, and rinsed twice in 2×SSC at room temperature, for 5 minutes each time. The sections were deproteinated in 20 µg/ml proteinase K (500 µl of 10 mg/ml in 250 ml RNAse-free RNAse buffer; 37° C., 15 minutes) for human embryo tissue, or 8× proteinase K (100 µl in 250 ml RNAse buffer, 37° C., 30 minutes) for formalin tissues. Subsequent rinsing in 0.5×SSC and dehydration were performed as described above.

C. Prehybridization

The slides were laid out in a plastic box lined with Box buffer (4×SSC, 50% formamide) The filter paper was saturated. The tissue was covered with 50 µl of hybridization buffer (3.75 g dextran sulfate+6 ml s.c. H$_2$O), vortexed, and heated in the microwave for 2 minutes with the cap loosened. After cooling on ice, 18.75 ml formamide, 3.75 ml 20×SSC, and 9 ml s.c. H$_2$O were added, and the tissue was vortexed well and incubated at 42° C. for 1-4 hours.

D. Hybridization $1.0 \times 10^6$ cpm probe and 1.0 µl tRNA (50 mg/ml stock) per slide were heated at 95° C. for 3 minutes. The slides were cooled on ice, and 48 µl hybridization buffer was added per slide. After vortexing, 50 µl $^{33}$P mix was added to 50 µl prehybridization on the slide. The slides were incubated overnight at 55° C.

E. Washes

Washing was done for 2×10 minutes with 2×SSC, EDTA at room temperature (400 ml 20×SSC+16 ml 0.25 M EDTA, $V_f$=4L), followed by RNAseA treatment at 37° C. for 30 minutes (500 µl of 10 mg/ml in 250 ml RNAse buffer=20 µg/ml). The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4L).

F. Oligonucleotides

In situ analysis was performed on DNA sequences disclosed herein. The oligonucleotides employed for these analyses are as follows.

```
(1) Mouse WISP-1 (Clone 568)
Notrim-p1:
                                      (SEQ ID NO: 147)
5'-GGA TTC TAA TAC GAC TCA CTA TAG GGC GTC CCT GGC

CAG TGC TGT GAG-3'

Notrim-p2:
                                      (SEQ ID NO: 148)
5'-CTA TGA AAT TAA CCC TCA CTA AAG GGA GGG CCA GGC

TTT GCT TCC ATT-3'

(2) Human WISP-1
hmWISP-1 p1:
                                      (SEQ ID NO: 149)
5'-GGA TTC TAA TAC GAC TCA CTA TAG GGC TGG AGG CAT

GGC ACA GGA AC-3' hmWISP-1 p2:
                                      (SEQ ID NO: 150)
5'-CTA TGA AAT TAA CCC TCA CTA AAG GGA TCC GGA TCA

GGC TTG GGT GTA-3'

(3) Mouse WISP-2 (Clone 1367.3)
1367.p1:
                                      (SEQ ID NO: 151)
5'-GGA TTC TAA TAC GAC TCA CTA TAG GGC AGC TTG GGA

TGG AGG TCT TTC-3'

1367.p2:
                                      (SEQ ID NO: 152)
5'-CTA TGA AAT TAA CCC TCA CTA AAG GGA GGG CAC TGG

GGT GGT GT-3'

(4) Human WISP-2 (DNA33473)
DNA33473-p1:
                                      (SEQ ID NO: 153)
5'-GGA TTC TAA TAC GAC TCA CTA TAG GGC GCG AGG ACG

GCG GCT TCA-3'

DNA33473-p2:
                                      (SEQ ID NO: 154)
5'-CTA TGA AAT TAA CCC TCA CTA AAG GGA AGA GTC GCG

GCC GCC CTT TTT-3'

(5) Human WISP-3
WISP3-p1
                                      (SEQ ID NO: 155)
5'-GGA TTC TAA TAC GAC TCA CTA TAG GGC GGG GCT CCT

CTT CTC CAC TCT-3'

WISP3-p2
                                      (SEQ ID NO: 156)
5'-CTA TGA AAT TAA CCC TCA CTA AAG GGA GCT GTC GCA

AGG CTG AAT GTA-3'
```

G. Results

In situ analysis was performed on the above DNA sequences disclosed herein. The results from these analyses are as follows.

(1) Mouse WISP-1
Expression in Mouse Tissues

Mouse Fetal Tissues: In situ hybridization of mouse WISP-1 showed strong expression in embryonic mesenchymal tissues. At E10.5 expression was observed in tissues that would develop into skeletal elements in the adult; this pattern was maintained at later stages of embryonic development. In later stages (E12.5 and E15.5), expression was highest in osteoblasts at the sites of bone formation. Expression was also observed in the embryonic heart, where the signal was particularly strong in the atria at E12.5 (atria were not included in sections at E15.5).

Mouse Adult Tissues: No expression was observed in any of the adult tissues examined, including heart, lung, kidney, adrenal, liver, pancreas, cerebrum, and cerebellum. These results do not correlate with the Northern data.

Additional sites of expression in the fetus were the walls of developing blood vessels and in fibroblast-like cells within the hepatic portal tract mesenchyme.

Expression in Normal and Wnt-1 Transgenic Tumors

Expression with the antisense probe was observed over fibroblast-like cells lying adjacent to the subcutaneous skeletal muscle in P10 (post-natal day 10 pups) and in pregnant females. Expression was not observed over breast epithelial cells at any of the time points examined in the study.

Expression of mouse WISP-1 was high in all three of the Wnt-1 transgenic tumors tested and appeared to be confined to the supporting fibroblast-like cells within the delicate connective tissue stroma. Some expression was seen over the tumor cells themselves; however, this likely represents overspill from tumor fibroblasts, rather than true expression by tumor cells.

In summary, mouse WISP-1 was expressed in embryonic skeletal mesenchyme and at sites of bone formation. It was additionally expressed in fibroblasts in the sub-cutus of growing pups and pregnant females. It is likely to play a role in osteogenesis, and may be involved in repair after injury. Expression was also observed in the embryonic heart.

(2) Human WISP-1
Expression in Human Tissues

Human Fetal Tissue The fetal tissues examined (E12-E16 weeks) included: placenta, umbilical cord, liver, kidney, adrenals, thyroid, lungs, heart, great vessels, oesophagus, stomach, small intestine, spleen, thymus, pancreas, brain, eye, spinal cord, body wall, pelvis, and lower limb.

Human WISP-1 exhibited expression at sites of connective tissue interfaces in the fetus, for example, developing portal tracts, fascial planes in muscle, and connective tissue surrounding developing skeletal elements and tendons. Expression also was seen in the epithelium of the developing renal cortex and in spindle-shaped fibroblast-like cells in the fetal adrenal. Human WISP-1 was strongly expressed by osteoblasts at sites of bone formation in the fetal limb.

Human Adult Tissue The adult tissues examined were: liver, kidney, adrenal, myocardium, aorta, spleen, lung, skin, chondrosarcoma, eye, stomach, gastric carcinoma, colon, colonic carcinoma, renal cell carcinoma, prostate, bladder mucosa, and gall bladder, as well as tissue with acetominophen-induced liver injury and hepatic cirrhosis.

No expression was seen in normal or diseased adult tissues in this study.

In summary, the overall pattern of expression of human WISP-1 was broadly similar to that observed for the mouse gene as noted above. The human WISP-1 probe did not cross react with the mouse embryo section.

Expression in Human Breast Carcinoma and Normal Breast Tissue

Human WISP-1 was negative on benign and malignant epithelial cells, but showed specific hybridization in mesenchmal cells, particularly in areas of tissue repair, including dystrophic ossification. Most positive cells had the morphology of fibroblasts; smooth muscle cells appeared to be negative.

In summary, this study shows expression of human WISP-1 RNA in mesenchymal cells involved in tissue repair and/or collagen deposition. The signal was particularly strong in benign fibroblast-like cells adjacent to either infiltrating breast carcinoma cells or tissue destruction due to benign, inflammatory conditions (duct rupture). Of note is the fact that deposition of benign osteoid seemed to correlate with strong expression of the RNA.

(3) Mouse WISP-2
Expression in Normal Mouse Tissues

Mouse Fetal Tissues: Expression of mouse WISP-2 was observed in osteoblasts in an E15.5 mouse embryo, within the developing mandible.

Mouse Adult Tissues: Expression of mouse WISP-2 was observed in stromal cells around the origin, and within the cusps of the mitral and tricuspid valves of the adult heart. Expression was also observed in the adventitial cells of the renal artery; expression was presumed to be present at this site in all arteries.

All other tissues were negative.
Expression in Wnt-1 Tumors

The results demonstrated specific expression of mouse WISP-2 in the stroma of all Wnt-1 tumors examined. There was a signal over mononuclear cells with open vesicular nuclei, possibly macrophages. No expression was observed in either the benign or the malignant epithelium.

(4) Human WISP-2
Expression in Human Tissues

Strong expression of the WISP-2-encoding gene was observed in dermal fibroblasts in normal adult skin. Additionally, strong expression was seen in two cirrhotic livers, at sites of active hepatic fibrosis. Moderate expression was found over fasiculata cells of adrenal cortex. This localization supports a role for human WISP-2 in extracellular matrix formation or turnover.
Expression in Human Breast Carcinoma and Normal Breast Tissue, and in Lung Carcinoma Human WISP-2 showed a similar hybridization pattern to human WISP-1 (described above) in the two breast tumors examined. It was negative on benign and malignant epithelial cells, but showed specific hybridization in mesenchmal cells, particularly in areas of tissue repair, including dystrophic ossification. The signal appeared to localize to the same cell population for both probes WISP-1 and WISP-2; however, in some areas (breast tumor 02), the signal for WISP-2 was significantly stronger than that for human WISP-1. Most positive cells had the morphology of fibroblasts; smooth muscle cells appeared to be negative. The signal for human WISP-2 was less intense in the lung tumor tissue; however, this section also showed less tissue repair compared with the breast tumor slides. Normal lung and kidney tissue were essentially negative for human WISP-2, as for human WISP-1.

In summary, this study shows expression of human WISP-2 RNA in mesenchymal cells involved in tissue repair and/or collagen deposition. The signal was particularly strong in benign fibroblast-like cells adjacent to either infiltrating breast carcinoma cells or tissue destruction due to benign, inflammatory conditions (duct rupture). Of note is the fact that deposition of benign osteoid seemed to correlate with strong expression of the RNA.

(5) Human WISP-3
Expression in Normal Adult and Fetal Tissues and in Human Breast Carcinoma and Normal Breast Tissue and in Colon Carcinoma The analysis shows strong expression of human WISP-3 in dermal fibroblasts in normal adult skin and in cirrhotic livers at sites of active hepatic fibrosis. This localization pattern supports a role for this growth factor in extracellular matrix formation and turnover.

The probe for human WISP-3 was negative on most tissues examined, it showed a weak, diffuse positivity on sections of an osteosarcoma; some of the positive cells do represent malignant cells. WISP-3 was negative on all normal and fetal tissues examined.

Example 17

Ability of WISP Polypeptides to Inhibit VEGF-Stimulated Proliferation of Endothelial Cell Growth The ability of mouse and human WISP-1 and human WISP-2 polypeptides to inhibit VEGF-stimulated proliferation of endothelial cells was tested. Specifically, bovine adrenal cortical capillary endothelial (ACE) cells (from primary culture, maximum 12-14 passages) were plated on 96-well microtiter plates (Amersham Life Science) at a density of 500 cells/well per 100 μL in low-glucose DMEM, 10% calf serum, 2 mM glutamine, 1× pen/strept, and fungizone, supplemented with 3 ng/mL VEGF. Controls were plated the same way but some did not include VEGF. A test sample of either mouse WISP-1, human WISP-1 conjugated to IgG, or human WISP-2 (PR0261) conjugated to poly-His was added in a 100-μl volume for a 200-μL final volume. Cells were incubated for 5-7 days at 37° C. The media were aspirated and the cells washed 1× with PBS. An acid phosphatase reaction mixture (100 μL, 0.1 M sodium acetate, pH 5.5, 0.1% TRITON-100TH, 10 mM p-nitrophenyl phosphate) was added. After incubation for 2 hours at 37° C., the reaction was stopped by addition of 10 μl, 1 N NaOH. OD was measured on a microtiter plate reader at 405 nm. Controls were: no cells, cells alone, cells+FGF (5 ng/mL), cells+VEGF (3 ng/mL), cells+VEGF (3 ng/ml)+TGF-β (1 ng/ml), and cells+VEGF (3 ng/mL)+LIF (5 ng/mL) (TGF-β at a 1 ng/ml concentration is known to block 70-90% of VEGF-stimulated cell proliferation.)

The results were assessed by calculating the percentage inhibition of VEGF (3 ng/ml)-stimulated cell proliferation, determined by measuring acid phosphatase activity at OD405 nm (1) relative to cells without stimulation, and (2) relative to the reference TGF-β inhibition of VEGF-stimulated activity. The results, as shown in Table X below, are indicative of the utility of the WISP polypeptides in cancer therapy and specifically in inhibiting tumor angiogenesis. The numerical values (relative inhibition) shown in Table X are determined by calculating the percent inhibition of VEGF-stimulated proliferation by the mouse WISP-1, human WISP-1-IgG, and human WISP-2-poly-His polypeptides relative to cells without stimulation and then dividing that percentage into the percent inhibition obtained by TGF-β at 1 ng/ml, which is known to block 70-90% of VEGF-stimulated cell proliferation. Human WISP-1 and human WISP-2 appear to be particularly useful as angiostatic agents.

TABLE X

| Polypeptide | Concentration (nM) | Relative Inhibition |
|---|---|---|
| Mouse WISP-1 | 0.1 | 113 |
| " | 1.0 | 108 |
| " | 10.0 | 109 |
| Human WISP-1-IgG | 1.1 | 1 |
| " | 11.0 | 0.95 |
| " | 110.0 | 0.9 |
| Human WisP-2-poly-His | 0.01 | 0.95 |
| " | 0.01% | 1.1 |
| " | 0.1 | 0.62 |
| " | 1.0 | 1.03 |
| " | 1.0 | 0.5 |
| " | 1.0 | 0.6 |

Deposit of Material

The following materials have been deposited with the American Type Culture Collection, University Blvd., Manassas, Va., USA (ATCC):

| Material | ATCC Dep. No. | Deposit Date |
|---|---|---|
| pRK5E.h.WIG-1.568.38 | 209533 | Dec. 10, 1997 |
| pRK5E.m.WIG-1.568.6his | 209537 | Dec. 10, 1997 |
| Plasmid (encoding human WISP-2) | 209391 | Oct. 17, 1997 |
| pRKE.m.WIG-2.1367.3 | 209538 | Dec. 10, 1997 |
| DNA56350-1176-2 | 209706 | Mar. 26, 1998 |
| DNA58800-1176-2 | 209707 | Mar. 26, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the cultures of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited materials is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiment is intended as a single illustration of certain aspects of the invention and any constructs that are functionally equivalent are within the scope of this invention. The deposits of materials herein do not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed:

1. An isolated chimeric, human or humanized antibody, or an antigen-binding fragment thereof, specifically binding to a WISP-1 polypeptide selected from the group consisting of polypeptides comprising
   (1) amino acid residues 23 to 367 or 1 to 367 of FIGS. 3A 3C (SEQ ID NOS:3 and 4, respectively);
   (2) amino acid residues 23 to 367 or 1 to 367 of FIGS. 3A 3C except for an isoleucine residue at position 184 rather than a valine residue (SEQ ID NOS:5 and 6, respectively);
   (3) amino acid residues 23 to 367 or 1 to 367 of FIGS. 3A 3C except for a serine residue at position 202 rather than an alanine residue (SEQ ID NOS:7 and 8, respectively);
   (4) amino acid residues 23 to 367 or 1 to 367 of FIGS. 3A 3C except for an isoleucine residue at position 184 rather than a valine residue and except for a serine residue at position 202 rather than an alanine residue (SEQ ID NOS:21 and 22, respectively);
   (5) the WISP-1 polypeptide encoded by the full-length coding sequence in ATCC Deposit No. 209533;
   (6) the WISP-1 polypeptide encoded by the nucleic acid sequence of SEQ ID NO: 23;
   (7) the WISP-1 polypeptide encoded by the nucleic acid sequence of SEQ ID NO: 24;
   (8) the WISP-1 polypeptide encoded by the nucleic acid sequence of SEQ ID NO: 25;
   (9) the WISP-1 polypeptide encoded by the nucleic acid sequence of SEQ ID NO: 26;
   (10) the WISP-1 polypeptide encoded by the nucleic acid sequence of SEQ ID. NO: 27;
   (11) the WISP-1 polypeptide encoded by the nucleic acid sequence of SEQ ID NO: 28; and

(12) the WISP-1 polypeptide encoded by the nucleic acid sequence of SEQ ID NO: 29, each with or without an N-terminal methionine, and a pharmaceutically acceptable carrier.

2. The isolated antibody of claim 1, which induces death of a cell overexpressing a WISP-1 polypeptide.

3. The isolated antibody of claim 2, wherein said cell is a cancer cell.

4. The isolated antibody, or antigen-binding fragment of claim 1, wherein said antigen-binding fragment is selected from the group consisting of Fv, Fab, Fab', F(ab')$_2$ fragments.

5. The isolated antibody, or antigen-binding fragment, of claim 1 which is monoclonal.

* * * * *

SEQUENCE LISTING

```
<160> NUMBER OF SEQ ID NOS: 156

<210> SEQ ID NO 1
<211> LENGTH: 2830
<212> TYPE: DNA
<213> ORGANISM: Homo sapiens

<400> SEQUENCE: 1
cccacgcgtc cgctgggccc agctcccccg agaggtggtc ggatcctctg ggctgctcgg      60
tcgatgcctg tgccactgac gtccaggcat gaggtggttc ctgccctgga cgctggcagc     120
agtgacagca gcagccgcca gcaccgtcct ggccacggcc ctctctccag cccctacgac     180
catggacttt actccagctc cactggagga cacctcctca cgcccccaat tctgcaagtg     240
gccatgtgag tgcccgccat ccccacccg ctgcccgctg ggggtcagcc tcatcacaga      300
tggctgtgag tgctgtaaga tgtgcgctca gcagcttggg gacaactgca cggaggctgc     360
catctgtgac ccccaccggg gcctctactg tgactacagc ggggaccgcc cgaggtacgc     420
aataggagtg tgtgcacagg tggtcggtgt gggctgcgtc ctggatgggg tgcgctacaa     480
caacggccag tccttccagc ctaactgcaa gtacaactgc acgtgcatcg acggcgcggt     540
gggctgcaca ccactgtgcc tccgagtgcg ccccccgcgt ctctggtgcc cccaccccgcg    600 gcgcgtgagc atacctggcc actgctgtga gcagtgggta tgtgaggacg acgccaagag     660
```

```
gccacgcaag accgcacccc gtgacacagg agccttcgat gctgtgggtg aggtggaggc    720
atggcacagg aactgcatag cctacacaag cccctggagc ccttgctcca ccagctgcgg    780
cctgggggtc tccactcgga tctccaatgt taacgcccag tgctggcctg agcaagagag    840
ccgcctctgc aacttgcggc catgcgatgt ggacatccat acactcatta aggcagggaa    900
gaagtgtctg gctgtgtacc agccagaggc atccatgaac ttcacacttg cgggctgcat    960
cagcacacgc tcctatcaac ccaagtactg tggagtttgc atggacaata ggtgctgcat   1020
cccctacaag tctaagacta cgacgtgtc cttccagtgt cctgatgggc ttggcttctc   1080
ccgccaggtc ctatggatta tgcctgcttc tgtaacctg agctgtagga atcccaatga   1140
catctttgct gacttggaat cctaccctga cttctcagaa attgccaact aggcaggcac   1200
aaatcttggg tcttggggac taacccaatg cctgtgaagc agtcagccct tatggccaat   1260
aacttttcac caatgagcct tagttaccct gatctggacc cttggcctcc atttctgtct   1320
ctaaccattc aaatgacgcc tgatggtgct gctcaggccc atgctatgag ttttctcctt   1380
gatatcattc agcatctact ctaaagaaaa atgcctgtct ctagctgttc tggactacac   1440
ccaagcctga tccagccttt ccaagtcact agaagtcctg ctggatcttg cctaaatccc   1500
aagaaatgga atcaggtaga cttttaatat cactaatttc ttctttagat gccaaccac   1560 aagactcttt gggtccattc agatgaatag atggaatttg gaacaataga ataatctatt   1620
atttggagcc tgccaagagg tactgtaatg ggtaattctg acgtcagcgc accaaaacta   1680
tcctgattcc aaatatgtat gcacctcaag gtcatcaaac atttgccaag tgagttgaat   1740
agttgcttaa ttttgatttt taatggaaag ttgtatccat taacctgggc attgttgagg   1800
ttaagtttct cttcacccct acactgtgaa gggtacagat taggtttgtc ccagtcagaa   1860 ataaatttg ataaacattc ctgttgatgg gaaaagcccc cagttaatac tccagagaca   1920
gggaaaggtc agcccatttc agaaggacca attgactctc acactgaatc agctgctgac   1980
tggcagggct ttgggcagtt ggccaggctc ttccttgaat cttctccctt gtcctgcttg   2040
ggttcatagg aattggtaag gcctctggac tggcctgtct ggcccctgag agtggtgccc   2100
tggaacactc ctctactctt acagagcctt gagagaccca gctgcagacc atgccagacc   2160
cactgaaatg accaagacag gttcaggtag gggtgtgggt caaaccaaga agtgggtgcc   2220
cttggtagca gcctggggtg acctctagag ctggaggctg tgggactcca ggggccccccg   2280 tgttcaggac acatctattg cagagactca tttcacagcc tttcgttctg ctgaccaaat   2340
ggccagtttt ctggtaggaa gatggaggtt taccagttgt ttagaaacag aaatagactt   2400
aataaaggtt taaagctgaa gaggttgaag ctaaaggaa aaggttgttg ttaatgaata   2460
tcaggctatt atttattgta ttaggaaaat ataatattta ctgttagaat tcttttattt   2520
agggcctttt ctgtgccaga cattgctctc agtgctttgc atgtattagc tcactgaatc   2580
ttcacgacaa tgttgagaag ttcccattat tatttctgtt cttacaaatg tgaaacggaa   2640
gctcatagag gtgagaaaac tcaaccagag tcacccagtt ggtgactggg aaagttagga   2700
ttcagatcga aattgactg tctttataac ccatatttc cccctgtttt tagagcttcc   2760
aaatgtgtca gaataggaaa acattgcaat aaatggcttg attttttaaa aaaaaaaaa   2820 aaaaaaaaaa                                                          2830

<210> SEQ ID NO 2
<211> LENGTH: 2830
<212> TYPE: DNA
<213> ORGANISM: Homo sapiens
```

<400> SEQUENCE: 2

```
ttttttttttt ttttttttttt tttaaaaaat caagccattt attgcaatgt tttcctattc      60
tgacacattt ggaagctcta aaaacagggg gaaaatatgg gttataaaga cagtccaatt      120
tcgatctgaa tcctaacttt cccagtcacc aactgggtga ctctggttga gttttctcac      180
ctctatgagc ttccgtttca catttgtaag aacagaaata ataatgggaa cttctcaaca      240
ttgtcgtgaa gattcagtga gctaatacat gcaaagcact gagagcaatg tctggcacag      300
aaaaggccct aaataaaaga attctaacag taaatattat attttcctaa tacaataaat      360
aatagcctga tattcattaa caacaacctt ttccttttag cttcaacctc ttcagcttta      420
aaccttatt aagtctattt ctgtttctaa caactggta aacctccatc ttcctaccag      480
aaaactggcc atttggtcag cagaacgaaa ggctgtgaaa tgagtctctg caatagatgt      540
gtcctgaaca cggggggcccc tggagtccca cagcctccag ctctagaggt caccccaggc      600
tgctaccaag gcacccact tcttggtttg acccacaccc ctacctgaac ctgtcttggt      660
catttcagtg ggtctggcat ggtctgcagc tgggtctctc aaggctctgt aagagtagag      720
gagtgttcca gggcaccact ctcaggggcc agacaggcca gtccagaggc cttaccaatt      780
cctatgaacc caagcaggac aagggagaag attcaaggaa gagcctggcc aactgcccaa      840
agccctgcca gtcagcagct gattcagtgt gagagtcaat tggtccttct gaaatgggct      900
gacctttccc tgtctctgga gtattaactg ggggcttttc ccatcaacag gaatgtttat      960
caaatttat ttctgactgg gacaaaccta atctgtaccc ttcacagtgt aggggtgaag     1020
agaaacttaa cctcaacaat gcccaggtta atggatacaa cttccatta aaaatcaaaa     1080
ttaagcaact attcaactca cttggcaaat gtttgatgac cttgaggtgc atacatattt     1140
ggaatcagga tagttttggt gcgctgacgt cagaattacc cattacagta cctcttggca     1200
ggctccaaat aatagattat tctattgttc caaattccat ctattcatct gaatggaccc     1260
aaagagtctt gtggtttggc atctaaagaa gaaattagtg atattaaaag tctacctgat     1320
tccatttctt gggatttagg caagatccag caggacttct agtgacttgg aaaggctgga     1380
tcaggcttgg gtgtagtcca gaacagctag agacaggcat ttttctttag agtagatgct     1440
gaatgatatc aaggagaaaa ctcatagcat gggcctgagc agcaccatca ggcgtcattt     1500
gaatggttag agacagaaat ggaggccaag ggtccagatc agggtaacta aggctcattg     1560
gtgaaaagtt attggccata agggctgact gcttcacagg cattgggtta gtccccaaga     1620
cccaagattt gtgcctgcct agttggcaat ttctgagaag tcagggtagg attccaagtc     1680
agcaaagatg tcattgggat tcctacagct caggttacag aagcaggcat taatccatag     1740
gacctggcgg gagaagccaa gcccatcagg acactggaag gacacgtcga tagtcttaga     1800
cttgtagggg atgcagcacc tattgtccat gcaaactcca cagtacttgg gttgatagga     1860
gcgtgtgctg atgcagcccg caagtgtgaa gttcatggat gcctctggct ggtacacagc     1920
cagacacttc ttccctgcct taatgagtgt atggatgtcc acatcgcatg gccgcaagtt     1980
gcagaggcgg ctctcttgct caggccagca ctgggcgtta acattggaga tccgagtgga     2040
gacccccagg ccgcagctgg tggagcaagg gctccagggg cttgtgtagg ctatgcagtt     2100
cctgtgccat gcctccacct cacccacagc atcgaaggct cctgtgtcac ggggtgcggt     2160
cttgcgtggc ctcttggcgt cgtcctcaca tacccactgc tcacagcagt ggccaggtat     2220
gctcacgcgc cgcgggtggg ggcaccgag acgcggggggg cgcactcgga ggcacagtgg     2280
tgtgcagccc accgcgccgt cgatgcacgt gcagttgtac ttgcagttag gctggaagga     2340
```

```
ctggccgttg ttgtagcgca ccccatccag gacgcagccc acaccgacca cctgtgcaca    2400
cactcctatt gcgtacctcg ggcggtcccc gctgtagtca cagtagaggc cccggtgggg    2460
gtcacagatg gcagcctccg tgcagttgtc cccaagctgc tgagcgcaca tcttacagca    2520
ctcacagcca tctgtgatga ggctgacccc cagcgggcag cggggtgggg atggcgggca    2580
ctcacatggc cacttgcaga attggggggcg tgaggaggtg tcctccagtg gagctggagt    2640
aaagtccatg gtcgtagggg ctggagagag ggccgtggcc aggacggtgc tggcggctgc    2700
tgctgtcact gctgccagcg tccagggcag gaaccacctc atgcctggac gtcagtggca    2760
caggcatcga ccgagcagcc cagaggatcc gaccacctct cgggggagct gggcccagcg    2820
gacgcgtggg                                                            2830
```

<210> SEQ ID NO 3
<211> LENGTH: 345
<212> TYPE: PRT
<213> ORGANISM: Homo sapiens

<400> SEQUENCE: 3

```
Thr Ala Leu Ser Pro Ala Pro Thr Thr Met Asp Phe Thr Pro Ala Pro
1               5                  10                  15

Leu Glu Asp Thr Ser Ser Arg Pro Gln Phe Cys Lys Trp Pro Cys Glu
            20                  25                  30

Cys Pro Pro Ser Pro Pro Arg Cys Pro Leu Gly Val Ser Leu Ile Thr
        35                  40                  45

Asp Gly Cys Glu Cys Cys Lys Met Cys Ala Gln Gln Leu Gly Asp Asn
    50                  55                  60

Cys Thr Glu Ala Ala Ile Cys Asp Pro His Arg Gly Leu Tyr Cys Asp
65                  70                  75                  80

Tyr Ser Gly Asp Arg Pro Arg Tyr Ala Ile Gly Val Cys Ala Gln Val
                85                  90                  95

Val Gly Val Gly Cys Val Leu Asp Gly Val Arg Tyr Asn Asn Gly Gln
            100                 105                 110

Ser Phe Gln Pro Asn Cys Lys Tyr Asn Cys Thr Cys Ile Asp Gly Ala
        115                 120                 125

Val Gly Cys Thr Pro Leu Cys Leu Arg Val Arg Pro Pro Arg Leu Trp
    130                 135                 140

Cys Pro His Pro Arg Arg Val Ser Ile Pro Gly His Cys Cys Glu Gln
145                 150                 155                 160

Trp Val Cys Glu Asp Asp Ala Lys Arg Pro Arg Lys Thr Ala Pro Arg
                165                 170                 175

Asp Thr Gly Ala Phe Asp Ala Val Gly Glu Val Glu Ala Trp His Arg
            180                 185                 190

Asn Cys Ile Ala Tyr Thr Ser Pro Trp Ser Pro Cys Ser Thr Ser Cys
        195                 200                 205

Gly Leu Gly Val Ser Thr Arg Ile Ser Asn Val Asn Ala Gln Cys Trp
    210                 215                 220

Pro Glu Gln Glu Ser Arg Leu Cys Asn Leu Arg Pro Cys Asp Val Asp
225                 230                 235                 240

Ile His Thr Leu Ile Lys Ala Gly Lys Lys Cys Leu Ala Val Tyr Gln
                245                 250                 255

Pro Glu Ala Ser Met Asn Phe Thr Leu Ala Gly Cys Ile Ser Thr Arg
            260                 265                 270

Ser Tyr Gln Pro Lys Tyr Cys Gly Val Cys Met Asp Asn Arg Cys Cys
        275                 280                 285
```

Ile Pro Tyr Lys Ser Lys Thr Ile Asp Val Ser Phe Gln Cys Pro Asp
290                 295                 300

Gly Leu Gly Phe Ser Arg Gln Val Leu Trp Ile Asn Ala Cys Phe Cys
305                 310                 315                 320

Asn Leu Ser Cys Arg Asn Pro Asn Asp Ile Phe Ala Asp Leu Glu Ser
            325                 330                 335

Tyr Pro Asp Phe Ser Glu Ile Ala Asn
            340                 345

<210> SEQ ID NO 4
<211> LENGTH: 367
<212> TYPE: PRT
<213> ORGANISM: Homo sapiens

<400> SEQUENCE: 4

Met Arg Trp Phe Leu Pro Trp Thr Leu Ala Ala Val Thr Ala Ala Ala
1               5                   10                  15

Ala Ser Thr Val Leu Ala Thr Ala Leu Ser Pro Ala Thr Thr Met
                20                  25                  30

Asp Phe Thr Pro Ala Pro Leu Glu Asp Thr Ser Ser Arg Pro Gln Phe
            35                  40                  45

Cys Lys Trp Pro Cys Glu Cys Pro Pro Ser Pro Arg Cys Pro Leu
50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
            115                 120                 125

Arg Tyr Asn Asn Gly Gln Ser Phe Gln Pro Asn Cys Lys Tyr Asn Cys
130                 135                 140

Thr Cys Ile Asp Gly Ala Val Gly Cys Thr Pro Leu Cys Leu Arg Val
145                 150                 155                 160

Arg Pro Pro Arg Leu Trp Cys Pro His Pro Arg Arg Val Ser Ile Pro
                165                 170                 175

Gly His Cys Cys Glu Gln Trp Val Cys Glu Asp Asp Ala Lys Arg Pro
            180                 185                 190

Arg Lys Thr Ala Pro Arg Asp Thr Gly Ala Phe Asp Ala Val Gly Glu
            195                 200                 205

Val Glu Ala Trp His Arg Asn Cys Ile Ala Tyr Thr Ser Pro Trp Ser
210                 215                 220

Pro Cys Ser Thr Ser Cys Gly Leu Gly Val Ser Thr Arg Ile Ser Asn
225                 230                 235                 240

Val Asn Ala Gln Cys Trp Pro Glu Gln Glu Ser Arg Leu Cys Asn Leu
                245                 250                 255

Arg Pro Cys Asp Val Asp Ile His Thr Leu Ile Lys Ala Gly Lys Lys
            260                 265                 270

Cys Leu Ala Val Tyr Gln Pro Glu Ala Ser Met Asn Phe Thr Leu Ala
            275                 280                 285

Gly Cys Ile Ser Thr Arg Ser Tyr Gln Pro Lys Tyr Cys Gly Val Cys
            290                 295                 300

Met Asp Asn Arg Cys Cys Ile Pro Tyr Lys Ser Lys Thr Ile Asp Val
305                 310                 315                 320

-continued

Ser Phe Gln Cys Pro Asp Gly Leu Gly Phe Ser Arg Gln Val Leu Trp
            325                 330                 335

Ile Asn Ala Cys Phe Cys Asn Leu Ser Cys Arg Asn Pro Asn Asp Ile
            340                 345                 350

Phe Ala Asp Leu Glu Ser Tyr Pro Asp Phe Ser Glu Ile Ala Asn
            355                 360             365

<210> SEQ ID NO 5
<211> LENGTH: 345
<212> TYPE: PRT
<213> ORGANISM: Homo sapiens

<400> SEQUENCE: 5

Thr Ala Leu Ser Pro Ala Pro Thr Thr Met Asp Phe Thr Pro Ala Pro
1               5                   10                  15

Leu Glu Asp Thr Ser Ser Arg Pro Gln Phe Cys Lys Trp Pro Cys Glu
                20                  25                  30

Cys Pro Pro Ser Pro Pro Arg Cys Pro Leu Gly Val Ser Leu Ile Thr
            35                  40                  45

Asp Gly Cys Glu Cys Cys Lys Met Cys Ala Gln Gln Leu Gly Asp Asn
        50                  55                  60

Cys Thr Glu Ala Ala Ile Cys Asp Pro His Arg Gly Leu Tyr Cys Asp
65                  70                  75                  80

Tyr Ser Gly Asp Arg Pro Arg Tyr Ala Ile Gly Val Cys Ala Gln Val
                85                  90                  95

Val Gly Val Gly Cys Val Leu Asp Gly Val Arg Tyr Asn Asn Gly Gln
            100                 105                 110

Ser Phe Gln Pro Asn Cys Lys Tyr Asn Cys Thr Cys Ile Asp Gly Ala
        115                 120                 125

Val Gly Cys Thr Pro Leu Cys Leu Arg Val Arg Pro Pro Arg Leu Trp
    130                 135                 140

Cys Pro His Pro Arg Arg Val Ser Ile Pro Gly His Cys Cys Glu Gln
145                 150                 155                 160

Trp Ile Cys Glu Asp Asp Ala Lys Arg Pro Arg Lys Thr Ala Pro Arg
                165                 170                 175

Asp Thr Gly Ala Phe Asp Ala Val Gly Glu Val Glu Ala Trp His Arg
            180                 185                 190

Asn Cys Ile Ala Tyr Thr Ser Pro Trp Ser Pro Cys Ser Thr Ser Cys
        195                 200                 205

Gly Leu Gly Val Ser Thr Arg Ile Ser Asn Val Asn Ala Gln Cys Trp
    210                 215                 220

Pro Glu Gln Glu Ser Arg Leu Cys Asn Leu Arg Pro Cys Asp Val Asp
225                 230                 235                 240

Ile His Thr Leu Ile Lys Ala Gly Lys Lys Cys Leu Ala Val Tyr Gln
                245                 250                 255

Pro Glu Ala Ser Met Asn Phe Thr Leu Ala Gly Cys Ile Ser Thr Arg
            260                 265                 270

Ser Tyr Gln Pro Lys Tyr Cys Gly Val Cys Met Asp Asn Arg Cys Cys
        275                 280                 285

Ile Pro Tyr Lys Ser Lys Thr Ile Asp Val Ser Phe Gln Cys Pro Asp
    290                 295                 300

Gly Leu Gly Phe Ser Arg Gln Val Leu Trp Ile Asn Ala Cys Phe Cys
305                 310                 315                 320

Asn Leu Ser Cys Arg Asn Pro Asn Asp Ile Phe Ala Asp Leu Glu Ser
                325                 330                 335

Tyr Pro Asp Phe Ser Glu Ile Ala Asn
            340                 345

<210> SEQ ID NO 6
<211> LENGTH: 345
<212> TYPE: PRT
<213> ORGANISM: Homo sapiens

<400> SEQUENCE: 6

Thr Ala Leu Ser Pro Ala Pro Thr Thr Met Asp Phe Thr Pro Ala Pro
1               5                   10                  15

Leu Glu Asp Thr Ser Ser Arg Pro Gln Phe Cys Lys Trp Pro Cys Glu
            20                  25                  30

Cys Pro Pro Ser Pro Pro Arg Cys Pro Leu Gly Val Ser Leu Ile Thr
        35                  40                  45

Asp Gly Cys Glu Cys Cys Lys Met Cys Ala Gln Gln Leu Gly Asp Asn
    50                  55                  60

Cys Thr Glu Ala Ala Ile Cys Asp Pro His Arg Gly Leu Tyr Cys Asp
65                  70                  75                  80

Tyr Ser Gly Asp Arg Pro Arg Tyr Ala Ile Gly Val Cys Ala Gln Val
                85                  90                  95

Val Gly Val Gly Cys Val Leu Asp Gly Val Arg Tyr Asn Asn Gly Gln
            100                 105                 110

Ser Phe Gln Pro Asn Cys Lys Tyr Asn Cys Thr Cys Ile Asp Gly Ala
        115                 120                 125

Val Gly Cys Thr Pro Leu Cys Leu Arg Val Arg Pro Pro Arg Leu Trp
    130                 135                 140

Cys Pro His Pro Arg Arg Val Ser Ile Pro Gly His Cys Cys Glu Gln
145                 150                 155                 160

Trp Val Cys Glu Asp Asp Ala Lys Arg Pro Arg Lys Thr Ala Pro Arg
                165                 170                 175

Asp Thr Gly Ser Phe Asp Ala Val Gly Glu Val Glu Ala Trp His Arg
            180                 185                 190

Asn Cys Ile Ala Tyr Thr Ser Pro Trp Ser Pro Cys Ser Thr Ser Cys
        195                 200                 205

Gly Leu Gly Val Ser Thr Arg Ile Ser Asn Val Asn Ala Gln Cys Trp
    210                 215                 220

Pro Glu Gln Glu Ser Arg Leu Cys Asn Leu Arg Pro Cys Asp Val Asp
225                 230                 235                 240

Ile His Thr Leu Ile Lys Ala Gly Lys Lys Cys Leu Ala Val Tyr Gln
                245                 250                 255

Pro Glu Ala Ser Met Asn Phe Thr Leu Ala Gly Cys Ile Ser Thr Arg
            260                 265                 270

Ser Tyr Gln Pro Lys Tyr Cys Gly Val Cys Met Asp Asn Arg Cys Cys
        275                 280                 285

Ile Pro Tyr Lys Ser Lys Thr Ile Asp Val Ser Phe Gln Cys Pro Asp
    290                 295                 300

Gly Leu Gly Phe Ser Arg Gln Val Leu Trp Ile Asn Ala Cys Phe Cys
305                 310                 315                 320

Asn Leu Ser Cys Arg Asn Pro Asn Asp Ile Phe Ala Asp Leu Glu Ser
                325                 330                 335

Tyr Pro Asp Phe Ser Glu Ile Ala Asn
            340                 345

<210> SEQ ID NO 7
<211> LENGTH: 367

```
<212> TYPE: PRT
<213> ORGANISM: Homo sapiens

<400> SEQUENCE: 7

Met Arg Trp Phe Leu Pro Trp Thr Leu Ala Ala Val Thr Ala Ala Ala
1               5                   10                  15

Ala Ser Thr Val Leu Ala Thr Ala Leu Ser Pro Ala Pro Thr Thr Met
            20                  25                  30

Asp Phe Thr Pro Ala Pro Leu Glu Asp Thr Ser Ser Arg Pro Gln Phe
        35                  40                  45

Cys Lys Trp Pro Cys Glu Cys Pro Pro Ser Pro Pro Arg Cys Pro Leu
    50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

Arg Tyr Asn Asn Gly Gln Ser Phe Gln Pro Asn Cys Lys Tyr Asn Cys
130                 135                 140

Thr Cys Ile Asp Gly Ala Val Gly Cys Thr Pro Leu Cys Leu Arg Val
145                 150                 155                 160

Arg Pro Pro Arg Leu Trp Cys Pro His Pro Arg Arg Val Ser Ile Pro
                165                 170                 175

Gly His Cys Cys Glu Gln Trp Ile Cys Glu Asp Asp Ala Lys Arg Pro
            180                 185                 190

Arg Lys Thr Ala Pro Arg Asp Thr Gly Ala Phe Asp Ala Val Gly Glu
        195                 200                 205

Val Glu Ala Trp His Arg Asn Cys Ile Ala Tyr Thr Ser Pro Trp Ser
210                 215                 220

Pro Cys Ser Thr Ser Cys Gly Leu Gly Val Ser Thr Arg Ile Ser Asn
225                 230                 235                 240

Val Asn Ala Gln Cys Trp Pro Glu Gln Glu Ser Arg Leu Cys Asn Leu
                245                 250                 255

Arg Pro Cys Asp Val Asp Ile His Thr Leu Ile Lys Ala Gly Lys Lys
            260                 265                 270

Cys Leu Ala Val Tyr Gln Pro Glu Ala Ser Met Asn Phe Thr Leu Ala
        275                 280                 285

Gly Cys Ile Ser Thr Arg Ser Tyr Gln Pro Lys Tyr Cys Gly Val Cys
290                 295                 300

Met Asp Asn Arg Cys Cys Ile Pro Tyr Lys Ser Lys Thr Ile Asp Val
305                 310                 315                 320

Ser Phe Gln Cys Pro Asp Gly Leu Gly Phe Ser Arg Gln Val Leu Trp
                325                 330                 335

Ile Asn Ala Cys Phe Cys Asn Leu Ser Cys Arg Asn Pro Asn Asp Ile
            340                 345                 350

Phe Ala Asp Leu Glu Ser Tyr Pro Asp Phe Ser Glu Ile Ala Asn
        355                 360                 365

<210> SEQ ID NO 8
<211> LENGTH: 367
<212> TYPE: PRT
<213> ORGANISM: Homo sapiens
```

<400> SEQUENCE: 8

| | | | | | | | | | | | | | | |
|---|---|---|---|---|---|---|---|---|---|---|---|---|---|---|
|Met|Arg|Trp|Phe|Leu|Pro|Trp|Thr|Leu|Ala|Ala|Val|Thr|Ala|Ala|
|1| | | |5| | | | |10| | | | |15|
|Ala|Ser|Thr|Val|Leu|Ala|Thr|Ala|Leu|Ser|Pro|Ala|Pro|Thr|Thr|Met|
| | | |20| | | | |25| | | | |30| | |
|Asp|Phe|Thr|Pro|Ala|Pro|Leu|Glu|Asp|Thr|Ser|Ser|Arg|Pro|Gln|Phe|
| | | |35| | | | |40| | | | |45| | |
|Cys|Lys|Trp|Pro|Cys|Glu|Cys|Pro|Pro|Ser|Pro|Pro|Arg|Cys|Pro|Leu|
| |50| | | | |55| | | | |60| | | | |
|Gly|Val|Ser|Leu|Ile|Thr|Asp|Gly|Cys|Glu|Cys|Cys|Lys|Met|Cys|Ala|
|65| | | | |70| | | | |75| | | | |80|
|Gln|Gln|Leu|Gly|Asp|Asn|Cys|Thr|Glu|Ala|Ala|Ile|Cys|Asp|Pro|His|
| | | | |85| | | | |90| | | | |95| |
|Arg|Gly|Leu|Tyr|Cys|Asp|Tyr|Ser|Gly|Asp|Arg|Pro|Arg|Tyr|Ala|Ile|
| | | |100| | | | |105| | | | |110| | |
|Gly|Val|Cys|Ala|Gln|Val|Val|Gly|Val|Gly|Cys|Val|Leu|Asp|Gly|Val|
| | | |115| | | | |120| | | | |125| | |
|Arg|Tyr|Asn|Asn|Gly|Gln|Ser|Phe|Gln|Pro|Asn|Cys|Lys|Tyr|Asn|Cys|
| | |130| | | | |135| | | | |140| | | |
|Thr|Cys|Ile|Asp|Gly|Ala|Val|Gly|Cys|Thr|Pro|Leu|Cys|Leu|Arg|Val|
|145| | | | |150| | | | |155| | | | |160|
|Arg|Pro|Pro|Arg|Leu|Trp|Cys|Pro|His|Pro|Arg|Val|Ser|Ile|Pro|
| | | | |165| | | | |170| | | | |175| |
|Gly|His|Cys|Cys|Glu|Gln|Trp|Val|Cys|Glu|Asp|Asp|Ala|Lys|Arg|Pro|
| | | |180| | | | |185| | | | |190| | |
|Arg|Lys|Thr|Ala|Pro|Arg|Asp|Thr|Gly|Ser|Phe|Asp|Ala|Val|Gly|Glu|
| | |195| | | | |200| | | | |205| | | |
|Val|Glu|Ala|Trp|His|Arg|Asn|Cys|Ile|Ala|Tyr|Thr|Ser|Pro|Trp|Ser|
| |210| | | | |215| | | | |220| | | | |
|Pro|Cys|Ser|Thr|Ser|Cys|Gly|Leu|Gly|Val|Ser|Thr|Arg|Ile|Ser|Asn|
|225| | | | |230| | | | |235| | | | |240|
|Val|Asn|Ala|Gln|Cys|Trp|Pro|Glu|Gln|Glu|Ser|Arg|Leu|Cys|Asn|Leu|
| | | |245| | | | |250| | | | |255| | |
|Arg|Pro|Cys|Asp|Val|Asp|Ile|His|Thr|Leu|Ile|Lys|Ala|Gly|Lys|Lys|
| | |260| | | | |265| | | | |270| | | |
|Cys|Leu|Ala|Val|Tyr|Gln|Pro|Glu|Ala|Ser|Met|Asn|Phe|Thr|Leu|Ala|
| |275| | | | |280| | | | |285| | | | |
|Gly|Cys|Ile|Ser|Thr|Arg|Ser|Tyr|Gln|Pro|Lys|Tyr|Cys|Gly|Val|Cys|
|290| | | | |295| | | | |300| | | | | |
|Met|Asp|Asn|Arg|Cys|Cys|Ile|Pro|Tyr|Lys|Ser|Lys|Thr|Ile|Asp|Val|
|305| | | |310| | | | |315| | | | |320| |
|Ser|Phe|Gln|Cys|Pro|Asp|Gly|Leu|Gly|Phe|Ser|Arg|Gln|Val|Leu|Trp|
| | | |325| | | | |330| | | | |335| | |
|Ile|Asn|Ala|Cys|Phe|Cys|Asn|Leu|Ser|Cys|Arg|Asn|Pro|Asn|Asp|Ile|
| | | |340| | | | |345| | | | |350| | |
|Phe|Ala|Asp|Leu|Glu|Ser|Tyr|Pro|Asp|Phe|Ser|Glu|Ile|Ala|Asn|
| | | |355| | | | |360| | | | |365| |

<210> SEQ ID NO 9
<211> LENGTH: 1766
<212> TYPE: DNA
<213> ORGANISM: Mus musculus
<220> FEATURE:
<221> NAME/KEY: modified_base
<222> LOCATION: (10)..(10)
<223> OTHER INFORMATION: Unknown nucleotide

<400> SEQUENCE: 9

```
taacaaggcn gtcctgcttg gagaggcatc cgcatcctct gggctgagcc gtagctcctg    60
tgacgctgac ttccaggcat gaggtggctc ctgccctgga cgctggcagc cgtggcagtc   120
ctgagggtgg gcaacatcct ggccacggcc ctctctccaa cccccacaac aatgaccttc   180
accccagcac cactagagga aacgactaca cgccccgaat tctgcaagtg gccatgtgag   240
tgcccacaat ccccacctcg ctgcccactg ggcgtcagcc taatcacaga tggctgtgaa   300
tgctgtaaga tatgtgccca gcagcttggg gacaactgca cagaggctgc catctgtgac   360
ccacaccggg gcctctactg cgattacagt ggggatcgcc cgaggtacgc aataggagtg   420
tgtgcacagg tggtcggtgt gggctgtgtc ctggatggcg tacgctacac caatggcgag   480
tccttccaac ccaactgcag gtacaactgt acctgcattg atggcacggt gggctgcaca   540
ccgctgtgcc taagcccag gccccacgc ctctggtgcc gccagccccg gcacgtgaga   600
gtccctggcc agtgctgtga gcagtgggtg tgtgatgatg acgcaaggag accacgccag   660
actgcactgt tggacaccag agcctttgca gcgtcaggcg ccgtggagca acggtatgag   720
aactgcatag cctacactag tccctggagc ccctgctcta ccacctgtgg cctaggtatc   780
tccactcgga tctctaacgt caatgcccgg tgctggccag agcaggaaag tcgcctctgc   840
aacctgcggc catgtgatgt ggacatccaa ctacacatca aggcagggaa gaaatgcctg   900
gctgtgtacc agccagagga ggccacgaac ttcactctcg caggctgtgt cagcacacgc   960
acctaccgac ccaagtactg cggagtctgt actgacaata ggtgttgcat cccctacaag  1020
tccaagacca tcagtgtgga tttccagtgt ccagaggggc caggtttctc ccggcaggtc  1080
ctatggatta atgcttgctt ctgcaacctg agctgcagga tcctaacga tatctttgct  1140
gacttggaat cttaccctga cttcgaagag attgccaatt aggtgggtgt gtggctcagg  1200
gtaaagttcc atgctgcaaa gcagccagcc ctttgtggtc caggacttca caattgagcc  1260
ttatttcatc tacttcctac tcgattctga attcccagtt tctgttcctg tttgacaat   1320
cgtaatggcc caggagagtg ctgctcaggc tcagacaatg ggttcctcct tggggacatt  1380
ctacatcatt ccaaggaaaa cacatctctg actgttcaca atggaagcaa agcctggccc  1440
agctagtctg gctccagcct gggcaagttg tcagaagttg tgatgggatt gtccaaggaa  1500
aagcatcagc tgaagaacca gtatcatgaa gtccttcctc agatgccaag cctagggatg  1560
ctgggatcct ttcagacaga tggatgggat tggggacaca ggataagct attattttac   1620
ccttgccaaa tgatactatc ctgggtattt ctgcctaaaa acataccaaa agtgttcttg  1680
ttccactgat ctgtatatca caagtcacca aacattttcc aggtgaggac ccatagttgt  1740
gtcattctgt tttgccaatt gaaaaa                                       1766
```

<210> SEQ ID NO 10
<211> LENGTH: 1766
<212> TYPE: DNA
<213> ORGANISM: Mus musculus
<220> FEATURE:
<221> NAME/KEY: modified_base
<222> LOCATION: (1757)..(1757)
<223> OTHER INFORMATION: Unknown nucleotide

<400> SEQUENCE: 10

```
tttttcaatt ggcaaaacag aatgacacaa ctatgggtcc tcacctggaa aatgtttggt    60
gacttgtgat atacagatca gtggaacaag aacactttg gtatgttttt aggcagaaat   120
acccaggata gtatcatttg gcaagggtaa aataatagct tattcctgtg tccccaatcc   180
```

```
catccatctg tctgaaagga tcccagcatc cctaggcttg gcatctgagg aaggacttca      240
tgatactggt tcttcagctg atgcttttcc ttggacaatc ccatcacaac ttctgacaac      300
ttgcccaggc tggagccaga ctagctgggc caggctttgc ttccattgtg aacagtcaga      360
gatgtgtttt ccttggaatg atgtagaatg tccccaagga ggaacccatt gtctgagcct      420
gagcagcact ctcctgggcc attacgattg tcaaaacagg aacagaaact gggaattcag      480
aatcgagtag gaagtagatg aaataaggct caattgtgaa gtcctggacc acaaagggct      540
ggctgctttg cagcatggaa ctttaccctg agccacacac ccacctaatt ggcaatctct      600
tcgaagtcag ggtaagattc caagtcagca agatatcgt taggattcct gcagctcagg       660
ttgcagaagc aagcattaat ccataggacc tgccgggaga aacctggccc ctctggacac      720
tggaaatcca cactgatggt cttggacttg taggggatga acaccctatt gtcagtacag      780
actccgcagt acttgggtcg gtaggtgcgt gtgctgacac agcctgcgag agtgaagttc      840
gtggcctcct ctggctggta cacagccagg catttcttcc ctgccttgat gtgtagttgg      900
atgtccacat cacatggccg caggttgcag aggcgacttt cctgctctgg ccagcaccgg      960
gcattgacgt tagagatccg agtggagata cctaggccac aggtggtaga gcaggggctc     1020
cagggactag tgtaggctat gcagttctca taccgttgct ccacggcgcc tgacgctgca     1080
aaggctctgt tgtccaacag tgcagtctgg cgtggtctcc ttgcgtcatc atcacacacc     1140
cactgctcac agcactggcc agggactctc acgtgccggg gctggcggca ccagaggcgt     1200
gggggcctgg ggcttaggca cagcggtgtg cagcccaccg tgccatcaat gcaggtacag     1260
ttgtacctgc agttgggttg gaaggactcg ccattggtgt agcgtacgcc atccaggaca     1320
cagcccacac cgaccacctg tgcacacact cctattgcgt acctcgggcg atccccactg     1380
taatcgcagt agaggccccg gtgtgggtca cagatggcag cctctgtgca gttgtcccca     1440
agctgctggg cacatatctt acagcattca cagccatctg tgattaggct gacgcccagt     1500
gggcagcgag gtggggattg tgggcactca catggccact tgcagaattc ggggcgtgta     1560
gtcgtttcct ctagtggtgc tggggtgaag gtcattgttg tgggggttgg agagagggcc     1620
gtggccagga tgttgcccac cctcaggact gccacggctg ccagcgtcca gggcaggagc     1680
cacctcatgc ctggaagtca gcgtcacagg agctacggct cagcccagag gatgcggatg     1740
cctctccaag caggacngcc ttgtta                                          1766

<210> SEQ ID NO 11
<211> LENGTH: 345
<212> TYPE: PRT
<213> ORGANISM: Mus musculus

<400> SEQUENCE: 11

Thr Ala Leu Ser Pro Thr Pro Thr Thr Met Thr Phe Thr Pro Ala Pro
1               5                  10                  15

Leu Glu Glu Thr Thr Thr Arg Pro Glu Phe Cys Lys Trp Pro Cys Glu
            20                  25                  30

Cys Pro Gln Ser Pro Pro Arg Cys Pro Leu Gly Val Ser Leu Ile Thr
        35                  40                  45

Asp Gly Cys Glu Cys Cys Lys Ile Cys Ala Gln Gln Leu Gly Asp Asn
    50                  55                  60

Cys Thr Glu Ala Ala Ile Cys Asp Pro His Arg Gly Leu Tyr Cys Asp
65                  70                  75                  80

Tyr Ser Gly Asp Arg Pro Arg Tyr Ala Ile Gly Val Cys Ala Gln Val
                85                  90                  95
```

Val Gly Val Gly Cys Val Leu Asp Gly Val Arg Tyr Thr Asn Gly Glu
            100                 105                 110

Ser Phe Gln Pro Asn Cys Arg Tyr Asn Cys Thr Cys Ile Asp Gly Thr
        115                 120                 125

Val Gly Cys Thr Pro Leu Cys Leu Ser Pro Arg Pro Arg Leu Trp
    130                 135                 140

Cys Arg Gln Pro Arg His Val Arg Val Pro Gly Gln Cys Cys Glu Gln
145                 150                 155                 160

Trp Val Cys Asp Asp Ala Arg Arg Pro Arg Gln Thr Ala Leu Leu
                165                 170                 175

Asp Thr Arg Ala Phe Ala Ala Ser Gly Ala Val Glu Gln Arg Tyr Glu
            180                 185                 190

Asn Cys Ile Ala Tyr Thr Ser Pro Trp Ser Pro Cys Ser Thr Thr Cys
            195                 200                 205

Gly Leu Gly Ile Ser Thr Arg Ile Ser Asn Val Asn Ala Arg Cys Trp
    210                 215                 220

Pro Glu Gln Glu Ser Arg Leu Cys Asn Leu Arg Pro Cys Asp Val Asp
225                 230                 235                 240

Ile Gln Leu His Ile Lys Ala Gly Lys Lys Cys Leu Ala Val Tyr Gln
                245                 250                 255

Pro Glu Glu Ala Thr Asn Phe Thr Leu Ala Gly Cys Val Ser Thr Arg
            260                 265                 270

Thr Tyr Arg Pro Lys Tyr Cys Gly Val Cys Thr Asp Asn Arg Cys Cys
        275                 280                 285

Ile Pro Tyr Lys Ser Lys Thr Ile Ser Val Asp Phe Gln Cys Pro Glu
290                 295                 300

Gly Pro Gly Phe Ser Arg Gln Val Leu Trp Ile Asn Ala Cys Phe Cys
305                 310                 315                 320

Asn Leu Ser Cys Arg Asn Pro Asn Asp Ile Phe Ala Asp Leu Glu Ser
                325                 330                 335

Tyr Pro Asp Phe Glu Glu Ile Ala Asn
            340                 345

<210> SEQ ID NO 12
<211> LENGTH: 367
<212> TYPE: PRT
<213> ORGANISM: Mus musculus

<400> SEQUENCE: 12

Met Arg Trp Leu Leu Pro Trp Thr Leu Ala Ala Val Ala Val Leu Arg
1               5                   10                  15

Val Gly Asn Ile Leu Ala Thr Ala Leu Ser Pro Thr Pro Thr Thr Met
            20                  25                  30

Thr Phe Thr Pro Ala Pro Leu Glu Glu Thr Thr Thr Arg Pro Glu Phe
        35                  40                  45

Cys Lys Trp Pro Cys Glu Cys Pro Gln Ser Pro Pro Arg Cys Pro Leu
    50                  55                  60

Gly Val Ser Leu Ile Thr Asp Gly Cys Glu Cys Cys Lys Ile Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

```
Arg Tyr Thr Asn Gly Glu Ser Phe Gln Pro Asn Cys Arg Tyr Asn Cys
        130                 135                 140

Thr Cys Ile Asp Gly Thr Val Gly Cys Thr Pro Leu Cys Leu Ser Pro
145                 150                 155                 160

Arg Pro Pro Arg Leu Trp Cys Arg Gln Pro Arg His Val Arg Val Pro
                165                 170                 175

Gly Gln Cys Cys Glu Gln Trp Val Cys Asp Asp Ala Arg Arg Pro
                180                 185                 190

Arg Gln Thr Ala Leu Leu Asp Thr Arg Ala Phe Ala Ala Ser Gly Ala
                195                 200                 205

Val Glu Gln Arg Tyr Glu Asn Cys Ile Ala Tyr Thr Ser Pro Trp Ser
        210                 215                 220

Pro Cys Ser Thr Thr Cys Gly Leu Gly Ile Ser Thr Arg Ile Ser Asn
225                 230                 235                 240

Val Asn Ala Arg Cys Trp Pro Glu Gln Glu Ser Arg Leu Cys Asn Leu
                245                 250                 255

Arg Pro Cys Asp Val Asp Ile Gln Leu His Ile Lys Ala Gly Lys Lys
                260                 265                 270

Cys Leu Ala Val Tyr Gln Pro Glu Glu Ala Thr Asn Phe Thr Leu Ala
        275                 280                 285

Gly Cys Val Ser Thr Arg Thr Tyr Arg Pro Lys Tyr Cys Gly Val Cys
290                 295                 300

Thr Asp Asn Arg Cys Cys Ile Pro Tyr Lys Ser Lys Thr Ile Ser Val
305                 310                 315                 320

Asp Phe Gln Cys Pro Glu Gly Pro Gly Phe Ser Arg Gln Val Leu Trp
                325                 330                 335

Ile Asn Ala Cys Phe Cys Asn Leu Ser Cys Arg Asn Pro Asn Asp Ile
                340                 345                 350

Phe Ala Asp Leu Glu Ser Tyr Pro Asp Phe Glu Glu Ile Ala Asn
        355                 360                 365

<210> SEQ ID NO 13
<211> LENGTH: 1293
<212> TYPE: DNA
<213> ORGANISM: Homo sapiens

<400> SEQUENCE: 13
cccacgcgtc cggctgggga catgagaggc acaccgaaga cccacctcct ggccttctcc      60
ctcctctgcc tcctctcaaa ggtgcgtacc cagctgtgcc cgacaccatg tacctgcccc     120
tggccacctc cccgatgccc gctgggagta ccctggtgc tggatggctg tggctgctgc     180
cgggtatgtg cacggcggct gggggagccc tgcgaccaac tccacgtctg cgacgccagc     240
cagggcctgg tctgccagcc cggggcagga cccggtggcc ggggggccct gtgcctcttg     300
gcagaggacg acagcagctg tgaggtgaac ggccgcctgt atcgggaagg ggagaccttc     360
cagcccact gcagcatccg ctgccgctgc gaggacggcg gcttcacctg cgtgccgctg     420
tgcagcgagg atgtgcggct gcccagctgg gactgccccc accccaggag ggtcgaggtc     480
ctgggcaagt gctgccctga gtgggtgtgc ggccaaggag ggggactggg gacccagccc     540
cttccagccc aaggacccca gttttctggc cttgtctctt ccctgccccc tggtgtcccc     600
tgcccagaat ggagcacggc ctggggaccc tgctcgacca cctgtgggct gggcatggcc     660
acccgggtgt ccaaccagaa ccgcttctgc cgactggaga cccagcgccg cctgtgcctg     720
tccaggccct gcccacccte cagggggtcgc agtccacaaa acagtgcctt ctagagccgg     780
```

-continued

```
gctgggaatg gggacacggt gtccaccatc cccagctggt ggccctgtgc ctgggccctg    840
ggctgatgga agatggtccg tgcccaggcc cttggctgca gcaacactt tagcttgggt    900 ccaccatgca gaacaccaat attaacacgc tgcctggtct gtctggatcc cgaggtatgg    960
cagaggtgca agacctagtc ccctttcctc taactcactg cctaggaggc tggccaaggt   1020
gtccagggtc ctctagccca ctccctgcct acacacacag cctatatcaa acatgcacac   1080
gggcgagctt tctctccgac ttccctggg caagagatgg gacaagcagt cccttaatat   1140
tgaggctgca gcaggtgctg ggctggactg gccatttttc tgggggtagg atgaagagaa   1200
ggcacacaga gattctggat ctcctgctgc cttttctgga gtttgtaaaa ttgttcctga   1260
atacaagcct atgcgtgaaa aaaaaaaaaa aaa                                1293
```

<210> SEQ ID NO 14
<211> LENGTH: 1293
<212> TYPE: DNA
<213> ORGANISM: Homo sapiens

<400> SEQUENCE: 14

```
tttttttttt ttttttcacg cataggcttg tattcaggaa caattttaca aactccagaa     60
aaggcagcag gagatccaga atctctgtgt gccttctctt catcctaccc ccagaaaaat    120
ggccagtcca gcccagcacc tgctgcagcc tcaatattaa gggactgctt gtcccatctc    180
ttgcccaggg gaagtcggag agaaagctcg cccgtgtgca tgtttgatat aggctgtgtg    240
tgtaggcagg gagtgggcta gaggaccctg gacaccttgg ccagcctcct aggcagtgag    300
ttagaggaaa ggggactagg tcttgcacct ctgccatacc tcgggatcca gacagaccag    360
gcagcgtgtt aatattggtg ttctgcatgg tggacccaag ctaaagtgtt gcctgcagcc    420
aagggcctgg gcacggacca tcttccatca gcccagggcc caggcacagg gccaccagct    480
ggggatggtg gacaccgtgt ccccattccc agcccggctc tagaaggcac tgttttgtgg    540
actgcgaccc ctggagggtg gcagggcct ggacaggcac aggcggcgct gggtctccag    600
tcggcagaag cggttctggt tggacacccg ggtggccatg cccagcccac aggtggtcga    660
gcagggtccc caggccgtgc tccattctgg gcaggggaca ccaggggca gggaagagac    720 aaggccagaa aactggggtc cttggctgg aaggggctgg gtcccagtc cccctccttg    780 gccgcacacc cactcaggc agcacttgcc caggacctcg accctcctgg ggtgggggca    840
gtcccagctg gcagccgca catcctcgct gcacagcggc acgcaggtga agccgccgtc    900
ctcgcagcgc agcggatgc tgcagtgggg ctggaaggtc tccccttccc gatacaggcg    960
gccgttcacc tcacagctgc tgtcgtcctc tgccaagagg cacagggccc ccggccacc   1020 gggtcctgcc ccgggctggc agaccaggcc ctggctggcg tcgcagacgt ggagttggtc   1080
gcagggctcc cccagccgcc gtgcacatac ccggcagcag ccacagccat ccagcaccag   1140
gggtactccc agcgggcatc ggggaggtgg ccaggggca gtacatggtg tcgggcacag   1200
ctgggtacgc acctttgaga ggaggcagag gagggagaag gccaggaggt gggtcttcgg   1260
tgtgcctctc atgtccccag ccggacgcgt ggg                                1293
```

<210> SEQ ID NO 15
<211> LENGTH: 227
<212> TYPE: PRT
<213> ORGANISM: Homo sapiens

<400> SEQUENCE: 15

```
Gln Leu Cys Pro Thr Pro Cys Thr Cys Pro Trp Pro Pro Pro Arg Cys
1               5                   10                  15
```

-continued

Pro Leu Gly Val Pro Leu Val Leu Asp Gly Cys Gly Cys Arg Val
            20                  25                  30

Cys Ala Arg Arg Leu Gly Glu Pro Cys Asp Gln Leu His Val Cys Asp
        35                  40                  45

Ala Ser Gln Gly Leu Val Cys Gln Pro Gly Ala Gly Pro Gly Gly Arg
 50                  55                  60

Gly Ala Leu Cys Leu Leu Ala Glu Asp Ser Ser Cys Glu Val Asn
 65                  70                  75                  80

Gly Arg Leu Tyr Arg Glu Gly Glu Thr Phe Gln Pro His Cys Ser Ile
                85                  90                  95

Arg Cys Arg Cys Glu Asp Gly Gly Phe Thr Cys Val Pro Leu Cys Ser
            100                 105                 110

Glu Asp Val Arg Leu Pro Ser Trp Asp Cys Pro His Pro Arg Arg Val
        115                 120                 125

Glu Val Leu Gly Lys Cys Cys Pro Glu Trp Val Cys Gly Gln Gly Gly
130                 135                 140

Gly Leu Gly Thr Gln Pro Leu Pro Ala Gln Gly Pro Gln Phe Ser Gly
145                 150                 155                 160

Leu Val Ser Ser Leu Pro Pro Gly Val Pro Cys Pro Glu Trp Ser Thr
                165                 170                 175

Ala Trp Gly Pro Cys Ser Thr Thr Cys Gly Leu Gly Met Ala Thr Arg
            180                 185                 190

Val Ser Asn Gln Asn Arg Phe Cys Arg Leu Glu Thr Gln Arg Arg Leu
        195                 200                 205

Cys Leu Ser Arg Pro Cys Pro Pro Ser Arg Gly Arg Ser Pro Gln Asn
210                 215                 220

Ser Ala Phe
225

<210> SEQ ID NO 16
<211> LENGTH: 250
<212> TYPE: PRT
<213> ORGANISM: Homo sapiens

<400> SEQUENCE: 16

Met Arg Gly Thr Pro Lys Thr His Leu Leu Ala Phe Ser Leu Leu Cys
1               5                   10                  15

Leu Leu Ser Lys Val Arg Thr Gln Leu Cys Pro Thr Pro Cys Thr Cys
            20                  25                  30

Pro Trp Pro Pro Pro Arg Cys Pro Leu Gly Val Pro Leu Val Leu Asp
        35                  40                  45

Gly Cys Gly Cys Arg Val Cys Ala Arg Arg Leu Gly Glu Pro Cys
 50                  55                  60

Asp Gln Leu His Val Cys Asp Ala Ser Gln Gly Leu Val Cys Gln Pro
65                  70                  75                  80

Gly Ala Gly Pro Gly Gly Arg Gly Ala Leu Cys Leu Leu Ala Glu Asp
                85                  90                  95

Asp Ser Ser Cys Glu Val Asn Gly Arg Leu Tyr Arg Glu Gly Glu Thr
            100                 105                 110

Phe Gln Pro His Cys Ser Ile Arg Cys Arg Cys Glu Asp Gly Gly Phe
        115                 120                 125

Thr Cys Val Pro Leu Cys Ser Glu Asp Val Arg Leu Pro Ser Trp Asp
130                 135                 140

Cys Pro His Pro Arg Arg Val Glu Val Leu Gly Lys Cys Cys Pro Glu
145                 150                 155                 160

```
Trp Val Cys Gly Gln Gly Gly Leu Gly Thr Gln Pro Leu Pro Ala
            165                 170                 175

Gln Gly Pro Gln Phe Ser Gly Leu Val Ser Ser Leu Pro Gly Val
            180                 185                 190

Pro Cys Pro Glu Trp Ser Thr Ala Trp Gly Pro Cys Ser Thr Cys
            195                 200                 205

Gly Leu Gly Met Ala Thr Arg Val Ser Asn Gln Asn Arg Phe Cys Arg
            210                 215                 220

Leu Glu Thr Gln Arg Arg Leu Cys Leu Ser Arg Pro Cys Pro Pro Ser
225                 230                 235                 240

Arg Gly Arg Ser Pro Gln Asn Ser Ala Phe
                245                 250

<210> SEQ ID NO 17
<211> LENGTH: 1734
<212> TYPE: DNA
<213> ORGANISM: Mus musculus

<400> SEQUENCE: 17
cccacgcgtc cgcgctcctg atctccagag gaccccgggc tgggacaggg gccttggcga      60
ggctgcagct gctgtggcag tagcttggga tggaggtctt tcttgctggg aactgaggag     120
ctgagaggct cctgtcaggc tcctgtccta aactcttggc acttgcggtg gcttgggctt     180
cacacactgt cagacacctt cttggtggcc tcctcggcct caggtttgaa gctggctcca     240
caagggacac ggtgacatga ggggcaaccc actgatccat cttctggcca tttccttcct     300
ctgcattctc tcaatggtgt attcccagct gtgcccagca ccctgtgcct gtccttggac     360
accaccccag tgcccaccgg gggtacccct ggtgctggat ggctgtggct gctgtcgagt     420
gtgtgcacgg aggctggggg agtcctgcga ccacctgcat gtctgcgacc ccagccaggg     480
cctggtttgt cagcctgggg caggcccag tggccgtggt gctgtgtgcc tcttcgaaga      540
ggatgacggg agctgtgagg tgaatggccg caggtacctg gatggggaga cctttaaacc     600
caattgcagg gttttgtgcc gctgtgatga cggtggtttc acctgcctgc cgctgtgcag     660
tgaggatgtg cggctgccca gctgggactg cccacgcccc aggagaatac aggtgccagg     720
aaggtgctgc cccagtggg tgtgtgacca ggcagtgatg cagccggcaa tccagccctc     780
ctcagcccaa ggacaccaac tttctgccct tgtcactcct gcatctgccg atggcccctg     840
tccaaactgg agcacagcct ggggcccctg ctcaaccacc tgtgggttgg gcatagccac     900
ccgagtatcc aaccagaacc gattctgcca actggagatc cagcgtcgcc tgtgtctgtc     960
cagaccctgc ctggcatcca ggagccacgg ctcatggaac agtgccttct agagccattg    1020
cggggatgtg gatacagggc ctgccattct cagcaaatgt ccctaggacc aggccctgga    1080
ctgatggtag atgcccctct ccatgctctt ggctgcagtt aactgtcctg ggtggattca    1140
gtgtccagag cctctgagcg atccctgctc tgtctgaggt gggggaagca ggtgaccagc    1200
tccatttctc tggattctga cccaggcttc tgggttctcc tggctagttc ctcaaaactt    1260
ccctgtatga aaaggacaac caaaaggacc tttaaagcta agctgtactg ggcaagcctg    1320
gccaccatgc tggggatagt gacagtaata ggtaccaggc agcagattgc ctgaaacatc    1380
caggtccctt cttggacttc tatgtgcttg tcccaaagat tatgggtgac cttgtaagtg    1440
tgcctttcct gatctgagaa caccctgccc ggctgggaag aattttctgg gaacatgaag    1500
agatggaatc acactattct taagagcgtt tgccaagtcc aggaacttga cctttgtatt    1560
tgtaaaaata cacatctctt aaatgctcac aaagcaagag gctccacact tctggcaggc    1620
```

```
cagggccttt tcttcagca tgagagagac aaggaacagt agagtaccct cctctggagg    1680
actggcccgg tctggaataa acacccaaat caagtgtgga aaaaaaaaaa aaaa         1734
```

<210> SEQ ID NO 18
<211> LENGTH: 1734
<212> TYPE: DNA
<213> ORGANISM: Mus musculus

<400> SEQUENCE: 18

```
ttttttttt  ttttccaca  cttgatttgg  gtgtttattc  cagaccgggc  cagtcctcca    60 gaggaggta  ctctactgtt  ccttgtctct  ctcatgctga  agagaaaggc  cctggcctgc   120
cagaagtgtg  gagcctcttg  ctttgtgagc  atttaagaga  tgtgtatttt  tacaaataca   180
aaggtcaagt  tcctggactt  ggcaaacgct  cttaagaata  gtgtgattcc  atctcttcat   240
gttcccagaa  aattcttccc  agccgggcag  ggtgttctca  gatcaggaaa  ggcacactta   300
caaggtcacc  cataatcttt  gggacaagca  catagaagtc  caagaaggga  cctggatgtt   360
tcaggcaatc  tgctgcctgg  tacctattac  tgtcactatc  cccagcatgg  tggccaggct   420
tgcccagtac  agcttagctt  taaaggtcct  tttggttgtc  cttttcatac  agggaagttt   480
tgaggaacta  gccaggagaa  cccagaagcc  tgggtcagaa  tccagagaaa  tggagctggt   540
cacctgcttc  ccccacctca  gacagagcag  ggatcgctca  gaggctctgg  acactgaatc   600
cacccaggac  agttaactgc  agccaagagc  atggagaggg  gcatctacca  tcagtccagg   660
gcctggtcct  agggacattt  gctgagaatg  gcaggccctg  tatccacatc  cccgcaatgg   720
ctctagaagg  cactgttcca  tgagccgtgg  ctcctggatg  ccaggcaggg  tctggacaga   780
cacaggcgac  gctggatctc  cagttggcag  aatcggttct  ggttggatac  tcgggtggct   840
atgcccaacc  cacaggtggt  tgagcagggg  ccccaggctg  tgctccagtt  tggacagggg   900
ccatcggcag  atgcaggagt  gacaagggca  gaaagttggt  gtccttgggc  tgaggagggc   960
tggattgccg  gctgcatcac  tgcctggtca  cacacccact  cggggcagca  ccttcctggc  1020
acctgtattc  tcctggggcg  tgggcagtcc  cagctgggca  gccgcacatc  ctcactgcac  1080
agcggcaggc  aggtgaaacc  accgtcatca  cagcggcaca  aaaccctgca  attgggttta  1140
aaggtctccc  catccaggta  cctgcggcca  ttcacctcac  agctcccgtc  atcctcttcg  1200
aagaggcaca  cagcaccacg  gccactgggg  cctgccccag  gctgacaaac  caggccctgg  1260
ctggggtcgc  agacatgcag  gtggtcgcag  gactccccca  gcctccgtgc  acacactcga  1320
cagcagccac  agccatccag  caccagggt   acccccggtg  ggcactgggg  tggtgtccaa  1380
ggacaggcac  agggtgctgg  gcacagctgg  gaatacacca  ttgagagaat  gcagaggaag  1440
gaaatggcca  gaagatggat  cagtgggttg  cccctcatgt  caccgtgtcc  cttgtggagc  1500
cagcttcaaa  cctgaggccg  aggaggccac  caagaaggtg  tctgacagtg  tgtgaagccc  1560
aagccaccgc  aagtgccaag  agtttaggac  aggagcctga  caggagcctc  tcagctcctc  1620
agttcccagc  aagaaagacc  tccatcccaa  gctactgcca  cagcagctgc  agcctcgcca  1680
aggcccctgt  cccagcccgg  ggtcctctgg  agatcaggag  cgcggacgcg  tggg         1734
```

<210> SEQ ID NO 19
<211> LENGTH: 228
<212> TYPE: PRT
<213> ORGANISM: Mus musculus

<400> SEQUENCE: 19

Gln Leu Cys Pro Ala Pro Cys Ala Cys Pro Trp Thr Pro Pro Gln Cys

```
                1               5                  10                 15
Pro Pro Gly Val Pro Leu Val Leu Asp Gly Cys Gly Cys Cys Arg Val
                20                 25                 30

Cys Ala Arg Arg Leu Gly Glu Ser Cys Asp His Leu His Val Cys Asp
                35                 40                 45

Pro Ser Gln Gly Leu Val Cys Gln Pro Gly Ala Gly Pro Ser Gly Arg
    50                 55                 60

Gly Ala Val Cys Leu Phe Glu Glu Asp Gly Ser Cys Glu Val Asn
65                 70                 75                 80

Gly Arg Arg Tyr Leu Asp Gly Glu Thr Phe Lys Pro Asn Cys Arg Val
                85                 90                 95

Leu Cys Arg Cys Asp Asp Gly Phe Thr Cys Leu Pro Leu Cys Ser
                100                105                110

Glu Asp Val Arg Leu Pro Ser Trp Asp Cys Pro Arg Pro Arg Arg Ile
                115                120                125

Gln Val Pro Gly Arg Cys Cys Pro Glu Trp Val Cys Asp Gln Ala Val
                130                135                140

Met Gln Pro Ala Ile Gln Pro Ser Ser Ala Gln Gly His Gln Leu Ser
145                150                155                160

Ala Leu Val Thr Pro Ala Ser Ala Asp Gly Pro Cys Pro Asn Trp Ser
                165                170                175

Thr Ala Trp Gly Pro Cys Ser Thr Thr Cys Gly Leu Gly Ile Ala Thr
                180                185                190

Arg Val Ser Asn Gln Asn Arg Phe Cys Gln Leu Glu Ile Gln Arg Arg
                195                200                205

Leu Cys Leu Ser Arg Pro Cys Leu Ala Ser Arg Ser His Gly Ser Trp
                210                215                220

Asn Ser Ala Phe
225

<210> SEQ ID NO 20
<211> LENGTH: 251
<212> TYPE: PRT
<213> ORGANISM: Mus musculus

<400> SEQUENCE: 20

Met Arg Gly Asn Pro Leu Ile His Leu Leu Ala Ile Ser Phe Leu Cys
1               5                  10                 15

Ile Leu Ser Met Val Tyr Ser Gln Leu Cys Pro Ala Pro Cys Ala Cys
                20                 25                 30

Pro Trp Thr Pro Pro Gln Cys Pro Pro Gly Val Pro Leu Val Leu Asp
                35                 40                 45

Gly Cys Gly Cys Cys Arg Val Cys Ala Arg Arg Leu Gly Glu Ser Cys
    50                 55                 60

Asp His Leu His Val Cys Asp Pro Ser Gln Gly Leu Val Cys Gln Pro
65                 70                 75                 80

Gly Ala Gly Pro Ser Gly Arg Gly Ala Val Cys Leu Phe Glu Glu Asp
                85                 90                 95

Asp Gly Ser Cys Glu Val Asn Gly Arg Arg Tyr Leu Asp Gly Glu Thr
                100                105                110

Phe Lys Pro Asn Cys Arg Val Leu Cys Arg Cys Asp Asp Gly Phe
                115                120                125

Thr Cys Leu Pro Leu Cys Ser Glu Asp Val Arg Leu Pro Ser Trp Asp
                130                135                140

Cys Pro Arg Pro Arg Arg Ile Gln Val Pro Gly Arg Cys Cys Pro Glu
```

```
                145                 150                 155                 160
Trp Val Cys Asp Gln Ala Val Met Gln Pro Ala Ile Gln Pro Ser Ser
                    165                 170                 175

Ala Gln Gly His Gln Leu Ser Ala Leu Val Thr Pro Ala Ser Ala Asp
                    180                 185                 190

Gly Pro Cys Pro Asn Trp Ser Thr Ala Trp Gly Pro Cys Ser Thr Thr
                    195                 200                 205

Cys Gly Leu Gly Ile Ala Thr Arg Val Ser Asn Gln Asn Arg Phe Cys
                    210                 215                 220

Gln Leu Glu Ile Gln Arg Arg Leu Cys Leu Ser Arg Pro Cys Leu Ala
225                 230                 235                 240

Ser Arg Ser His Gly Ser Trp Asn Ser Ala Phe
                    245                 250

<210> SEQ ID NO 21
<211> LENGTH: 345
<212> TYPE: PRT
<213> ORGANISM: Homo sapiens

<400> SEQUENCE: 21

Thr Ala Leu Ser Pro Ala Pro Thr Thr Met Asp Phe Thr Pro Ala Pro
1               5                   10                  15

Leu Glu Asp Thr Ser Ser Arg Pro Gln Phe Cys Lys Trp Pro Cys Glu
                20                  25                  30

Cys Pro Pro Ser Pro Pro Arg Cys Pro Leu Gly Val Ser Leu Ile Thr
            35                  40                  45

Asp Gly Cys Glu Cys Cys Lys Met Cys Ala Gln Gln Leu Gly Asp Asn
        50                  55                  60

Cys Thr Glu Ala Ala Ile Cys Asp Pro His Arg Gly Leu Tyr Cys Asp
65                  70                  75                  80

Tyr Ser Gly Asp Arg Pro Arg Tyr Ala Ile Gly Val Cys Ala Gln Val
                85                  90                  95

Val Gly Val Gly Cys Val Leu Asp Gly Val Arg Tyr Asn Asn Gly Gln
            100                 105                 110

Ser Phe Gln Pro Asn Cys Lys Tyr Asn Cys Thr Cys Ile Asp Gly Ala
        115                 120                 125

Val Gly Cys Thr Pro Leu Cys Leu Arg Val Arg Pro Pro Arg Leu Trp
    130                 135                 140

Cys Pro His Pro Arg Arg Val Ser Ile Pro Gly His Cys Cys Glu Gln
145                 150                 155                 160

Trp Ile Cys Glu Asp Asp Ala Lys Arg Pro Arg Lys Thr Ala Pro Arg
                165                 170                 175

Asp Thr Gly Ser Phe Asp Ala Val Gly Glu Val Glu Ala Trp His Arg
            180                 185                 190

Asn Cys Ile Ala Tyr Thr Ser Pro Trp Ser Pro Cys Ser Thr Ser Cys
        195                 200                 205

Gly Leu Gly Val Ser Thr Arg Ile Ser Asn Val Asn Ala Gln Cys Trp
    210                 215                 220

Pro Glu Gln Glu Ser Arg Leu Cys Asn Leu Arg Pro Cys Asp Val Asp
225                 230                 235                 240

Ile His Thr Leu Ile Lys Ala Gly Lys Lys Cys Leu Ala Val Tyr Gln
                245                 250                 255

Pro Glu Ala Ser Met Asn Phe Thr Leu Ala Gly Cys Ile Ser Thr Arg
            260                 265                 270

Ser Tyr Gln Pro Lys Tyr Cys Gly Val Cys Met Asp Asn Arg Cys Cys
```

```
                    275                 280                 285
Ile Pro Tyr Lys Ser Lys Thr Ile Asp Val Ser Phe Gln Cys Pro Asp
            290                 295                 300

Gly Leu Gly Phe Ser Arg Gln Val Leu Trp Ile Asn Ala Cys Phe Cys
305                 310                 315                 320

Asn Leu Ser Cys Arg Asn Pro Asn Asp Ile Phe Ala Asp Leu Glu Ser
                325                 330                 335

Tyr Pro Asp Phe Ser Glu Ile Ala Asn
            340                 345

<210> SEQ ID NO 22
<211> LENGTH: 367
<212> TYPE: PRT
<213> ORGANISM: Homo sapiens

<400> SEQUENCE: 22

Met Arg Trp Phe Leu Pro Trp Thr Leu Ala Ala Val Thr Ala Ala Ala
1               5                   10                  15

Ala Ser Thr Val Leu Ala Thr Ala Leu Ser Pro Ala Pro Thr Thr Met
            20                  25                  30

Asp Phe Thr Pro Ala Pro Leu Glu Asp Thr Ser Ser Arg Pro Gln Phe
        35                  40                  45

Cys Lys Trp Pro Cys Glu Cys Pro Pro Ser Pro Pro Arg Cys Pro Leu
    50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

Arg Tyr Asn Asn Gly Gln Ser Phe Gln Pro Asn Cys Lys Tyr Asn Cys
    130                 135                 140

Thr Cys Ile Asp Gly Ala Val Gly Cys Thr Pro Leu Cys Leu Arg Val
145                 150                 155                 160

Arg Pro Pro Arg Leu Trp Cys Pro His Pro Arg Arg Val Ser Ile Pro
                165                 170                 175

Gly His Cys Cys Glu Gln Trp Ile Cys Glu Asp Asp Ala Lys Arg Pro
            180                 185                 190

Arg Lys Thr Ala Pro Arg Asp Thr Gly Ser Phe Asp Ala Val Gly Glu
        195                 200                 205

Val Glu Ala Trp His Arg Asn Cys Ile Ala Tyr Thr Ser Pro Trp Ser
    210                 215                 220

Pro Cys Ser Thr Ser Cys Gly Leu Gly Val Ser Thr Arg Ile Ser Asn
225                 230                 235                 240

Val Asn Ala Gln Cys Trp Pro Glu Gln Glu Ser Arg Leu Cys Asn Leu
                245                 250                 255

Arg Pro Cys Asp Val Asp Ile His Thr Leu Ile Lys Ala Gly Lys Lys
            260                 265                 270

Cys Leu Ala Val Tyr Gln Pro Glu Ala Ser Met Asn Phe Thr Leu Ala
        275                 280                 285

Gly Cys Ile Ser Thr Arg Ser Tyr Gln Pro Lys Tyr Cys Gly Val Cys
    290                 295                 300

Met Asp Asn Arg Cys Cys Ile Pro Tyr Lys Ser Lys Thr Ile Asp Val
```

```
                   305                 310                 315                 320
Ser Phe Gln Cys Pro Asp Gly Leu Gly Phe Ser Arg Gln Val Leu Trp
                325                 330                 335

Ile Asn Ala Cys Phe Cys Asn Leu Ser Cys Arg Asn Pro Asn Asp Ile
            340                 345                 350

Phe Ala Asp Leu Glu Ser Tyr Pro Asp Phe Ser Glu Ile Ala Asn
                355                 360                 365

<210> SEQ ID NO 23
<211> LENGTH: 1403
<212> TYPE: DNA
<213> ORGANISM: Homo sapiens

<400> SEQUENCE: 23
gccagtctgg gcccagctcc cccgagaggt ggtcggatcc tctgggctgc tcggtcgatg      60
cctgtgccac tgacgtccag gcatgaggtg gttcctgccc tggacgctgg cagcagtgac     120
agcagcagcc gccagcaccg tcctggccac ggccctctct ccagccccta cgaccatgga     180
ctttacccca gctccactgg aggacacctc ctcacgcccc caattctgca agtggccatg     240
tgagtgcccg ccatccccac cccgctgccc gctgggggtc agcctcatca cagatggctg     300
tgagtgctgt aagatgtgcg ctcagcagct tggggacaac tgcacggagg ctgccatctg     360 tgaccccac cggggcctct actgtgacta gcggggac cgcccgagag gtggtcggtg     420
tgggctgcgt cctggatggg gtgcgctaca caacggcca gtccttccag cctaactgca     480
agtacaactg cacgtgcatc gacgcgcgg tgggctgcac accactgtgc ctccgagtgc     540
gccccccgcg tctctggtgc cccaccccgc ggcgcgtgag catacctggc cactgctgtg     600
agcagtgggg atgtgaggac gacgccaaga ggccacgcaa gaccgcaccc cgtgacacag     660
gagccttcga tgctgtgggt gaggtggagg catggcacag gaactgcata gcctacacaa     720
gcccctggag cccttgctcc accagctgcg gcctgggggt ctccactcgg atctccaatg     780
ttaacgccca gtgctggcct gagcaagaga gccgcctctg caacttgcgg ccatgcgatg     840
tggacatcca tacactcatt aaggcaggga agaagtgtct ggctgtgtac cagccagagg     900
catccatgaa cttcacactt gcgggctgca tcagcacacg ctcctatcaa cccaagtact     960
gtggagtttg catggacaat aggtgctgca tccctacaa gtctaagact atcgacgtgt    1020
ccttccagtg tcctgatggg cttggcttct cccgccaggt cctatggatt aatgcctgct    1080
tctgtaacct gagctgtagg aatcccaatg acatctttgc tgacttggaa tcctaccctg    1140
acttctcaga aattgccaac taggcaggca caaatcttgg gtcttgggga ctaacccaat    1200
gcctgtgaag cagtcagccc ttatggccaa taacttttca ccaatgagcc ttagttaccc    1260
tgatctggac ccttggcctc catttctgtc tctaaccatt caaatgacgc ctgatggtgc    1320
tgctcaggcc catgctatga gttttctcct tgatatcatt cagcatctac tctaaagaaa    1380
aatgcctgtc tctagctgtt ctg                                            1403

<210> SEQ ID NO 24
<211> LENGTH: 693
<212> TYPE: DNA
<213> ORGANISM: Homo sapiens

<400> SEQUENCE: 24
tttaattaaa cccccaaggg ctgcggaagg agcatatctg gtgctcctga tgggccggcc      60
agtctgggcc cagctccccc gagaggtggt cggatcctct gggctgctcg gtcgatgcct     120
gtgccactga cgtccaggca tgaggtggtt cctgccctgg acgctggcag cagtgacagc     180
```

| | |
|---|---|
| agcagccgcc agcaccgtcc tggccacggc cctctctcca gcccctacga ccatggactt | 240 |
| taccccagct ccactggagg acacctcctc acgcccccaa ttctgcaagt ggccatgtga | 300 |
| gtgcccgcca tccccacccc gctgcccgct ggggtcagc ctcatcacag atggctgtga | 360 |
| gtgctgtaag atgtgcgctc agcagcttgg ggacaactgc acggaggctg ccatctgtga | 420 |
| cccccaccgg ggcctctact gtgactacag cggggaccgc cgaggtacg caataggagt | 480 |
| gtgtgcacgc agggaagaag tgtctggctg tgtaccagcc agaggcatcc atgaacttca | 540 |
| cacttgcggg ctgcatcagc acacgctcct atcaacccaa gtactgtgga gtttgcatgg | 600 |
| acaacaggtg ctgcatcccc tacaagtcta agactatcga cgtgtccttc agtgtcctg | 660 |
| atgggcttgg cttctcccgc caggtcctat gga | 693 |

<210> SEQ ID NO 25
<211> LENGTH: 683
<212> TYPE: DNA
<213> ORGANISM: Homo sapiens

<400> SEQUENCE: 25

| | |
|---|---|
| cagaatttga actgggatcc acctgtctct aaagatgggt ttcctcccat gcttccacac | 60 |
| tgcctctctt gatcagaaac atacaaggag ctgagaacat gtcctccact ccctgggtac | 120 |
| ctttgctggt tagaagccaa cttgctgtcc tgtggggagg tacagccaat ttctgtgttc | 180 |
| ctctgagttc tggggaccgc agaccttagt gtggtgaaag tgagcgttgg gggctggtgg | 240 |
| gagctgtaga ttcatgcaga ttctgttccc cacacacaga tgctgtgggt gaggtggagg | 300 |
| catggcacag gaactgcata gcctacacaa gcccctggag cccttgctcc accagctgcg | 360 |
| gcctgggggt ctccactcgg atctccaatg ttaacgccca gtgctggcct gagcaagaga | 420 |
| gccgcctctg caacttgcgg ccatgcgatg tggacatcca tacactcatt aaggcaggga | 480 |
| agaagtgtct ggctgtgtac cagccagagg catccatgaa cttcacactt gcgggctgca | 540 |
| tcagcacacg ctcctatcaa cccaagtact gtggagtttg catggacaat aggtgctgca | 600 |
| tcccctacaa gtctaagact atcgacgtgt ccttccagtg tcctgatggg cttggcttct | 660 |
| cccgccaggt cgtatggatt aat | 683 |

<210> SEQ ID NO 26
<211> LENGTH: 1202
<212> TYPE: DNA
<213> ORGANISM: Homo sapiens

<400> SEQUENCE: 26

| | |
|---|---|
| gtctgggccc agctccccg agaggtggtc ggatcctctg gctgctcgg tcgatgcctg | 60 |
| tgccactgac gtccaggcat gaggtggttc ctgccctgga cgctggcagc agtgacagca | 120 |
| gcagccgcca gcaccgtcct ggccacggcc ctctctccag cccctacgac catggacttt | 180 |
| accccagctc cactggagga cacctcctca cgcccccaat tctgcaagtg gccatgtgag | 240 |
| tgcccgccat ccccaccccg ctgcccgctg gggtcagcc tcatcacaga tggctgtgag | 300 |
| tgctgtaaga tgtgcgctca gcagcttggg gacaactgca cggaggctgc catctgtgac | 360 |
| ccccaccggg gcctctactg tgactacagc ggggaccgcc gaggtacgc aataggagtg | 420 |
| tgtgcacgca gggaagaagt gtctggctgt gtaccagcca gaggcatcca tgaacttcac | 480 |
| acttgcgggc tgcatcagca cacgctccta tcaacccaag tactgtggag tttgcatgga | 540 |
| caacaggtgc tgcatcccct acaagtctaa gactatcgac gtgtccttcc agtgtcctga | 600 |
| tgggcttggc ttctcccgcc aggtcctatg gattaatgcc tgcttctgta acctgagctg | 660 |

```
taggaatccc aatgacatct tgctgacttg gaatcctacc ctgacttctc agaaattgc     720 caactaggca ggcacaaatc ttgggtcttg ggactaacc caatgcctgt gaagcagtca    780
gcccttatgg ccaataactt ttcaccaatg agccttagtt accctgatct ggacccttgg   840
cctccatttc tgtctctaac cattcaaatg acgcctgatg gtgctgctca ggcccatgct   900
atgagttttc tccttgatat cattcagcat ctactctaaa gaaaatgcc tgtctctagc    960 tgttctggac tacacccaag cctgatccag ccttttccaag tcactagaag tcctgctgga 1020
tcttgcctaa atcccaagaa atggaatcag gtagactttt aatatcacta atttcttctt  1080
tagatgccaa accacaagac tctttgggtc cattcagatg aatagatgga atttggaaca  1140
atagaataat ctattatttg gagcctgcca agaggtactg taatgggtaa ttctgacgtc  1200
ag                                                                 1202

<210> SEQ ID NO 27
<211> LENGTH: 1183
<212> TYPE: DNA
<213> ORGANISM: Homo sapiens

<400> SEQUENCE: 27
cagaacagct agagacaggc attttctctt agagtagatg ctgaatgata tcaaggagaa    60
aactcatagc atgggcctga gcagcaccat caggcgtcat ttgaatggtt agagacagaa   120
atggaggcca agggtccaga tcagggtaac taaggctcat tggtgaaaag ttattggcca   180
taagggctga ctgcttcaca ggcattgggt tagtccccaa gacccaagat tgtgcctgc   240 ctagttggca atttctgaga agtcagggta ggattccaag tcagcaaaga tgtcattggg  300
attcctacag ctcaggttac agaagcaggc attaatccat aggacctggc gggagaagcc  360
aagcccatca ggacactgga aggacacgtc gatagtctta gacttgtagg ggatgcagca   420
cctattgtcc atgcaaactc cacagtactt gggttgatag gagcgtgtgc tgatgcagcc  480
cgcaagtgtg aagttcatgg atgcctctgg ctggtacaca gccagacact tcttccctgc   540
cttaatgagt gtatggatgt ccacatcgca tggccgcaag ttgcagaggc ggctctcttg   600
ctcaggccag cactgggcgt taacattgga gatccgagtg gagaccccca ggccgcagct   660
ggtggagcaa gggctccagg ggcttgtgta ggctatgcag ttcctgtgcc atgcctccac   720
ctcacccaca gcatctgtgt gtggggaaca gaatctgcat gaatctacag ctcccaccag   780
cccccaacgc tcactttcac cacactaagg tctgcggtcc ccagaactca gaggaacaca   840
gaaattggct gtacctcccc acaggacagc aagttggctt ctaaccagca aaggtaccca   900
gggagtggag acatgttctc agctccttg tatgtttctg atcaagagag gcagtgtgga   960
agcatgggag gaaacccatc tttagagaca ggtggatccc agttcaaatt ctgctctacc  1020
acctacaagc tgtgtgatct tagataaccc accctgggcc tgtctcccca ttagaacaat  1080
aacacctgcc tgtgcggctg gcaacacaat aataagggcc tagattttta ctgagtatgc  1140
atcaatcatc cttgctaagt gctgggaatg ggactttttt ttt                    1183

<210> SEQ ID NO 28
<211> LENGTH: 546
<212> TYPE: DNA
<213> ORGANISM: Homo sapiens

<400> SEQUENCE: 28
cctgatctgg acccttggcc tccaattctg tctgtaacca ttcaaatgac gcctggtggt    60
gctgctcagg cccatagcaa ggttcagcct ggttaagtcc aagctgaatt agcggccgcg   120
```

| | |
|---|---|
| tcgacagtag gagtgtgtgc acatgctgtg ggtgaggtgg aggcatggca caggaactgc | 180 |
| atagcctaca caagcccctg gagcccttgc tccaccagct gcggcctggg ggtctccact | 240 |
| cggatctcca atgttaacgc ccagtgctgg cctgagcaag agagccgcct ctgcaacttg | 300 |
| cggccatgcg atgtggacat ccatacactc attaaggcag ggaagaagtg tctggctgtg | 360 |
| taccagccag aggcatccat gaacttcaca cttgcgggct gcatcagcac acgctccat | 420 |
| caacccaagt actgtggagt ttgcatggac aataggtgct gcatcccta caagtctaag | 480 |
| actatcgacg tgtccttcca gtgtcctgat gggcttggct tctcccgcca ggtcctatgg | 540 |
| attaat | 546 |

<210> SEQ ID NO 29
<211> LENGTH: 1101
<212> TYPE: DNA
<213> ORGANISM: Homo sapiens

<400> SEQUENCE: 29

| | |
|---|---|
| ggcccagctc ccccgagagg tggtcggatc ctctgggctg ctcggtcgat gcctgtgcca | 60 |
| ctgacgtcca ggcatgaggt ggttcctgcc ctggacgctg gcagcagtga cagcagcagc | 120 |
| cgccagcacc gtcctggcca cggccctctc tccagcccct acgaccatgg actttacccc | 180 |
| agctccactg gaggacacct cctcacgccc ccaattctgc aagtggccat gtgagtgccc | 240 |
| gccatcccca ccccgctgcc cgctgggggt cagcctcatc acagatggct gtgagtgctg | 300 |
| taagatgtgc gctcagcagc ttggggacaa ctgcacggag gctgccatct gtgacccca | 360 |
| ccggggcctc tactgtgact acagcgggga ccgcccgaga ggtggtcggt gtgggctgcg | 420 |
| tcctggatgg ggtgcgctac aacaacggcc agtccttcca gcctaactgc aagtacaact | 480 |
| gcacgtgcat cgacggcgcg gtgggctgca caccactgtg cctccgagtg cgcccccgc | 540 |
| gtctctggtg cccccacccg cggcgcgtga gcatacctgg ccactgctgt gagcagtgga | 600 |
| tatgtgagga cgacgccaag aggccacgca agaccgcacc ccgtgacaca ggagccttcg | 660 |
| atgccagaag cgcccgctcc ctcagagatg tgacaaccaa atcatctcc agacctttcc | 720 |
| aaatacaccc taggagacaa aattgctcgg tggagaagca gtcctgtgag gacaggagga | 780 |
| ggcgtggagg aaagctttgt ccccagcagc cccaggaag caaggcagct ctcccaccac | 840 |
| cacctcccca ggagggccac acgagggtca cggggggagc agggaggcgg aagctgtctg | 900 |
| ccattgtgtc tggcccagtg accctgttct gaccgagcac aagcggagcc ctgcctagc | 960 |
| cgagatgctg tgggtgaggt ggaggcatgg cacaggaact gcatagccta cacaagcccc | 1020 |
| tggagcccctt gctccaccag ctgcggcctg ggggtctcca ctcggatctc caatgttaac | 1080 |
| gcccagtgct ggcctgagca a | 1101 |

<210> SEQ ID NO 30
<211> LENGTH: 1335
<212> TYPE: DNA
<213> ORGANISM: Homo sapiens
<220> FEATURE:
<221> NAME/KEY: modified_base
<222> LOCATION: (1205)..(1205)
<223> OTHER INFORMATION: Unknown nucleotide
<220> FEATURE:
<221> NAME/KEY: modified_base
<222> LOCATION: (1318)..(1318)
<223> OTHER INFORMATION: Unknown nucleotide

<400> SEQUENCE: 30

| | |
|---|---|
| gtggggtttg cagaggagac aggggagctt tgtgtacccg gagcaatgaa caagcggcga | 60 |

| | |
|---|---|
| cttctctacc cctcagggtg gctccacggt cccagcgaca tgcagggget cctcttctcc | 120 |
| actcttctgc ttgctggcct ggcacagttc tgctgcaggg tacagggcac tggaccatta | 180 |
| gatacaacac ctgaaggaag gcctggagaa gtgtcagatg cacctcagcg taaacagttt | 240 |
| tgtcactggc cctgcaaatg ccctcagcag aagccccgtt gccctcctgg agtgagcctg | 300 |
| gtgagagatg gctgtggatg ctgtaaaatc tgtgccaagc aaccagggga aatctgcaat | 360 |
| gaagctgacc tctgtgaccc acacaaaggg ctgtattgtg actactcagt agacaggcct | 420 |
| aggtacgaga ctggagtgtg tgcataccct tgtagctgttg ggtgcgagtt caaccaggta | 480 |
| cattatcata atggccaagt gtttcagccc aacccttgt tcagctgcct ctgtgtgagt | 540 |
| ggggccattg gatgcacacc tctgttcata ccaaagctgg ctggcagtca ctgctctgga | 600 |
| gctaaaggtg gaaagaagtc tgatcagtca aactgtagcc tggaaccatt actacagcag | 660 |
| ctttcaacaa gctacaaaac aatgccagct tatagagatc tcccacttat ttggaaaaaa | 720 |
| aaatgtcttg tgcaagcaac aaaatggact ccctgctcca gaacatgtgg gatgggaata | 780 |
| tctaacaggg tgaccaatga aacagcaac tgtgaaatga aaaagagaa aagactgtgt | 840 |
| tacattcagc cttgcgacag caatatatta agacaataa agattcccaa aggaaaaaca | 900 |
| tgccaaccta ctttccaact ctccaaagct gaaaatttg tcttttctgg atgctcaagt | 960 |
| actcagagtt acaaacccac ttttttgtgga atatgcttgg ataagagatg ctgtatccct | 1020 |
| aataagtcta aaatgattac tattcaattt gattgcccaa atgaggggtc atttaaatgg | 1080 |
| aagatgctgt ggattacatc ttgtgtgtgt cagagaaact gcagagaacc tggagatata | 1140 |
| ttttctgagc tcaagattct gtaaaaccaa gcaaatgggg gaaaagttag tcaatcctgt | 1200 |
| catanaataa aaaaattagt gagtataaaa tggtggcaaa tctactttgt ttaaaacagt | 1260 |
| atgaatgcct attctcagat cactacattt aaggcattag aaactttaa aaagttanct | 1320 |
| taaaaatata cataa | 1335 |

<210> SEQ ID NO 31
<211> LENGTH: 1335
<212> TYPE: DNA
<213> ORGANISM: Homo sapiens
<220> FEATURE:
<221> NAME/KEY: modified_base
<222> LOCATION: (18)..(18)
<223> OTHER INFORMATION: Unknown nucleotide
<220> FEATURE:
<221> NAME/KEY: modified_base
<222> LOCATION: (131)..(131)
<223> OTHER INFORMATION: Unknown nucleotide

<400> SEQUENCE: 31

| | |
|---|---|
| ttatgtatat ttttaagnta acttttaaa agtttctaat gccttaaatg tagtgatctg | 60 |
| agaataggca ttcatactgt tttaaacaaa gtagatttgc caccatttta tactcactaa | 120 |
| ttttttatt ntatgacagg attgactaac ttttccccca tttgcttggt tttacagaat | 180 |
| cttgagctca gaaatatat ctccaggttc tctgcagttt ctctgacaca cacaagatgt | 240 |
| aatccacagc atcttccatt taaatgaccc ctcatttggg caatcaaatt gaatagtaat | 300 |
| cattttagac ttattaggga tacagcatct cttatccaag catattccac aaaaagtggg | 360 |
| tttgtaactc tgagtacttg agcatccaga aaagacaaat ttttcagctt tggagagttg | 420 |
| gaaagtaggt tggcatgttt ttcctttggg aatctttatt gtctttaata tattgctgtc | 480 |
| gcaaggctga atgtaacaca gtcttttctc ttttctcatt tcacagttgc tgttttcatt | 540 |
| ggtcaccctg ttagatattc ccatcccaca tgttctggag cagggagtcc attttgttgc | 600 |

-continued

```
ttgcacaaga catttttttt tccaaataag tgggagatct ctataagctg gcattgtttt    660
gtagcttgtt gaaagctgct gtagtaatgg ttccaggcta cagtttgact gatcagactt    720 cttttccacct ttagctccag agcagtgact gccagccagc tttggtatga acagaggtgt    780
gcatccaatg gccccactca cacagaggca gctgaacaag gggttgggct gaaacacttg    840
gccattatga taatgtacct ggttgaactc gcacccaaca gctacaaggt atgcacacac    900
tccagtctcg tacctaggcc tgtctactga gtagtcacaa tacagcccctt tgtgtgggtc    960 acagaggtca gcttcattgc agatttcccc tggttgcttg gcacagattt tacagcatcc   1020
acagccatct ctcaccaggc tcactccagg agggcaacgg ggcttctgct gagggcattt   1080
gcagggccag tgacaaaact gtttacgctg aggtgcatct gacacttctc caggccttcc   1140
ttcaggtgtt gtatctaatg gtccagtgcc ctgtaccctg cagcagaact gtgccaggcc   1200
agcaagcaga agagtggaga agaggagccc ctgcatgtcg ctgggaccgt ggagccaccc   1260 tgagggtag agaagtcgcc gcttgttcat tgctccgggt acacaaagct cccctgtctc   1320
ctctgcaaac cccac                                                    1335
```

<210> SEQ ID NO 32
<211> LENGTH: 339
<212> TYPE: PRT
<213> ORGANISM: Homo sapiens

<400> SEQUENCE: 32

```
Gln Phe Cys Cys Arg Val Gln Gly Thr Gly Pro Leu Asp Thr Thr Pro
1               5                   10                  15

Glu Gly Arg Pro Gly Glu Val Ser Asp Ala Pro Gln Arg Lys Gln Phe
            20                  25                  30

Cys His Trp Pro Cys Lys Cys Pro Gln Gln Lys Pro Arg Cys Pro Pro
        35                  40                  45

Gly Val Ser Leu Val Arg Asp Gly Cys Gly Cys Cys Lys Ile Cys Ala
    50                  55                  60

Lys Gln Pro Gly Glu Ile Cys Asn Glu Ala Asp Leu Cys Asp Pro His
65                  70                  75                  80

Lys Gly Leu Tyr Cys Asp Tyr Ser Val Asp Arg Pro Arg Tyr Glu Thr
                85                  90                  95

Gly Val Cys Ala Tyr Leu Val Ala Val Gly Cys Glu Phe Asn Gln Val
            100                 105                 110

His Tyr His Asn Gly Gln Val Phe Gln Pro Asn Pro Leu Phe Ser Cys
        115                 120                 125

Leu Cys Val Ser Gly Ala Ile Gly Cys Thr Pro Leu Phe Ile Pro Lys
    130                 135                 140

Leu Ala Gly Ser His Cys Ser Gly Ala Lys Gly Gly Lys Lys Ser Asp
145                 150                 155                 160

Gln Ser Asn Cys Ser Leu Glu Pro Leu Leu Gln Leu Ser Thr Ser
                165                 170                 175

Tyr Lys Thr Met Pro Ala Tyr Arg Asp Leu Pro Leu Ile Trp Lys Lys
            180                 185                 190

Lys Cys Leu Val Gln Ala Thr Lys Trp Thr Pro Cys Ser Arg Thr Cys
        195                 200                 205

Gly Met Gly Ile Ser Asn Arg Val Thr Asn Glu Asn Ser Asn Cys Glu
    210                 215                 220

Met Arg Lys Glu Lys Arg Leu Cys Tyr Ile Gln Pro Cys Asp Ser Asn
225                 230                 235                 240
```

```
Ile Leu Lys Thr Ile Lys Ile Pro Lys Gly Lys Thr Cys Gln Pro Thr
                245                 250                 255

Phe Gln Leu Ser Lys Ala Glu Lys Phe Val Phe Ser Gly Cys Ser Ser
            260                 265                 270

Thr Gln Ser Tyr Lys Pro Thr Phe Cys Gly Ile Cys Leu Asp Lys Arg
        275                 280                 285

Cys Cys Ile Pro Asn Lys Ser Lys Met Ile Thr Ile Gln Phe Asp Cys
    290                 295                 300

Pro Asn Glu Gly Ser Phe Lys Trp Lys Met Leu Trp Ile Thr Ser Cys
305                 310                 315                 320

Val Cys Gln Arg Asn Cys Arg Glu Pro Gly Asp Ile Phe Ser Glu Leu
                325                 330                 335

Lys Ile Leu

<210> SEQ ID NO 33
<211> LENGTH: 372
<212> TYPE: PRT
<213> ORGANISM: Homo sapiens

<400> SEQUENCE: 33

Met Asn Lys Arg Arg Leu Leu Tyr Pro Ser Gly Trp Leu His Gly Pro
1               5                   10                  15

Ser Asp Met Gln Gly Leu Leu Phe Ser Thr Leu Leu Leu Ala Gly Leu
            20                  25                  30

Ala Gln Phe Cys Cys Arg Val Gln Gly Thr Gly Pro Leu Asp Thr Thr
        35                  40                  45

Pro Glu Gly Arg Pro Gly Glu Val Ser Asp Ala Pro Gln Arg Lys Gln
    50                  55                  60

Phe Cys His Trp Pro Cys Lys Cys Pro Gln Gln Lys Pro Arg Cys Pro
65                  70                  75                  80

Pro Gly Val Ser Leu Val Arg Asp Gly Cys Gly Cys Cys Lys Ile Cys
                85                  90                  95

Ala Lys Gln Pro Gly Glu Ile Cys Asn Glu Ala Asp Leu Cys Asp Pro
            100                 105                 110

His Lys Gly Leu Tyr Cys Asp Tyr Ser Val Asp Arg Pro Arg Tyr Glu
        115                 120                 125

Thr Gly Val Cys Ala Tyr Leu Val Ala Val Gly Cys Glu Phe Asn Gln
    130                 135                 140

Val His Tyr His Asn Gly Gln Val Phe Gln Pro Asn Pro Leu Phe Ser
145                 150                 155                 160

Cys Leu Cys Val Ser Gly Ala Ile Gly Cys Thr Pro Leu Phe Ile Pro
                165                 170                 175

Lys Leu Ala Gly Ser His Cys Ser Gly Ala Lys Gly Gly Lys Lys Ser
            180                 185                 190

Asp Gln Ser Asn Cys Ser Leu Glu Pro Leu Leu Gln Gln Leu Ser Thr
        195                 200                 205

Ser Tyr Lys Thr Met Pro Ala Tyr Arg Asp Leu Pro Leu Ile Trp Lys
    210                 215                 220

Lys Lys Cys Leu Val Gln Ala Thr Lys Trp Thr Pro Cys Ser Arg Thr
225                 230                 235                 240

Cys Gly Met Gly Ile Ser Asn Arg Val Thr Asn Glu Asn Ser Asn Cys
                245                 250                 255

Glu Met Arg Lys Glu Lys Arg Leu Cys Tyr Ile Gln Pro Cys Asp Ser
            260                 265                 270

Asn Ile Leu Lys Thr Ile Lys Ile Pro Lys Gly Lys Thr Cys Gln Pro
```

```
                         275                 280                 285
Thr Phe Gln Leu Ser Lys Ala Glu Lys Phe Val Phe Ser Gly Cys Ser
    290                 295                 300

Ser Thr Gln Ser Tyr Lys Pro Thr Phe Cys Gly Ile Cys Leu Asp Lys
305                 310                 315                 320

Arg Cys Cys Ile Pro Asn Lys Ser Lys Met Ile Thr Ile Gln Phe Asp
                325                 330                 335

Cys Pro Asn Glu Gly Ser Phe Lys Trp Lys Met Leu Trp Ile Thr Ser
                340                 345                 350

Cys Val Cys Gln Arg Asn Cys Arg Glu Pro Gly Asp Ile Phe Ser Glu
                355                 360                 365

Leu Lys Ile Leu
    370

<210> SEQ ID NO 34
<211> LENGTH: 1212
<212> TYPE: DNA
<213> ORGANISM: Homo sapiens

<400> SEQUENCE: 34
cacggtccca gcgacatgca ggggctcctc ttctccactc ttctgcttgc tggcctggca      60
cagttctgct gcagggtaca gggcactgga ccattagata caacacctga aggaaggcct     120
ggagaagtgt cagatgcacc tcagcgtaaa cagttttgtc actggccctg caaatgccct     180
cagcagaagc cccgttgccc tcctggagtg agcctggtga gagatggctg tggatgctgt     240
aaaatctgtg ccaagcaacc aggggaaatc tgcaatgaag ctgacctctg tgacccacac     300
aaagggctgt attgtgacta ctcagtagac aggcctaggt acgagactgg agtgtgtgca     360
taccttgtag ctgttgggtg cgagttcaac caggtacatt atcataatgg ccaagtgttt     420
cagcccaacc ccttgttcag ctgcctctgt gtgagtgggg ccattggatg cacacctctg     480
ttcataccaa agctggctgg cagtcactgc tctggagcta aaggtggaaa gaagtctgat     540
cagtcaaact gtagcctgga accattacta cagcagcttt caacaagcta caaacaatg     600 ccagcttata gaaatctccc acttatttgg aaaaaaaaat gtcttgtgca agcaacaaaa     660
tggactccct gctccagaac atgtgggatg ggaatatcta acagggtgac caatgaaaac     720
agcaactgtg aaatgagaaa agagaaaaga ctgtgttaca ttcagccttg cgacagcaat     780
atattaaaga caataaagat tcccaaagga aaacatgcc aacctacttt ccaactctcc     840
aaagctgaaa aatttgtctt ttctggatgc tcaagtactc agagttacaa acccactttt     900
tgtggaatat gcttggataa gagatgctgt atccctaata agtctaaaat gattactatt    960
caatttgatt gccaaatga gggtcatttt aaatggaaga tgctgtggat acatcttgt    1020 gtgtgtcaga gaaactgcag agaacctgga gatatattt ctgagctcaa gattctgtaa   1080
aaccaagcaa atgggggaaa agttagtcaa tcctgtcata taataaaaaa attagtgagt    1140
aaaaaaaaaa aaaaaaaaaa aaaaaaaaaa aaaaaaaaaa aaaaaaaaaa agaaaaaaaa    1200
aaaaaaaaaa aa                                                       1212

<210> SEQ ID NO 35
<211> LENGTH: 1212
<212> TYPE: DNA
<213> ORGANISM: Homo sapiens

<400> SEQUENCE: 35
tttttttttt tttttttttt cttttttttt tttttttttt tttttttttt tttttttttt     60
```

```
tttttttttt ttactcacta atttttttat tatatgacag gattgactaa cttttccccc      120
atttgcttgg ttttacagaa tcttgagctc agaaaatata tctccaggtt tctctgcagtt     180 tctctgacac acacaagatg taatccacag catcttccat ttaaatgacc cctcatttgg      240
gcaatcaaat tgaatagtaa tcattttaga cttattaggg atacagcatc tcttatccaa      300
gcatattcca caaaagtgg gtttgtaact ctgagtactt gagcatccag aaaagacaaa       360
tttttcagct ttggagagtt ggaaagtagg ttggcatgtt tttcctttgg gaatctttat      420
tgtctttaat atattgctgt cgcaaggctg aatgtaacac agtctttct cttttctcat       480 ttcacagttg ctgttttcat tggtcaccct gttagatatt cccatcccac atgttctgga     540
gcagggagtc catttgttg cttgcacaag acattttttt ttccaaataa gtgggagatt      600
tctataagct ggcattgttt tgtagcttgt tgaaagctgc tgtagtaatg gttccaggct     660
acagtttgac tgatcagact tctttccacc tttagctcca gagcagtgac tgccagccag    720
ctttggtatg aacagaggtg tgcatccaat ggccccactc acacagaggc agctgaacaa     780
ggggttgggc tgaaacactt ggccattatg ataatgtacc tggttgaact cgcacccaac    840
agctacaagg tatgcacaca ctccagtctc gtacctaggc ctgtctactg agtagtcaca    900
atacagccct ttgtgtgggt cacagaggtc agcttcattg cagatttccc ctggttgctt    960
ggcacagatt ttacagcatc cacagccatc tctcaccagg ctcactccag gagggcaacg  1020
gggcttctgc tgagggcatt tgcagggcca gtgacaaaac tgtttacgct gaggtgcatc   1080
tgacacttct ccaggccttc cttcaggtgt tgtatctaat ggtccagtgc cctgtaccct   1140
gcagcagaac tgtgccaggc cagcaagcag aagagtggag aagaggagcc cctgcatgtc   1200
gctgggaccg tg                                                        1212
```

<210> SEQ ID NO 36
<211> LENGTH: 339
<212> TYPE: PRT
<213> ORGANISM: Homo sapiens

<400> SEQUENCE: 36

Gln Phe Cys Cys Arg Val Gln Gly Thr Gly Pro Leu Asp Thr Thr Pro
1               5                   10                  15

Glu Gly Arg Pro Gly Glu Val Ser Asp Ala Pro Gln Arg Lys Gln Phe
            20                  25                  30

Cys His Trp Pro Cys Lys Cys Pro Gln Gln Lys Pro Arg Cys Pro Pro
        35                  40                  45

Gly Val Ser Leu Val Arg Asp Gly Cys Gly Cys Cys Lys Ile Cys Ala
    50                  55                  60

Lys Gln Pro Gly Glu Ile Cys Asn Glu Ala Asp Leu Cys Asp Pro His
65                  70                  75                  80

Lys Gly Leu Tyr Cys Asp Tyr Ser Val Asp Arg Pro Arg Tyr Glu Thr
                85                  90                  95

Gly Val Cys Ala Tyr Leu Val Ala Val Gly Cys Glu Phe Asn Gln Val
            100                 105                 110

His Tyr His Asn Gly Gln Val Phe Gln Pro Asn Pro Leu Phe Ser Cys
        115                 120                 125

Leu Cys Val Ser Gly Ala Ile Gly Cys Thr Pro Leu Phe Ile Pro Lys
    130                 135                 140

Leu Ala Gly Ser His Cys Ser Gly Ala Lys Gly Gly Lys Lys Ser Asp
145                 150                 155                 160

Gln Ser Asn Cys Ser Leu Glu Pro Leu Leu Gln Leu Ser Thr Ser
                165                 170                 175

```
Tyr Lys Thr Met Pro Ala Tyr Arg Asn Leu Pro Leu Ile Trp Lys Lys
            180                 185                 190

Lys Cys Leu Val Gln Ala Thr Lys Trp Thr Pro Cys Ser Arg Thr Cys
        195                 200                 205

Gly Met Gly Ile Ser Asn Arg Val Thr Asn Glu Asn Ser Asn Cys Glu
    210                 215                 220

Met Arg Lys Glu Lys Arg Leu Cys Tyr Ile Gln Pro Cys Asp Ser Asn
225                 230                 235                 240

Ile Leu Lys Thr Ile Lys Ile Pro Lys Gly Lys Thr Cys Gln Pro Thr
                245                 250                 255

Phe Gln Leu Ser Lys Ala Glu Lys Phe Val Phe Ser Gly Cys Ser Ser
            260                 265                 270

Thr Gln Ser Tyr Lys Pro Thr Phe Cys Gly Ile Cys Leu Asp Lys Arg
        275                 280                 285

Cys Cys Ile Pro Asn Lys Ser Lys Met Ile Thr Ile Gln Phe Asp Cys
    290                 295                 300

Pro Asn Glu Gly Ser Phe Lys Trp Lys Met Leu Trp Ile Thr Ser Cys
305                 310                 315                 320

Val Cys Gln Arg Asn Cys Arg Glu Pro Gly Asp Ile Phe Ser Glu Leu
                325                 330                 335

Lys Ile Leu

<210> SEQ ID NO 37
<211> LENGTH: 354
<212> TYPE: PRT
<213> ORGANISM: Homo sapiens

<400> SEQUENCE: 37

Met Gln Gly Leu Leu Phe Ser Thr Leu Leu Leu Ala Gly Leu Ala Gln
1               5                   10                  15

Phe Cys Cys Arg Val Gln Gly Thr Gly Pro Leu Asp Thr Thr Pro Glu
            20                  25                  30

Gly Arg Pro Gly Glu Val Ser Asp Ala Pro Gln Arg Lys Gln Phe Cys
        35                  40                  45

His Trp Pro Cys Lys Cys Pro Gln Gln Lys Pro Arg Cys Pro Pro Gly
    50                  55                  60

Val Ser Leu Val Arg Asp Gly Cys Gly Cys Cys Lys Ile Cys Ala Lys
65                  70                  75                  80

Gln Pro Gly Glu Ile Cys Asn Glu Ala Asp Leu Cys Asp Pro His Lys
                85                  90                  95

Gly Leu Tyr Cys Asp Tyr Ser Val Asp Arg Pro Arg Tyr Glu Thr Gly
            100                 105                 110

Val Cys Ala Tyr Leu Val Ala Val Gly Cys Glu Phe Asn Gln Val His
        115                 120                 125

Tyr His Asn Gly Gln Val Phe Gln Pro Asn Pro Leu Phe Ser Cys Leu
    130                 135                 140

Cys Val Ser Gly Ala Ile Gly Cys Thr Pro Leu Phe Ile Pro Lys Leu
145                 150                 155                 160

Ala Gly Ser His Cys Ser Gly Ala Lys Gly Gly Lys Ser Asp Gln
                165                 170                 175

Ser Asn Cys Ser Leu Glu Pro Leu Leu Gln Leu Ser Thr Ser Tyr
            180                 185                 190

Lys Thr Met Pro Ala Tyr Arg Asn Leu Pro Leu Ile Trp Lys Lys Lys
        195                 200                 205
```

```
Cys Leu Val Gln Ala Thr Lys Trp Thr Pro Cys Ser Arg Thr Cys Gly
        210                 215                 220

Met Gly Ile Ser Asn Arg Val Thr Asn Glu Asn Ser Asn Cys Glu Met
225                 230                 235                 240

Arg Lys Glu Lys Arg Leu Cys Tyr Ile Gln Pro Cys Asp Ser Asn Ile
                245                 250                 255

Leu Lys Thr Ile Lys Ile Pro Lys Gly Lys Thr Cys Gln Pro Thr Phe
        260                 265                 270

Gln Leu Ser Lys Ala Glu Lys Phe Val Phe Ser Gly Cys Ser Ser Thr
    275                 280                 285

Gln Ser Tyr Lys Pro Thr Phe Cys Gly Ile Cys Leu Asp Lys Arg Cys
    290                 295                 300

Cys Ile Pro Asn Lys Ser Lys Met Ile Thr Ile Gln Phe Asp Cys Pro
305                 310                 315                 320

Asn Glu Gly Ser Phe Lys Trp Lys Met Leu Trp Ile Thr Ser Cys Val
                325                 330                 335

Cys Gln Arg Asn Cys Arg Glu Pro Gly Asp Ile Phe Ser Glu Leu Lys
                340                 345                 350

Ile Leu

<210> SEQ ID NO 38
<211> LENGTH: 738
<212> TYPE: DNA
<213> ORGANISM: Homo sapiens

<400> SEQUENCE: 38
ccgaagaccc acctcctggc cttctccctc tctgcctcc tctcaaaggt gcgtacccag        60
ctgtgcccga caccatgtac ctgccccctgg ccacctcccc gatgcccgct gggagtaccc     120
ctggtgctgg atggctgtgg ctgctgccgg gtatgtgcac ggcggctggg ggagccctgc     180
gaccaactcc acgtctgcga cgccagccag ggcctggtct gccagcccgg ggcaggaccc     240
ggtggccggg gggccctgtg cctcttggca gaggacgaca gcagctgtga ggtgaacggc     300
cgcctgtatc gggaagggga gaccttccag ccccactgca gcatccgctg ccgctgcgag     360
gacggcggct tcacctgcgt gccgctgtgc agcgaggatg tgcggctgcc cagctgggac     420
tgcccccacc ccaggagggt cgaggtcctg ggcaagtgct gccctgagtg ggtgtgcggc     480
caaggagggg gactggggac ccagccccctt ccagcccaag accccagtt ttctggcctt     540 gtctcttccc tgcccctgg tgtccctgc cagaatgga gcacggcctg ggaccctgc         600 tcgaccacct gtgggctggg catggccacc cgggtgtcca accagaaccg cttctgccga     660
ctggagaccc agcgccgcct gtgcctgtcc aggccctgcc caccctccag gggtcgcagt     720
ccacaaaaca gtgccttc                                                   738

<210> SEQ ID NO 39
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
ctgcagggga catgagaggc acaccgaaga cccacctcct ggccttctcc ctcctctgcc       60
tcctctcaaa ggtgcgtacc cagctgtgcc cgacaccatg tacctgcccc tggccacctc     120
cccgatgccc gctgggagta ccctggtgg tggatggctg tggctgctgc cgggtatgtg     180
```

-continued

```
cacggcgggct gggggagccc tgcgaccaac tccacgtctg cgacgccagc cagggcctgg      240
tctgccagcc cggggcagga cccggtggcc ggggggccct gtgcctcttg gcagaggacg      300
acagcagctg tgaggtgaac ggccgcctgt atcgggaagg ggagaccttc cagccccact      360
gcagcatccg ctgccgctgc gaggacgcg gcttcacctg cgtgccgctg tgcagcgagg      420
atgtgcggct gcccagctgg gactgccccc accccaggag ggtcgaggtc ctgggcaagt      480
gctgccctga gtgggtgtgc ggccaaggag ggggactggg gaccagccct tccagcccaa      540 ggacccagt tttctggcct tgtctcttcc ctgcccctg gtgtccctg cccagaatgg      600 agcacggcct ggggaccctg ctcgaccacc tgtgggctgg gcatggccac ccgggtgtcc      660
aaccagaacc gcttctgccg actggagacc cagcgccgcc tgtgcctgtc caggccctgc      720
ccaccctcca ggggtcgcag tccacaaaac agtgccttct agagccgggc tgggaatggg      780
gacacggtgt ccaccatccc cagctggtgg ccctgtgcct gggccctggg ctgatggaag      840
a                                                                      841
```

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttttgtacaa gctt                                                        14

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctaatacgac tcactatagg gctcgagcgg ccgcccgggc aggt                        44

<210> SEQ ID NO 42
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgtagcgtga agacgacaga aagggcgtgg tgcggagggc ggt                         43

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acctgcccgg                                                             10

<210> SEQ ID NO 44
<211> LENGTH: 11
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 44
accgccctcc g                                                          11

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctaatacgac tcactatagg gc                                              22

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgtagcgtga agacgacaga a                                               21

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tcgagcggcc gcccgggcag gt                                              22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agggcgtggt gcggagggcg gt                                              22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
accacagtcc atgccatcac                                                 20

<210> SEQ ID NO 50
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 50
tccaccaccc tgttgctgta                                                20

<210> SEQ ID NO 51
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
tgtaatacga ctcactatag ggcgaattgg gcccgacgtc gcatgctccc ggccgccatg      60
gccgcgggat tatcactagt gcggccgcct gcaggtcgac catatgggag agctcccaac    120
gcgttggatg catagcttga gtattctata gtgtcaccta aat                      163

<210> SEQ ID NO 52
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atttaggtga cactatagaa tactcaagct atgcatccaa cgcgttggga gctctcccat      60
atggtcgacc tgcaggcggc cgcactagtg attatcccgc ggccatggcg ccgggagca     120 tgcgacgtcg ggcccaattc gccctatagt gagtcgtatt aca                      163

<210> SEQ ID NO 53
<211> LENGTH: 10325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ttcgagctcg cccgacattg attattgact agagtcgatc accggttatt aatagtaatc      60
aattacgggg tcatagttca tagcccatat atggagttcc gcgttacata acttacggta    120
aatgccccgc ctggctgacc gcccaacgac ccccgcccat tgacgtcaat aatgacgtat    180
gttcccatag taacgccaat agggactttc cattgacgtc aatgggtgga gtatttacgg    240
taaactgccc acttggcagt acatcaagtg tatcatatgc caagtacgcc ccctattgac    300
gtcaatgacg gtaaatggcc cgcctggcat tatgcccagt acatgacctt atgggacttt    360
cctacttggc agtacatcta cgtattagtc atcgctatta ccatggtgat gcggttttgg    420
cagtacatca atgggcgtgg atagcggttt gactcacggg gatttccaag tctccacccc    480
attgacgtca atgggagttt gttttggcac caaaatcaac gggactttcc aaaatgtcgt    540
aacaactccg ccccattgac gcaaatgggc ggtaggcgtg tacggtggga ggtctatata    600
agcagagctc gtttagtgaa ccgtcagatc gcctggagac gccatccacg ctgttttgac    660
ctgggcccgg ccgaggccgc ctcggcctct gagctattcc agaagtagtg aggaggcttt    720
tttggaggcc taggcttttg caaaaagcta gcttatccgg ccgggaacgg tgcattggaa    780
cgcggattcc ccgtgccaag agtgacgtaa gtaccgccta tagagcgact agtccaccat    840

```
gaccgagtac aagcccacgg tgcgcctcgc cacccgcgac gacgtcccgc gggccgtacg    900
cacccctcgcc gccgcgttcg ccgactaccc cgccacgcgc cacaccgtag acccggaccg    960
ccacatcgag cgggtcaccg agctgcaaga actcttcctc acgcgcgtcg ggctcgacat   1020
cggcaaggtg tgggtcgcgg acgacggcgc cgcggtggcg gtctggacca cgccggagag   1080
cgtcgaagcg ggggcggtgt tcgccgagat cggcccgcgc atggccgagt tgagcggttc   1140
ccggctggcc gcgcagcaac agatggaagg cctcctggcg ccgcaccggc caaggagcc    1200
cgcgtggttc ctggccaccg tcggcgtctc gcccgaccac cagggcaagg gtctgggcag   1260
cgccgtcgtg ctccccggag tggaggcggc cgagcgcgcc ggggtgcccg ccttcctgga   1320
gacctccgcg ccccgcaacc tccccttcta cgagcggctc ggcttcaccg tcaccgccga   1380
cgtcgagtgc ccgaaggacc gcgcgacctg gtgcatgacc cgcaagcccg gtgccaacat   1440
ggttcgacca ttgaactgca tcgtcgccgt gtcccaaaat atggggattg gcaagaacgg   1500
agacctaccc tgccctccgc tcaggaacgc gttcaagtac ttccaaagaa tgaccacaac   1560
ctcttcagtg gaaggtaaac agaatctggt gattatgggt aggaaaacct ggttctccat   1620
tcctgagaag aatcgacctt taaaggacag aattaatata gttctcagta gagaactcaa   1680
agaaccacca cgaggagctc attttcttgc caaaagtttg gatgatgcct taagactat    1740
tgaacaaccg gaattggcaa gtaaagtaga catggtttgg atagtcggag gcagttctgt   1800
ttaccaggaa gccatgaatc aaccaggcca ccttagactc tttgtgacaa ggatcatgca   1860
ggaatttgaa agtgacacgt ttttcccaga aattgatttg gggaaatata aacctctccc   1920
agaatacccca ggcgtcctct ctgaggtcca ggaggaaaaa ggcatcaagt ataagtttga   1980
agtctacgag aagaaagact aacgttaact gctcccctcc taaagctatg cattttata    2040
agaccatggg acttttgctg gctttagatc cccttggctt cgttagaacg cagctacaat   2100
taatacataa ccttatgtat catacacata cgatttaggt gacactatag ataacatcca   2160
ctttgccttt ctctccacag gtgtccactc ccaggtccaa ctgcacctcg gttctatcga   2220
ttgaattccc cggggatcct ctagagtcga cctgcagaag cttcgatggc cgccatggcc   2280
caacttgttt attgcagctt ataatggtta caaataaagc aatagcatca caaatttcac   2340
aaataaagca tttttttcac tgcattctag ttgtggtttg tccaaactca tcaatgtatc   2400
ttatcatgtc tggatcgatc gggaattaat tcggcgcagc accatggcct gaaataacct   2460
ctgaaagagg aacttggtta ggtaccgact agtcgcgtta cataacttac ggtaaatggc   2520
ccgcctggct gaccgcccaa cgaccccgc ccattgacgt caataatgac gtatgttccc    2580
atagtaacgc caatagggac tttccattga cgtcaatggg tggagtattt acggtaaact   2640
gcccacttgg cagtacatca agtgtatcat atgccaagta cgccccctat tgacgtcaat   2700
gacggtaaat ggcccgcctg gcattatgcc cagtacatga ccttatggga ctttcctact   2760
tggcagtaca tctacgtatt agtcatcgct attaccatgg tgatgcggtt ttggcagtac   2820
atcaatgggc gtggatagcg gtttgactca cggggatttc caagtctcca ccccattgac   2880
gtcaatggga gtttgttttg actagtagca aggtcgccac gcacaagatc aatattaaca   2940
atcagtcatc tctctttagc aataaaaagg tgaaaaatta cattttaaaa atgacaccat   3000
agacgatgta tgaaaataat ctacttggaa ataaatctag gcaaagaagt gcaagactgt   3060
tacccagaaa acttacaaat tgtaaatgag aggttagtga agatttaaat gaatgaagat   3120
ctaaataaac ttataaattg tgagagaaat taatgaatgt ctaagttaat gcagaaacgg   3180
agagacatac tatattcatg aactaaaaga cttaatattg tgaaggtata cttctttttc   3240
```

```
acataaattt gtagtcaata tgttcacccc aaaaaagctg tttgttaact tgtcaacctc   3300
atttcaaaat gtatatagaa agcccaaaga caataacaaa atatattcttg tagaacaaaa   3360 tgggaaagaa tgttccacta aatatcaaga tttagagcaa agcatgagat gtgtggggat   3420
agacagtgag gctgataaaa tagagtagag ctcagaaaca gacccattga tatatgtaag   3480
tgacctatga aaaaaatatg gcattttaca atgggaaaat gatgatcttt ttcttttta   3540 gaaaaacagg gaaatatatt tatatgtaaa aaataaaagg gaacccatat gtcataccat   3600
acacacaaaa aaattccagt gaattataag tctaaatgga gaaggcaaaa ctttaaatct   3660
tttagaaaat aatatagaag catgccatca tgacttcagt gtagagaaaa atttcttatg   3720
actcaaagtc ctaaccacaa agaaaagatt gttaattaga ttgcatgaat attaagactt   3780
atttttaaaa ttaaaaaacc attaagaaaa gtcaggccat agaatgacag aaaatatttg   3840
caacacccca gtaaagagaa ttgtaatatg cagattataa aaagaagtct tacaaatcag   3900
taaaaaataa aactagacaa aaatttgaac agatgaaaga gaaactctaa ataatcatta   3960
cacatgagaa actcaatctc agaaatcaga gaactatcat tgcatataca ctaaattaga   4020
gaaatattaa aaggctaagt aacatctgtg gcaatattga tggtatataa ccttgatatg   4080
atgtgatgag aacagtactt tacccatgg gcttcctccc caaaccctta ccccagtata   4140
aatcatgaca aatatacttt aaaaaccatt accctatatc taaccagtac tcctcaaaac   4200
tgtcaaggtc atcaaaaata agaaaagtct gaggaactgt caaaactaag aggaacccaa   4260
ggagacatga gaattatatg taatgtggca ttctgaatga gatcccagaa cagaaaaaga   4320
acagtagcta aaaaactaat gaaatataaa taaagtttga actttagttt tttttaaaaa   4380
agagtagcat taacacggca aagtcatttt catatttttc ttgaacatta agtacaagtc   4440
tataattaaa aatttttaa atgtagtctg gaacattgcc agaaacagaa gtacagcagc   4500
tatctgtgct gtcgcctaac tatccatagc tgattggtct aaaatgagat acatcaacgc   4560
tcctccatgt tttttgtttt cttttaaat gaaaaacttt attttttaag aggagtttca   4620
ggttcatagc aaaattgaga ggaaggtaca ttcaagctga ggaagttttc ctctattcct   4680
agtttactga gagattgcat catgaatggg tgttaaattt tgtcaaatgc ttttctgtg   4740 tctatcaata tgaccatgtg attttcttct ttaacctgtt gatgggacaa attacgttaa   4800
ttgattttca aacgttgaac caccctaca tatctggaat aaattctact tggttgtggt   4860 gtatatttt tgatacattc ttggattctt tttgctaata ttttgttgaa aatgtttgta   4920
tctttgttca tgagagatat tggtctgttg ttttttttc ttgtaatgtc attttctagt   4980
tccggtatta aggtaatgct ggcctagttg aatgatttag gaagtattcc ctctgcttct   5040
gtcttctgag gtaccgcggc cgcccgtcgt tttacaacgt cgtgactggg aaaaccctgg   5100
cgttacccaa cttaatcgcc ttgcagcaca tccccctttc gccagctggc gtaatagcga   5160
agaggcccgc accgatcgcc cttcccaaca gttgcgcagc ctgaatggcg aatggcgcct   5220
gatgcggtat tttctcctta cgcatctgtg cggtatttca caccgcatac gtcaaagcaa   5280
ccatagtacg cgccctgtag cggcgcatta agcgcggcgg gtgtggtggt tacgcgcagc   5340
gtgaccgcta cacttgccag cgccctagcg cccgctcctt tcgctttctt cccttccttt   5400
ctcgccacgt tcgccggctt tccccgtcaa gctctaaatc gggggctccc tttagggttc   5460
cgatttagtg ctttacggca cctcgacccc aaaaaacttg atttgggtga tggttcacgt   5520
agtgggccat cgccctgata gacggttttt cgccctttga cgttggagtc acgttcttt   5580 aatagtggac tcttgttcca aactggaaca acactcaacc ctatctcggg ctattctttt   5640
```

```
gatttataag ggattttgcc gatttcggcc tattggttaa aaaatgagct gatttaacaa    5700
aaatttaacg cgaattttaa caaaatatta acgtttacaa ttttatggtg cactctcagt    5760
acaatctgct ctgatgccgc atagttaagc cagccccgac acccgccaac acccgctgac    5820
gcgccctgac gggcttgtct gctcccggca tccgcttaca gacaagctgt gaccgtctcc    5880
gggagctgca tgtgtcagag gttttcaccg tcatcaccga aacgcgcgag acgaaagggc    5940
ctcgtgatac gcctattttt ataggttaat gtcatgataa taatggtttc ttagacgtca    6000
ggtggcactt ttcggggaaa tgtgcgcgga acccctattt gtttatttttt ctaaatacat    6060 tcaaatatgt atccgctcat gagacaataa ccctgataaa tgcttcaata atattgaaaa    6120
aggaagagta tgagtattca acatttccgt gtcgccctta ttcccttttt tgcggcattt    6180
tgccttcctg ttttgctca cccagaaacg ctggtgaaag taaaagatgc tgaagatcag    6240
ttgggtgcac gagtgggtta catcgaactg gatctcaaca gcggtaagat ccttgagagt    6300
tttcgccccg aagaacgttt tccaatgatg agcacttttta aagttctgct atgtggcgcg    6360
gtattatccc gtattgacgc cgggcaagag caactcggtc gccgcataca ctattctcag    6420
aatgacttgg ttgagtactc accagtcaca gaaaagcatc ttacgatgg catgacagta    6480 agagaattat gcagtgctgc cataaccatg agtgataaca ctgcggccaa cttacttctg    6540
acaacgatcg gaggaccgaa ggagctaacc gcttttttgc acaacatggg ggatcatgta    6600
actcgccttg atcgttggga accggagctg aatgaagcca taccaaacga cgagcgtgac    6660
accacgatgc ctgtagcaat ggcaacaacg ttgcgcaaac tattaactgg cgaactactt    6720
actctagctt cccggcaaca attaatagac tggatggagg cggataaagt tgcaggacca    6780
cttctgcgct cggcccttcc ggctggctgg tttattgctg ataaatctgg agccggtgag    6840
cgtgggtctc gcggtatcat tgcagcactg gggccagatg gtaagccctc ccgtatcgta    6900
gttatctaca cgacggggag tcaggcaact atggatgaac gaaatagaca gatcgctgag    6960
ataggtgcct cactgattaa gcattggtaa ctgtcagacc aagtttactc atatatactt    7020
tagattgatt taaaacttca ttttttaattt aaaaggatct aggtgaagat cctttttgat    7080
aatctcatga ccaaaatccc ttaacgtgag ttttcgttcc actgagcgtc agaccccgta    7140
gaaaagatca aaggatcttc ttgagatcct ttttttctgc gcgtaatctg ctgcttgcaa    7200
acaaaaaaac caccgctacc agcggtggtt tgtttgccgg atcaagagct accaactctt    7260
tttccgaagg taactggctt cagcagagcg cagataccaa atactgtcct tctagtgtag    7320
ccgtagttag gccaccactt caagaactct gtagcaccgc ctacatacct cgctctgcta    7380
atcctgttac cagtggctgc tgccagtggc gataagtcgt gtcttaccgg gttggactca    7440
agacgatagt taccggataa ggcgcagcgg tcgggctgaa cggggggttc gtgcacacag    7500
cccagcttgg agcgaacgac ctacaccgaa ctgagatacc tacagcgtga gctatgagaa    7560
agcgccacgc ttcccgaagg gagaaaggcg gacaggtatc cggtaagcgg cagggtcgga    7620
acaggagagc gcacgaggga gcttccaggg ggaaacgcct ggtatcttta tagtcctgtc    7680
gggtttcgcc acctctgact tgagcgtcga tttttgtgat gctcgtcagg ggggcggagc    7740
ctatggaaaa acgccagcaa cgcggccttt ttacggttcc tggccttttg ctggccttt    7800 gctcacatgt tctttcctgc gttatcccct gattctgtgg ataaccgtat taccgccttt    7860
gagtgagctg ataccgctcg ccgcagccga acgaccgagc gcagcgagtc agtgagcgag    7920
gaagcggaag agcccgcggg caaggtcgcc acgcacaaga tcaatattaa caatcagtca    7980
tctctcttta gcaataaaaa ggtgaaaaat tacattttaa aaatgacacc atagacgatg    8040
```

```
tatgaaaata atctacttgg aaataaatct aggcaaagaa gtgcaagact gttacccaga    8100
aaacttacaa attgtaaatg agaggttagt gaagatttaa atgaatgaag atctaaataa    8160
acttataaat tgtgagagaa attaatgaat gtctaagtta atgcagaaac ggagagacat    8220
actatattca tgaactaaaa gacttaatat tgtgaaggta actttctttt tcacataaat    8280
ttgtagtcaa tatgttcacc ccaaaaaagc tgtttgttaa cttgtcaacc tcatttcaaa    8340
atgtatatag aaagcccaaa gacaataaca aaaatattct tgtagaacaa aatgggaaag    8400
aatgttccac taaatatcaa gatttagagc aaagcatgag atgtgtgggg atagacagtg    8460
aggctgataa aatagagtag agctcagaaa cagacccatt gatatatgta agtgacctat    8520
gaaaaaaata tggcatttta caatgggaaa atgatgatct ttttcttttt tagaaaaaca    8580
gggaaatata tttatatgta aaaaataaaa gggaacccat atgtcatacc atacacacaa    8640
aaaaattcca gtgaattata agtctaaatg gagaaggcaa aactttaaat cttttagaaa    8700 ataaatataga agcatgccat catgacttca gtgtagagaa aaatttctta tgactcaaag    8760
tcctaaccac aaagaaaaga ttgttaatta gattgcatga atattaagac ttattttaa    8820 aattaaaaaa ccattaagaa aagtcaggcc atagaatgac agaaaatatt tgcaacaccc    8880
cagtaaagag aattgtaata tgcagattat aaaagaagt cttacaaatc agtaaaaaat    8940
aaaactagac aaaaatttga acagatgaaa gagaaactct aaataatcat tacacatgag    9000
aaactcaatc tcagaaatca gagaactatc attgcatata cactaaatta gagaaatatt    9060
aaaaggctaa gtaacatctg tggcaatatt gatggtatat aaccttgata tgatgtgatg    9120
agaacagtac tttaccccat gggcttcctc cccaaaccct taccccagta taaatcatga    9180
caaatatact ttaaaaacca ttaccctata tctaaccagt actcctcaaa actgtcaagg    9240
tcatcaaaaa taagaaaagt ctgaggaact gtcaaaacta agaggaaccc aaggagacat    9300
gagaattata tgtaatgtgg cattctgaat gagatcccag aacagaaaaa gaacagtagc    9360
taaaaaacta atgaaatata aataaagttt gaactttagt ttttttaaa aaagagtagc    9420 attaacacgg caaagtcatt ttcatatttt tcttgaacat taagtacaag tctataatta    9480 aaaattttt aaatgtagtc tggaacattg ccagaaacag aagtacagca gctatctgtg    9540
ctgtcgccta actatccata gctgattggt ctaaaatgag atacatcaac gctcctccat    9600 gtttttgtt ttcttttaa atgaaaaact ttatttttta agaggagttt caggttcata    9660
gcaaaattga gaggaaggta cattcaagct gaggaagttt tcctctattc ctagtttact    9720
gagagattgc atcatgaatg ggtgttaaat tttgtcaaat gcttttctg tgtctatcaa    9780 tatgaccatg tgatttctt ctttaacctg ttgatgggac aaattacgtt aattgatttt    9840
caaacgttga accaccctta catatctgga ataaattcta cttggttgtg gtgtatattt    9900
tttgatacat tcttggattc tttttgctaa tattttgttg aaaatgtttg tatctttgtt    9960
catgagagat attggtctgt tgttttcttt tcttgtaatg tcattttcta gttccggtat   10020
taaggtaatg ctggcctagt tgaatgattt aggaagtatt ccctctgctt ctgtcttctg   10080
aagcggaaga gcgcccaata cgcaaaccgc ctctccccgc gcgttggccg attcattaat   10140
gcagctggca cgacaggttt cccgactgga aagcgggcag tgagcgcaac gcaattaatg   10200
tgagttagct cactcattag gcaccccagg ctttacactt tatgcttccg gctcgtatgt   10260
tgtgtggaat tgtgagcgga taacaatttc acacaggaaa cagctatgac atgattacga   10320
attaa                                                              10325
```

<210> SEQ ID NO 54

<211> LENGTH: 10379
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

| | | | | | |
|---|---|---|---|---|---|
| aagctttact | cgtaaagcga | gttgaaggat | catatttagt | tgcgtttatg | agataagatt | 60 |
| gaaagcacgt | gtaaaatgtt | tcccgcgcgt | tggcacaact | atttacaatg | cggccaagtt | 120 |
| ataaaagatt | ctaatctgat | atgttttaaa | acacctttgc | ggcccgagtt | gtttgcgtac | 180 |
| gtgactagcg | aagaagatgt | gtggaccgca | gaacagatag | taaaacaaaa | ccctagtatt | 240 |
| ggagcaataa | tcgatttaac | caacacgtct | aaatattatg | atggtgtgca | ttttttgcgg | 300 |
| gcgggcctgt | tatacaaaaa | aattcaagta | cctggccaga | ctttgccgcc | tgaaagcata | 360 |
| gttcaagaat | ttattgacac | ggtaaaagaa | tttacagaaa | agtgtcccgg | catgttggtg | 420 |
| ggcgtgcact | gcacacacgg | tattaatcgc | accggttaca | tggtgtgcag | atatttaatg | 480 |
| cacaccctgg | gtattgcgcc | gcaggaagcc | atagatagat | tcgaaaaagc | cagaggtcac | 540 |
| aaaattgaaa | gacaaaatta | cgttcaagat | ttattaattt | aattaatatt | atttgcattc | 600 |
| tttaacaaat | actttatcct | attttcaaat | tgttgcgctt | cttccagcga | accaaaacta | 660 |
| tgcttcgctt | gctccgttta | gcttgtagcc | gatcagtggc | gttgttccaa | tcgacggtag | 720 |
| gattaggccg | gatattctcc | accacaatgt | tggcaacgtt | gatgttacgt | ttatgctttt | 780 |
| ggttttccac | gtacgtcttt | tggccggtaa | tagccgtaaa | cgtagtgccg | tcgcgcgtca | 840 |
| cgcacaacac | cggatgtttg | cgcttgtccg | cggggtattg | aaccgcgcga | tccgacaaat | 900 |
| ccaccacttt | ggcaactaaa | tcggtgacct | gcgcgtcttt | tttctgcatt | atttcgtctt | 960 |
| tcttttgcat | ggtttcctgg | aagccggtgt | acatgcggtt | tagatcagtc | atgacgcgcg | 1020 |
| tgacctgcaa | atctttggcc | tcgatctgct | tgtccttgat | ggcaacgatg | cgttcaataa | 1080 |
| actcttgttt | tttaacaagt | tcctcggttt | tttgcgccac | caccgcttgc | agcgcgtttg | 1140 |
| tgtgctcggt | gaatgtcgca | atcagcttag | tcaccaactg | tttgctctcc | tcctcccgtt | 1200 |
| gtttgatcgc | gggatcgtac | ttgccggtgc | agagcacttg | aggaattact | tcttctaaaa | 1260 |
| gccattcttg | taattctatg | gcgtaaggca | atttggactt | cataatcagc | tgaatcacgc | 1320 |
| cggatttagt | aatgagcact | gtatgcggct | gcaaatacag | cgggtcgccc | cttttcacga | 1380 |
| cgctgttaga | ggtagggccc | ccattttgga | tggtctgctc | aaataacgat | ttgtatttat | 1440 |
| tgtctacatg | aacacgtata | gctttatcac | aaactgtata | ttttaaactg | ttagcgacgt | 1500 |
| ccttggccac | gaaccggacc | tgttggtcgc | gctctagcac | gtaccgcagg | ttgaacgtat | 1560 |
| cttctccaaa | tttaaattct | ccaattttaa | cgcgagccat | tttgatacac | gtgtgtcgat | 1620 |
| tttgcaacaa | ctattgtttt | ttaacgcaaa | ctaaacttat | tgtggtaagc | aataattaaa | 1680 |
| tatggggaa | catgcgccgc | tacaacactc | gtcgttatga | acgcagacgg | cgccggtctc | 1740 |
| ggcgcaagcg | gctaaaacgt | gttgcgcgtt | caacgcggca | acatcgcaa | aagccaatag | 1800 |
| tacagttttg | atttgcatat | taacggcgat | ttttaaatt | atcttattta | ataaatagtt | 1860 |
| atgacgccta | caactccccg | cccgcgttga | ctcgctgcac | ctcgagcagt | tcgttgacgc | 1920 |
| cttcctccgt | gtggccgaac | acgtcgagcg | ggtggtcgat | gaccagcggc | gtgccgcacg | 1980 |
| cgacgcacaa | gtatctgtac | accgaatgat | cgtcgggcga | aggcacgtcg | gcctccaagt | 2040 |
| ggcaatattg | gcaaattcga | aaatatatac | agttgggttg | tttgcgcata | tctatcgtgg | 2100 |
| cgttgggcat | gtacgtccga | acgttgattt | gcatgcaagc | cgaaattaaa | tcattgcgat | 2160 |

```
tagtgcgatt aaaacgttgt acatcctcgc ttttaatcat gccgtcgatt aaatcgcgca    2220
atcgagtcaa gtgatcaaag tgtggaataa tgttttcttt gtattcccga gtcaagcgca    2280
gcgcgtattt taacaaacta gccatcttgt aagttagttt catttaatgc aactttatcc    2340
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gttttttacga agcgatgaca    2520 tgaccccccgt agtgacaacg atcacgccca aaagaactgc cgactacaaa attaccgagt    2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaagaaa    2940 aatgtcgtcg acatgctgaa caacaagatt aatatgcctc cgtgtataaa aaaatattg    3000 aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aatgaaaac tgtcgacaag    3240 ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aattttattt tcacataaac    3480
tagacgcctt gtcgtcttct tcttcgtatt ccttctcttt ttcattttc tcctcataaa    3540 aattaacata gttattatcg tatccatata tgtatctatc gtatagagta aattttttgt    3600
tgtcataaat atatatgtct ttttaatgg ggtgtatagt accgctgcgc atagtttttc    3660
tgtaatttac aacagtgcta ttttctggta gttcttcgga gtgtgttgct ttaattatta    3720
aatttatata atcaatgaat tgggatcgt cggttttgta caatatgttg ccggcatagt    3780
acgcagcttc ttctagttca attacaccat ttttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atccgcggcc    4140
gcgaattcta aaccaccatg gctagcaggc ctgacaaaac tcacacatgc ccaccgtgcc    4200
cagcacctga actcctgggg ggaccgtcag tcttcctctt ccccccaaaa cccaaggaca    4260
ccctcatgat ctcccggacc cctgaggtca catgcgtggt ggtggacgtg agccacgaag    4320
accctgaggt caagttcaac tggtacgtgg acggcgtgga ggtgcataat gccaagacaa    4380
agccgcggga ggagcagtac aacagcacgt accgtgtggt cagcgtcctc accgtcctgc    4440
accaggactg gctgaatggc aaggagtaca agtgcaaggt ctccaacaaa gccctcccag    4500
cccccatcga gaaaaccatc tccaaagcca aagggcagcc ccgagaacca caggtgtaca    4560
```

```
ccctgccccc atcccgggaa gagatgacca agaaccaggt cagcctgacc tgcctggtca   4620
aaggcttcta tcccagcgac atcgccgtgg agtgggagag caatgggcag ccggagaaca   4680
actacaagac cacgcctccc gtgctggact ccgacggctc cttcttcctc tacagcaagc   4740
tcaccgtgga caagagcagg tggcagcagg ggaacgtctt ctcatgctcc gtgatgcatg   4800
aggctctgca caaccactac acgcagaaga gcctctccct gtctccgggt aaatgacata   4860
gggcatcatc atcatcatca tcatcattaa ttctagacta gtctgcagat ctgatccttt   4920
cctgggaccc ggcaagaacc aaaaactcac tctcttcaag gaaatccgta atgttaaacc   4980
cgacacgatg aagcttgtcg ttggatggaa aggaaaagag ttctacaggg aaacttggac   5040
ccgcttcatg gaagacagct tccccattgt taacgaccaa gaagtgatgg atgttttcct   5100
tgttgtcaac atgcgtccca ctagacccaa ccgttgttac aaattcctgg cccaacacgc   5160
tctgcgttgc gaccccgact atgtacctca tgacgtgatt aggatcgtcg agccttcatg   5220
ggtgggcagc aacaacgagt accgcatcag cctggctaag aagggcggcg gctgcccaat   5280
aatgaacctt cactctgagt acaccaactc gttcgaacag ttcatcgatc gtgtcatctg   5340
ggagaacttc tacaagccca tcgtttacat cggtaccgac tctgctgaag aggaggaaat   5400
tctccttgaa gtttccctgg tgttcaaagt aaaggagttt gcaccagacg cacctctgtt   5460
cactggtccg gcgtattaaa acacgataca ttgttattag tacatttatt aagcgctaga   5520
ttctgtgcgt tgttgattta cagacaattg ttgtacgtat tttaataatt cattaaattt   5580
ataatcttta gggtggtatg ttagagcgaa aatcaaatga ttttcagcgt ctttatatct   5640
gaatttaaat attaaatcct caatagattt gtaaaatagg tttcgattag tttcaaacaa   5700
gggttgtttt tccgaaccga tggctggact atctaatgga ttttcgctca acgccacaaa   5760
acttgccaaa tcttgtagca gcaatctagc tttgtcgata ttcgtttgtg ttttgttttg   5820
taataaaggt tcgacgtcgt tcaaaatatt atgcgctttt gtatttcttt catcactgtc   5880
gttagtgtac aattgactcg acgtaaacac gttaaataaa gcttggacat atttaacatc   5940
gggcgtgtta gctttattag gccgattatc gtcgtcgtcc caaccctcgt cgttagaagt   6000
tgcttccgaa gacgattttg ccatagccac acgacgccta ttaattgtgt cggctaacac   6060
gtccgcgatc aaatttgtag ttgagctttt tggaattatt tctgattgcg ggcgttttg    6120 ggcgggtttc aatctaactg tgcccgattt taattcagac aacacgttag aaagcgatgg   6180
tgcaggcggt ggtaacattt cagacggcaa atctactaat ggcggcggtg gtggagctga   6240
tgataaatct accatcggtg gaggcgcagg cggggctggc ggcggaggcg gaggcggagg   6300
tggtggcggt gatgcagacg gcggtttagg ctcaaatgtc tctttaggca acacagtcgg   6360
cacctcaact attgtactgg tttcgggcgc cgttttggt ttgaccggtc tgagacgagt    6420
gcgatttttt tcgtttctaa tagcttccaa caattgttgt ctgtcgtcta aaggtgcagc   6480
gggttgaggt tccgtcggca ttggtggagc gggcggcaat tcagacatcg atggtggtgg   6540
tggtggtgga ggcgctggaa tgttaggcac gggagaaggt ggtggcggcg gtgccgccgg   6600
tataatttgt tctggttag tttgttcgcg cacgattgtg ggcaccggcg caggcgccgc   6660
tggctgcaca acggaaggtc gtctgcttcg aggcagcgct gggtggtgtg gcaattcaat   6720
attataattg gaatacaaat cgtaaaaatc tgctataagc attgtaattt cgctatcgtt   6780
taccgtgccg atatttaaca accgctcaat gtaagcaatt gtattgtaaa gagattgtct   6840
caagctccgc acgccgataa caagcctttt cattttact acagcattgt agtggcgaga    6900
cacttcgctg tcgtcgacgt acatgtatgc tttgttgtca aaaacgtcgt tggcaagctt   6960
```

```
taaaatattt aaaagaacat ctctgttcag caccactgtg ttgtcgtaaa tgttgttttt    7020
gataatttgc gcttccgcag tatcgacacg ttcaaaaaat tgatgcgcat caattttgtt    7080
gttcctatta ttgaataaat aagattgtac agattcatat ctacgattcg tcatggccac    7140
cacaaatgct acgctgcaaa cgctggtaca attttacgaa aactgcaaaa acgtcaaaac    7200
tcggtataaa ataatcaacg ggcgctttgg caaaatatct attttatcgc acaagcccac    7260
tagcaaattg tatttgcaga aaacaatttc ggcgcacaat tttaacgctg acgaaataaa    7320
agttcaccag ttaatgagcg accacccaaa ttttataaaa atctatttta atcacggttc    7380
catcaacaac caagtgatcg tgatggacta cattgactgt cccgatttat ttgaaacact    7440
acaaattaaa ggcgagcttt cgtaccaact tgttagcaat attattagac agctgtgtga    7500
agcgctcaac gatttgcaca agcacaattt catacacaac gacataaaac tcgaaaatgt    7560
cttatatttc gaagcacttg atcgcgtgta tgtttgcgat tacggattgt gcaaacacga    7620
aaactcactt agcgtgcacg acggcacgtt ggagtatttt agtccggaaa aaattcgaca    7680
cacaactatg cacgtttcgt ttgactggta cgcggcgtgt taacatacaa gttgctaacc    7740
ggcggttcgt aatcatggtc atagctgttt cctgtgtgaa attgttatcc gctcacaatt    7800
ccacacaaca tacgagccgg aagcataaag tgtaaagcct ggggtgccta atgagtgagc    7860
taactcacat taattgcgtt gcgctcactg cccgctttcc agtcgggaaa cctgtcgtgc    7920
cagctgcatt aatgaatcgg ccaacgcgcg gggagaggcg gtttgcgtat gggcgctct    7980 tccgcttcct cgctcactga ctcgctgcgc tcggtcgttc ggctgcggcg agcggtatca    8040
gctcactcaa aggcggtaat acggttatcc acagaatcag gggataacgc aggaaagaac    8100
atgtgagcaa aaggccagca aaaggccagg aaccgtaaaa aggccgcgtt gctggcgttt    8160
ttccataggc tccgccccc tgacgagcat cacaaaaatc gacgctcaag tcagaggtgg    8220
cgaaacccga caggactata aagataccag gcgtttcccc ctggaagctc cctcgtgcgc    8280
tctcctgttc cgaccctgcc gcttaccgga tacctgtccg cctttctccc ttcgggaagc    8340
gtggcgcttt ctcatagctc acgctgtagg tatctcagtt cggtgtaggt cgttcgctcc    8400
aagctgggct gtgtgcacga accccccgtt cagcccgacc gctgcgcctt atccggtaac    8460
tatcgtcttg agtccaaccc ggtaagacac gacttatcgc cactggcagc agccactggt    8520
aacaggatta gcagagcgag gtatgtaggc ggtgctacag agttcttgaa gtggtggcct    8580
aactacggct acactagaag gacagtattt ggtatctgcg ctctgctgaa gccagttacc    8640
ttcggaaaaa gagttggtag ctcttgatcc ggcaaacaaa ccaccgctgg tagcggtggt    8700
ttttttgttt gcaagcagca gattacgcgc agaaaaaaag gatctcaaga agatcctttg    8760
atcttttcta cggggtctga cgctcagtgg aacgaaaact cacgttaagg attttggtc    8820 atgagattat caaaaaggat cttcacctag atccttttaa attaaaaatg aagttttaaa    8880
tcaatctaaa gtatatatga gtaaacttgg tctgacagtt accaatgctt aatcagtgag    8940
gcacctatct cagcgatctg tctatttcgt tcatccatag ttgcctgact ccccgtcgtg    9000
tagataacta cgatacggga gggcttacca tctggcccca gtgctgcaat gataccgcga    9060
gacccacgct caccggctcc agatttatca gcaataaacc agccagccgg aagggccgag    9120
cgcagaagtg gtcctgcaac tttatccgcc tccatccagt ctattaattg ttgccggaa    9180 gctagagtaa gtagttcgcc agttaatagt ttgcgcaacg ttgttgccat tgctacaggc    9240
atcgtggtgt cacgctcgtc gtttggtatg gcttcattca gctccggttc ccaacgatca    9300
aggcgagtta catgatcccc catgttgtgc aaaaaagcgg ttagctcctt cggtcctccg    9360
```

```
atcgttgtca gaagtaagtt ggccgcagtg ttatcactca tggttatggc agcactgcat    9420
aattctctta ctgtcatgcc atccgtaaga tgcttttctg tgactggtga gtactcaacc    9480
aagtcattct gagaatagtg tatgcggcga ccgagttgct cttgcccggc gtcaatacgg    9540
gataataccg cgccacatag cagaacttta aaagtgctca tcattggaaa acgttcttcg    9600
gggcgaaaac tctcaaggat cttaccgctg ttgagatcca gttcgatgta acccactcgt    9660
gcacccaact gatcttcagc atcttttact ttcaccagcg tttctgggtg agcaaaaaca    9720
ggaaggcaaa atgccgcaaa aaagggaata agggcgacac ggaaatgttg aatactcata    9780
ctcttccttt ttcaatatta ttgaagcatt tatcagggtt attgtctcat gagcggatac    9840
atatttgaat gtatttagaa aaataaacaa atagggttc cgcgcacatt tccccgaaaa    9900
gtgccacctg acgtctaaga accattatt atcatgacat taacctataa aataggcgt     9960 atcacgaggc cctttcgtct cgcgcgtttc ggtgatgacg tgaaaacct ctgacacatg     10020 cagctcccgg agacggtcac agcttgtctg taagcggatg ccgggagcag acaagcccgt    10080
cagggcgcgt cagcgggtgt tggcgggtgt cggggctggc ttaactatgc ggcatcagag    10140
cagattgtac tgagagtgca ccatatatgc ggtgtgaaat accgcacaga tgcgtaagga    10200
gaaaataccg catcaggcgc cattcgccat tcaggctgcg caactgttgg gaagggcgat    10260
cggtgcgggc ctcttcgcta ttacgccagc tggcgaaagg gggatgtgct gcaaggcgat    10320
taagttgggt aacgccaggg ttttcccagt cacgacgttg taaaacgacg ccagtgcc     10379
```

<210> SEQ ID NO 55
<211> LENGTH: 9690
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 55

```
aagctttact cgtaaagcga gttgaaggat catatttagt tgcgtttatg agataagatt      60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca ttttttgcgg    300
gcgggcctgt tatacaaaaa aattcaagta cctggccaga cttgtccgcc tgaaagcata    360
gttcaagaat ttattgacac ggtaaaagaa tttacagaaa agtgtccgg catgttggtg     420 ggcgtgcact gcacacacgg tattaatcgc accggttaca tggtgtgcag atatttaatg    480
cacaccctgg gtattgcgcc gcaggaagcc atagatagat cgaaaaagc cagaggtcac    540 aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt ttttctgcatt atttcgtctt    960 tcttttgcat ggtttcctgg aagccggtgt acatgcggtt tagatcagtc atgacgcgcg   1020
```

```
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccatttggga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat ttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gttttacga agcgatgaca   2520 tgaccccgt agtgacaacg atcacgccca aaagaactgc cgactacaaa attaccgagt   2580
atgtcggtga cgttaaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaatattg   3000 aacgatttga agaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaaccacca aactgccaaa aatgaaaaac tgtcgacaag   3240
ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
catttgtagt attatctata attgaaaacg cgtagttata atcgctgagg taatatttaa   3420
```

```
aatcattttc aaatgattca cagttaattt gcgacaatat aattttattt tcacataaac   3480
tagacgcctt gtcgtcttct tcttcgtatt ccttctcttt ttcatttttc tcctcataaa   3540
aattaacata gttattatcg tatccatata tgtatctatc gtatagagta aatttttgt    3600
tgtcataaat atatatgtct ttttttaatgg ggtgtatagt accgctgcgc atagttttc   3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tcccttttct atactattgt   3900
ctgcgagcag ttgtttgttg ttaaaaataa cagccattgt aatgagacgc acaaactaat   3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atccgcggcc   4140
gcgaattcta aaccaccatg ggcagctgcc cgggcatcat catcatcatc atcatcatta   4200
attctagact agtctgcaga tctgatcctt tcctgggacc cggcaagaac caaaaactca   4260
ctctcttcaa ggaaatccgt aatgttaaac ccgacacgat gaagcttgtc gttggatgga   4320
aaggaaaaga gttctacagg gaaacttgga cccgcttcat ggaagacagc ttccccattg   4380
ttaacgacca agaagtgatg gatgttttcc ttgttgtcaa catgcgtccc actagaccca   4440
accgttgtta caaattcctg gcccaacacg ctctgcgttg cgaccccgac tatgtacctc   4500
atgacgtgat taggatcgtc gagccttcat gggtgggcag caacaacgag taccgcatca   4560
gcctggctaa gaagggcggc ggctgcccaa taatgaacct tcactctgag tacaccaact   4620
cgttcgaaca gttcatcgat cgtgtcatct gggagaactt ctacaagccc atcgtttaca   4680
tcggtaccga ctctgctgaa gaggaggaaa ttctccttga gtttccctg gtgttcaaag    4740
taaaggagtt tgcaccagac gcacctctgt tcactggtcc ggcgtattaa aacacgatac   4800
attgttatta gtacatttat taagcgctag attctgtgcg ttgttgattt acagacaatt   4860
gttgtacgta ttttaataat tcattaaatt tataatcttt agggtggtat gttagagcga   4920
aaatcaaatg attttcagcg tctttatatc tgaatttaaa tattaaatcc tcaatagatt   4980
tgtaaaatag gtttcgatta gtttcaaaca agggttgtt ttccgaaccg atggctggac    5040
tatctaatgg attttcgctc aacgccacaa aacttgccaa atcttgtagc agcaatctag   5100
ctttgtcgat attcgtttgt gttttgtttt gtaataaagg ttcgacgtcg ttcaaaatat   5160
tatgcgcttt tgtatttctt tcatcactgt cgttagtgta caattgactc gacgtaaaca   5220
cgttaaataa agcttggaca tatttaacat cgggcgtgtt agctttatta ggccgattat   5280
cgtcgtcgtc ccaaccctcg tcgttagaag ttgcttccga agacgatttt gccatagcca   5340
cacgacgcct attaattgtg tcggctaaca cgtccgcgat caaatttgta gttgagcttt   5400
ttggaattat ttctgattgc gggcgttttt gggcgggttt caatctaact gtgcccgatt   5460
ttaattcaga caacacgtta gaaagcgatg gtgcaggcgg tggtaacatt tcagacggca   5520
aatctactaa tggcggcggt ggtggagctg atgataaatc taccatcggt ggaggcgcag   5580
gcggggctgg cggcggaggc ggaggcggag gtggtggcgg tgatgcagac ggcggtttag   5640
gctcaaatgt ctctttaggc aacacagtcg gcacctcaac tattgtactg gtttcgggcg   5700
ccgttttttgg tttgaccggt ctgagacgag tgcgatttt ttcgtttcta atagcttcca   5760
acaattgttg tctgtcgtct aaaggtgcag cgggttgagg ttccgtcggc attggtggag   5820
```

```
cgggcggcaa ttcagacatc gatggtggtg gtggtggtgg aggcgctgga atgttaggca    5880
cgggagaagg tggtggcggc ggtgccgccg gtataatttg ttctggttta gtttgttcgc    5940
gcacgattgt gggcaccggc gcaggcgccg ctggctgcac aacggaaggt cgtctgcttc    6000
gaggcagcgc ttggggtggt ggcaattcaa tattataatt ggaatacaaa tcgtaaaaat    6060
ctgctataag cattgtaatt tcgctatcgt ttaccgtgcc gatatttaac aaccgctcaa    6120
tgtaagcaat tgtattgtaa agagattgtc tcaagctccg cacgccgata caagcctttt    6180
tcatttttac tacagcattg tagtggcgag acacttcgct gtcgtcgacg tacatgtatg    6240
ctttgttgtc aaaaacgtcg ttggcaagct ttaaaatatt taaaagaaca tctctgttca    6300
gcaccactgt gttgtcgtaa atgttgtttt tgataatttg cgcttccgca gtatcgacac    6360
gttcaaaaaa ttgatgcgca tcaattttgt tgttcctatt attgaataaa taagattgta    6420
cagattcata tctacgattc gtcatggcca ccacaaatgc tacgctgcaa acgctggtac    6480
aattttacga aaactgcaaa aacgtcaaaa ctcggtataa aataatcaac gggcgctttg    6540
gcaaaatatc tattttatcg cacaagccca ctagcaaatt gtatttgcag aaaacaattt    6600
cggcgcacaa ttttaacgct gacgaaataa aagttcacca gttaatgagc gaccacccaa    6660
atttttataaa aatctatttt aatcacggtt ccatcaacaa ccaagtgatc gtgatggact    6720
acattgactg tcccgattta tttgaaacac tacaaattaa aggcgagctt tcgtaccaac    6780
ttgttagcaa tattattaga cagctgtgtg aagcgctcaa cgatttgcac aagcacaatt    6840
tcatacacaa cgacataaaa ctcgaaaatg tcttatatt cgaagcactt gatcgcgtgt    6900
atgtttgcga ttacggattg tgcaaacacg aaaactcact agcgtgcac gacggcacgt    6960
tggagtattt tagtccggaa aaaattcgac acacaactat gcacgtttcg tttgactggt    7020
acgcggcgtg ttaacataca agttgctaac cggcggttcg taatcatggt catagctgtt    7080
tcctgtgtga aattgttatc cgctcacaat tccacacaac atacgagccg gaagcataaa    7140
gtgtaaagcc tgggtgcct aatgagtgag ctaactcaca ttaattgcgt tgcgctcact    7200
gcccgctttc cagtcgggaa acctgtcgtg ccagctgcat taatgaatcg gccaacgcgc    7260
ggggagaggc ggtttgcgta ttgggcgctc ttccgcttcc tcgctcactg actcgctgcg    7320
ctcggtcgtt cggctgcggc gagcggtatc agctcactca aaggcggtaa tacggttatc    7380
cacagaatca ggggataacg caggaaagaa catgtgagca aaaggccagc aaaaggccag    7440
gaaccgtaaa aaggccgcgt tgctggcgtt tttccatagg ctccgccccc ctgacgagca    7500
tcacaaaaat cgacgctcaa gtcagaggtg gcgaaacccg acaggactat aaagatacca    7560
ggcgtttccc cctggaagct ccctcgtgcg ctctcctgtt ccgaccctgc cgcttaccgg    7620
atacctgtcc gcctttctcc cttcgggaag cgtggcgctt tctcatagct cacgctgtag    7680
gtatctcagt tcggtgtagg tcgttcgctc caagctgggc tgtgtgcacg aaccccccgt    7740
tcagcccgac cgctgcgcct tatccggtaa ctatcgtctt gagtccaacc cggtaagaca    7800
cgacttatcg ccactggcag cagccactgg taacaggatt agcagagcga ggtatgtagg    7860
cggtgctaca gagttcttga agtggtggcc taactacggc tacactagaa ggacagtatt    7920
tggtatctgc gctctgctga agccagttac cttcggaaaa agagttggta gctcttgatc    7980
cggcaaacaa accaccgctg gtagcggtgg tttttttgtt tgcaagcagc agattacgcg    8040
cagaaaaaaa ggatctcaag aagatccttt gatcttttct acggggtctg acgctcagtg    8100
gaacgaaaac tcacgttaag ggattttggt catgagatta tcaaaaagga tcttcaccta    8160
gatcctttta aattaaaaat gaagttttaa atcaatctaa agtatatatg agtaaacttg    8220
```

```
gtctgacagt taccaatgct taatcagtga ggcacctatc tcagcgatct gtctatttcg    8280
ttcatccata gttgcctgac tccccgtcgt gtagataact acgatacggg agggcttacc    8340
atctggcccc agtgctgcaa tgataccgcg agacccacgc tcaccggctc cagatttatc    8400
agcaataaac cagccagccg gaagggccga gcgcagaagt ggtcctgcaa ctttatccgc    8460
ctccatccag tctattaatt gttgccggga agctagagta agtagttcgc cagttaatag    8520
tttgcgcaac gttgttgcca ttgctacagg catcgtggtg tcacgctcgt cgtttggtat    8580
ggcttcattc agctccggtt cccaacgatc aaggcgagtt acatgatccc ccatgttgtg    8640
caaaaaagcg gttagctcct tcggtcctcc gatcgttgtc agaagtaagt tggccgcagt    8700
gttatcactc atggttatgg cagcactgca taattctctt actgtcatgc catccgtaag    8760
atgcttttct gtgactggtg agtactcaac caagtcattc tgagaatagt gtatgcggcg    8820
accgagttgc tcttgcccgg cgtcaatacg ggataatacc gcgccacata gcagaacttt    8880
aaaagtgctc atcattggaa aacgttcttc ggggcgaaaa ctctcaagga tcttaccgct    8940
gttgagatcc agttcgatgt aacccactcg tgcacccaac tgatcttcag catcttttac    9000
tttcaccagc gtttctgggt gagcaaaaac aggaaggcaa aatgccgcaa aaagggaat    9060
aagggcgaca cggaaatgtt gaatactcat actcttcctt tttcaatatt attgaagcat    9120
ttatcagggt tattgtctca tgagcggata catatttgaa tgtatttaga aaataaaca    9180
aatagggtt ccgcgcacat ttccccgaaa agtgccacct gacgtctaag aaaccattat    9240
tatcatgaca ttaacctata aaataggcg tatcacgagg cccttttcgtc tcgcgcgttt    9300
cggtgatgac ggtgaaaacc tctgacacat gcagctcccg gagacggtca cagcttgtct    9360
gtaagcggat gccgggagca gacaagcccg tcagggcgcg tcagcgggtg ttggcgggtg    9420
tcggggctgg cttaactatg cggcatcaga gcagattgta ctgagagtgc accatatatg    9480
cggtgtgaaa taccgcacag atgcgtaagg agaaaatacc gcatcaggcg ccattcgcca    9540
ttcaggctgc gcaactgttg ggaagggcga tcggtgcggg cctcttcgct attacgccag    9600
ctggcgaaag ggggatgtgc tgcaaggcga ttaagttggg taacgccagg gttttcccag    9660
tcacgacgtt gtaaaacgac ggccagtgcc                                       9690
```

<210> SEQ ID NO 56
<211> LENGTH: 249
<212> TYPE: PRT
<213> ORGANISM: Homo sapiens

<400> SEQUENCE: 56

Arg Gly Thr Pro Lys Thr His Leu Leu Ala Phe Ser Leu Leu Cys Leu
1               5                   10                  15

Leu Ser Lys Val Arg Thr Gln Leu Cys Pro Thr Pro Cys Thr Cys Pro
            20                  25                  30

Trp Pro Pro Arg Cys Pro Leu Gly Val Pro Leu Val Leu Asp Gly
        35                  40                  45

Cys Gly Cys Cys Arg Val Cys Ala Arg Arg Leu Gly Glu Pro Cys Asp
    50                  55                  60

Gln Leu His Val Cys Asp Ala Ser Gln Gly Leu Val Cys Gln Pro Gly
65                  70                  75                  80

Ala Gly Pro Gly Gly Arg Gly Ala Leu Cys Leu Leu Ala Glu Asp Asp
                85                  90                  95

Ser Ser Cys Glu Val Asn Gly Arg Leu Tyr Arg Glu Gly Glu Thr Phe
            100                 105                 110

Gln Pro His Cys Ser Ile Arg Cys Arg Cys Glu Asp Gly Gly Phe Thr

```
                115                 120                 125
Cys Val Pro Leu Cys Ser Glu Asp Val Arg Leu Pro Ser Trp Asp Cys
    130                 135                 140

Pro His Pro Arg Arg Val Glu Val Leu Gly Lys Cys Cys Pro Glu Trp
145                 150                 155                 160

Val Cys Gly Gln Gly Gly Leu Gly Thr Gln Pro Leu Pro Ala Gln
                165                 170                 175

Gly Pro Gln Phe Ser Gly Leu Val Ser Ser Leu Pro Pro Gly Val Pro
                180                 185                 190

Cys Pro Glu Trp Ser Thr Ala Trp Gly Pro Cys Ser Thr Thr Cys Gly
                195                 200                 205

Leu Gly Met Ala Thr Arg Val Ser Asn Gln Asn Arg Phe Cys Arg Leu
    210                 215                 220

Glu Thr Gln Arg Arg Leu Cys Leu Ser Arg Pro Cys Pro Pro Ser Arg
225                 230                 235                 240

Gly Arg Ser Pro Gln Asn Ser Ala Phe
                245

<210> SEQ ID NO 57
<211> LENGTH: 248
<212> TYPE: PRT
<213> ORGANISM: Homo sapiens

<400> SEQUENCE: 57

Gly Thr Pro Lys Thr His Leu Leu Ala Phe Ser Leu Leu Cys Leu Leu
1               5                   10                  15

Ser Lys Val Arg Thr Gln Leu Cys Pro Thr Pro Cys Thr Cys Pro Trp
                20                  25                  30

Pro Pro Pro Arg Cys Pro Leu Gly Val Pro Leu Val Leu Asp Gly Cys
                35                  40                  45

Gly Cys Cys Arg Val Cys Ala Arg Arg Leu Gly Glu Pro Cys Asp Gln
    50                  55                  60

Leu His Val Cys Asp Ala Ser Gln Gly Leu Val Cys Gln Pro Gly Ala
65                  70                  75                  80

Gly Pro Gly Gly Arg Gly Ala Leu Cys Leu Leu Ala Glu Asp Asp Ser
                85                  90                  95

Ser Cys Glu Val Asn Gly Arg Leu Tyr Arg Glu Gly Glu Thr Phe Gln
                100                 105                 110

Pro His Cys Ser Ile Arg Cys Arg Cys Glu Asp Gly Gly Phe Thr Cys
                115                 120                 125

Val Pro Leu Cys Ser Glu Asp Val Arg Leu Pro Ser Trp Asp Cys Pro
    130                 135                 140

His Pro Arg Arg Val Glu Val Leu Gly Lys Cys Cys Pro Glu Trp Val
145                 150                 155                 160

Cys Gly Gln Gly Gly Gly Leu Gly Thr Gln Pro Leu Pro Ala Gln Gly
                165                 170                 175

Pro Gln Phe Ser Gly Leu Val Ser Ser Leu Pro Pro Gly Val Pro Cys
                180                 185                 190

Pro Glu Trp Ser Thr Ala Trp Gly Pro Cys Ser Thr Thr Cys Gly Leu
                195                 200                 205

Gly Met Ala Thr Arg Val Ser Asn Gln Asn Arg Phe Cys Arg Leu Glu
    210                 215                 220

Thr Gln Arg Arg Leu Cys Leu Ser Arg Pro Cys Pro Pro Ser Arg Gly
225                 230                 235                 240

Arg Ser Pro Gln Asn Ser Ala Phe
```

<210> SEQ ID NO 58
<211> LENGTH: 247
<212> TYPE: PRT
<213> ORGANISM: Homo sapiens

<400> SEQUENCE: 58

```
Thr Pro Lys Thr His Leu Leu Ala Phe Ser Leu Leu Cys Leu Leu Ser
1               5                   10                  15

Lys Val Arg Thr Gln Leu Cys Pro Thr Pro Cys Thr Cys Pro Trp Pro
            20                  25                  30

Pro Pro Arg Cys Pro Leu Gly Val Pro Leu Val Leu Asp Gly Cys Gly
        35                  40                  45

Cys Cys Arg Val Cys Ala Arg Arg Leu Gly Glu Pro Cys Asp Gln Leu
    50                  55                  60

His Val Cys Asp Ala Ser Gln Gly Leu Val Cys Gln Pro Gly Ala Gly
65                  70                  75                  80

Pro Gly Gly Arg Gly Ala Leu Cys Leu Leu Ala Glu Asp Asp Ser Ser
                85                  90                  95

Cys Glu Val Asn Gly Arg Leu Tyr Arg Glu Gly Glu Thr Phe Gln Pro
            100                 105                 110

His Cys Ser Ile Arg Cys Arg Cys Glu Asp Gly Gly Phe Thr Cys Val
        115                 120                 125

Pro Leu Cys Ser Glu Asp Val Arg Leu Pro Ser Trp Asp Cys Pro His
    130                 135                 140

Pro Arg Arg Val Glu Val Leu Gly Lys Cys Cys Pro Glu Trp Val Cys
145                 150                 155                 160

Gly Gln Gly Gly Gly Leu Gly Thr Gln Pro Leu Pro Ala Gln Gly Pro
                165                 170                 175

Gln Phe Ser Gly Leu Val Ser Ser Leu Pro Pro Gly Val Pro Cys Pro
            180                 185                 190

Glu Trp Ser Thr Ala Trp Gly Pro Cys Ser Thr Thr Cys Gly Leu Gly
        195                 200                 205

Met Ala Thr Arg Val Ser Asn Gln Asn Arg Phe Cys Arg Leu Glu Thr
    210                 215                 220

Gln Arg Arg Leu Cys Leu Ser Arg Pro Cys Pro Pro Ser Arg Gly Arg
225                 230                 235                 240

Ser Pro Gln Asn Ser Ala Phe
                245
```

<210> SEQ ID NO 59
<211> LENGTH: 246
<212> TYPE: PRT
<213> ORGANISM: Homo sapiens

<400> SEQUENCE: 59

```
Pro Lys Thr His Leu Leu Ala Phe Ser Leu Leu Cys Leu Leu Ser Lys
1               5                   10                  15

Val Arg Thr Gln Leu Cys Pro Thr Pro Cys Thr Cys Pro Trp Pro Pro
            20                  25                  30

Pro Arg Cys Pro Leu Gly Val Pro Leu Val Leu Asp Gly Cys Gly Cys
        35                  40                  45

Cys Arg Val Cys Ala Arg Arg Leu Gly Glu Pro Cys Asp Gln Leu His
    50                  55                  60

Val Cys Asp Ala Ser Gln Gly Leu Val Cys Gln Pro Gly Ala Gly Pro
65                  70                  75                  80
```

```
Gly Gly Arg Gly Ala Leu Cys Leu Leu Ala Glu Asp Asp Ser Ser Cys
                85                  90                  95

Glu Val Asn Gly Arg Leu Tyr Arg Glu Gly Glu Thr Phe Gln Pro His
            100                 105                 110

Cys Ser Ile Arg Cys Arg Cys Glu Asp Gly Gly Phe Thr Cys Val Pro
            115                 120                 125

Leu Cys Ser Glu Asp Val Arg Leu Pro Ser Trp Asp Cys Pro His Pro
    130                 135                 140

Arg Arg Val Glu Val Leu Gly Lys Cys Cys Pro Glu Trp Val Cys Gly
145                 150                 155                 160

Gln Gly Gly Gly Leu Gly Thr Gln Pro Leu Pro Ala Gln Gly Pro Gln
                165                 170                 175

Phe Ser Gly Leu Val Ser Ser Leu Pro Pro Gly Val Pro Cys Pro Glu
            180                 185                 190

Trp Ser Thr Ala Trp Gly Pro Cys Ser Thr Thr Cys Gly Leu Gly Met
            195                 200                 205

Ala Thr Arg Val Ser Asn Gln Asn Arg Phe Cys Arg Leu Glu Thr Gln
        210                 215                 220

Arg Arg Leu Cys Leu Ser Arg Pro Cys Pro Pro Ser Arg Gly Arg Ser
225                 230                 235                 240

Pro Gln Asn Ser Ala Phe
                245

<210> SEQ ID NO 60
<211> LENGTH: 245
<212> TYPE: PRT
<213> ORGANISM: Homo sapiens

<400> SEQUENCE: 60

Lys Thr His Leu Leu Ala Phe Ser Leu Leu Cys Leu Leu Ser Lys Val
1               5                   10                  15

Arg Thr Gln Leu Cys Pro Thr Pro Cys Thr Cys Pro Trp Pro Pro Pro
            20                  25                  30

Arg Cys Pro Leu Gly Val Pro Leu Val Leu Asp Gly Cys Gly Cys Cys
        35                  40                  45

Arg Val Cys Ala Arg Arg Leu Gly Glu Pro Cys Asp Gln Leu His Val
    50                  55                  60

Cys Asp Ala Ser Gln Gly Leu Val Cys Gln Pro Gly Ala Gly Pro Gly
65                  70                  75                  80

Gly Arg Gly Ala Leu Cys Leu Leu Ala Glu Asp Asp Ser Ser Cys Glu
                85                  90                  95

Val Asn Gly Arg Leu Tyr Arg Glu Gly Glu Thr Phe Gln Pro His Cys
            100                 105                 110

Ser Ile Arg Cys Arg Cys Glu Asp Gly Gly Phe Thr Cys Val Pro Leu
        115                 120                 125

Cys Ser Glu Asp Val Arg Leu Pro Ser Trp Asp Cys Pro His Pro Arg
    130                 135                 140

Arg Val Glu Val Leu Gly Lys Cys Cys Pro Glu Trp Val Cys Gly Gln
145                 150                 155                 160

Gly Gly Gly Leu Gly Thr Gln Pro Leu Pro Ala Gln Gly Pro Gln Phe
                165                 170                 175

Ser Gly Leu Val Ser Ser Leu Pro Pro Gly Val Pro Cys Pro Glu Trp
            180                 185                 190

Ser Thr Ala Trp Gly Pro Cys Ser Thr Thr Cys Gly Leu Gly Met Ala
            195                 200                 205
```

Thr Arg Val Ser Asn Gln Asn Arg Phe Cys Arg Leu Glu Thr Gln Arg
    210                 215                 220

Arg Leu Cys Leu Ser Arg Pro Cys Pro Pro Ser Arg Gly Arg Ser Pro
225                 230                 235                 240

Gln Asn Ser Ala Phe
            245

<210> SEQ ID NO 61
<211> LENGTH: 244
<212> TYPE: PRT
<213> ORGANISM: Homo sapiens

<400> SEQUENCE: 61

Thr His Leu Leu Ala Phe Ser Leu Leu Cys Leu Leu Ser Lys Val Arg
1               5                   10                  15

Thr Gln Leu Cys Pro Thr Pro Cys Thr Cys Pro Trp Pro Pro Pro Arg
            20                  25                  30

Cys Pro Leu Gly Val Pro Leu Val Leu Asp Gly Cys Gly Cys Cys Arg
        35                  40                  45

Val Cys Ala Arg Arg Leu Gly Glu Pro Cys Asp Gln Leu His Val Cys
50                  55                  60

Asp Ala Ser Gln Gly Leu Val Cys Gln Pro Gly Ala Gly Pro Gly Gly
65                  70                  75                  80

Arg Gly Ala Leu Cys Leu Leu Ala Glu Asp Asp Ser Ser Cys Glu Val
                85                  90                  95

Asn Gly Arg Leu Tyr Arg Glu Gly Glu Thr Phe Gln Pro His Cys Ser
            100                 105                 110

Ile Arg Cys Arg Cys Glu Asp Gly Gly Phe Thr Cys Val Pro Leu Cys
        115                 120                 125

Ser Glu Asp Val Arg Leu Pro Ser Trp Asp Cys Pro His Pro Arg Arg
130                 135                 140

Val Glu Val Leu Gly Lys Cys Cys Pro Glu Trp Val Cys Gly Gln Gly
145                 150                 155                 160

Gly Gly Leu Gly Thr Gln Pro Leu Pro Ala Gln Gly Pro Gln Phe Ser
                165                 170                 175

Gly Leu Val Ser Ser Leu Pro Pro Gly Val Pro Cys Pro Glu Trp Ser
            180                 185                 190

Thr Ala Trp Gly Pro Cys Ser Thr Thr Cys Gly Leu Gly Met Ala Thr
        195                 200                 205

Arg Val Ser Asn Gln Asn Arg Phe Cys Arg Leu Glu Thr Gln Arg Arg
210                 215                 220

Leu Cys Leu Ser Arg Pro Cys Pro Pro Ser Arg Gly Arg Ser Pro Gln
225                 230                 235                 240

Asn Ser Ala Phe

<210> SEQ ID NO 62
<211> LENGTH: 243
<212> TYPE: PRT
<213> ORGANISM: Homo sapiens

<400> SEQUENCE: 62

His Leu Leu Ala Phe Ser Leu Leu Cys Leu Leu Ser Lys Val Arg Thr
1               5                   10                  15

Gln Leu Cys Pro Thr Pro Cys Thr Cys Pro Trp Pro Pro Pro Arg Cys
            20                  25                  30

Pro Leu Gly Val Pro Leu Val Leu Asp Gly Cys Gly Cys Cys Arg Val

```
                35                  40                  45
Cys Ala Arg Arg Leu Gly Glu Pro Cys Asp Gln Leu His Val Cys Asp
        50                  55                  60
Ala Ser Gln Gly Leu Val Cys Gln Pro Gly Ala Gly Pro Gly Gly Arg
65                  70                  75                  80
Gly Ala Leu Cys Leu Leu Ala Glu Asp Asp Ser Ser Cys Glu Val Asn
                85                  90                  95
Gly Arg Leu Tyr Arg Glu Gly Glu Thr Phe Gln Pro His Cys Ser Ile
                100                 105                 110
Arg Cys Arg Cys Glu Asp Gly Gly Phe Thr Cys Val Pro Leu Cys Ser
                115                 120                 125
Glu Asp Val Arg Leu Pro Ser Trp Asp Cys Pro His Pro Arg Arg Val
        130                 135                 140
Glu Val Leu Gly Lys Cys Cys Pro Glu Trp Val Cys Gly Gln Gly Gly
145                 150                 155                 160
Gly Leu Gly Thr Gln Pro Leu Pro Ala Gln Gly Pro Gln Phe Ser Gly
                165                 170                 175
Leu Val Ser Ser Leu Pro Pro Gly Val Pro Cys Pro Glu Trp Ser Thr
                180                 185                 190
Ala Trp Gly Pro Cys Ser Thr Thr Cys Gly Leu Gly Met Ala Thr Arg
                195                 200                 205
Val Ser Asn Gln Asn Arg Phe Cys Arg Leu Glu Thr Gln Arg Arg Leu
        210                 215                 220
Cys Leu Ser Arg Pro Cys Pro Pro Ser Arg Gly Arg Ser Pro Gln Asn
225                 230                 235                 240

Ser Ala Phe

<210> SEQ ID NO 63
<211> LENGTH: 242
<212> TYPE: PRT
<213> ORGANISM: Homo sapiens

<400> SEQUENCE: 63

Leu Leu Ala Phe Ser Leu Leu Cys Leu Leu Ser Lys Val Arg Thr Gln
1               5                   10                  15
Leu Cys Pro Thr Pro Cys Thr Cys Pro Trp Pro Pro Arg Cys Pro
                20                  25                  30
Leu Gly Val Pro Leu Val Leu Asp Gly Cys Gly Cys Arg Val Cys
                35                  40                  45
Ala Arg Arg Leu Gly Glu Pro Cys Asp Gln Leu His Val Cys Asp Ala
        50                  55                  60
Ser Gln Gly Leu Val Cys Gln Pro Gly Ala Gly Pro Gly Gly Arg Gly
65                  70                  75                  80
Ala Leu Cys Leu Leu Ala Glu Asp Asp Ser Ser Cys Glu Val Asn Gly
                85                  90                  95
Arg Leu Tyr Arg Glu Gly Glu Thr Phe Gln Pro His Cys Ser Ile Arg
                100                 105                 110
Cys Arg Cys Glu Asp Gly Gly Phe Thr Cys Val Pro Leu Cys Ser Glu
                115                 120                 125
Asp Val Arg Leu Pro Ser Trp Asp Cys Pro His Pro Arg Arg Val Glu
        130                 135                 140
Val Leu Gly Lys Cys Cys Pro Glu Trp Val Cys Gly Gln Gly Gly Gly
145                 150                 155                 160
Leu Gly Thr Gln Pro Leu Pro Ala Gln Gly Pro Gln Phe Ser Gly Leu
                165                 170                 175
```

Val Ser Ser Leu Pro Pro Gly Val Pro Cys Pro Glu Trp Ser Thr Ala
            180                 185                 190

Trp Gly Pro Cys Ser Thr Thr Cys Gly Leu Gly Met Ala Thr Arg Val
            195                 200                 205

Ser Asn Gln Asn Arg Phe Cys Arg Leu Glu Thr Gln Arg Arg Leu Cys
            210                 215                 220

Leu Ser Arg Pro Cys Pro Pro Ser Arg Gly Arg Ser Pro Gln Asn Ser
225                 230                 235                 240

Ala Phe

<210> SEQ ID NO 64
<211> LENGTH: 241
<212> TYPE: PRT
<213> ORGANISM: Homo sapiens

<400> SEQUENCE: 64

Leu Ala Phe Ser Leu Leu Cys Leu Leu Ser Lys Val Arg Thr Gln Leu
1               5                   10                  15

Cys Pro Thr Pro Cys Thr Cys Pro Trp Pro Pro Arg Cys Pro Leu
            20                  25                  30

Gly Val Pro Leu Val Leu Asp Gly Cys Gly Cys Cys Arg Val Cys Ala
            35                  40                  45

Arg Arg Leu Gly Glu Pro Cys Asp Gln Leu His Val Cys Asp Ala Ser
50                  55                  60

Gln Gly Leu Val Cys Gln Pro Gly Ala Gly Pro Gly Gly Arg Gly Ala
65                  70                  75                  80

Leu Cys Leu Leu Ala Glu Asp Asp Ser Ser Cys Glu Val Asn Gly Arg
                85                  90                  95

Leu Tyr Arg Glu Gly Glu Thr Phe Gln Pro His Cys Ser Ile Arg Cys
            100                 105                 110

Arg Cys Glu Asp Gly Gly Phe Thr Cys Val Pro Leu Cys Ser Glu Asp
            115                 120                 125

Val Arg Leu Pro Ser Trp Asp Cys Pro His Pro Arg Arg Val Glu Val
130                 135                 140

Leu Gly Lys Cys Cys Pro Glu Trp Val Cys Gly Gln Gly Gly Gly Leu
145                 150                 155                 160

Gly Thr Gln Pro Leu Pro Ala Gln Gly Pro Gln Phe Ser Gly Leu Val
                165                 170                 175

Ser Ser Leu Pro Pro Gly Val Pro Cys Pro Glu Trp Ser Thr Ala Trp
            180                 185                 190

Gly Pro Cys Ser Thr Thr Cys Gly Leu Gly Met Ala Thr Arg Val Ser
            195                 200                 205

Asn Gln Asn Arg Phe Cys Arg Leu Glu Thr Gln Arg Arg Leu Cys Leu
            210                 215                 220

Ser Arg Pro Cys Pro Pro Ser Arg Gly Arg Ser Pro Gln Asn Ser Ala
225                 230                 235                 240

Phe

<210> SEQ ID NO 65
<211> LENGTH: 240
<212> TYPE: PRT
<213> ORGANISM: Homo sapiens

<400> SEQUENCE: 65

Ala Phe Ser Leu Leu Cys Leu Leu Ser Lys Val Arg Thr Gln Leu Cys
1               5                   10                  15

```
Pro Thr Pro Cys Thr Cys Pro Trp Pro Pro Arg Cys Pro Leu Gly
            20                  25                  30

Val Pro Leu Val Leu Asp Gly Cys Gly Cys Cys Arg Val Cys Ala Arg
                35                  40                  45

Arg Leu Gly Glu Pro Cys Asp Gln Leu His Val Cys Asp Ala Ser Gln
        50                  55                  60

Gly Leu Val Cys Gln Pro Gly Ala Gly Pro Gly Gly Arg Gly Ala Leu
65                  70                  75                  80

Cys Leu Leu Ala Glu Asp Asp Ser Ser Cys Glu Val Asn Gly Arg Leu
                85                  90                  95

Tyr Arg Glu Gly Glu Thr Phe Gln Pro His Cys Ser Ile Arg Cys Arg
                100                 105                 110

Cys Glu Asp Gly Gly Phe Thr Cys Val Pro Leu Cys Ser Glu Asp Val
            115                 120                 125

Arg Leu Pro Ser Trp Asp Cys Pro His Pro Arg Arg Val Glu Val Leu
130                 135                 140

Gly Lys Cys Cys Pro Glu Trp Val Cys Gly Gln Gly Gly Leu Gly
145                 150                 155                 160

Thr Gln Pro Leu Pro Ala Gln Gly Pro Gln Phe Ser Gly Leu Val Ser
                165                 170                 175

Ser Leu Pro Pro Gly Val Pro Cys Pro Glu Trp Ser Thr Ala Trp Gly
            180                 185                 190

Pro Cys Ser Thr Thr Cys Gly Leu Gly Met Ala Thr Arg Val Ser Asn
            195                 200                 205

Gln Asn Arg Phe Cys Arg Leu Glu Thr Gln Arg Arg Leu Cys Leu Ser
210                 215                 220

Arg Pro Cys Pro Pro Ser Arg Gly Arg Ser Pro Gln Asn Ser Ala Phe
225                 230                 235                 240

<210> SEQ ID NO 66
<211> LENGTH: 239
<212> TYPE: PRT
<213> ORGANISM: Homo sapiens

<400> SEQUENCE: 66

Phe Ser Leu Leu Cys Leu Leu Ser Lys Val Arg Thr Gln Leu Cys Pro
1               5                   10                  15

Thr Pro Cys Thr Cys Pro Trp Pro Pro Arg Cys Pro Leu Gly Val
            20                  25                  30

Pro Leu Val Leu Asp Gly Cys Gly Cys Cys Arg Val Cys Ala Arg Arg
                35                  40                  45

Leu Gly Glu Pro Cys Asp Gln Leu His Val Cys Asp Ala Ser Gln Gly
        50                  55                  60

Leu Val Cys Gln Pro Gly Ala Gly Pro Gly Gly Arg Gly Ala Leu Cys
65                  70                  75                  80

Leu Leu Ala Glu Asp Asp Ser Ser Cys Glu Val Asn Gly Arg Leu Tyr
                85                  90                  95

Arg Glu Gly Glu Thr Phe Gln Pro His Cys Ser Ile Arg Cys Arg Cys
                100                 105                 110

Glu Asp Gly Gly Phe Thr Cys Val Pro Leu Cys Ser Glu Asp Val Arg
            115                 120                 125

Leu Pro Ser Trp Asp Cys Pro His Pro Arg Arg Val Glu Val Leu Gly
130                 135                 140

Lys Cys Cys Pro Glu Trp Val Cys Gly Gln Gly Gly Gly Leu Gly Thr
145                 150                 155                 160
```

Gln Pro Leu Pro Ala Gln Gly Pro Gln Phe Ser Gly Leu Val Ser Ser
            165                 170                 175

Leu Pro Pro Gly Val Pro Cys Pro Glu Trp Ser Thr Ala Trp Gly Pro
            180                 185                 190

Cys Ser Thr Thr Cys Gly Leu Gly Met Ala Thr Arg Val Ser Asn Gln
            195                 200                 205

Asn Arg Phe Cys Arg Leu Glu Thr Gln Arg Arg Leu Cys Leu Ser Arg
            210                 215                 220

Pro Cys Pro Pro Ser Arg Gly Arg Ser Pro Gln Asn Ser Ala Phe
225                 230                 235

<210> SEQ ID NO 67
<211> LENGTH: 238
<212> TYPE: PRT
<213> ORGANISM: Homo sapiens

<400> SEQUENCE: 67

Ser Leu Leu Cys Leu Leu Ser Lys Val Arg Thr Gln Leu Cys Pro Thr
1               5                   10                  15

Pro Cys Thr Cys Pro Trp Pro Pro Arg Cys Pro Leu Gly Val Pro
            20                  25                  30

Leu Val Leu Asp Gly Cys Gly Cys Arg Val Cys Ala Arg Arg Leu
            35                  40                  45

Gly Glu Pro Cys Asp Gln Leu His Val Cys Asp Ala Ser Gln Gly Leu
    50                  55                  60

Val Cys Gln Pro Gly Ala Gly Pro Gly Gly Arg Gly Ala Leu Cys Leu
65                  70                  75                  80

Leu Ala Glu Asp Asp Ser Ser Cys Glu Val Asn Gly Arg Leu Tyr Arg
                85                  90                  95

Glu Gly Glu Thr Phe Gln Pro His Cys Ser Ile Arg Cys Arg Cys Glu
            100                 105                 110

Asp Gly Gly Phe Thr Cys Val Pro Leu Cys Ser Glu Asp Val Arg Leu
            115                 120                 125

Pro Ser Trp Asp Cys Pro His Pro Arg Arg Val Glu Val Leu Gly Lys
    130                 135                 140

Cys Cys Pro Glu Trp Val Cys Gly Gln Gly Gly Gly Leu Gly Thr Gln
145                 150                 155                 160

Pro Leu Pro Ala Gln Gly Pro Gln Phe Ser Gly Leu Val Ser Ser Leu
                165                 170                 175

Pro Pro Gly Val Pro Cys Pro Glu Trp Ser Thr Ala Trp Gly Pro Cys
            180                 185                 190

Ser Thr Thr Cys Gly Leu Gly Met Ala Thr Arg Val Ser Asn Gln Asn
            195                 200                 205

Arg Phe Cys Arg Leu Glu Thr Gln Arg Arg Leu Cys Leu Ser Arg Pro
            210                 215                 220

Cys Pro Pro Ser Arg Gly Arg Ser Pro Gln Asn Ser Ala Phe
225                 230                 235

<210> SEQ ID NO 68
<211> LENGTH: 237
<212> TYPE: PRT
<213> ORGANISM: Homo sapiens

<400> SEQUENCE: 68

Leu Leu Cys Leu Leu Ser Lys Val Arg Thr Gln Leu Cys Pro Thr Pro
1               5                   10                  15

```
Cys Thr Cys Pro Trp Pro Pro Pro Arg Cys Pro Leu Gly Val Pro Leu
                20                  25                  30

Val Leu Asp Gly Cys Gly Cys Cys Arg Val Cys Ala Arg Arg Leu Gly
            35                  40                  45

Glu Pro Cys Asp Gln Leu His Val Cys Asp Ala Ser Gln Gly Leu Val
        50                  55                  60

Cys Gln Pro Gly Ala Gly Pro Gly Arg Gly Ala Leu Cys Leu Leu
65                  70                  75                  80

Ala Glu Asp Asp Ser Ser Cys Glu Val Asn Gly Arg Leu Tyr Arg Glu
                85                  90                  95

Gly Glu Thr Phe Gln Pro His Cys Ser Ile Arg Cys Arg Cys Glu Asp
            100                 105                 110

Gly Gly Phe Thr Cys Val Pro Leu Cys Ser Glu Asp Val Arg Leu Pro
        115                 120                 125

Ser Trp Asp Cys Pro His Pro Arg Arg Val Glu Val Leu Gly Lys Cys
130                 135                 140

Cys Pro Glu Trp Val Cys Gly Gln Gly Gly Gly Leu Gly Thr Gln Pro
145                 150                 155                 160

Leu Pro Ala Gln Gly Pro Gln Phe Ser Gly Leu Val Ser Ser Leu Pro
                165                 170                 175

Pro Gly Val Pro Cys Pro Glu Trp Ser Thr Ala Trp Gly Pro Cys Ser
            180                 185                 190

Thr Thr Cys Gly Leu Gly Met Ala Thr Arg Val Ser Asn Gln Asn Arg
        195                 200                 205

Phe Cys Arg Leu Glu Thr Gln Arg Arg Leu Cys Leu Ser Arg Pro Cys
210                 215                 220

Pro Pro Ser Arg Gly Arg Ser Pro Gln Asn Ser Ala Phe
225                 230                 235

<210> SEQ ID NO 69
<211> LENGTH: 236
<212> TYPE: PRT
<213> ORGANISM: Homo sapiens

<400> SEQUENCE: 69

Leu Cys Leu Leu Ser Lys Val Arg Thr Gln Leu Cys Pro Thr Pro Cys
1               5                   10                  15

Thr Cys Pro Trp Pro Pro Pro Arg Cys Pro Leu Gly Val Pro Leu Val
                20                  25                  30

Leu Asp Gly Cys Gly Cys Cys Arg Val Cys Ala Arg Arg Leu Gly Glu
            35                  40                  45

Pro Cys Asp Gln Leu His Val Cys Asp Ala Ser Gln Gly Leu Val Cys
        50                  55                  60

Gln Pro Gly Ala Gly Pro Gly Arg Gly Ala Leu Cys Leu Leu Ala
65                  70                  75                  80

Glu Asp Asp Ser Ser Cys Glu Val Asn Gly Arg Leu Tyr Arg Glu Gly
                85                  90                  95

Glu Thr Phe Gln Pro His Cys Ser Ile Arg Cys Arg Cys Glu Asp Gly
            100                 105                 110

Gly Phe Thr Cys Val Pro Leu Cys Ser Glu Asp Val Arg Leu Pro Ser
        115                 120                 125

Trp Asp Cys Pro His Pro Arg Arg Val Glu Val Leu Gly Lys Cys Cys
130                 135                 140

Pro Glu Trp Val Cys Gly Gln Gly Gly Gly Leu Gly Thr Gln Pro Leu
145                 150                 155                 160
```

```
Pro Ala Gln Gly Pro Gln Phe Ser Gly Leu Val Ser Ser Leu Pro Pro
                165                 170                 175

Gly Val Pro Cys Pro Glu Trp Ser Thr Ala Trp Gly Pro Cys Ser Thr
            180                 185                 190

Thr Cys Gly Leu Gly Met Ala Thr Arg Val Ser Asn Gln Asn Arg Phe
        195                 200                 205

Cys Arg Leu Glu Thr Gln Arg Arg Leu Cys Leu Ser Arg Pro Cys Pro
    210                 215                 220

Pro Ser Arg Gly Arg Ser Pro Gln Asn Ser Ala Phe
225                 230                 235

<210> SEQ ID NO 70
<211> LENGTH: 235
<212> TYPE: PRT
<213> ORGANISM: Homo sapiens

<400> SEQUENCE: 70

Cys Leu Leu Ser Lys Val Arg Thr Gln Leu Cys Pro Thr Pro Cys Thr
1               5                   10                  15

Cys Pro Trp Pro Pro Arg Cys Pro Leu Gly Val Pro Leu Val Leu
            20                  25                  30

Asp Gly Cys Gly Cys Arg Val Cys Ala Arg Arg Leu Gly Glu Pro
        35                  40                  45

Cys Asp Gln Leu His Val Cys Asp Ala Ser Gln Gly Leu Val Cys Gln
    50                  55                  60

Pro Gly Ala Gly Pro Gly Gly Arg Gly Ala Leu Cys Leu Leu Ala Glu
65                  70                  75                  80

Asp Asp Ser Ser Cys Glu Val Asn Gly Arg Leu Tyr Arg Glu Gly Glu
                85                  90                  95

Thr Phe Gln Pro His Cys Ser Ile Arg Cys Arg Cys Glu Asp Gly Gly
            100                 105                 110

Phe Thr Cys Val Pro Leu Cys Ser Glu Asp Val Arg Leu Pro Ser Trp
        115                 120                 125

Asp Cys Pro His Pro Arg Arg Val Glu Val Leu Gly Lys Cys Cys Pro
    130                 135                 140

Glu Trp Val Cys Gly Gln Gly Gly Leu Gly Thr Gln Pro Leu Pro
145                 150                 155                 160

Ala Gln Gly Pro Gln Phe Ser Gly Leu Val Ser Ser Leu Pro Pro Gly
                165                 170                 175

Val Pro Cys Pro Glu Trp Ser Thr Ala Trp Gly Pro Cys Ser Thr Thr
            180                 185                 190

Cys Gly Leu Gly Met Ala Thr Arg Val Ser Asn Gln Asn Arg Phe Cys
        195                 200                 205

Arg Leu Glu Thr Gln Arg Arg Leu Cys Leu Ser Arg Pro Cys Pro Pro
    210                 215                 220

Ser Arg Gly Arg Ser Pro Gln Asn Ser Ala Phe
225                 230                 235

<210> SEQ ID NO 71
<211> LENGTH: 234
<212> TYPE: PRT
<213> ORGANISM: Homo sapiens

<400> SEQUENCE: 71

Leu Leu Ser Lys Val Arg Thr Gln Leu Cys Pro Thr Pro Cys Thr Cys
1               5                   10                  15

Pro Trp Pro Pro Pro Arg Cys Pro Leu Gly Val Pro Leu Val Leu Asp
```

```
                     20                  25                  30
Gly Cys Gly Cys Cys Arg Val Cys Ala Arg Arg Leu Gly Glu Pro Cys
                 35                  40                  45

Asp Gln Leu His Val Cys Asp Ala Ser Gln Gly Leu Val Cys Gln Pro
 50                  55                  60

Gly Ala Gly Pro Gly Gly Arg Gly Ala Leu Cys Leu Ala Glu Asp
 65                  70                  75                  80

Asp Ser Ser Cys Glu Val Asn Gly Arg Leu Tyr Arg Glu Gly Glu Thr
                 85                  90                  95

Phe Gln Pro His Cys Ser Ile Arg Cys Arg Cys Glu Asp Gly Gly Phe
                100                 105                 110

Thr Cys Val Pro Leu Cys Ser Glu Asp Val Arg Leu Pro Ser Trp Asp
            115                 120                 125

Cys Pro His Pro Arg Arg Val Glu Val Leu Gly Lys Cys Cys Pro Glu
        130                 135                 140

Trp Val Cys Gly Gln Gly Gly Leu Gly Thr Gln Pro Leu Pro Ala
145                 150                 155                 160

Gln Gly Pro Gln Phe Ser Gly Leu Val Ser Ser Leu Pro Pro Gly Val
                165                 170                 175

Pro Cys Pro Glu Trp Ser Thr Ala Trp Gly Pro Cys Ser Thr Thr Cys
            180                 185                 190

Gly Leu Gly Met Ala Thr Arg Val Ser Asn Gln Asn Arg Phe Cys Arg
                195                 200                 205

Leu Glu Thr Gln Arg Arg Leu Cys Leu Ser Arg Pro Cys Pro Pro Ser
            210                 215                 220

Arg Gly Arg Ser Pro Gln Asn Ser Ala Phe
225                 230

<210> SEQ ID NO 72
<211> LENGTH: 233
<212> TYPE: PRT
<213> ORGANISM: Homo sapiens

<400> SEQUENCE: 72

Leu Ser Lys Val Arg Thr Gln Leu Cys Pro Thr Cys Thr Cys Pro
  1               5                  10                  15

Trp Pro Pro Arg Cys Pro Leu Gly Val Pro Leu Val Leu Asp Gly
                 20                  25                  30

Cys Gly Cys Cys Arg Val Cys Ala Arg Arg Leu Gly Glu Pro Cys Asp
                 35                  40                  45

Gln Leu His Val Cys Asp Ala Ser Gln Gly Leu Val Cys Gln Pro Gly
 50                  55                  60

Ala Gly Pro Gly Gly Arg Gly Ala Leu Cys Leu Ala Glu Asp Asp
 65                  70                  75                  80

Ser Ser Cys Glu Val Asn Gly Arg Leu Tyr Arg Glu Gly Glu Thr Phe
                 85                  90                  95

Gln Pro His Cys Ser Ile Arg Cys Arg Cys Glu Asp Gly Gly Phe Thr
                100                 105                 110

Cys Val Pro Leu Cys Ser Glu Asp Val Arg Leu Pro Ser Trp Asp Cys
            115                 120                 125

Pro His Pro Arg Arg Val Glu Val Leu Gly Lys Cys Cys Pro Glu Trp
        130                 135                 140

Val Cys Gly Gln Gly Gly Leu Gly Thr Gln Pro Leu Pro Ala Gln
145                 150                 155                 160

Gly Pro Gln Phe Ser Gly Leu Val Ser Ser Leu Pro Pro Gly Val Pro
```

```
                    165                 170                 175

Cys Pro Glu Trp Ser Thr Ala Trp Gly Pro Cys Ser Thr Thr Cys Gly
            180                 185                 190

Leu Gly Met Ala Thr Arg Val Ser Asn Gln Asn Arg Phe Cys Arg Leu
            195                 200                 205

Glu Thr Gln Arg Arg Leu Cys Leu Ser Arg Pro Cys Pro Pro Ser Arg
            210                 215                 220

Gly Arg Ser Pro Gln Asn Ser Ala Phe
225                 230

<210> SEQ ID NO 73
<211> LENGTH: 232
<212> TYPE: PRT
<213> ORGANISM: Homo sapiens

<400> SEQUENCE: 73

Ser Lys Val Arg Thr Gln Leu Cys Pro Thr Pro Cys Thr Cys Pro Trp
1               5                   10                  15

Pro Pro Pro Arg Cys Pro Leu Gly Val Pro Leu Val Leu Asp Gly Cys
            20                  25                  30

Gly Cys Cys Arg Val Cys Ala Arg Leu Gly Glu Pro Cys Asp Gln
            35                  40                  45

Leu His Val Cys Asp Ala Ser Gln Gly Leu Val Cys Gln Pro Gly Ala
 50                  55                  60

Gly Pro Gly Gly Arg Gly Ala Leu Cys Leu Leu Ala Glu Asp Asp Ser
65                  70                  75                  80

Ser Cys Glu Val Asn Gly Arg Leu Tyr Arg Glu Gly Glu Thr Phe Gln
                85                  90                  95

Pro His Cys Ser Ile Arg Cys Arg Cys Glu Asp Gly Gly Phe Thr Cys
            100                 105                 110

Val Pro Leu Cys Ser Glu Asp Val Arg Leu Pro Ser Trp Asp Cys Pro
            115                 120                 125

His Pro Arg Arg Val Glu Val Leu Gly Lys Cys Cys Pro Glu Trp Val
            130                 135                 140

Cys Gly Gln Gly Gly Gly Leu Gly Thr Gln Pro Leu Pro Ala Gln Gly
145                 150                 155                 160

Pro Gln Phe Ser Gly Leu Val Ser Ser Leu Pro Pro Gly Val Pro Cys
                165                 170                 175

Pro Glu Trp Ser Thr Ala Trp Gly Pro Cys Ser Thr Thr Cys Gly Leu
            180                 185                 190

Gly Met Ala Thr Arg Val Ser Asn Gln Asn Arg Phe Cys Arg Leu Glu
            195                 200                 205

Thr Gln Arg Arg Leu Cys Leu Ser Arg Pro Cys Pro Pro Ser Arg Gly
            210                 215                 220

Arg Ser Pro Gln Asn Ser Ala Phe
225                 230

<210> SEQ ID NO 74
<211> LENGTH: 231
<212> TYPE: PRT
<213> ORGANISM: Homo sapiens

<400> SEQUENCE: 74

Lys Val Arg Thr Gln Leu Cys Pro Thr Pro Cys Thr Cys Pro Trp Pro
1               5                   10                  15

Pro Pro Arg Cys Pro Leu Gly Val Pro Leu Val Leu Asp Gly Cys Gly
            20                  25                  30
```

Cys Cys Arg Val Cys Ala Arg Arg Leu Gly Glu Pro Cys Asp Gln Leu
                35                  40                  45

His Val Cys Asp Ala Ser Gln Gly Leu Val Cys Gln Pro Gly Ala Gly
     50                  55                  60

Pro Gly Gly Arg Gly Ala Leu Cys Leu Leu Ala Glu Asp Asp Ser Ser
 65                  70                  75                  80

Cys Glu Val Asn Gly Arg Leu Tyr Arg Glu Gly Glu Thr Phe Gln Pro
                 85                  90                  95

His Cys Ser Ile Arg Cys Arg Cys Glu Asp Gly Gly Phe Thr Cys Val
                100                 105                 110

Pro Leu Cys Ser Glu Asp Val Arg Leu Pro Ser Trp Asp Cys Pro His
            115                 120                 125

Pro Arg Arg Val Glu Val Leu Gly Lys Cys Cys Pro Glu Trp Val Cys
            130                 135                 140

Gly Gln Gly Gly Gly Leu Gly Thr Gln Pro Leu Pro Ala Gln Gly Pro
145                 150                 155                 160

Gln Phe Ser Gly Leu Val Ser Ser Leu Pro Pro Gly Val Pro Cys Pro
                165                 170                 175

Glu Trp Ser Thr Ala Trp Gly Pro Cys Ser Thr Thr Cys Gly Leu Gly
            180                 185                 190

Met Ala Thr Arg Val Ser Asn Gln Asn Arg Phe Cys Arg Leu Glu Thr
            195                 200                 205

Gln Arg Arg Leu Cys Leu Ser Arg Pro Cys Pro Pro Ser Arg Gly Arg
210                 215                 220

Ser Pro Gln Asn Ser Ala Phe
225                 230

<210> SEQ ID NO 75
<211> LENGTH: 230
<212> TYPE: PRT
<213> ORGANISM: Homo sapiens

<400> SEQUENCE: 75

Val Arg Thr Gln Leu Cys Pro Thr Pro Cys Thr Cys Pro Trp Pro Pro
 1               5                   10                  15

Pro Arg Cys Pro Leu Gly Val Pro Leu Val Leu Asp Gly Cys Gly Cys
            20                  25                  30

Cys Arg Val Cys Ala Arg Arg Leu Gly Glu Pro Cys Asp Gln Leu His
                35                  40                  45

Val Cys Asp Ala Ser Gln Gly Leu Val Cys Gln Pro Gly Ala Gly Pro
 50                  55                  60

Gly Gly Arg Gly Ala Leu Cys Leu Leu Ala Glu Asp Asp Ser Ser Cys
 65                  70                  75                  80

Glu Val Asn Gly Arg Leu Tyr Arg Glu Gly Glu Thr Phe Gln Pro His
                 85                  90                  95

Cys Ser Ile Arg Cys Arg Cys Glu Asp Gly Gly Phe Thr Cys Val Pro
                100                 105                 110

Leu Cys Ser Glu Asp Val Arg Leu Pro Ser Trp Asp Cys Pro His Pro
            115                 120                 125

Arg Arg Val Glu Val Leu Gly Lys Cys Cys Pro Glu Trp Val Cys Gly
            130                 135                 140

Gln Gly Gly Gly Leu Gly Thr Gln Pro Leu Pro Ala Gln Gly Pro Gln
145                 150                 155                 160

Phe Ser Gly Leu Val Ser Ser Leu Pro Pro Gly Val Pro Cys Pro Glu
                165                 170                 175

```
Trp Ser Thr Ala Trp Gly Pro Cys Ser Thr Thr Cys Gly Leu Gly Met
            180                 185                 190

Ala Thr Arg Val Ser Asn Gln Asn Arg Phe Cys Arg Leu Glu Thr Gln
        195                 200                 205

Arg Arg Leu Cys Leu Ser Arg Pro Cys Pro Pro Ser Arg Gly Arg Ser
    210                 215                 220

Pro Gln Asn Ser Ala Phe
225                 230

<210> SEQ ID NO 76
<211> LENGTH: 229
<212> TYPE: PRT
<213> ORGANISM: Homo sapiens

<400> SEQUENCE: 76

Arg Thr Gln Leu Cys Pro Thr Pro Cys Thr Cys Pro Trp Pro Pro Pro
1               5                   10                  15

Arg Cys Pro Leu Gly Val Pro Leu Val Leu Asp Gly Cys Gly Cys Cys
            20                  25                  30

Arg Val Cys Ala Arg Arg Leu Gly Glu Pro Cys Asp Gln Leu His Val
        35                  40                  45

Cys Asp Ala Ser Gln Gly Leu Val Cys Gln Pro Gly Ala Gly Pro Gly
50                  55                  60

Gly Arg Gly Ala Leu Cys Leu Ala Glu Asp Asp Ser Ser Cys Glu
65                  70                  75                  80

Val Asn Gly Arg Leu Tyr Arg Glu Gly Glu Thr Phe Gln Pro His Cys
                85                  90                  95

Ser Ile Arg Cys Arg Cys Glu Asp Gly Gly Phe Thr Cys Val Pro Leu
            100                 105                 110

Cys Ser Glu Asp Val Arg Leu Pro Ser Trp Asp Cys Pro His Pro Arg
        115                 120                 125

Arg Val Glu Val Leu Gly Lys Cys Cys Pro Glu Trp Val Cys Gly Gln
    130                 135                 140

Gly Gly Gly Leu Gly Thr Gln Pro Leu Pro Ala Gln Gly Pro Gln Phe
145                 150                 155                 160

Ser Gly Leu Val Ser Ser Leu Pro Pro Gly Val Pro Cys Pro Glu Trp
                165                 170                 175

Ser Thr Ala Trp Gly Pro Cys Ser Thr Thr Cys Gly Leu Gly Met Ala
            180                 185                 190

Thr Arg Val Ser Asn Gln Asn Arg Phe Cys Arg Leu Glu Thr Gln Arg
        195                 200                 205

Arg Leu Cys Leu Ser Arg Pro Cys Pro Pro Ser Arg Gly Arg Ser Pro
    210                 215                 220

Gln Asn Ser Ala Phe
225

<210> SEQ ID NO 77
<211> LENGTH: 228
<212> TYPE: PRT
<213> ORGANISM: Homo sapiens

<400> SEQUENCE: 77

Thr Gln Leu Cys Pro Thr Pro Cys Thr Cys Pro Trp Pro Pro Pro Arg
1               5                   10                  15

Cys Pro Leu Gly Val Pro Leu Val Leu Asp Gly Cys Gly Cys Cys Arg
            20                  25                  30
```

-continued

Val Cys Ala Arg Arg Leu Gly Glu Pro Cys Asp Gln Leu His Val Cys
         35                  40                  45

Asp Ala Ser Gln Gly Leu Val Cys Gln Pro Gly Ala Gly Pro Gly Gly
 50                  55                  60

Arg Gly Ala Leu Cys Leu Leu Ala Glu Asp Asp Ser Ser Cys Glu Val
 65                  70                  75                  80

Asn Gly Arg Leu Tyr Arg Glu Gly Glu Thr Phe Gln Pro His Cys Ser
                 85                  90                  95

Ile Arg Cys Arg Cys Glu Asp Gly Gly Phe Thr Cys Val Pro Leu Cys
            100                 105                 110

Ser Glu Asp Val Arg Leu Pro Ser Trp Asp Cys Pro His Pro Arg Arg
        115                 120                 125

Val Glu Val Leu Gly Lys Cys Cys Pro Glu Trp Val Cys Gly Gln Gly
    130                 135                 140

Gly Gly Leu Gly Thr Gln Pro Leu Pro Ala Gln Gly Pro Gln Phe Ser
145                 150                 155                 160

Gly Leu Val Ser Ser Leu Pro Pro Gly Val Pro Cys Pro Glu Trp Ser
                165                 170                 175

Thr Ala Trp Gly Pro Cys Ser Thr Thr Cys Gly Leu Gly Met Ala Thr
            180                 185                 190

Arg Val Ser Asn Gln Asn Arg Phe Cys Arg Leu Glu Thr Gln Arg Arg
        195                 200                 205

Leu Cys Leu Ser Arg Pro Cys Pro Pro Ser Arg Gly Arg Ser Pro Gln
    210                 215                 220

Asn Ser Ala Phe
225

<210> SEQ ID NO 78
<211> LENGTH: 250
<212> TYPE: PRT
<213> ORGANISM: Homo sapiens

<400> SEQUENCE: 78

Arg Gly Asn Pro Leu Ile His Leu Leu Ala Ile Ser Phe Leu Cys Ile
  1               5                  10                  15

Leu Ser Met Val Tyr Ser Gln Leu Cys Pro Ala Pro Cys Ala Cys Pro
             20                  25                  30

Trp Thr Pro Pro Gln Cys Pro Pro Gly Val Pro Leu Val Leu Asp Gly
         35                  40                  45

Cys Gly Cys Cys Arg Val Cys Ala Arg Arg Leu Gly Glu Ser Cys Asp
 50                  55                  60

His Leu His Val Cys Asp Pro Ser Gln Gly Leu Val Cys Gln Pro Gly
 65                  70                  75                  80

Ala Gly Pro Ser Gly Arg Gly Ala Val Cys Leu Phe Glu Glu Asp Asp
                 85                  90                  95

Gly Ser Cys Glu Val Asn Gly Arg Arg Tyr Leu Asp Gly Glu Thr Phe
            100                 105                 110

Lys Pro Asn Cys Arg Val Leu Cys Arg Cys Asp Asp Gly Gly Phe Thr
        115                 120                 125

Cys Leu Pro Leu Cys Ser Glu Asp Val Arg Leu Pro Ser Trp Asp Cys
    130                 135                 140

Pro Arg Pro Arg Arg Ile Gln Val Pro Gly Arg Cys Cys Pro Glu Trp
145                 150                 155                 160

Val Cys Asp Gln Ala Val Met Gln Pro Ala Ile Gln Pro Ser Ser Ala
                165                 170                 175

```
Gln Gly His Gln Leu Ser Ala Leu Val Thr Pro Ala Ser Ala Asp Gly
            180                 185                 190

Pro Cys Pro Asn Trp Ser Thr Ala Trp Gly Pro Cys Ser Thr Thr Cys
        195                 200                 205

Gly Leu Gly Ile Ala Thr Arg Val Ser Asn Gln Asn Arg Phe Cys Gln
    210                 215                 220

Leu Glu Ile Gln Arg Arg Leu Cys Leu Ser Arg Pro Cys Leu Ala Ser
225                 230                 235                 240

Arg Ser His Gly Ser Trp Asn Ser Ala Phe
                245                 250

<210> SEQ ID NO 79
<211> LENGTH: 249
<212> TYPE: PRT
<213> ORGANISM: Homo sapiens

<400> SEQUENCE: 79

Gly Asn Pro Leu Ile His Leu Leu Ala Ile Ser Phe Leu Cys Ile Leu
1               5                   10                  15

Ser Met Val Tyr Ser Gln Leu Cys Pro Ala Pro Cys Ala Cys Pro Trp
            20                  25                  30

Thr Pro Pro Gln Cys Pro Pro Gly Val Pro Leu Val Leu Asp Gly Cys
        35                  40                  45

Gly Cys Cys Arg Val Cys Ala Arg Arg Leu Gly Glu Ser Cys Asp His
    50                  55                  60

Leu His Val Cys Asp Pro Ser Gln Gly Leu Val Cys Gln Pro Gly Ala
65                  70                  75                  80

Gly Pro Ser Gly Arg Gly Ala Val Cys Leu Phe Glu Glu Asp Asp Gly
                85                  90                  95

Ser Cys Glu Val Asn Gly Arg Arg Tyr Leu Asp Gly Glu Thr Phe Lys
            100                 105                 110

Pro Asn Cys Arg Val Leu Cys Arg Cys Asp Asp Gly Gly Phe Thr Cys
        115                 120                 125

Leu Pro Leu Cys Ser Glu Asp Val Arg Leu Pro Ser Trp Asp Cys Pro
130                 135                 140

Arg Pro Arg Arg Ile Gln Val Pro Gly Arg Cys Cys Pro Glu Trp Val
145                 150                 155                 160

Cys Asp Gln Ala Val Met Gln Pro Ala Ile Gln Pro Ser Ser Ala Gln
                165                 170                 175

Gly His Gln Leu Ser Ala Leu Val Thr Pro Ala Ser Ala Asp Gly Pro
            180                 185                 190

Cys Pro Asn Trp Ser Thr Ala Trp Gly Pro Cys Ser Thr Thr Cys Gly
        195                 200                 205

Leu Gly Ile Ala Thr Arg Val Ser Asn Gln Asn Arg Phe Cys Gln Leu
    210                 215                 220

Glu Ile Gln Arg Arg Leu Cys Leu Ser Arg Pro Cys Leu Ala Ser Arg
225                 230                 235                 240

Ser His Gly Ser Trp Asn Ser Ala Phe
                245

<210> SEQ ID NO 80
<211> LENGTH: 248
<212> TYPE: PRT
<213> ORGANISM: Homo sapiens

<400> SEQUENCE: 80

Asn Pro Leu Ile His Leu Leu Ala Ile Ser Phe Leu Cys Ile Leu Ser
```

```
                1               5                  10                 15
        Met Val Tyr Ser Gln Leu Cys Pro Ala Pro Cys Ala Cys Pro Trp Thr
                               20                 25                 30
        Pro Pro Gln Cys Pro Pro Gly Val Pro Leu Val Leu Asp Gly Cys Gly
                       35                 40                 45
        Cys Cys Arg Val Cys Ala Arg Arg Leu Gly Glu Ser Cys Asp His Leu
               50                 55                 60
        His Val Cys Asp Pro Ser Gln Gly Leu Val Cys Gln Pro Gly Ala Gly
        65                 70                 75                 80
        Pro Ser Gly Arg Gly Ala Val Cys Leu Phe Glu Glu Asp Gly Ser
                       85                 90                 95
        Cys Glu Val Asn Gly Arg Arg Tyr Leu Asp Gly Glu Thr Phe Lys Pro
                       100                105                110
        Asn Cys Arg Val Leu Cys Arg Cys Asp Asp Gly Gly Phe Thr Cys Leu
                       115                120                125
        Pro Leu Cys Ser Glu Asp Val Arg Leu Pro Ser Trp Asp Cys Pro Arg
                       130                135                140
        Pro Arg Arg Ile Gln Val Pro Gly Arg Cys Cys Pro Glu Trp Val Cys
        145                150                155                160
        Asp Gln Ala Val Met Gln Pro Ala Ile Gln Pro Ser Ser Ala Gln Gly
                               165                170                175
        His Gln Leu Ser Ala Leu Val Thr Pro Ala Ser Ala Asp Gly Pro Cys
                       180                185                190
        Pro Asn Trp Ser Thr Ala Trp Gly Pro Cys Ser Thr Thr Cys Gly Leu
                       195                200                205
        Gly Ile Ala Thr Arg Val Ser Asn Gln Asn Arg Phe Cys Gln Leu Glu
                       210                215                220
        Ile Gln Arg Arg Leu Cys Leu Ser Arg Pro Cys Leu Ala Ser Arg Ser
        225                230                235                240
        His Gly Ser Trp Asn Ser Ala Phe
                       245

<210> SEQ ID NO 81
<211> LENGTH: 247
<212> TYPE: PRT
<213> ORGANISM: Homo sapiens

<400> SEQUENCE: 81

Pro Leu Ile His Leu Leu Ala Ile Ser Phe Leu Cys Ile Leu Ser Met
        1               5                  10                 15
        Val Tyr Ser Gln Leu Cys Pro Ala Pro Cys Ala Cys Pro Trp Thr Pro
                       20                 25                 30
        Pro Gln Cys Pro Pro Gly Val Pro Leu Val Leu Asp Gly Cys Gly Cys
                       35                 40                 45
        Cys Arg Val Cys Ala Arg Arg Leu Gly Glu Ser Cys Asp His Leu His
               50                 55                 60
        Val Cys Asp Pro Ser Gln Gly Leu Val Cys Gln Pro Gly Ala Gly Pro
        65                 70                 75                 80
        Ser Gly Arg Gly Ala Val Cys Leu Phe Glu Glu Asp Gly Ser Cys
                       85                 90                 95
        Glu Val Asn Gly Arg Arg Tyr Leu Asp Gly Glu Thr Phe Lys Pro Asn
                       100                105                110
        Cys Arg Val Leu Cys Arg Cys Asp Asp Gly Gly Phe Thr Cys Leu Pro
                       115                120                125
        Leu Cys Ser Glu Asp Val Arg Leu Pro Ser Trp Asp Cys Pro Arg Pro
```

```
                130                 135                 140
Arg Arg Ile Gln Val Pro Gly Arg Cys Cys Pro Glu Trp Val Cys Asp
145                 150                 155                 160

Gln Ala Val Met Gln Pro Ala Ile Gln Pro Ser Ser Ala Gln Gly His
                165                 170                 175

Gln Leu Ser Ala Leu Val Thr Pro Ala Ser Ala Asp Gly Pro Cys Pro
                180                 185                 190

Asn Trp Ser Thr Ala Trp Gly Pro Cys Ser Thr Cys Gly Leu Gly
                195                 200                 205

Ile Ala Thr Arg Val Ser Asn Gln Asn Arg Phe Cys Gln Leu Glu Ile
                210                 215                 220

Gln Arg Arg Leu Cys Leu Ser Arg Pro Cys Leu Ala Ser Arg Ser His
225                 230                 235                 240

Gly Ser Trp Asn Ser Ala Phe
                245

<210> SEQ ID NO 82
<211> LENGTH: 246
<212> TYPE: PRT
<213> ORGANISM: Homo sapiens

<400> SEQUENCE: 82

Leu Ile His Leu Leu Ala Ile Ser Phe Leu Cys Ile Leu Ser Met Val
1               5                   10                  15

Tyr Ser Gln Leu Cys Pro Ala Pro Cys Ala Cys Pro Trp Thr Pro Pro
                20                  25                  30

Gln Cys Pro Pro Gly Val Pro Leu Val Leu Asp Gly Cys Gly Cys Cys
                35                  40                  45

Arg Val Cys Ala Arg Arg Leu Gly Glu Ser Cys Asp His Leu His Val
        50                  55                  60

Cys Asp Pro Ser Gln Gly Leu Val Cys Gln Pro Gly Ala Gly Pro Ser
65                  70                  75                  80

Gly Arg Gly Ala Val Cys Leu Phe Glu Glu Asp Asp Gly Ser Cys Glu
                85                  90                  95

Val Asn Gly Arg Arg Tyr Leu Asp Gly Glu Thr Phe Lys Pro Asn Cys
                100                 105                 110

Arg Val Leu Cys Arg Cys Asp Asp Gly Gly Phe Thr Cys Leu Pro Leu
                115                 120                 125

Cys Ser Glu Asp Val Arg Leu Pro Ser Trp Asp Cys Pro Arg Pro Arg
        130                 135                 140

Arg Ile Gln Val Pro Gly Arg Cys Cys Pro Glu Trp Val Cys Asp Gln
145                 150                 155                 160

Ala Val Met Gln Pro Ala Ile Gln Pro Ser Ser Ala Gln Gly His Gln
                165                 170                 175

Leu Ser Ala Leu Val Thr Pro Ala Ser Ala Asp Gly Pro Cys Pro Asn
                180                 185                 190

Trp Ser Thr Ala Trp Gly Pro Cys Ser Thr Cys Gly Leu Gly Ile
                195                 200                 205

Ala Thr Arg Val Ser Asn Gln Asn Arg Phe Cys Gln Leu Glu Ile Gln
                210                 215                 220

Arg Arg Leu Cys Leu Ser Arg Pro Cys Leu Ala Ser Arg Ser His Gly
225                 230                 235                 240

Ser Trp Asn Ser Ala Phe
                245
```

```
<210> SEQ ID NO 83
<211> LENGTH: 245
<212> TYPE: PRT
<213> ORGANISM: Homo sapiens

<400> SEQUENCE: 83

Ile His Leu Leu Ala Ile Ser Phe Leu Cys Ile Leu Ser Met Val Tyr
1               5                   10                  15

Ser Gln Leu Cys Pro Ala Pro Cys Ala Cys Pro Trp Thr Pro Pro Gln
            20                  25                  30

Cys Pro Pro Gly Val Pro Leu Val Leu Asp Gly Cys Gly Cys Cys Arg
        35                  40                  45

Val Cys Ala Arg Arg Leu Gly Glu Ser Cys Asp His Leu His Val Cys
    50                  55                  60

Asp Pro Ser Gln Gly Leu Val Cys Gln Pro Gly Ala Gly Pro Ser Gly
65                  70                  75                  80

Arg Gly Ala Val Cys Leu Phe Glu Glu Asp Asp Gly Ser Cys Glu Val
                85                  90                  95

Asn Gly Arg Arg Tyr Leu Asp Gly Glu Thr Phe Lys Pro Asn Cys Arg
            100                 105                 110

Val Leu Cys Arg Cys Asp Asp Gly Phe Thr Cys Leu Pro Leu Cys
        115                 120                 125

Ser Glu Asp Val Arg Leu Pro Ser Trp Asp Cys Pro Arg Pro Arg Arg
    130                 135                 140

Ile Gln Val Pro Gly Arg Cys Cys Pro Glu Trp Val Cys Asp Gln Ala
145                 150                 155                 160

Val Met Gln Pro Ala Ile Gln Pro Ser Ser Ala Gln Gly His Gln Leu
                165                 170                 175

Ser Ala Leu Val Thr Pro Ala Ser Ala Asp Gly Pro Cys Pro Asn Trp
            180                 185                 190

Ser Thr Ala Trp Gly Pro Cys Ser Thr Thr Cys Gly Leu Gly Ile Ala
        195                 200                 205

Thr Arg Val Ser Asn Gln Asn Arg Phe Cys Gln Leu Glu Ile Gln Arg
    210                 215                 220

Arg Leu Cys Leu Ser Arg Pro Cys Leu Ala Ser Arg Ser His Gly Ser
225                 230                 235                 240

Trp Asn Ser Ala Phe
                245

<210> SEQ ID NO 84
<211> LENGTH: 244
<212> TYPE: PRT
<213> ORGANISM: Homo sapiens

<400> SEQUENCE: 84

His Leu Leu Ala Ile Ser Phe Leu Cys Ile Leu Ser Met Val Tyr Ser
1               5                   10                  15

Gln Leu Cys Pro Ala Pro Cys Ala Cys Pro Trp Thr Pro Pro Gln Cys
            20                  25                  30

Pro Pro Gly Val Pro Leu Val Leu Asp Gly Cys Gly Cys Cys Arg Val
        35                  40                  45

Cys Ala Arg Arg Leu Gly Glu Ser Cys Asp His Leu His Val Cys Asp
    50                  55                  60

Pro Ser Gln Gly Leu Val Cys Gln Pro Gly Ala Gly Pro Ser Gly Arg
65                  70                  75                  80

Gly Ala Val Cys Leu Phe Glu Glu Asp Asp Gly Ser Cys Glu Val Asn
                85                  90                  95
```

```
Gly Arg Arg Tyr Leu Asp Gly Glu Thr Phe Lys Pro Asn Cys Arg Val
            100                 105                 110

Leu Cys Arg Cys Asp Asp Gly Gly Phe Thr Cys Leu Pro Leu Cys Ser
        115                 120                 125

Glu Asp Val Arg Leu Pro Ser Trp Asp Cys Pro Arg Pro Arg Arg Ile
130                 135                 140

Gln Val Pro Gly Arg Cys Cys Pro Glu Trp Val Cys Asp Gln Ala Val
145                 150                 155                 160

Met Gln Pro Ala Ile Gln Pro Ser Ser Ala Gln Gly His Gln Leu Ser
                165                 170                 175

Ala Leu Val Thr Pro Ala Ser Ala Asp Gly Pro Cys Pro Asn Trp Ser
            180                 185                 190

Thr Ala Trp Gly Pro Cys Ser Thr Thr Cys Gly Leu Gly Ile Ala Thr
        195                 200                 205

Arg Val Ser Asn Gln Asn Arg Phe Cys Gln Leu Glu Ile Gln Arg Arg
210                 215                 220

Leu Cys Leu Ser Arg Pro Cys Leu Ala Ser Arg Ser His Gly Ser Trp
225                 230                 235                 240

Asn Ser Ala Phe

<210> SEQ ID NO 85
<211> LENGTH: 243
<212> TYPE: PRT
<213> ORGANISM: Homo sapiens

<400> SEQUENCE: 85

Leu Leu Ala Ile Ser Phe Leu Cys Ile Leu Ser Met Val Tyr Ser Gln
1               5                   10                  15

Leu Cys Pro Ala Pro Cys Ala Cys Pro Trp Thr Pro Pro Gln Cys Pro
            20                  25                  30

Pro Gly Val Pro Leu Val Leu Asp Gly Cys Gly Cys Cys Arg Val Cys
        35                  40                  45

Ala Arg Arg Leu Gly Glu Ser Cys Asp His Leu His Val Cys Asp Pro
50                  55                  60

Ser Gln Gly Leu Val Cys Gln Pro Gly Ala Gly Pro Ser Gly Arg Gly
65                  70                  75                  80

Ala Val Cys Leu Phe Glu Glu Asp Asp Ser Cys Glu Val Asn Gly
                85                  90                  95

Arg Arg Tyr Leu Asp Gly Glu Thr Phe Lys Pro Asn Cys Arg Val Leu
            100                 105                 110

Cys Arg Cys Asp Asp Gly Gly Phe Thr Cys Leu Pro Leu Cys Ser Glu
        115                 120                 125

Asp Val Arg Leu Pro Ser Trp Asp Cys Pro Arg Pro Arg Arg Ile Gln
130                 135                 140

Val Pro Gly Arg Cys Cys Pro Glu Trp Val Cys Asp Gln Ala Val Met
145                 150                 155                 160

Gln Pro Ala Ile Gln Pro Ser Ser Ala Gln Gly His Gln Leu Ser Ala
                165                 170                 175

Leu Val Thr Pro Ala Ser Ala Asp Gly Pro Cys Pro Asn Trp Ser Thr
            180                 185                 190

Ala Trp Gly Pro Cys Ser Thr Thr Cys Gly Leu Gly Ile Ala Thr Arg
        195                 200                 205

Val Ser Asn Gln Asn Arg Phe Cys Gln Leu Glu Ile Gln Arg Arg Leu
210                 215                 220
```

```
Cys Leu Ser Arg Pro Cys Leu Ala Ser Arg Ser His Gly Ser Trp Asn
225                 230                 235                 240

Ser Ala Phe

<210> SEQ ID NO 86
<211> LENGTH: 242
<212> TYPE: PRT
<213> ORGANISM: Homo sapiens

<400> SEQUENCE: 86

Leu Ala Ile Ser Phe Leu Cys Ile Leu Ser Met Val Tyr Ser Gln Leu
1               5                   10                  15

Cys Pro Ala Pro Cys Ala Cys Pro Trp Thr Pro Gln Cys Pro Pro
            20                  25                  30

Gly Val Pro Leu Val Leu Asp Gly Cys Gly Cys Arg Val Cys Ala
                35                  40                  45

Arg Arg Leu Gly Glu Ser Cys Asp His Leu His Val Cys Asp Pro Ser
    50                  55                  60

Gln Gly Leu Val Cys Gln Pro Gly Ala Gly Pro Ser Gly Arg Gly Ala
65                  70                  75                  80

Val Cys Leu Phe Glu Glu Asp Asp Gly Ser Cys Glu Val Asn Gly Arg
                85                  90                  95

Arg Tyr Leu Asp Gly Glu Thr Phe Lys Pro Asn Cys Arg Val Leu Cys
            100                 105                 110

Arg Cys Asp Asp Gly Gly Phe Thr Cys Leu Pro Leu Cys Ser Glu Asp
        115                 120                 125

Val Arg Leu Pro Ser Trp Asp Cys Pro Arg Pro Arg Arg Ile Gln Val
    130                 135                 140

Pro Gly Arg Cys Cys Pro Glu Trp Val Cys Asp Gln Ala Val Met Gln
145                 150                 155                 160

Pro Ala Ile Gln Pro Ser Ser Ala Gln Gly His Gln Leu Ser Ala Leu
                165                 170                 175

Val Thr Pro Ala Ser Ala Asp Gly Pro Cys Pro Asn Trp Ser Thr Ala
            180                 185                 190

Trp Gly Pro Cys Ser Thr Thr Cys Gly Leu Gly Ile Ala Thr Arg Val
        195                 200                 205

Ser Asn Gln Asn Arg Phe Cys Gln Leu Glu Ile Gln Arg Arg Leu Cys
    210                 215                 220

Leu Ser Arg Pro Cys Leu Ala Ser Arg Ser His Gly Ser Trp Asn Ser
225                 230                 235                 240

Ala Phe

<210> SEQ ID NO 87
<211> LENGTH: 241
<212> TYPE: PRT
<213> ORGANISM: Homo sapiens

<400> SEQUENCE: 87

Ala Ile Ser Phe Leu Cys Ile Leu Ser Met Val Tyr Ser Gln Leu Cys
1               5                   10                  15

Pro Ala Pro Cys Ala Cys Pro Trp Thr Pro Gln Cys Pro Pro Gly
            20                  25                  30

Val Pro Leu Val Leu Asp Gly Cys Gly Cys Arg Val Cys Ala Arg
                35                  40                  45

Arg Leu Gly Glu Ser Cys Asp His Leu His Val Cys Asp Pro Ser Gln
    50                  55                  60
```

```
Gly Leu Val Cys Gln Pro Gly Ala Gly Pro Ser Gly Arg Gly Ala Val
 65                  70                  75                  80

Cys Leu Phe Glu Glu Asp Asp Gly Ser Cys Glu Val Asn Gly Arg Arg
                 85                  90                  95

Tyr Leu Asp Gly Glu Thr Phe Lys Pro Asn Cys Arg Val Leu Cys Arg
            100                 105                 110

Cys Asp Asp Gly Gly Phe Thr Cys Leu Pro Leu Cys Ser Glu Asp Val
            115                 120                 125

Arg Leu Pro Ser Trp Asp Cys Pro Arg Pro Arg Ile Gln Val Pro
        130                 135                 140

Gly Arg Cys Cys Pro Glu Trp Val Cys Asp Gln Ala Val Met Gln Pro
145                 150                 155                 160

Ala Ile Gln Pro Ser Ser Ala Gln Gly His Gln Leu Ser Ala Leu Val
                165                 170                 175

Thr Pro Ala Ser Ala Asp Gly Pro Cys Pro Asn Trp Ser Thr Ala Trp
            180                 185                 190

Gly Pro Cys Ser Thr Thr Cys Gly Leu Gly Ile Ala Thr Arg Val Ser
            195                 200                 205

Asn Gln Asn Arg Phe Cys Gln Leu Glu Ile Gln Arg Arg Leu Cys Leu
        210                 215                 220

Ser Arg Pro Cys Leu Ala Ser Arg Ser His Gly Ser Trp Asn Ser Ala
225                 230                 235                 240

Phe

<210> SEQ ID NO 88
<211> LENGTH: 240
<212> TYPE: PRT
<213> ORGANISM: Homo sapiens

<400> SEQUENCE: 88

Ile Ser Phe Leu Cys Ile Leu Ser Met Val Tyr Ser Gln Leu Cys Pro
  1               5                  10                  15

Ala Pro Cys Ala Cys Pro Trp Thr Pro Pro Gln Cys Pro Pro Gly Val
                 20                  25                  30

Pro Leu Val Leu Asp Gly Cys Gly Cys Cys Arg Val Cys Ala Arg Arg
             35                  40                  45

Leu Gly Glu Ser Cys Asp His Leu His Val Cys Asp Pro Ser Gln Gly
         50                  55                  60

Leu Val Cys Gln Pro Gly Ala Gly Pro Ser Gly Arg Gly Ala Val Cys
 65                  70                  75                  80

Leu Phe Glu Glu Asp Asp Gly Ser Cys Glu Val Asn Gly Arg Arg Tyr
                 85                  90                  95

Leu Asp Gly Glu Thr Phe Lys Pro Asn Cys Arg Val Leu Cys Arg Cys
            100                 105                 110

Asp Asp Gly Gly Phe Thr Cys Leu Pro Leu Cys Ser Glu Asp Val Arg
            115                 120                 125

Leu Pro Ser Trp Asp Cys Pro Arg Pro Arg Arg Ile Gln Val Pro Gly
        130                 135                 140

Arg Cys Cys Pro Glu Trp Val Cys Asp Gln Ala Val Met Gln Pro Ala
145                 150                 155                 160

Ile Gln Pro Ser Ser Ala Gln Gly His Gln Leu Ser Ala Leu Val Thr
                165                 170                 175

Pro Ala Ser Ala Asp Gly Pro Cys Pro Asn Trp Ser Thr Ala Trp Gly
            180                 185                 190

Pro Cys Ser Thr Thr Cys Gly Leu Gly Ile Ala Thr Arg Val Ser Asn
```

```
            195                 200                 205
Gln Asn Arg Phe Cys Gln Leu Glu Ile Gln Arg Arg Leu Cys Leu Ser
        210                 215                 220

Arg Pro Cys Leu Ala Ser Arg Ser His Gly Ser Trp Asn Ser Ala Phe
225                 230                 235                 240

<210> SEQ ID NO 89
<211> LENGTH: 239
<212> TYPE: PRT
<213> ORGANISM: Homo sapiens

<400> SEQUENCE: 89

Ser Phe Leu Cys Ile Leu Ser Met Val Tyr Ser Gln Leu Cys Pro Ala
1               5                   10                  15

Pro Cys Ala Cys Pro Trp Thr Pro Pro Gln Cys Pro Pro Gly Val Pro
            20                  25                  30

Leu Val Leu Asp Gly Cys Gly Cys Cys Arg Val Cys Ala Arg Arg Leu
        35                  40                  45

Gly Glu Ser Cys Asp His Leu His Val Cys Asp Pro Ser Gln Gly Leu
    50                  55                  60

Val Cys Gln Pro Gly Ala Gly Pro Ser Gly Arg Gly Ala Val Cys Leu
65                  70                  75                  80

Phe Glu Glu Asp Asp Gly Ser Cys Glu Val Asn Gly Arg Arg Tyr Leu
                85                  90                  95

Asp Gly Glu Thr Phe Lys Pro Asn Cys Arg Val Leu Cys Arg Cys Asp
            100                 105                 110

Asp Gly Gly Phe Thr Cys Leu Pro Leu Cys Ser Glu Asp Val Arg Leu
        115                 120                 125

Pro Ser Trp Asp Cys Pro Arg Pro Arg Arg Ile Gln Val Pro Gly Arg
    130                 135                 140

Cys Cys Pro Glu Trp Val Cys Asp Gln Ala Val Met Gln Pro Ala Ile
145                 150                 155                 160

Gln Pro Ser Ser Ala Gln Gly His Gln Leu Ser Ala Leu Val Thr Pro
                165                 170                 175

Ala Ser Ala Asp Gly Pro Cys Pro Asn Trp Ser Thr Ala Trp Gly Pro
            180                 185                 190

Cys Ser Thr Thr Cys Gly Leu Gly Ile Ala Thr Arg Val Ser Asn Gln
        195                 200                 205

Asn Arg Phe Cys Gln Leu Glu Ile Gln Arg Arg Leu Cys Leu Ser Arg
    210                 215                 220

Pro Cys Leu Ala Ser Arg Ser His Gly Ser Trp Asn Ser Ala Phe
225                 230                 235

<210> SEQ ID NO 90
<211> LENGTH: 238
<212> TYPE: PRT
<213> ORGANISM: Homo sapiens

<400> SEQUENCE: 90

Phe Leu Cys Ile Leu Ser Met Val Tyr Ser Gln Leu Cys Pro Ala Pro
1               5                   10                  15

Cys Ala Cys Pro Trp Thr Pro Pro Gln Cys Pro Pro Gly Val Pro Leu
            20                  25                  30

Val Leu Asp Gly Cys Gly Cys Cys Arg Val Cys Ala Arg Arg Leu Gly
        35                  40                  45

Glu Ser Cys Asp His Leu His Val Cys Asp Pro Ser Gln Gly Leu Val
    50                  55                  60
```

```
Cys Gln Pro Gly Ala Gly Pro Ser Gly Arg Gly Ala Val Cys Leu Phe
 65                  70                  75                  80

Glu Glu Asp Asp Gly Ser Cys Glu Val Asn Gly Arg Arg Tyr Leu Asp
                 85                  90                  95

Gly Glu Thr Phe Lys Pro Asn Cys Arg Val Leu Cys Arg Cys Asp Asp
             100                 105                 110

Gly Gly Phe Thr Cys Leu Pro Leu Cys Ser Glu Asp Val Arg Leu Pro
         115                 120                 125

Ser Trp Asp Cys Pro Arg Pro Arg Ile Gln Val Pro Gly Arg Cys
130                 135                 140

Cys Pro Glu Trp Val Cys Asp Gln Ala Val Met Gln Pro Ala Ile Gln
145                 150                 155                 160

Pro Ser Ser Ala Gln Gly His Gln Leu Ser Ala Leu Val Thr Pro Ala
                165                 170                 175

Ser Ala Asp Gly Pro Cys Pro Asn Trp Ser Thr Ala Trp Gly Pro Cys
            180                 185                 190

Ser Thr Thr Cys Gly Leu Gly Ile Ala Thr Arg Val Ser Asn Gln Asn
        195                 200                 205

Arg Phe Cys Gln Leu Glu Ile Gln Arg Arg Leu Cys Leu Ser Arg Pro
    210                 215                 220

Cys Leu Ala Ser Arg Ser His Gly Ser Trp Asn Ser Ala Phe
225                 230                 235

<210> SEQ ID NO 91
<211> LENGTH: 237
<212> TYPE: PRT
<213> ORGANISM: Homo sapiens

<400> SEQUENCE: 91

Leu Cys Ile Leu Ser Met Val Tyr Ser Gln Leu Cys Pro Ala Pro Cys
 1               5                  10                  15

Ala Cys Pro Trp Thr Pro Pro Gln Cys Pro Pro Gly Val Pro Leu Val
                 20                  25                  30

Leu Asp Gly Cys Gly Cys Cys Arg Val Cys Ala Arg Arg Leu Gly Glu
             35                  40                  45

Ser Cys Asp His Leu His Val Cys Asp Pro Ser Gln Gly Leu Val Cys
         50                  55                  60

Gln Pro Gly Ala Gly Pro Ser Gly Arg Gly Ala Val Cys Leu Phe Glu
 65                  70                  75                  80

Glu Asp Asp Gly Ser Cys Glu Val Asn Gly Arg Arg Tyr Leu Asp Gly
                 85                  90                  95

Glu Thr Phe Lys Pro Asn Cys Arg Val Leu Cys Arg Cys Asp Asp Gly
            100                 105                 110

Gly Phe Thr Cys Leu Pro Leu Cys Ser Glu Asp Val Arg Leu Pro Ser
        115                 120                 125

Trp Asp Cys Pro Arg Pro Arg Ile Gln Val Pro Gly Arg Cys Cys
    130                 135                 140

Pro Glu Trp Val Cys Asp Gln Ala Val Met Gln Pro Ala Ile Gln Pro
145                 150                 155                 160

Ser Ser Ala Gln Gly His Gln Leu Ser Ala Leu Val Thr Pro Ala Ser
                165                 170                 175

Ala Asp Gly Pro Cys Pro Asn Trp Ser Thr Ala Trp Gly Pro Cys Ser
            180                 185                 190

Thr Thr Cys Gly Leu Gly Ile Ala Thr Arg Val Ser Asn Gln Asn Arg
        195                 200                 205
```

```
Phe Cys Gln Leu Glu Ile Gln Arg Arg Leu Cys Leu Ser Arg Pro Cys
    210                 215                 220

Leu Ala Ser Arg Ser His Gly Ser Trp Asn Ser Ala Phe
225                 230                 235
```

<210> SEQ ID NO 92
<211> LENGTH: 236
<212> TYPE: PRT
<213> ORGANISM: Homo sapiens

<400> SEQUENCE: 92

```
Cys Ile Leu Ser Met Val Tyr Ser Gln Leu Cys Pro Ala Pro Cys Ala
1               5                   10                  15

Cys Pro Trp Thr Pro Pro Gln Cys Pro Pro Gly Val Pro Leu Val Leu
                20                  25                  30

Asp Gly Cys Gly Cys Cys Arg Val Cys Ala Arg Arg Leu Gly Glu Ser
            35                  40                  45

Cys Asp His Leu His Val Cys Asp Pro Ser Gln Gly Leu Val Cys Gln
    50                  55                  60

Pro Gly Ala Gly Pro Ser Gly Arg Gly Ala Val Cys Leu Phe Glu Glu
65                  70                  75                  80

Asp Asp Gly Ser Cys Glu Val Asn Gly Arg Arg Tyr Leu Asp Gly Glu
                85                  90                  95

Thr Phe Lys Pro Asn Cys Arg Val Leu Cys Arg Cys Asp Asp Gly Gly
                100                 105                 110

Phe Thr Cys Leu Pro Leu Cys Ser Glu Asp Val Arg Leu Pro Ser Trp
            115                 120                 125

Asp Cys Pro Arg Pro Arg Arg Ile Gln Val Pro Gly Arg Cys Cys Pro
    130                 135                 140

Glu Trp Val Cys Asp Gln Ala Val Met Gln Pro Ala Ile Gln Pro Ser
145                 150                 155                 160

Ser Ala Gln Gly His Gln Leu Ser Ala Leu Val Thr Pro Ala Ser Ala
                165                 170                 175

Asp Gly Pro Cys Pro Asn Trp Ser Thr Ala Trp Gly Pro Cys Ser Thr
            180                 185                 190

Thr Cys Gly Leu Gly Ile Ala Thr Arg Val Ser Asn Gln Asn Arg Phe
        195                 200                 205

Cys Gln Leu Glu Ile Gln Arg Arg Leu Cys Leu Ser Arg Pro Cys Leu
    210                 215                 220

Ala Ser Arg Ser His Gly Ser Trp Asn Ser Ala Phe
225                 230                 235
```

<210> SEQ ID NO 93
<211> LENGTH: 235
<212> TYPE: PRT
<213> ORGANISM: Homo sapiens

<400> SEQUENCE: 93

```
Ile Leu Ser Met Val Tyr Ser Gln Leu Cys Pro Ala Pro Cys Ala Cys
1               5                   10                  15

Pro Trp Thr Pro Pro Gln Cys Pro Pro Gly Val Pro Leu Val Leu Asp
                20                  25                  30

Gly Cys Gly Cys Cys Arg Val Cys Ala Arg Arg Leu Gly Glu Ser Cys
            35                  40                  45

Asp His Leu His Val Cys Asp Pro Ser Gln Gly Leu Val Cys Gln Pro
    50                  55                  60
```

Gly Ala Gly Pro Ser Gly Arg Gly Ala Val Cys Leu Phe Glu Glu Asp
65                  70                  75                  80

Asp Gly Ser Cys Glu Val Asn Gly Arg Arg Tyr Leu Asp Gly Glu Thr
            85                  90                  95

Phe Lys Pro Asn Cys Arg Val Leu Cys Arg Cys Asp Asp Gly Gly Phe
                100                 105                 110

Thr Cys Leu Pro Leu Cys Ser Glu Asp Val Arg Leu Pro Ser Trp Asp
            115                 120                 125

Cys Pro Arg Pro Arg Arg Ile Gln Val Pro Gly Arg Cys Cys Pro Glu
        130                 135                 140

Trp Val Cys Asp Gln Ala Val Met Gln Pro Ala Ile Gln Pro Ser Ser
145                 150                 155                 160

Ala Gln Gly His Gln Leu Ser Ala Leu Val Thr Pro Ala Ser Ala Asp
                165                 170                 175

Gly Pro Cys Pro Asn Trp Ser Thr Ala Trp Gly Pro Cys Ser Thr Thr
            180                 185                 190

Cys Gly Leu Gly Ile Ala Thr Arg Val Ser Asn Gln Asn Arg Phe Cys
        195                 200                 205

Gln Leu Glu Ile Gln Arg Leu Cys Leu Ser Arg Pro Cys Leu Ala
    210                 215                 220

Ser Arg Ser His Gly Ser Trp Asn Ser Ala Phe
225                 230                 235

<210> SEQ ID NO 94
<211> LENGTH: 234
<212> TYPE: PRT
<213> ORGANISM: Homo sapiens

<400> SEQUENCE: 94

Leu Ser Met Val Tyr Ser Gln Leu Cys Pro Ala Pro Cys Ala Cys Pro
1               5                   10                  15

Trp Thr Pro Pro Gln Cys Pro Pro Gly Val Pro Leu Val Leu Asp Gly
            20                  25                  30

Cys Gly Cys Cys Arg Val Cys Ala Arg Arg Leu Gly Glu Ser Cys Asp
        35                  40                  45

His Leu His Val Cys Asp Pro Ser Gln Gly Leu Val Cys Gln Pro Gly
    50                  55                  60

Ala Gly Pro Ser Gly Arg Gly Ala Val Cys Leu Phe Glu Glu Asp Asp
65                  70                  75                  80

Gly Ser Cys Glu Val Asn Gly Arg Arg Tyr Leu Asp Gly Glu Thr Phe
            85                  90                  95

Lys Pro Asn Cys Arg Val Leu Cys Arg Cys Asp Asp Gly Gly Phe Thr
                100                 105                 110

Cys Leu Pro Leu Cys Ser Glu Asp Val Arg Leu Pro Ser Trp Asp Cys
            115                 120                 125

Pro Arg Pro Arg Arg Ile Gln Val Pro Gly Arg Cys Cys Pro Glu Trp
        130                 135                 140

Val Cys Asp Gln Ala Val Met Gln Pro Ala Ile Gln Pro Ser Ser Ala
145                 150                 155                 160

Gln Gly His Gln Leu Ser Ala Leu Val Thr Pro Ala Ser Ala Asp Gly
                165                 170                 175

Pro Cys Pro Asn Trp Ser Thr Ala Trp Gly Pro Cys Ser Thr Thr Cys
            180                 185                 190

Gly Leu Gly Ile Ala Thr Arg Val Ser Asn Gln Asn Arg Phe Cys Gln
        195                 200                 205

```
Leu Glu Ile Gln Arg Arg Leu Cys Leu Ser Arg Pro Cys Leu Ala Ser
    210                 215                 220

Arg Ser His Gly Ser Trp Asn Ser Ala Phe
225                 230
```

<210> SEQ ID NO 95
<211> LENGTH: 233
<212> TYPE: PRT
<213> ORGANISM: Homo sapiens

<400> SEQUENCE: 95

```
Ser Met Val Tyr Ser Gln Leu Cys Pro Ala Pro Cys Ala Cys Pro Trp
1               5                   10                  15

Thr Pro Pro Gln Cys Pro Pro Gly Val Pro Leu Val Leu Asp Gly Cys
            20                  25                  30

Gly Cys Cys Arg Val Cys Ala Arg Arg Leu Gly Glu Ser Cys Asp His
        35                  40                  45

Leu His Val Cys Asp Pro Ser Gln Gly Leu Val Cys Gln Pro Gly Ala
50                  55                  60

Gly Pro Ser Gly Arg Gly Ala Val Cys Leu Phe Glu Glu Asp Asp Gly
65                  70                  75                  80

Ser Cys Glu Val Asn Gly Arg Arg Tyr Leu Asp Gly Glu Thr Phe Lys
                85                  90                  95

Pro Asn Cys Arg Val Leu Cys Arg Cys Asp Asp Gly Gly Phe Thr Cys
            100                 105                 110

Leu Pro Leu Cys Ser Glu Asp Val Arg Leu Pro Ser Trp Asp Cys Pro
        115                 120                 125

Arg Pro Arg Arg Ile Gln Val Pro Gly Arg Cys Cys Pro Glu Trp Val
130                 135                 140

Cys Asp Gln Ala Val Met Gln Pro Ala Ile Gln Pro Ser Ser Ala Gln
145                 150                 155                 160

Gly His Gln Leu Ser Ala Leu Val Thr Pro Ala Ser Ala Asp Gly Pro
                165                 170                 175

Cys Pro Asn Trp Ser Thr Ala Trp Gly Pro Cys Ser Thr Thr Cys Gly
            180                 185                 190

Leu Gly Ile Ala Thr Arg Val Ser Asn Gln Asn Arg Phe Cys Gln Leu
        195                 200                 205

Glu Ile Gln Arg Arg Leu Cys Leu Ser Arg Pro Cys Leu Ala Ser Arg
210                 215                 220

Ser His Gly Ser Trp Asn Ser Ala Phe
225                 230
```

<210> SEQ ID NO 96
<211> LENGTH: 232
<212> TYPE: PRT
<213> ORGANISM: Homo sapiens

<400> SEQUENCE: 96

```
Met Val Tyr Ser Gln Leu Cys Pro Ala Pro Cys Ala Cys Pro Trp Thr
1               5                   10                  15

Pro Pro Gln Cys Pro Pro Gly Val Pro Leu Val Leu Asp Gly Cys Gly
            20                  25                  30

Cys Cys Arg Val Cys Ala Arg Arg Leu Gly Glu Ser Cys Asp His Leu
        35                  40                  45

His Val Cys Asp Pro Ser Gln Gly Leu Val Cys Gln Pro Gly Ala Gly
50                  55                  60

Pro Ser Gly Arg Gly Ala Val Cys Leu Phe Glu Glu Asp Asp Gly Ser
```

```
                65                  70                  75                  80
Cys Glu Val Asn Gly Arg Arg Tyr Leu Asp Gly Glu Thr Phe Lys Pro
                    85                  90                  95
Asn Cys Arg Val Leu Cys Arg Cys Asp Asp Gly Gly Phe Thr Cys Leu
                    100                 105                 110
Pro Leu Cys Ser Glu Asp Val Arg Leu Pro Ser Trp Asp Cys Pro Arg
                    115                 120                 125
Pro Arg Arg Ile Gln Val Pro Gly Arg Cys Cys Pro Glu Trp Val Cys
            130                 135                 140
Asp Gln Ala Val Met Gln Pro Ala Ile Gln Pro Ser Ser Ala Gln Gly
145                 150                 155                 160
His Gln Leu Ser Ala Leu Val Thr Pro Ala Ser Ala Asp Gly Pro Cys
                    165                 170                 175
Pro Asn Trp Ser Thr Ala Trp Gly Pro Cys Ser Thr Thr Cys Gly Leu
                    180                 185                 190
Gly Ile Ala Thr Arg Val Ser Asn Gln Asn Arg Phe Cys Gln Leu Glu
                    195                 200                 205
Ile Gln Arg Arg Leu Cys Leu Ser Arg Pro Cys Leu Ala Ser Arg Ser
            210                 215                 220
His Gly Ser Trp Asn Ser Ala Phe
225                 230

<210> SEQ ID NO 97
<211> LENGTH: 231
<212> TYPE: PRT
<213> ORGANISM: Homo sapiens

<400> SEQUENCE: 97

Val Tyr Ser Gln Leu Cys Pro Ala Pro Cys Ala Cys Pro Trp Thr Pro
1               5                   10                  15
Pro Gln Cys Pro Pro Gly Val Pro Leu Val Leu Asp Gly Cys Gly Cys
                20                  25                  30
Cys Arg Val Cys Ala Arg Arg Leu Gly Glu Ser Cys Asp His Leu His
                35                  40                  45
Val Cys Asp Pro Ser Gln Gly Leu Val Cys Gln Pro Gly Ala Gly Pro
            50                  55                  60
Ser Gly Arg Gly Ala Val Cys Leu Phe Glu Glu Asp Asp Gly Ser Cys
65                  70                  75                  80
Glu Val Asn Gly Arg Arg Tyr Leu Asp Gly Glu Thr Phe Lys Pro Asn
                    85                  90                  95
Cys Arg Val Leu Cys Arg Cys Asp Asp Gly Gly Phe Thr Cys Leu Pro
                    100                 105                 110
Leu Cys Ser Glu Asp Val Arg Leu Pro Ser Trp Asp Cys Pro Arg Pro
                    115                 120                 125
Arg Arg Ile Gln Val Pro Gly Arg Cys Cys Pro Glu Trp Val Cys Asp
            130                 135                 140
Gln Ala Val Met Gln Pro Ala Ile Gln Pro Ser Ser Ala Gln Gly His
145                 150                 155                 160
Gln Leu Ser Ala Leu Val Thr Pro Ala Ser Ala Asp Gly Pro Cys Pro
                    165                 170                 175
Asn Trp Ser Thr Ala Trp Gly Pro Cys Ser Thr Thr Cys Gly Leu Gly
                    180                 185                 190
Ile Ala Thr Arg Val Ser Asn Gln Asn Arg Phe Cys Gln Leu Glu Ile
                    195                 200                 205
Gln Arg Arg Leu Cys Leu Ser Arg Pro Cys Leu Ala Ser Arg Ser His
```

Gly Ser Trp Asn Ser Ala Phe
225                 230

<210> SEQ ID NO 98
<211> LENGTH: 230
<212> TYPE: PRT
<213> ORGANISM: Homo sapiens

<400> SEQUENCE: 98

Tyr Ser Gln Leu Cys Pro Ala Pro Cys Ala Cys Pro Trp Thr Pro Pro
1               5                   10                  15

Gln Cys Pro Pro Gly Val Pro Leu Val Leu Asp Gly Cys Gly Cys Cys
                20                  25                  30

Arg Val Cys Ala Arg Arg Leu Gly Glu Ser Cys Asp His Leu His Val
            35                  40                  45

Cys Asp Pro Ser Gln Gly Leu Val Cys Gln Pro Gly Ala Gly Pro Ser
50                  55                  60

Gly Arg Gly Ala Val Cys Leu Phe Glu Glu Asp Asp Gly Ser Cys Glu
65                  70                  75                  80

Val Asn Gly Arg Arg Tyr Leu Asp Gly Glu Thr Phe Lys Pro Asn Cys
                85                  90                  95

Arg Val Leu Cys Arg Cys Asp Asp Gly Gly Phe Thr Cys Leu Pro Leu
            100                 105                 110

Cys Ser Glu Asp Val Arg Leu Pro Ser Trp Asp Cys Pro Arg Pro Arg
        115                 120                 125

Arg Ile Gln Val Pro Gly Arg Cys Cys Pro Glu Trp Val Cys Asp Gln
    130                 135                 140

Ala Val Met Gln Pro Ala Ile Gln Pro Ser Ser Ala Gln Gly His Gln
145                 150                 155                 160

Leu Ser Ala Leu Val Thr Pro Ala Ser Ala Asp Gly Pro Cys Pro Asn
                165                 170                 175

Trp Ser Thr Ala Trp Gly Pro Cys Ser Thr Thr Cys Gly Leu Gly Ile
            180                 185                 190

Ala Thr Arg Val Ser Asn Gln Asn Arg Phe Cys Gln Leu Glu Ile Gln
        195                 200                 205

Arg Arg Leu Cys Leu Ser Arg Pro Cys Leu Ala Ser Arg Ser His Gly
    210                 215                 220

Ser Trp Asn Ser Ala Phe
225                 230

<210> SEQ ID NO 99
<211> LENGTH: 229
<212> TYPE: PRT
<213> ORGANISM: Homo sapiens

<400> SEQUENCE: 99

Ser Gln Leu Cys Pro Ala Pro Cys Ala Cys Pro Trp Thr Pro Pro Gln
1               5                   10                  15

Cys Pro Pro Gly Val Pro Leu Val Leu Asp Gly Cys Gly Cys Cys Arg
                20                  25                  30

Val Cys Ala Arg Arg Leu Gly Glu Ser Cys Asp His Leu His Val Cys
            35                  40                  45

Asp Pro Ser Gln Gly Leu Val Cys Gln Pro Gly Ala Gly Pro Ser Gly
50                  55                  60

Arg Gly Ala Val Cys Leu Phe Glu Glu Asp Asp Gly Ser Cys Glu Val
65                  70                  75                  80

```
Asn Gly Arg Arg Tyr Leu Asp Gly Glu Thr Phe Lys Pro Asn Cys Arg
                85                  90                  95

Val Leu Cys Arg Cys Asp Asp Gly Phe Thr Cys Leu Pro Leu Cys
            100                 105                 110

Ser Glu Asp Val Arg Leu Pro Ser Trp Asp Cys Pro Arg Pro Arg Arg
        115                 120                 125

Ile Gln Val Pro Gly Arg Cys Cys Pro Glu Trp Val Cys Asp Gln Ala
    130                 135                 140

Val Met Gln Pro Ala Ile Gln Pro Ser Ser Ala Gln Gly His Gln Leu
145                 150                 155                 160

Ser Ala Leu Val Thr Pro Ala Ser Ala Asp Gly Pro Cys Pro Asn Trp
                165                 170                 175

Ser Thr Ala Trp Gly Pro Cys Ser Thr Thr Cys Gly Leu Gly Ile Ala
            180                 185                 190

Thr Arg Val Ser Asn Gln Asn Arg Phe Cys Gln Leu Glu Ile Gln Arg
        195                 200                 205

Arg Leu Cys Leu Ser Arg Pro Cys Leu Ala Ser Arg Ser His Gly Ser
    210                 215                 220

Trp Asn Ser Ala Phe
225

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccagccagag gaggccacga ac                                                22

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gtacttgggt cggtaggtgc gtgt                                              24

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gtggcccatg ctctggcaga ggg                                               23

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
```

```
gactggagca aggtcgtcct cgcc                                              24
```

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104

```
gcaccaccca caaggaagcc atcc                                              24
```

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105

```
gacgaaaggg aagccggcat cacc                                              24
```

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106

```
gagaaggtcg tgttcgagca aacc                                              24
```

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107

```
cttctcgtgt acttcctgtg cctg                                              24
```

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
cacgtcagct ggcgttgcca gctc                                              24
```

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Pro Glu Glu Ala Thr Asn Phe Thr Leu Ala Gly Cys Val Ser Thr

```
1               5                  10                 15
Arg Thr Tyr Arg Pro Lys Tyr
            20
```

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggccctggcc tgccagaagt gtgg                                           24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gtgtgccttt cctgatctga gaac                                           24

<210> SEQ ID NO 112
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtgattccat ctcttcatgt tcccagaaaa ttcttcccag ccgggcaggg               50

<210> SEQ ID NO 113
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ccagccagag gaggccacga acttcactct cgcaggctgt gtcagcacac gcacctaccg    60
acccaagtac                                                           70

<210> SEQ ID NO 114
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gccgctggag cccttgctcc accagctgcg gcctggggt ctccactcgg                50

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aaaggtgcgt acccagctgt gcc    23

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggtcttggcg aagacggctg acct    24

<210> SEQ ID NO 117
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cctggtgctg gatggctgtg gctgctgccg ggtatgtgca cggcggctgg g    51

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gtcttgtgca agcaacaaaa tggactcc    28

<210> SEQ ID NO 119
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gctgtcgcaa ggctgaatgt aacacag    27

<210> SEQ ID NO 120
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gctccagaac atgtgggatg ggaatatcta acagggtgac caatgaaaac    50

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cctggagtga gcctggtgag aga                                          23

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
acaatacagc cctttgtgtg ggtcaca                                      27

<210> SEQ ID NO 123
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tggttgcttg gcacagattt tacagcatcc acagccatct ctca                   44

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgacttccag gcatgaggtg gctcctg                                      27

<210> SEQ ID NO 125
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
attggcaatc tcttcgaagt cagggtaaga ttcc                              34

<210> SEQ ID NO 126
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ggtacgtcta gactaattgg caatctcttc gaagtcaggg                        40

<210> SEQ ID NO 127
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127 tttcccttg gatcctaaac caacatgagg tggctcctgc cc                      42

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cagattggtg ctggatatgc                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
actgccttga ttactcctac                                              20

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agttgcagat gtggctct                                                18

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
agtccaagag tctcagca                                                18

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
acaactggaa gcactgga                                                18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tcttattcca gaggaacc                                                18

```
<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tccctgtacg cttctggtcg ta                                            22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tctcaaagtc caaagccaca ta                                            22

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cacagttcca gcaaatac                                                 18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggaatcaggc ggtacagt                                                 18

<210> SEQ ID NO 138
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agcctttcca agtcactaga agtcctgctg g                                  31

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctggactaca cccaagcctg a                                             21

<210> SEQ ID NO 140
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
catttcttgg gatttaggca aga                                            23

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tctagcccac tccctgcct                                                 19

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gaagtcggag agaaagctcg c                                              21

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cacacacagc ctatatcaaa catgcacacg                                     30

<210> SEQ ID NO 144
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cttgagactg aaagatttag ccataatgta aactgcct                            38

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
caaatgcaac ctcacaacct tg                                             22

<210> SEQ ID NO 146
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 146
ttcttttatg cccaaagtcc aatt                                           24

<210> SEQ ID NO 147
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggattctaat acgactcact atagggcgtc cctggccagt gctgtgag                 48

<210> SEQ ID NO 148
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ctatgaaatt aaccctcact aaagggaggg ccaggctttg cttccatt                 48

<210> SEQ ID NO 149
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggattctaat acgactcact atagggctgg aggcatggca caggaac                  47

<210> SEQ ID NO 150
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ctatgaaatt aaccctcact aaagggatcc ggatcaggct tgggtgta                 48

<210> SEQ ID NO 151
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggattctaat acgactcact atagggcagc ttgggatgga ggtctttc                 48

<210> SEQ ID NO 152
<211> LENGTH: 44
<212> TYPE: DNA
<213> ORGANISM: Artificial Sequence
<220> FEATURE:
<223> OTHER INFORMATION: Description of Artificial Sequence: Synthetic
```

-continued

```
        oligonucleotide

<400> SEQUENCE: 152
ctatgaaatt aaccctcact aaagggaggg cactggggtg gtgt                    44

<210> SEQ ID NO 153
<211> LENGTH: 45
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 153
ggattctaat acgactcact atagggcgcg aggacggcgg cttca                   45

<210> SEQ ID NO 154
<211> LENGTH: 48
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 154
ctatgaaatt aaccctcact aaagggaaga gtcgcggccg ccctttt                 48

<210> SEQ ID NO 155
<211> LENGTH: 48
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 155
ggattctaat acgactcact atagggcggg gctcctcttc tccactct                48

<210> SEQ ID NO 156
<211> LENGTH: 48
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 156
ctatgaaatt aaccctcact aaagggagct gtcgcaaggc tgaatgta                48
```